(12) United States Patent
Salemme et al.

(10) Patent No.: US 8,993,714 B2
(45) Date of Patent: *Mar. 31, 2015

(54) STREPTAVIDIN MACROMOLECULAR ADAPTOR AND COMPLEXES THEREOF

(75) Inventors: Francis Raymond Salemme, Yardley, PA (US); Patricia C. Weber, Yardley, PA (US)

(73) Assignee: Imiplex LLC, Yardley, PA (US)

( * ) Notice: Subject to any disclaimer, the term of this patent is extended or adjusted under 35 U.S.C. 154(b) by 803 days.

This patent is subject to a terminal disclaimer.

(21) Appl. No.: 12/766,658

(22) Filed: Apr. 23, 2010

(65) Prior Publication Data

US 2010/0329930 A1 Dec. 30, 2010

Related U.S. Application Data

(63) Continuation-in-part of application No. PCT/US2008/012174, filed on Oct. 27, 2008.

(60) Provisional application No. 60/996,089, filed on Oct. 26, 2007, provisional application No. 61/173,114, filed on Apr. 27, 2009.

(51) Int. Cl.
*C07K 14/00* (2006.01)
*C07K 16/00* (2006.01)
*C07K 14/36* (2006.01)
*G01N 33/53* (2006.01)

(52) U.S. Cl.
CPC ............... *C07K 16/00* (2013.01); *C07K 14/36* (2013.01); *G01N 33/53* (2013.01)
USPC .............................................. 530/300; 514/2

(58) Field of Classification Search
None
See application file for complete search history.

(56) References Cited

U.S. PATENT DOCUMENTS

| 4,839,293 | A | 6/1989 | Cantor et al. |
|---|---|---|---|
| 4,933,275 | A | 6/1990 | Wands et al. |
| 5,258,627 | A | 11/1993 | Turin |
| 5,672,691 | A | 9/1997 | Kopetzki et al. |
| 5,891,993 | A | 4/1999 | Dawson et al. |
| 5,948,668 | A | 9/1999 | Hartman et al. |
| 5,948,688 | A | 9/1999 | Weber et al. |
| 6,022,951 | A | 2/2000 | Sano et al. |
| 6,156,493 | A | 12/2000 | Stayton |
| 6,165,750 | A | 12/2000 | Stayton |
| 6,211,388 | B1 | 4/2001 | Tsuji et al. |
| 6,218,506 | B1 | 4/2001 | Krafft et al. |
| 6,232,085 | B1 | 5/2001 | Pantoliano et al. |
| 6,268,158 | B1 | 7/2001 | Pantoliano et al. |
| 6,291,192 | B1 | 9/2001 | Pantoliano et al. |
| 6,485,984 | B1 | 11/2002 | Kim |
| 6,490,532 | B1 | 12/2002 | Hogue et al. |
| 6,492,492 | B1 | 12/2002 | Stayton |
| 6,653,127 | B1 | 11/2003 | Malcolm et al. |
| 6,743,771 | B2 | 6/2004 | Douglas et al. |
| 6,756,039 | B1 | 6/2004 | Yeates et al. |
| 6,849,458 | B2 | 2/2005 | Pantoliano et al. |
| 6,859,736 | B2 | 2/2005 | Blankenbecler et al. |
| 7,039,621 | B2 | 5/2006 | Agrafiotis et al. |
| 7,045,537 | B1 | 5/2006 | Woolfson et al. |
| 7,122,321 | B2 | 10/2006 | Pantoliano et al. |
| 7,138,255 | B2 | 11/2006 | Vodyanoy et al. |
| 7,139,739 | B2 | 11/2006 | Agrafiotis et al. |
| 7,144,991 | B2 | 12/2006 | Goshorn et al. |
| 7,188,055 | B2 | 3/2007 | Agrafiotis et al. |
| 7,217,557 | B1 | 5/2007 | Noel et al. |
| 7,803,575 | B2 | 9/2010 | Borchert et al. |
| 2001/0047074 | A1 | 11/2001 | Kissel et al. |
| 2002/0037908 | A1 | 3/2002 | Douglas et al. |
| 2003/0027194 | A1 | 2/2003 | Kurz et al. |
| 2003/0077803 | A1 | 4/2003 | Walker et al. |
| 2003/0171257 | A1 | 9/2003 | Stirbl et al. |
| 2003/0198967 | A1 | 10/2003 | Matson et al. |
| 2004/0014186 | A1 | 1/2004 | Kumar |
| 2004/0152872 | A1 | 8/2004 | Wohlfahrt et al. |
| 2005/0027103 | A1 | 2/2005 | Tang et al. |
| 2005/0048078 | A1 | 3/2005 | Sakasegawa et al. |
| 2005/0053525 | A1 | 3/2005 | Segal et al. |
| 2005/0130258 | A1 | 6/2005 | Trent et al. |
| 2005/0192757 | A1 | 9/2005 | Umeyama et al. |
| 2005/0221343 | A1 | 10/2005 | Waldo et al. |
| 2006/0003381 | A1 | 1/2006 | Gilmore et al. |
| 2006/0009620 | A1 | 1/2006 | Woolfson et al. |
| 2006/0030053 | A1 | 2/2006 | Seymour et al. |
| 2006/0089808 | A1 | 4/2006 | Agrafiotis et al. |
| 2006/0134072 | A1 | 6/2006 | Pedrozo et al. |
| 2007/0087356 | A1 | 4/2007 | Chatterjee et al. |

(Continued)

FOREIGN PATENT DOCUMENTS

WO WO-2006/058226 A2 6/2006
WO WO-2008/112980 A2 9/2008

(Continued)

OTHER PUBLICATIONS

Cloutier et al., "Streptabody, a highly avidity molecule made by tetramerization of in vivo biotinylated, a phage display-selected scFv fragments on streptavidin", Molecular Immunology 37: 1067-1077 (2000).*
Schaffer et al., "The structure of secondary cell wall polymers: how Gram-positive bacteria stick their cell walls together", Microbiology (2005) 151:643-651.*
Green, "A Spectrophotometric Assay for Avidin and Biotin Based on Binding of Dyes by Avidin", Biochem. J. (1965) 94:23c-24c.*
Peel et al., "Short Communications: Inactivation by Substrate plus Oxygen of the Pyruvate Dehydrogenase of a Strictly Anaerobic Bacterium", Biochem. J. (1965) 94:21c-22c.*
Drexler (ed.) et al., "Productive Nanosystems: A Technology Roadmap 2007", Battelle Memorial Institute and Foresight Nanotech Institute, 2007.*

(Continued)

*Primary Examiner* — Anand Desai
(74) *Attorney, Agent, or Firm* — Venable LLP; Lars H. Genieser; Michael A. Golin

(57) ABSTRACT

A streptavidin macromolecular adaptor (SAMA) protein may be used for the controlled assembly of nanostructure building blocks and struts including streptavidin:SAMA complexes.

50 Claims, 47 Drawing Sheets

(56) References Cited

U.S. PATENT DOCUMENTS

| | | | |
|---|---|---|---|
| 2007/0178572 A1 | 8/2007 | Gamblin et al. | |
| 2007/0256250 A1 | 11/2007 | Knight | |
| 2008/0003662 A1 | 1/2008 | Trachtenberg | |
| 2008/0248972 A1 | 10/2008 | Nishizawa et al. | |
| 2010/0256342 A1* | 10/2010 | Salemme et al. | 530/391.1 |
| 2011/0085939 A1* | 4/2011 | Salemme et al. | 422/68.1 |
| 2012/0059156 A1* | 3/2012 | Salemme et al. | 530/387.3 |
| 2014/0178962 A1* | 6/2014 | Salemme et al. | 435/177 |

FOREIGN PATENT DOCUMENTS

| | | |
|---|---|---|
| WO | WO-2009/055068 A1 | 4/2009 |
| WO | WO-2010/019725 A2 | 2/2010 |

OTHER PUBLICATIONS

Office Action issued in U.S. Appl. No. 12/892,911 dated Sep. 11, 2014.*
Office Action issued in U.S. Appl. No. 13/319,989 dated Jun. 2, 2014.*
Restriction Requirement in U.S. Appl. No. 12/589,529 dated Jul. 26, 2011.*
Restriction Requirement in U.S. Appl. No. 12/892,911 dated Apr. 3, 2014.*
Restriction Requirement in U.S. Appl. No. 13/319,989 dated May 17, 2013.*
Filing Receipt in U.S. Appl. No. 13/398,820 dated Mar. 1, 2012.*
Restriction Requirement in U.S. Appl. No. 13/797,283 dated May 15, 2014.*
Restriction Requirement in U.S. Appl. No. 13/797,283 dated Oct. 16, 2014.*
Adams et al., "Structure of the Pleckstrin Homology Domain from Phospholipase C Delta in Complex with Inositol Trisphosphate" Protein Data Bank, Code: 1MAIL, Last Modified on Feb. 24, 2009 (www.rcsb.org/pdb/explore/explore.do?structureId=1mai).
Benach et al., "The 2.35 A structure of the TenA homolog from *Pyrococcus furiosus* supports an enzymatic function in thiamine metabolism" (2005) *Acta Crystallogr.,Sect.D* 61: 589-598 (pdb code:1rtw).
Blum et al., "An engineered virus as a scaffold for three-dimensional self-assembly on the nanoscale" *Small* (2005)1:702.
Blum et al., "Cowpea mosaic virus as a scaffold for 3-D patterning of gold nanoparticles" *Nano Lett* (2004)4:867.
Case et al., "The Amber biomolecular simulation programs" (2005) *J. Computat. Chem.* 26, 1668-1688 (//amber.scripps.edu/).
Castro et al., "Homogeneous biocatalysis in organic solvents and water-organic mixtures" *Crit Rev Biotechnol* (2003)23:195-231.
Chatterji et al., "A virus-based nanoblock with tunable electrostatic properties" *Nano Lett* (2005)5:597.
Chatterji et al., "New addresses on an addressable virus nanoblock; uniquely reactive Lys residues on cowpea mosaic virus" *Chem Biol* (2004)11:855.
Cherny et al., "Analysis of Various Sequence-Specific Triplexes by Electron and Atomic Force Microscopies" *Biophysical J* (1998)74:1015-1023.
Cosgrove et al., "The structural basis of sirtuin substrate affinity" (2006) *Biochemistry* 45: 7511-7521 (pdb code: 2h2i).
Deng Y, Wang Y, Holtz B, Li J, Traaseth N, Veglia G, Stottrup BJ, Elde R, Pei, Guo A, Zhu X-Y "Fluidic and Air-Stable Supported Lipid Bilayer and Cell-Mimicking Microarrays" *J Am Chem Soc* (2008) Apr. 12, 2008 web publication.
Eigler et al., "Positioning single atoms with a scanning tunnelling microscope" *Nature* (1990)344:524-526.
Esposito et al., "Structural study of a single-point mutant of *Sulfolobus solfataricus* alcohol dehydrogenase with enhanced activity" (2003) *Febs Lett.* 539: 14-18 (pdb code: 1nto).
Falkner et al., "Virus crystals as nanocomposite scaffolds" *J Am Chem Soc* (2005)127:5274.
Fitzpatrick et al., "Enzyme Crystal Structure in a Neat Organic Solvent" *Proc Nat Acad Sci USA* (1993)90:8653.
Gonzalez et al., "Interaction of Biotin with Streptavidin" *J Biol Chem* (1997)272:112288-11294.
Green NM "A Spectrophotometric Assay for Avidin and Biotin Based on Binding of Dyes by Avidin" *Biochem J* (1965)294:23c-24c.
Green NM "Avidin and Streptavidin" *Meth Enzymol* (1990)243:51-67.
Green NM "Avidin" *Adv Prot Chem* (1975)29:85-133.
Gupta MN, Roy I "Enzymes in organic media: Forms, functions and applications" *Eur J Biochem* (2004)271:2575-2583.
Hartmann et al., "Imaging and manipulation properties of nanoparticles in scanning tunneling microscopy" *Nanotechnology* (1996)7:376-380.
Hatzor-de Picciotto et al., "Arrays of $Cu^{2+}$-Complexed Organic Clusters Grown on Gold Nano Dots" (2007) Journal of Experimental Nanoscience, 2: 3-11.
Hla et al., "STM Control of Chemical Reactions: Single-Molecule Synthesis" *Annu Rev Phys Chem* (2003)54:307-309.
Hofmann et al., "Iminobiotin affinity columns and their application to retrieval of streptavidin" *Proc Natl Acad Sci USA* (1980)77:4666-4668.
Humphrey et al., "VMD: visual molecular dynamics" J Mol Graph. Feb. 1996;14(1):33-8-27-8. Retrieved From: //www.ks.uiuc.edu/Research/vmd/.
International Preliminary Report on Patentability issued in International Application No. PCT/US2009/053628 dated Nov. 1, 2011.
International Preliminary Report on Patentability issued in International Application No. PCT/US2008/012174 dated Apr. 27, 2010.
International Preliminary Report on Patentability issued in International Application No. PCT/US2010/034248 dated Nov. 15, 2011.
International Search Report issued in International Application No. PCT/US2008/012174 dated Feb. 2, 2009.
International Search Report issued in International Application No. PCT/US2009/053628 dated Jul. 14, 2010.
International Search Report issued in International Application No. PCT/US2010/034248 dated Aug. 19, 2010.
International Technology Roadmap for Semiconductors (//www.itrs.net/reports.html), pp. 1-3, accessed Sep. 25, 2012.
Izard et al., "Principles of quasi-equivalence and Euclidean geometry govern the assembly of cubic and dodecahedral cores of pyruvate dehydrogenase complexes" (1999) *Proc. Natl. Acad. Sci. USA* 96: 1240-1245 (pdb code: 1b5s).
Jones A "O: A Macromolecule Modeling Environment," Crystallographic and Modeling Methods in Molecular Design, 1990, pp. 189-199.
Jones, et al., "Using known substructures in protein model building and crystallography," The EMBO Journal, vol. 5, No. 4, 1986 pp. 819-822.
Judy JW, "Microelectromechanical systems (MEMS): fabrication, design and applications" (2001) *Smart Mater. Struct.* 10 1115-1134.
Kim et al., "Crystal structure of a small heat-shock protein" (1998) *Nature* 394: 595-599 (pdb code: 1shs).
Kisker et al., "A left-hand beta-helix revealed by the crystal structure of a carbonic anhydrase from the archaeon *Methanosarcina thermophila*" (1996) EMBO J. v15 pp. 2323-30 (pdb code: 1thj).
Kitago et al., "Structure of 5'-deoxy-5'-methylthioadenosine phosphorylase homologue from *Sulfolobus tokodaii*" Protein Data Bank, Code: 1V4N, Last Modified on Feb. 24, 2009 (www.rcsb.org/pdb/explore/explore.do?structureId=1v4n).
Lawrence et al., "Shape complementarity at protein/protein interfaces" *J Mol Biol* (1993)234:946-950.
Lee et al., "Protein Nanoarrays Generated by Dip-Pen Nanolithography" *Science* (2002)295:1702-1705.
Lee et al., "The interpretation of protein structures: Estimation of static accessibility" (1971) *J. Mol. Biol.* 55, 379-400.
Levene et al., "Zero-Mode Waveguides for Single-Molecule Analysis at High Concentrations" (2003) Science 299: 682-686.
Liu et al., "Nanofabrication of Self-Assembled Monolayers Using Scanning Probe Lithography" *Nanotechnology* (1996)7:376-380.
Liu et al., "Positioning protein molecules on surfaces: A nanoengineering approach to supramolecular chemistry" *Proc Nat Acad Sci* (2002)99:5165-5170.
Loo et al., "Effect of reducing disulfide-cotaining proteins on electrospray ionization spectra" *Anal Chem* (1990)62:693-698.

(56) References Cited

OTHER PUBLICATIONS

Massant et al., "Refined structure of *Pyrococcus furiosus* ornithine carbamoyltransferase at 1.87 A" (2003) *Acta Crystallogr.*, Sect.D 59: 2140-2149 (pdb code: 1pvv).
Medalsy et al., "SP1 Protein-Based Nanostructures and Arrays" (2008) *Nano Lett.*, 8 (2), 473-477.
Merrifield et al., "An instrument for automated synthesis of peptides" *Anal Chem* (1966)38:1905-1914.
Merrifield et al., "Automated Peptide Synthesis" *Nature* (1965)207:522-523.
Ni et al., "Structure of the arginine repressor from *Bacillus stearothermophilus*." (1999) *Nat.Struct.Biol.* 6: 427-432 (pdb code: 1b4b).
Nordlund, HR, et. al. Construction of a Dual Chain Pseudotetrameric Chicken Avidin by Combining Two Circularly Permuted Avidins J. Biol. Chem. 279:36715-36719 (2004).
Padilla et al., "Nanohedra: Using symmetry to design self-assembling protein cages, layers, crystals, and filaments" *Proc Nat Acad Sci USA* (2001)98:2217-2221.
Pantoliano et al., "High Density Miniaturized Thermal Shift Assay as a General Strategy for Drug Discovery" *J Biomol Screening* (2001)6:429-440.
Phillips et al., "The Biological Frontiers of Physics" Physics Today (May 2006) p. 38-43.
Protein Data Bank. www.rcsb.org/pdb/, pp. 1-2, accessed Sep. 25, 2012.
Ringler et al., "Self-Assembly of Proteins into Designed Networks" *Science* (2003)302:106-109.
Rogers et al., "Recent progress in Soft Lithography" (2005) *Materials Today* 8:50-56.
Rothemund PWK "Folding DNA to create nanoscale shapes and patterns" *Nature* (2006)440:297-302.
Rupley et al., "Protein hydration and function" *Adv Protein Chem* (1991)41:37-172.
Saridakis et al., "Insights into ligand binding and catalysis of a central step in NAD+ synthesis: structures of *Methanobacterium thermoautotrophicum* NMN adenylyltransferase complexes." (2001) *J.Biol.Chem.* 276: 7225-7232 (pdb code: 1hyb).
Saveanu et al., "Structural and nucleotide-binding properties of YajQ and YnaF, two *Escherichia coli* proteins of unknown function" *Prot Sci* (2002)11:2551-2560.
Schulten K "VMD" //www.ks.uiuc.edu/Research/vmd/, pp. 1-2, accessed Sep. 25, 2012.
Schwarzenbacher et al. "Crystal structure of a phosphoribosylaminoimidazole mutase PurE (TM0446) from *Thermotoga maritima* at 1.77 A resolution" (2004) *Proteins* 55: 474-478 (pdb code: 1o4v).
Schwarzenbacher et al., "Crystals Structure of Uronate Isomerase (TM0064) From *Thermotoga maritima* at 2.85 A Resolution" *Proteins: Struct, Funct & Bioinform* (2003)53:142-145.
Seeman NC "From Genes to Machines: DNA Nanomechanical Devices" *Trends in Biochemical Sciences* (2005a)30:119-235.
Seeman NC "Structural DNA Nanotechnology: An Overview" Methods in Molecular Biology 303: Bionanotechnology Protocols, Editors, Sandra J. Rosenthal and David W. Wright, Humana Press, Totowa, NJ (2005b) pp. 143-166.
Shih et al., "1.7-kilobase single-stranded DNA that folds into a nanoscale octahedron" *Nature* (2004)427:618-621.
Siegele "Universal Stress Proteins in *Escherichia coli*" *J Bacteriol* (2005) 187:6253-6254.
Skerra et al., "Use of the Strep-tag and Streptavidin for Detection and Purification of Recombinant Proteins" *Meth. Enzymology* (2000)326:271-204.
Sleytr et al., "S Layers as Basic Building Block for a Molecular Construction Kit" (2008) *FEBS J.* 274:323-334.
Sligar et al., "Protein engineering for molecular electronics" *Curr Opin Biotechnol* (1992)3:388-393.
Smith et al., Surface Plasmon Resonance Imaging as a Tool to Monitor Biomolecular Interactions in an Array Based Format. *Appl. Spectroscopy*, 2003, 57, 320A-332A.
Soukka et al., "Utilization of Kinetically Enhanced Monovalent Binding Affinity by Immunoassays Based on Multivalent Nanoparticle-Antibody Bioconjugates" *Anal Chem* (2001) 73:2254-2260.
Sousa et al., "Structure of the universal stress protein of *Haemophilus influenzae*" *Structure* (2001)9:1135-1141.
Teplyakov et al., "Crystal structure of inorganic pyrophosphatase from *Thermus thermophilus*" (1994) *Protein Sci.* 3: 1098-1107 (pdb code: 2prd).
Wada et al., "Crystal Structure of IPP isomerase at P43212" Protein Data Bank, Code: 1VCG, Last Modified on Jul. 13, 2011 (www.rcsb.org/pdb/explore/explore.do?structureId=1vcg).
Weber et al., "Crystallographic and Thermodynamic Comparison of Natural and Synthetic Ligands Bound to Streptavidin" *J Amer Chem Soc* (1992)114:3197-3200.
Weber et al., "Structural Origins of High Affinity Biotin Binding to Streptavidin" *Science* (1989)243:85-88.
Weber et al., "Structure-Based Design of Synthetic Azobenzene Ligands for Streptavidin" *J Amer Chem Soc* (1994)116:2717-2724.
Weber S (1999) //jcrystal.com/steffenweber/gallery/Fullerenes/Fullerenes.html, pp. 1-4, accessed Sep. 25, 2012.
Whitesides et al., "Beyond molecules: Self-assembly of mesoscopic and macroscopic components" *Proc Nat Acad Sci USA* (2002)99:4769-4774.
Whitesides et al., "Molecular Self Assembly and Nanochemistry: A chemical strategy for the synthesis for the synthesis of nanostructures" (1991) *Science* 254, 1312-1319.
Xia et al., "Soft Lithography" (1998) *Annu. Rev. Mater. Sci.* 28, 153-184.
Zaks et al., "Enzymatic catalysis in nonaqueous solvents" *J Biol Chem* (1988)263:3194-3201.
Zarembinski et al., "Structure-based assignment of the biochemical function of a hypothetical protein: A test case of structural genomics" *Proc Natl Acad Sci USA* (1998)95:15189-15193.
Zhu et al., "Crystal Structure of Tt0030 from *Thermus thermophilus*" Protein Data Bank, Code: 2IEL, Last Modified on Feb. 24, 2007 (www.rcsb.org/pdb/explore/explore.do?structureId=2iel).
Restriction Requirement issued in U.S. Appl. No. 12/589,529 dated Jul. 26, 2011.
Dotan et al., "Self-Assembly of a Tetrahedral Lectin into Predesigned Diamondlike Protein Crystals," Angewandte Chemie International Edition, vol. 38, Iss. 16, pp. 2363-2366 (1999) and online abstract at http:/www3.interscience.wiley.com/cgi-bin/abstract/63001579/ABSTRACT accessed Jul. 29, 2005.
Livnah et al., "Three-dimensional structures of avidin and the avidin-biotin complex," Proc. Natl. Acad. Sci. USA, vol. 90, pp. 5076-5080 (1993).
Restriction Requirement issued in U.S. Appl. No. 13/319,989 dated Nov. 21, 2013.
Ringler et al., "Self-Assembly of Proteins into Designed Networks", Science, 302 (2003) 106-109: Supporting Online Material, 8 pages.
Halford, "Catalyst Goes Viral", Chemical & Engineering News, (Jun. 14, 2010) 13.
Adams et al., "Structure and properties of the atypical iron superoxide dismutase from *Methanobacterium thermoautotrophicum*" To be published (2002) (pdb code:1ma1).
Alber et al., "Kinetic and Spectroscopic Characterization of the Gamma-Carbonic Anhydrase from the Methanoarchaeon *Methanosarcina* thermophile" Biochemistry (1999)38:13119-13128.
Allert et al., "Computational design of receptors for an organophosphate surrogate of the nerve agent soman" Proc Natl Acad Sci USA (2004)101:7907-7912.
Asada et al., 2007 Protein Data Bank Entry 2cu0.
Ashwell et al., Uronic Acid Metabolism in Bacteria I. Purification and Properties of Uronic Acid Isomerase in *Escherichia coli* J Biol Chem (1960)235:1559-1565.
Barat et al., "Metabolic biotinylation of recombinant antibody by biotin ligase retained in the endoplasmic reticulum" Biomol Eng (2007)24:283-291.
Biteau et al., "ATP-dependent reduction of cysteine-sulfinic acid by S. cerevisiae sulphlredoxin" Nature (2003)425:980-984.

(56) References Cited

OTHER PUBLICATIONS

Carvalho-Alves et al., "Stoichiometric Photolabeling of Two Distinct Low and High Affinity nucleotide Sites in Sarcoplasmic Reticulum ATPase" J Biol Chem (1985) 260:4282-4287.

Chapman-Smith et al., "Molecular Biology of biotin attachment to proteins" J Nutr (1999)129:477S-484S.

Collins et al., "Crystals structure of a heptameric Sm-like protein complex from archea: Implications for the structure and evolution of snRNPs" J Mol Biol (2001) 309:915-923.

Cornell et al., "A Second Generation Force Field for the Simulation of Proteins, Nucleic Acids, and Organic Molecules" J Am Chem Soc (1995) 117:51795197.

Das et al., "Macromolecular Modeling with Rosetta" Annu Rev Biochem (2008) 77:363-382.

Ebihara et al., "Structure-based functional identification of a novel heme-binding protein from Thermus thermophilus HBB" J Struct Funct Genom (2005) 6:21-32.

Ermolova et al., "Site-Directed Alkylation of Cysteine Replacements in the Lactose Permease of *Escherichia coli*: Helices I, II, VI, and XI" Biochemistry (2006) 45:4182-4189.

Faust et al., "Synthesis of a Protein-reactive ATP analog and Its Application for the Affinity Labeling of Rabbit-Muscle Actin" Eur J Biochem (1974) 43:273-279.

Finzel et al., "Molecular Modeling with Substructure Libraries Derived from Known Protein Structures" In Crystallographic and Modeling Methods in Molecular Design (S Ealick & C Bugg eds.) Springer Verlag, New York (1990) pp.175-189.

Ge et al., "Enzyme-Based CO2 Capture for Air Recovery Subsystems" Life Support & Biosphere Science (2002) 8:181-189.

Green NM "A Spectrophotometric Assay for Avidin and Biotin Based on Binding of Dyes by Avidin" Biophys J (1965)294:23c-24c.

Guex N "Swiss-PdbViewer: A new fast and easy to use PDB viewer for the Macintosh" Experientia (1996) 52:A26.

Guex et al., "Protein Modelling for All" Trends Biochem Sci (1999) 24:364-367.

Hernandez et al., "Dynamic Protein Complexes: Insights from Mass Spectrometry" J Biol Chem (2001) 276:46685-46688.

Holmberg et al., "The biotin-streptavidin interaction can be reversibly broken using water at elevated temperatures" Electrophoresis (2005) 3:501-10.

Horlick et al., "Permuteins of interleukin 1β: A simplified approach for the construction of permuted proteins having new termini" Prot Eng (1992) 5:427-431.

Horovitz et al., "An accurate method for determination of receptor-ligand and enzyme-inhibitor dissociation constants from displacement curves" Proc Natl Acad Sci USA (1987) 84:6654-6658.

Jacobson et al., "ATP binding to a protease-resistant core of actin" Proc Nat Acad Sci (1976) 73:2742-2746.

Jaenicke R "Stability and folding of ultrastable proteins: eye lens crystallins and enzymes from thermophiles" FASEB J (1996) 10:84-92.

Jeyakanthan et al., "Observation of a calcium-binding site in the gamma-class carbonic anhydrase from Pyrococcus horikoshii" Acta Cryst D (2008)64:1012-1019 (pdb code: 1v3w).

Kay et al., "High Throughput Biotinylation of Proteins" Meth Mol Biol (2009)498:185-198.

Khalifah RG "Carbon dioxide hydration activity of carbonic anhydrase. I. Stop-flow kinetic studies on the native human isoenzymes B and C" J Biol Chem (1971) 246:2561-2573.

Kirk et al., "Optimising the recovery of recombinant thermostable proteins expressed in mesophilic hosts" J Biotechnol (1995) 42:177-84.

Krishnaswamy et al., "Free energies of protein-protein association determined by electrospray ionization mass spectrometry correlate accurately with values obtained by solution methods" Protein Sci (2006) 15:1465-1475.

Kumar et al., "Factors enhancing protein thermostability" Prot Eng (2000) 13:179-191.

Kurzban et al., "The Quaternary Structure of Streptavidin in Urea" J Biol Chem (1991) 266:14470-14477.

Lepock et al., "Contribution of Conformational Stability and Reversibility of Unfolding to the Increased Thermostability of Human and Bovine Superoxide Dismutase Mutated at Free Cysteines" J Biol Chem (1990) 265:21612-21618.

Maren TH, "A simplified micromethod for the determination of carbonic anhydrase and its inhibitors" J Pharmacol Exp Ther (1960) 130:26-29.

Matulis et al., "Thermodynamic Stability of Carbonic Anhydrase: Measurements of Binding Affinity and Stoichiometry Using ThermoFluor" Biochemistry (2005) 44:5258-66.

Merrifield RB "Solid Phase peptide Synthesis. I. The Synthesis of a Tetrapeptide" J Am Chem Soc (1963) 85:2149-2154.

Mohan et al., "Continuum model calculations of solvation energies: Accurate evaluation of electrostatic contributions" J Phys Chem (1992) 96:6428-36.

Mohan et al., "Docking: Successes and Challenges" Curr Pharmaceutical Design (2005) 11:323-34.

Neves-Peterse et al., "Photonic activation of disulfide bridges achieves oriented protein immobilization on biosensor surfaces" Prot Sci (2006) 15:343-351.

Pantazatos et al., "Rapid refinement of crystallographic protein construct definition employing enhanced hydrogen/deuterium exchange MS" Proc Natl Acad Sci USA (2004) 101:751-756.

Potier et al., "Using nondenaturing mass spectrometry to detect fortuitous ligands in orphan nuclear receptors" Protein Sci (2003) 12:725-733.

Repo et al., "Binding properties of HABA-type azo derivatives to avidin and avidin-related protein 4" Chem Biol (2006) 10:1029-1039.

Riddles et al., "Reassessment of Ellman's Reagent" Meth Enzymol (1983) 91:49-60.

Salemme FR "Conformational Flexibility and Amide Exchange Stability in Protein B-Sheets" Nature (1982) 299:754-756.

Sano et al., "Cooperative Biotin Binding by Streptavidin Electrophoretic Behavior and Subunit Association of Streptavidin in the Presence of 6M Urea" J Biol Chem (1990b) 265:3369-3373.

Sano et al., "Expression of a cloned streptavidin gene in *Escherichia coli*" Proc Natl Acad Sci USA (1990a) 87:142-146.

Sano et al., "Recombinant Core Streptavidins A Minimum-sized Core Streptavidin has Enhanced Structural Stability and Higher Accessibility to Biotinylated Macromolecules" J Biol Chem (1995) 270:28204-28209.

Sasaki et al., "Two-dimensional arrangement of a functional protein by cysteine-gold interaction: enzyme activity and characterization of a protein monolayer on a gold substrate" Biophysical Journal (1979) 72:1842-1848.

Shimkus et al., "A chemically cleavable biotinylated nucleotide: Usefulness in the recovery of protein-DNA complexes from avidin affinity columns" Proc Natl Acad Sci USA (1985) 82:2593-2597.

Sorensen et al., "Production of recombinant thermostable proteins expressed in *Escherichia coli*: completion of protein synthesis is the bottleneck" J Chromatogr B Analyt Technol Biomed Life Sci (2003) 786:207-214.

Spraggon et al., "On the use of DXMS to produce more crystallizable proteins: Structures of the T. maritima proteins TM0160 and TM1171" Prot Sci (2004) 13:3187-3199.

Spura et al., "Biotinylation of Substituted Cysteines in the Nicotinic Acetylcholine Receptor Reveals Distinct Binding Modes for a-Bungarotoxin and Erabutoxin" J Biol Chem (2000) 275:22452-22460.

Suter "Isolation and Characterization of Highly Purified Streptavidin Obtained in a Two-Step Purification Procedure from Streptomyces avidinii Grown in a Synthetic Medium" J Immunol Meth (1988) 113:83-91.

Taremi et al., "Construction and Expression of a Novel Fully Activated Recombinant Single-chain Hepatitis C Virus Protease" Prot Sci (1998) 7:2143-2149.

Thompson LD, Weber PC "Expression of Streptavidin from a Synthetic Gene" Gene (1993)136:243-6.

Waner et al., "Thermal and Sodium Dodecylsulfate Induced Transitions of Streptavidin" Biophys J (2004) 87:2701-2713.

(56) References Cited

OTHER PUBLICATIONS

Wasserman et al., "A Molecular Dynamics Investigation of the Elastomeric Restoring Force in Elastin" Biopolymers (1990) 29:1613-1631.

Wendoloski et al., "Molecular Dynamics Simulation of a Phospholipid Micelle" Science (1989) 243:636-638.

Wendoloski et al., "PROBIT: A Statistical Approach to Modeling Proteins from Partial Coordinate Data Using Substructure Libraries" J Mol Graphics (1992)10:124-126.

Woo et al., Reversing the inactivation of peroxlredoxins caused by cysteine sulfinic acid formation Science (2003) 300:653-658.

Wu et al., "Engineering Soluble Monomeric Streptavidin with Reversible Biotin Binding Capability" J Biol Chem (2005) 280:23225-23231.

Wu et al., "Binding of ATP to brain glutamate decarboxylase as studied by affinity chromatography" J Neurochem (1984) 42:1607-1612.

Yamashita et al., "Type 2 isopentenyl diphosphate isomerase from a thermoacidophilic archaeon Sulfolobus Shibatae" Eur J Biochem (2004) 271:1087-1093.

Yu et al., "Crystal structures of catalytic complexes of the Fe(II)-oxoglutarate-dependent DNA repair enzyme AlkB give insight into promiscuous substrate recognition and oxidation chemistry" Nature (2006) 439:879-884.

Zhang et al., "Determination of amide hydrogen exchange by mass spectrometry: a new tool for protein structure elucidation" Prot Sci (1993) 2:522-531.

Zimmerman et al., "Characterization of CamH from Methanosarcina thermophila, founding member of a subclass of the gamma class of carbonic anhydrases" J Bacteriol (2010) 192:1353-1360.

Zofall et al., "Two novel dATP analogs for DNA photoaffinity labeling" Nuc Acids Res (2000) 28:4382-4390.

Office Action issued in U.S. Appl. No. 13/319,989 dated Feb. 5, 2015.

* cited by examiner

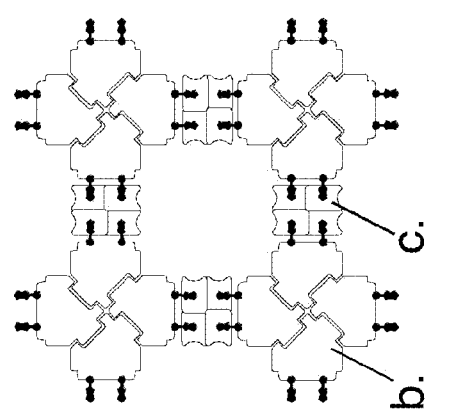
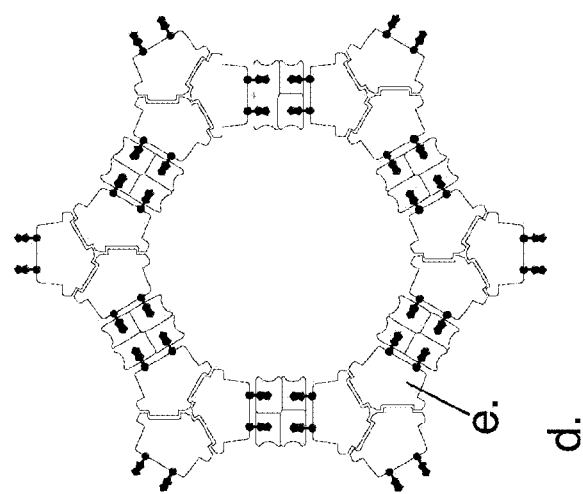
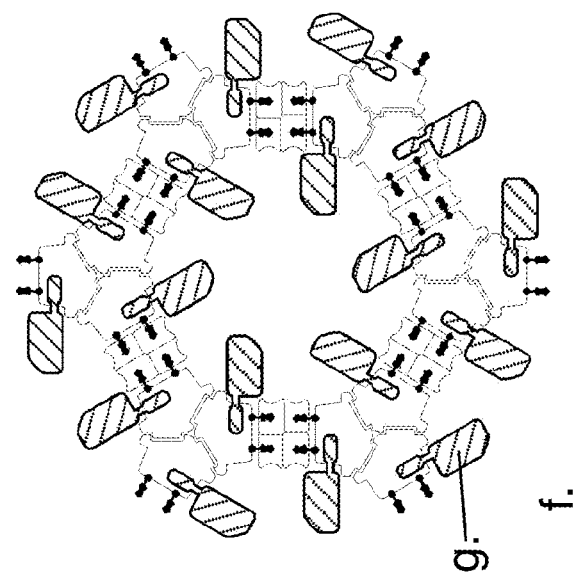
Fig 3.

Figure 10.

Sequence A:

```
          10         20         30         40         50         60
MSVMYKKILY PTDFSETAEI ALKHVKAFKT LKAEEVILLH VIDEREIKKR DIFSLLLGVA
          70         80         90        100        110        120
GLNKSVEEFE NELKNKLTEE AKNKMENIKK ELEDVGFKVK DIIVVGIPHE EIVKIAEDEG
         130        140        150        160
VDIIIMGSHG KTNLKEILLG SVTENVIKKS NKPVLVVKRK NS  (SEQ ID NO: 11)
```

Sequences B1 through B8:

Native sequence is disclosed as SEQ ID NO: 11. B1 through B8 are disclosed as SEQ ID NOS 14-21, respectively.

```
                     10         20         30         40         50
Native:   MSVMYKKILY PTDFSETAEI ALKHVKAFKT LKAEEVILLH VIDEREIKKR
SAMA:     ---------- ---------- --------C- CCC------- ----------
                     60         70         80         90        100        110
DIFSLLLGVA GLNKSVEEFE NELKNKLTEE AKNKMENIKK ELEDVGFKVK DIIVVGIPHE
---------- ---------- ---------- ---------- --CCCC---- ----------
                    120        130        140        150        160
EIVKIAEDEG VDIIIMGSHG KTNLKEILLG SVTENVIKKS NKPVLVVKRK NS
---------- ---------- ---------- ---------- ---------- --
```

(-- Designates Amino Acid Identity)

Sequences C1, C2, etc. comprise the following connected sequence variants:

[D0 $_{(k)}$ D1 $_{(k)}$ SG $_{(n)}$ D0 $_{(k)}$ D2 $_{(k)}$ SG $_{(n)}$ D0 $_{(k)}$ D3 $_{(k)}$ SG $_{(n)}$ D0 $_{(k)}$ D4 $_{(k)}$ SG $_{(n)}$ D0 $_{(k)}$ D5 $_{(k)}$ SG $_{(n)}$

D0 $_{(k)}$ (Sequence B1 to B8) D0 $_{(k)}$ SG $_{(n)}$ E1 $_{(k)}$ D0 $_{(k)}$ SG $_{(n)}$ E2 $_{(k)}$ D0 $_{(k)}$ SG $_{(n)}$ E3 $_{(k)}$ D0 $_{(k)}$ SG $_{(n)}$ E4 $_{(k)}$ D0 $_{(k)}$ SG $_{(n)}$ E5 $_{(k)}$ ]   (SEQ ID NO: 22)

Where: k = 0-1, and where n = 0-6

Sequence D0: [IEGR] (FXa Protease Cleavage Site) (SEQ ID NO: 23)

Sequence D1 = Sequence E5: [H$_{(m)}$] where m = 0-10 (Histidine Tag) (SEQ ID NO: 24)

Sequence D2 = Sequence E4: [WSHPQFEK] (StrepTag) (SEQ ID NO: 25)

Sequence D3 = Sequence E3: (Ig Binding sequence) (SEQ ID NO: 26)
[AQHDEAQQNAFYQVLNMPNLNADQRNGFIQSLKDDPSQSANVLGEAQKLNDSQAPK]

Sequence D4 = Sequence E2: (Ig Binding sequence) (SEQ ID NO: 27)
[MTYKLILNGKTLKGETTTEAVDAATAEKVFKQYANDNGVDGEWTYDDATKTFTVTE]

Sequence D5 = Sequence E1: (Ig Binding sequence) (SEQ ID NO: 28)
[MDPGDASELTPAVTTYKLVINGKTLKGETTTKAVDAETAEKAFKQYANDNGVDGVWTYD
DATKTFTVTEMVTEVPVASKR]

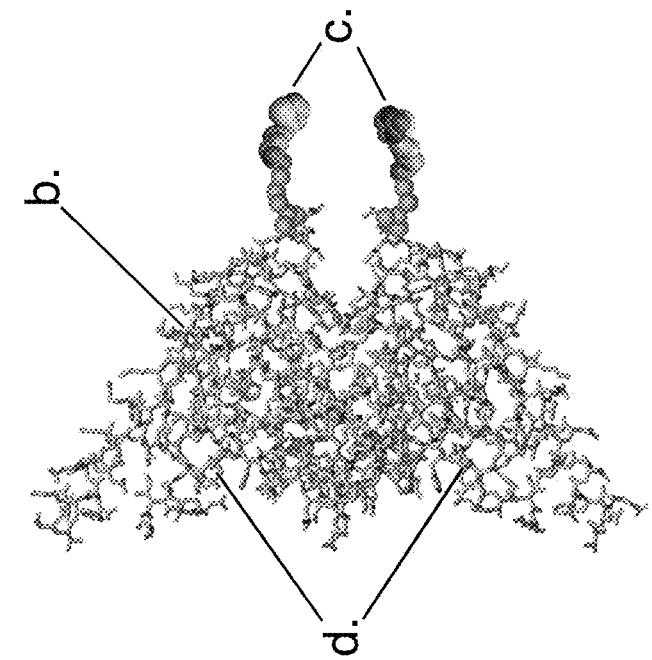
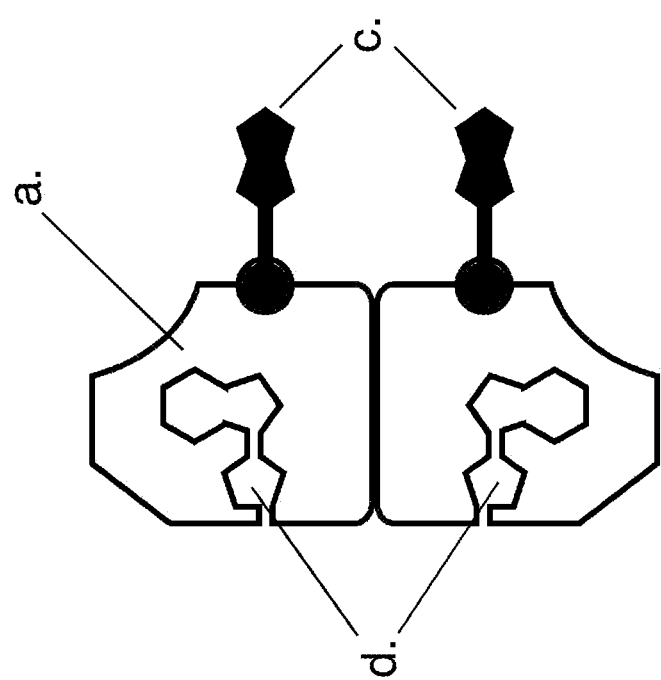
Fig 11.

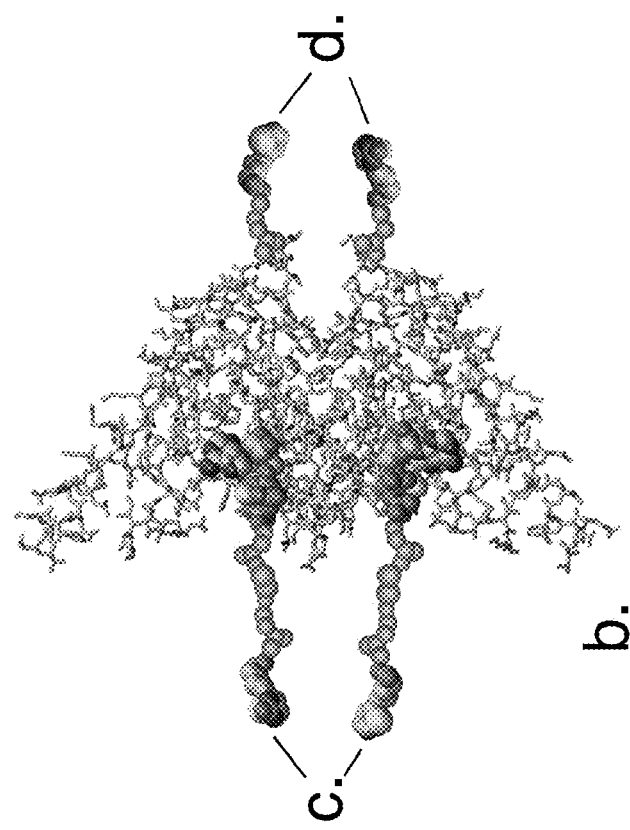
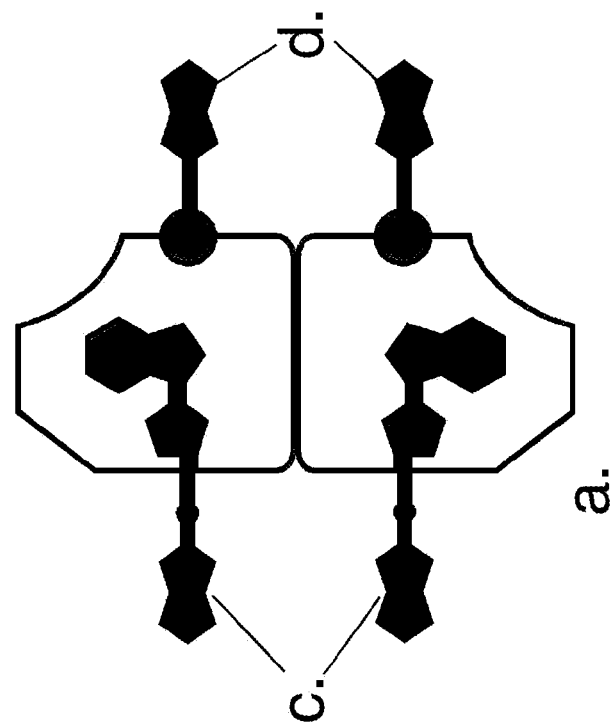
Fig 14.

| | Reagent Chemical Structure | Schematic & Description |
|---|---|---|
| a1 | | Biotin – linking reagent: (EZ-Link Sulfo-NHS-SS-Biotin) Sulfosuccinimidyl 2-(biotinamido)-ethyl-1, 3-dithiopropionate |
| a2 | | Biotin – linking reagent: (EZ-Link HPDP) |
| a3 | | Biotin – linking reagent: (MAL PEO3) |
| a4 | | Biotin – linking reagent: (MAL PEO11) |
| a5 | | Thiol - functionalized biotin linking reagent |

Fig 23 (Part 1).

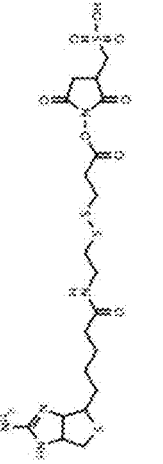
Fig 23 (Part 2).

| | Reagent Chemical Structure | Schematic & Description |
|---|---|---|
| c1 | | 2-Azido-ATP photolabel linked to Biotin: 2-Azidoadenosine 5'-triphosphate [g]-5(biotinamido)pentylamine (2N3ATP[g]Biotinpentylamine) |
| c2 | | 8-Azido-ATP photolabel linked to Biotin: 8-Azidoadenosine 5'-triphosphate [g]-5(biotinamido)pentylamine (8N3ATP[g]Biotinpentylamine) |
| d1 | | 2-Azido-ATP photolabel - Thiol-reactive reagent |
| d2 | | 8-Azido-ATP photolabel - Thiol-reactive reagent |

Fig 23 (Part 3).

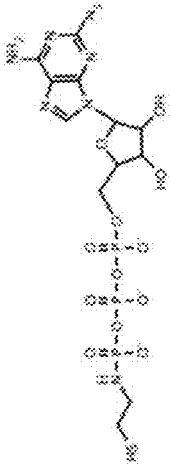
Fig 23 (Part 4).

| | Reagent Chemical Structure | Schematic & Description |
|---|---|---|
| g | | S-S linked biotin-(2-azido ATP): bifunctional crosslinking reagent |
| h | | S-S linked di-photo ATP (2-azido ATP): bifunctional crosslinking reagent |
| i | | Biotin Displacement Detection Dye: HABA: 4'-hydroxyazobenzene-2-carboxylic acid. |
| j | | Fluorescent ATP Label for monitoring ATP binding: EDANS-ATP Reagent |

Figure 23 (Part 5).

a.  b.  c.  d.

STREPTAVIDIN MACROMOLECULAR ADAPTOR AND COMPLEXES THEREOF

This application is a continuation-in-part of International Application No. PCT/US2008/012174, filed Oct. 27, 2008, which claims the benefit of U.S. Provisional Application No. 60/996,089, filed Oct. 26, 2007, and this application claims the benefit of U.S. Provisional Application No. 61/173,114, filed Apr. 27, 2009 the specifications of which are hereby incorporated by reference.

This invention was made with government support under grant numbers 1 R43 GM080805-01A1 and 1 R43 GM077743-01A1 awarded by the National Institutes of Health. The government has certain rights in the invention.

The instant application contains a Sequence Listing which has been submitted in ASCII format via EFS-Web and is hereby incorporated by reference in its entirety. Said ASCII copy, created on Sep. 9, 2010, is named 85213286.txt and is 50,385 bytes in size.

BACKGROUND OF THE INVENTION

Miniaturization is required for the improvement of existing technologies and the enablement of new ones. For example, increases in the speed and processing power of computing machinery are dependent on further miniaturization. Silicon semiconductor devices, are presently fabricated by a "top down" sequential patterning technology using photolithography, far-ultraviolet lithography, or, more recently, electron beam lithography. Although progress with this technology has been made to produce ever smaller devices, it is generally recognized that the reliable production of structures with consistent sub-10 nanometer features probably lies beyond the capabilities of top-down silicon fabrication technology.

Several companies are developing nanotechnology based on carbon or silicon-based nanostructures, functionalized carbon nanotubes, or buckyballs. An alternative approach to the development of self-assembled nanostructures makes use of proteins.

In Ringler & Schulz 2003 a two-dimensional lattice was assembled through interaction of proteins with a self-assembled monolayer. This work had several limitations. Many non-uniform, defective structures were formed. An inability to drive reactions to completion resulted in unreacted sites that can lead to both incomplete assembly or subsequent reaction in an unexpected manner. The near irreversibility of the streptavidin-biotin interaction created a tendency for macromolecules to aggregate or polymerize uncontrollably.

SUMMARY OF THE INVENTION

A biotin-residue functionalized streptavidin macromolecular adaptor (SAMA) protein may include two designated surface amino acid residues and two biotin or biotin derivative groups. Each biotin or biotin derivative group can be covalently bonded to a designated surface amino acid residue, and each biotin or biotin derivative group can be positioned to bind with a separate biotin binding site of a pair of biotin binding sites on a streptavidin tetramer. The SAMA protein can be a protein that was not previously known.

In an embodiment according to the invention, a biotin-nucleotide functionalized streptavidin macromolecular adaptor (SAMA) protein includes two binding sites and two bifunctional crosslinking reagents. Each bifunctional crosslinking reagent can include a first moiety and a second moiety. The first moiety can be biotin, iminobiotin, derivatives of these, or chemical analogs of these. The second moiety can be a nucleotide, an enzyme inhibitor, an enzyme substrate, an enzyme cofactor, derivatives of these, or chemical analogs of these. For example, a biotin-ligand crosslinking reagent can include a biotin-type moiety and a ligand moiety. Each first moiety can be positioned to bind with a separate biotin binding site of a pair of biotin binding sites on a streptavidin tetramer. Each second moiety can be bound to a binding site of the SAMA protein. The binding sites can, for example, be separated by a distance of about 20.5 Angstroms. A binding site can be, for example, an adenosine triphosphate (ATP) binding site. For example, a streptavidin macromolecular adaptor (SAMA) can be formed of two subunits, and the designated surface amino acid residue on the first subunit, the designated surface amino acid residue on the second subunit, the binding site on the first subunit, and the binding site on the second unit can lie in about the same plane.

In an embodiment according to the invention, a biotin-residue, biotin-nucleotide functionalized streptavidin macromolecular adaptor (SAMA) protein includes two binding sites, at least two designated surface amino acid residues, two biotin or biotin derivative groups, and two bifunctional crosslinking reagents. Each bifunctional crosslinking reagent includes a first moiety and a second moiety. Each biotin or biotin derivative group is covalently bonded to a designated surface amino acid residue. Each biotin or biotin derivative group is positioned to bind with a separate biotin binding site of a pair of biotin binding sites on a streptavidin tetramer. The first moiety can be biotin, iminobiotin, derivatives of these, or chemical analogs of these. The second moiety can be a nucleotide, an enzyme inhibitor, an enzyme substrate, an enzyme cofactor, derivatives of these, or chemical analogs of these. Each first moiety can be positioned to bind with a separate biotin binding site of a pair of biotin binding sites on a streptavidin tetramer. Each second moiety can be bound to a binding site of the SAMA protein.

In an embodiment according to the invention, a biotin-residue linked 1:1 streptavidin:SAMA complex includes a streptavidin tetramer having biotin binding sites, a SAMA protein having two binding sites and comprising at least two designated surface amino acid residues, and two biotin or biotin derivative groups. Each biotin or biotin derivative group can be covalently bonded to a designated surface amino acid residue. Each biotin or biotin derivative group can be bound to a separate biotin binding site of a pair of biotin binding sites on the streptavidin tetramer.

In an embodiment according to the invention, a biotin-nucleotide linked 1:1 streptavidin:SAMA complex includes a streptavidin tetramer having biotin binding sites, a SAMA protein having at least two binding sites and comprising at least two designated surface amino acid residues, and two bifunctional crosslinking reagents, each comprising a first moiety and a second moiety. The first moiety can be selected from the group consisting of biotin, iminobiotin, derivatives of these, and chemical analogs of these. The second moiety can be selected from the group consisting of a nucleotide, an enzyme inhibitor, an enzyme substrate, an enzyme cofactor, derivatives of these, and chemical analogs of these. Each first moiety can be bound to a separate biotin binding site of a pair of biotin binding sites on the streptavidin tetramer. Each second moiety can be bound to a binding site of the SAMA protein.

In an embodiment according to the invention, a strut includes at least two biotin-residue linked 1:1 streptavidin: SAMA complexes. Each biotin-residue linked 1:1 streptavidin:SAMA complex can be attached to at least one and at most two 1:1 streptavidin:SAMA complexes. A first and second attached biotin-residue linked 1:1 streptavidin:SAMA complex can includes two bifunctional crosslinking reagents, each comprising a first moiety and a second moiety. The first moiety can be biotin, iminobiotin, derivatives of these, or chemical analogs of these. The second moiety can be a nucleotide, an enzyme inhibitor, an enzyme substrate, an enzyme cofactor, derivatives of these, or chemical analogs of these. Each first moiety can be bound to a separate biotin binding site of a pair of biotin binding sites on the streptavidin tetramer of the first biotin-residue linked 1:1 streptavidin: SAMA complex. Each second moiety can be bound to a separate binding site of a pair of binding sites on the SAMA protein of the second biotin-residue linked 1:1 streptavidin: SAMA complex.

In an embodiment according to the invention, a strut includes at least two proteins or protein multimers. Each of the at least two proteins or protein multimers can be linked to at least one and at most two of the at least two proteins or protein multimers. The dissociation constant for two linked proteins or protein multimers can be less than about $10^{-11}$ M. The linked proteins can lie along a common axis, and the linked proteins can be substantially rigid.

In an embodiment according to the invention, a nucleotide-linked antibody biosensor includes a substrate functionalized with biotin or biotin derivative groups, a strut, and an antibody having 2 Fc chain termini. Two biotin binding sites of a streptavidin of the strut can be bound with the biotin or biotin derivative groups with which the substrate is functionalized. Each Fc chain terminus can be functionalized with a nucleotide or nucleotide derivative. Each nucleotide or nucleotide derivative with which an Fc chain terminus is functionalized can be bound to a binding site of a pair of binding sites on a SAMA of the strut.

In an embodiment according to the invention, a biotin-linked antibody biosensor includes a substrate functionalized with nucleotides or nucleotide derivatives, a strut, and an antibody having two Fc chain termini. Two binding sites of a SAMA of the strut can be bound with the nucleotide or nucleotide derivative groups with which the substrate is functionalized. Each Fc chain terminus can be functionalized with a biotin or biotin derivative. Each biotin or biotin derivative with which an Fc chain terminus is functionalized can be bound to a biotin binding site of a pair of biotin binding sites on a streptavidin of the strut.

A method according to the invention includes providing a SAMA protein having at least two designated surface amino acid residues, for example, a SAMA protein that includes a dimer having two subunits, each subunit having a designated surface amino acid residue, mixing the SAMA protein with a thiol-reactive biotinylation reagent to form a reaction solution, allowing the SAMA protein and the thiol-reactive biotinylation reagent to react to form a biotin-residue functionalized SAMA protein; and purifying the reaction solution to obtain a substantially pure biotin-residue functionalized SAMA protein. Each biotin of the biotin-residue functionalized SAMA protein can be positioned to bind with a separate biotin binding site of a pair of biotin binding sites on a streptavidin tetramer. Alternatively, the SAMA protein provided can include a pair of binding sites, a pair of designated surface amino acid residues, and a first end and a second end. The second end can be opposed to the first end, and a dyad axis can span from the first end to the second end. Each member of the pair of binding sites can be symmetric about the dyad axis at the first end, and each member of the pair of designated surface amino acid residues can be symmetric about the dyad axis at the second end. The thiol-reactive biotinylation reagent can be capable of bonding with the designated surface amino acid residue.

A method according to the invention includes providing a SAMA protein having two binding sites, mixing the SAMA protein with a bifunctional crosslinking reagent having a first moiety and a second moiety to form a reaction solution, allowing the SAMA protein and the bifunctional crosslinking reagent to react to form a biotin-nucleotide functionalized SAMA protein, and purifying the reaction solution to obtain a substantially pure biotin-nucleotide functionalized SAMA protein. The first moiety can be biotin, iminobiotin, derivatives of these, or chemical analogs of these. The second moiety can be a nucleotide, an enzyme inhibitor, an enzyme substrate, an enzyme cofactor, derivatives of these, or chemical analogs of these. Each first moiety of the biotin-nucleotide functionalized SAMA protein moiety can be positioned to bind with a separate biotin binding site of a pair of biotin binding sites on a streptavidin tetramer.

In an embodiment according to the invention, a binding sequence linked antibody sensor includes a substrate functionalized with nucleotides or nucleotide derivatives, a SAMA protein, and an antibody. The SAMA protein can include a symmetric dimer, a binding domain comprised of a binding polypeptide chain, and a linker peptide. The dimer can include two polypeptide chains. The binding polypeptide chain can be covalently bonded to the linker peptide, and the linker peptide can be covalently bonded to the polypeptide chain. The binding polypeptide chain of the biotin-residue functionalized SAMA protein can be an antibody binding polypeptide. The biotin-residue functionalized SAMA protein can comprise at least two binding sites. The at least two binding sites of the biotin-residue functionalized SAMA protein can be bound with the nucleotide or nucleotide derivatives with which the substrate is functionalized. The antibody can be bound to the antibody binding polypeptide.

In an embodiment according to the invention, a binding sequence linked antibody sensor can include a substrate functionalized with biotin or biotin derivative groups, a biotin-residue functionalized SAMA protein, a streptavidin tetramer having biotin binding sites, and an antibody. The binding polypeptide chain of the biotin-residue functionalized SAMA protein can be an antibody binding polypeptide. The biotin or biotin derivative group of the biotin-residue functionalized SAMA protein can be bound to a separate biotin binding site of a pair of biotin binding sites on the streptavidin tetramer. A pair of biotin binding sites on the streptavidin tetramer can be bound with the biotin or biotin derivative groups with which the substrate is functionalized, The antibody can be bound to the antibody binding polypeptide.

In an embodiment according to the invention, a biotin binding site exposed assembly includes a substrate functionalized with nucleotides or nucleotide derivatives, a first SAMA protein having two binding sites and two designated surface amino acid residues with a nucleotide or nucleotide derivative bound to each designated surface amino acid residue, and a biotin-residue linked 1:1 streptavidin:SAMA complex. The nucleotides or nucleotide derivatives of the substrate can be bound to each binding site of the first SAMA protein. Each nucleotide or nucleotide derivative of the first SAMA protein can be bound to a binding site of the SAMA protein of the biotin-residue linked 1:1 streptavidin:SAMA complex.

In an embodiment according to the invention, a binding site exposed assembly includes a substrate functionalized with nucleotides or nucleotide derivatives, a first SAMA protein having two binding sites and two designated surface amino acid residues with a biotin or biotin derivative bound to each designated surface amino acid residue, and a biotin-residue linked 1:1 streptavidin:SAMA complex. The nucleotides or nucleotide derivatives of the substrate can be bound to each binding site of the first SAMA protein. Each biotin or biotin derivative of the first SAMA protein can be bound to a biotin binding site of the streptavidin tetramer of the biotin-residue linked 1:1 streptavidin:SAMA complex.

In an embodiment according to the invention, an iminobiotin exposed assembly includes a substrate functionalized with nucleotides or nucleotide derivatives and a SAMA protein having two binding sites and two designated surface amino acid residues with an iminobiotin linked to each designated surface amino acid residue.

In an embodiment according to the invention, a streptavidin macromolecular adaptor (SAMA) protein includes a dimer having two polypeptide chains. Each polypeptide chain can include a designated surface amino acid residue that is a cysteine residue. The designated surface amino acid residue can be located such that when a biotin or biotin derivative group is covalently bonded to the designated surface amino acid residue, each biotin or biotin derivative group on the dimer is positioned to bind with a separate biotin binding site of a pair of biotin binding sites on a streptavidin tetramer. The SAMA protein can be a protein whose amino acid sequence is not identical to a previously known protein. The SAMA protein may be a natural sequence that has been modified to substitute any cysteine residues in the natural sequence by an alternative amino acid.

In an embodiment according to the invention, a streptavidin macromolecular adaptor (SAMA) protein includes a dimer having 2 polypeptide chains. Each polypeptide chain includes a designated surface amino acid residue that can be, for example, cysteine, lysine, histidine, arginine, methionine, tyrosine, serine, or threonine. The designated surface amino acid residue can be located such that when a biotin or biotin derivative group is covalently bonded to the designated surface amino acid residue, each biotin or biotin derivative group on the dimer is positioned to bind with a separate biotin binding site of a pair of biotin binding sites on a streptavidin tetramer. The SAMA protein can be a protein whose amino acid sequence is not identical to a previously known protein. The SAMA protein may be a natural sequence that has been modified to substitute any cysteines, lysine, histidine, arginine, methionine, tyrosine, serine, or threonine residues in the natural sequence by an alternative amino acid.

A method according to the invention of identifying a streptavidin macromolecular adaptor (SAMA) framework protein includes analyzing protein coordinate sets from at least one publicly available database and/or the Protein Data Bank and identifying protein dimers that are 2-fold symmetric and have two ligand-binding pockets. The two ligand-binding pockets can be separated by a distance within ±10 Angstroms of the distance between two biotin binding sites on a streptavidin tetramer. For example, the two ligand-binding pockets are separated by a distance of from about 10 Angstroms to about 30 Angstroms. For example, the two ligand-binding pockets are separated by a distance of from about 15 Angstroms to about 25 Angstroms.

In an embodiment according to the invention, a streptavidin:SAMA complex can include a streptavidin tetramer having a pair of biotin binding sites and a SAMA protein having a pair of binding sites and having a pair of designated surface amino acid residues. Two biotin-type groups can be covalently bonded to a designated surface amino acid residue and can be bound to a biotin binding site of the pair of biotin binding sites of the streptavidin tetramer to link the streptavidin and SAMA proteins together. Two bifunctional crosslinking reagents, each comprising a biotin-type moiety bound to a biotin binding site of the pair of biotin binding sites of the streptavidin tetramer and a second moiety bound to a binding site of the pair of binding sites of the SAMA protein can be used to link the streptavidin and SAMA proteins together. The SAMA protein can have a dyad axis that spans from a first end of the SAMA protein to a second end of the SAMA protein. The second end of the SAMA protein can be opposed to the first end of the SAMA protein. Each member of the pair of binding sites on the SAMA protein can be symmetric about the dyad axis at the first end of the SAMA protein, and each member of the pair of designated surface amino acid residues on the SAMA protein can be symmetric about the dyad axis at the second end of the SAMA protein. The second moiety can include, for example, a nucleotide, an enzyme inhibitor, an enzyme substrate, an enzyme cofactor, derivatives of these, and/or chemical analogs of these. The streptavidin tetramer can have a dyad axis. Each member of a pair of biotin binding sites on the streptavidin can be symmetric about the dyad axis. The dyad axis of the streptavidin tetramer can be colinear with the dyad axis of a SAMA protein.

In an embodiment according to the invention, a strut can include at least two proteins or protein multimers. Each of the at least two proteins or protein multimers can be linked to at least one and at most two of the at least two proteins or protein multimers. The dissociation constant for two linked proteins or protein multimers can be less than about $10^{-11}$ M. The at least two proteins can lie along a common axis. The linked at least two proteins can be substantially rigid.

In an embodiment according to the invention, an iminobiotin exposed assembly can include a substrate functionalized with nucleotides or nucleotide derivatives and a SAMA protein having two binding sites and two designated surface amino acid residues with an iminobiotin linked to each designated surface amino acid residue.

In an embodiment according to the invention, a SAMA protein can include a functional polypeptide sequence. The functional polypeptide sequence can be covalently bound to an amino or carboxy terminus of the subunit. The functional polypeptide sequence can be within a surface loop of one or two polypeptide chains. For example, the functional polypeptide sequence can be an Fab sequence (a sequence from or similar to a fragment antigen binding (Fab) region of an antibody).

In an embodiment according to the invention, a binding site exposed assembly includes a substrate functionalized with nucleotides or nucleotide derivatives, a first SAMA protein having two binding sites and two designated surface amino acid residues with a biotin or biotin derivative bound to each designated surface amino acid residue, and a biotin-residue linked 1:1 streptavidin:SAMA complex. The nucleotides or nucleotide derivatives of the substrate can be bound to each binding site of the first SAMA protein. Each biotin or biotin derivative of the first SAMA protein can be bound to a biotin binding site of the streptavidin tetramer of the biotin-residue linked 1:1 streptavidin:SAMA complex.

In an embodiment according to the invention, an iminobiotin exposed assembly includes a substrate functionalized with nucleotides or nucleotide derivatives and a SAMA protein having two binding sites and two designated surface amino acid residues with an iminobiotin linked to each designated surface amino acid residue.

In an embodiment according to the invention, a kit includes a nanostructure building block and a linking compound. For example, the linking compound can be a biotin-ligand crosslinking reagent, such as a biotin-nucleotide crosslinking reagent (e.g., FIGS. 23c1-23c2 and FIG. 23g), a biotin-biotin crosslinking reagent (e.g., FIGS. 23f1-23f2), a ligand-ligand crosslinking reagent (e.g., FIG. 23h), can be a biotinylation reagent (e.g., the compounds of FIGS. 23a1-23a5 and FIGS. 23b1-23b5), such as a thiol-reactive biotinylation reagent (e.g., FIGS. 23a1 and 23b1), or can be a ligand functionalization reagent, such as a thiol reactive-nucleotide reagent (e.g., FIGS. 23d1-23d2).

BRIEF DESCRIPTION OF THE DRAWINGS

FIG. 3 presents cartoons of two-dimensional lattices formed using three-fold and four-fold symmetric nodes.

FIG. 10 presents SAMA amino acid sequences based on the MJ0577 protein.

FIG. 11 presents a cartoon and a molecular model of a biotinylated SAMA based on the MJ0577 protein.

FIG. 14 presents a cartoon and a molecular model of a SAMA based on the MJ0577 protein incorporating four biotin groups introduced through reaction with crosslinking reagents.

FIG. 23 shows chemical structures and schematic illustrations of reagents used in streptavidin:SAMA nanostructure assembly.

DETAILED DESCRIPTION

Figure 1:
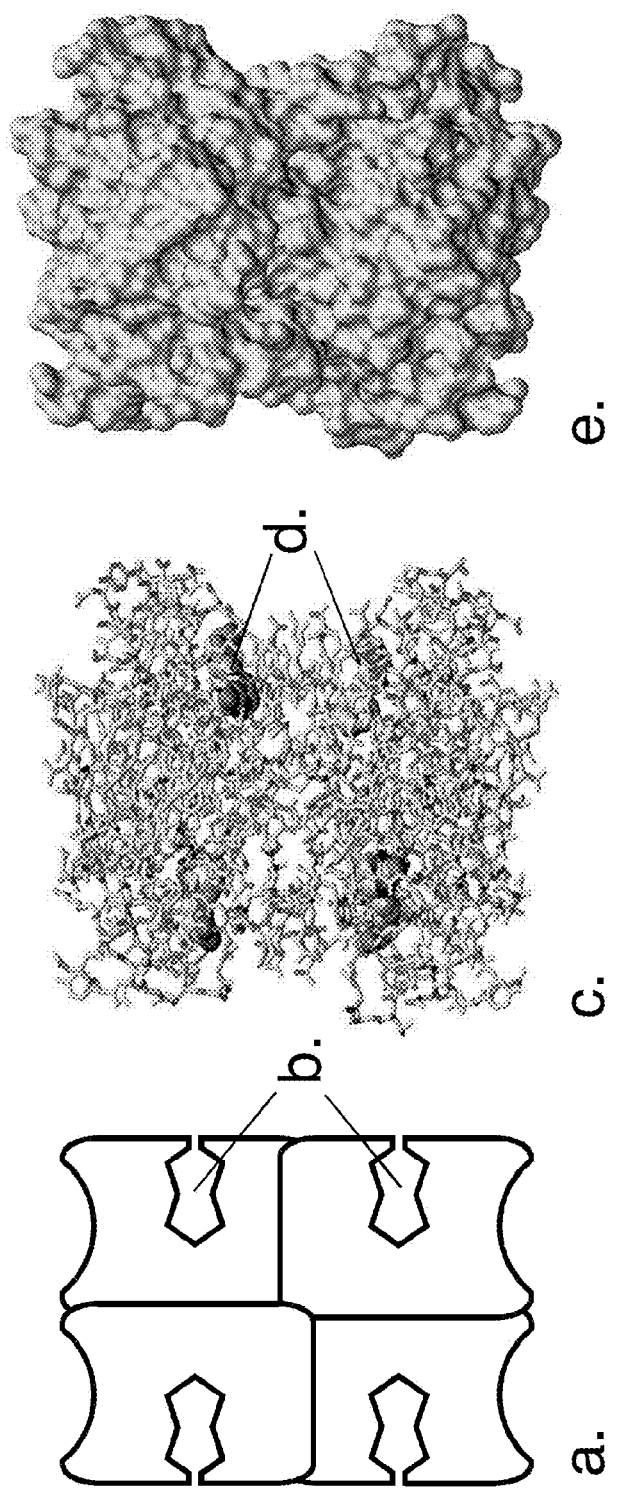
FIG. 1 shows a cartoon and a molecular model of the streptavidin tetramer indicating biotin ligand binding sites.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

In this document, an amino acid may be indicated by its standard one-letter abbreviation, as understood by one of skill in the art. For example, a polypeptide sequence may be represented by a string of letters.

Overview of Components and Approach

An objective of the work leading to the present invention, of which several embodiments are presented in this text, is the development of biomolecular components allowing for the systematic and precise fabrication of complex nanodevices with two and three-dimensional architectures. Proteins, typically having (subunit) dimensions in the range of 5 to 20 nm (or the equivalent, 50 to 200 Angstrom units), and other organic molecules serve as the biomolecular components, and allow for unprecedented miniaturization of devices. By providing proteins with three or more points of controllable attachment, a limited set of a small number of biomolecular components allows for construction of an unlimited number of structures, over the design of which a user has full control. Thus, the biomolecular components will advance research and development into nanodevice applications. The control over assembly with and reproducible precision of structures formed by these biomolecular components will allow for the fabrication of nanodevices of unprecedented complexity, extent, and diversity.

"Parts Box" Philosophy

The biomolecular components can include molecular-scale "struts" and "nodes". Struts are components that basically function as linear structural elements or linear connectors. Different struts or arrays of struts can be used to establish predetermined distances in a structure. Nodes are connectors that have multiple, for example, three or more, attachment points with defined geometry. Nodes can be linked together, for example, by struts, to establish the topology of a structure.

Thus, with the struts and nodes, structures with two-dimensional and three-dimensional geometry, such as lattices, can be constructed. These lattices can have utility themselves and/or can be further functionalized through chemical modification or the incorporation of additional specific binding proteins.

Assembly of biomolecular components such as struts and nodes can proceed in stages that provide the user with the efficiency and parallel nature characteristic of "bottom-up" self-assembly and the control and ability to form asymmetric and complex structures characteristic of "top-down" manufacturing. Because a limited number of biomolecular components can be combined to produce any one of an unlimited number of structures, attention can be focused on developing a small number of these biomolecular components that serve as a "parts box". Because only a limited number of biomolecular components and associated assembly techniques need be designed, produced, and tested, economies of scale can be achieved, so that inexpensive development and production of nanodevices can be realized. That is, the compositions and methods discussed herein apply the philosophies of interchangeable parts and mass production, which drove unprecedented economic expansion in the last two centuries, to the nanoscale. Providing such a "parts box" of biomolecular components allows users to experiment with a range of structures and thereby facilitates the development of a new generation of functional nanodevices, biosensors, and biomaterials, potentially finding broad application in areas as diverse as biomedical devices and nanoelectronic applications.

Use of Proteins

Proteins have a number of advantages for use as biomolecular components, including, but not limited to the following. Proteins already exist in nature as functional polypeptide units with well-defined three-dimensional structures, so that effort can focus on tailoring them as building blocks for specific applications, rather than having to develop building blocks from scratch. A very large number of proteins exist, and the detailed atomic structure of many are known, and certain proteins, with minimal tailoring, can perform as a desired building block.

Naturally occurring proteins have diverse and sophisticated functionality. They can show high interaction specificity and manifest catalytic properties. They can exhibit interesting and useful optical, magnetic, and redox properties, for example, by incorporating metal centers and a wide variety of prosthetic groups. Such metal centers and prosthetic groups can, as well as the polypeptide sequence itself, be tailored to produce a protein having a desired functionality.

In nature, DNA encodes a polypeptide sequence that spontaneously and reproducibly folds to form a predetermined three-dimensional protein of thousands of atoms of which each atom is precisely placed. Because proteins as building blocks are reproducible and have precise configuration, they can be relied upon as components in the construction of extensive and complex structures. Naturally occurring proteins frequently form cooperative hierarchical assemblies of great structural and functional complexity. These natural assemblies can be studied to derive assembly techniques and simplify the development of analogous artificial structures having an intended purpose.

The techniques for modifying proteins by the techniques of molecular biology and synthetic organic chemistry are well established. For example, a selected amino acid unit of a natural protein can be substituted with a different natural amino acid, or with an artificial amino acid. Reliable production of large numbers of proteins is a well-established biotechnical procedure. Thus proteins are excellent candidates for a "parts box" with which the philosophies of interchangeable parts and mass production can be applied at the nanoscale.

Applications

The diverse and sophisticated functionality of naturally occurring proteins allow them to perform a wide range of processing and signal transduction functions in nature, including catalysis, chemomechanical, electromechanical, optomechanical, and optoelectronic transduction for sensing and actuation purposes. This suggests the diverse range of man-made devices that can be produced with a "parts box" of proteins as biomolecular components.

A "parts box" of proteins may initially be applied to make devices that are analogous to or in some way emulate natural systems. For example, two- and three-dimensional structures formed from struts and nodes, as described herein, may be applied in the fields of biosensors and diagnostics. The specific immobilization and precise geometric control facilitated by strut-node technology presented herein, along with the functionality inherent in proteins, can enable the development of new kinds of sensors incorporating, for example, multiple antibodies specifically immobilized in patterned arrays.

Other applications may not have direct natural analogs, but are intended to interact with natural biological systems. For example, the strut-node technology presented herein can be used in devices that couple directly to living systems, for example, that provide an interface between semiconductor substrates and living organisms and nanostructures. Such devices could, for example, be used for prostheses.

Applications of a "parts box" of proteins as biomolecular components are not limited to devices analogous to or for interacting with natural biological systems. For example, structures can be assembled from the struts and nodes described herein that emulate the architecture and functions of silicon-based microprocessor architecture and computer memory.

Biomolecular Components

Protein Stability and Selection

The three-dimensional atomic structures of over 25,000 proteins are known (see, www.rcsb.org), providing an extensive set from which biomolecular components having desired structural and functional characteristics can be selected for a "parts box" (see, scop.mrc-lmb.cam.ac.uk/scop/). Moreover, the tools of recombinant DNA technology enable the synthesis of virtually any polypeptide sequence or functional domain fusion, providing the basis for rapidly designing and optimizing novel assemblies from engineered biological macromolecules.

Although not widely recognized, numerous studies show that the structural and functional properties of proteins that normally function in aqueous solution are preserved intact when the protein is dehydrated to the level of a few water molecules per protein molecule (Rupley & Careri 1991; Zaks & Klibanov 1988; Fitzpatrick et al. 1993; Castro & Knubovets 2003; Gupta & Roy 2004). Many examples exist of structural proteins, for example spider silk, that form essentially solid-state structural materials and have thermal stabilities in excess of 100° C. In addition, many proteins that form unusually stable complexes (Weber et al. 1992), or that carry out the biological functions of thermophilic organisms that live in hot environments also have thermal stabilities in excess of 100° C., an environment not very dissimilar from the maximum operating temperatures for conventional semiconductor devices.

Several biomolecular components that described herein are based on proteins of thermostable bacteria of known three-dimensional crystal structure. The proteins provide several advantages in node production, handling and purification. The enzymatic binding sites of proteins used as nodes can provide additional sites for functionalization of the nanostructure through covalent binding of inhibitors linked to other chemical moieties or proteins.

Struts

Two fundamental nanoscale biomolecular components of a "parts box" from which a structure, for example, a device, can be assembled are "struts" and "nodes". Struts are molecular components that function as linear connectors. Nodes connect struts and orient them with defined geometries.

A strut can be formed from streptavidin (FIG. 1), a tetrameric protein of 60 kiloDalton molecular weight secreted by the bacterium *Streptomyces avidinii*. The streptavidin tetramer has D2 symmetry and 4 binding sites for the vitamin biotin. FIG. 1 shows a cartoon and a molecular model of the streptavidin tetramer indicating biotin ligand binding sites. Part a shows a schematic of a streptavidin tetramer (streptavidin) which has binding sites for 4 biotin groups. Part b designates the location of a pair of biotin binding sites on the same "side" of the tetramer that are spaced approximately 20.5 Angstroms apart. Part c shows an all atom (excluding hydrogen atoms) stick bond representation of the streptavidin tetramer, including four bound biotin molecules in space-filling representation. Part d designates two of the four bound biotins on the same "side" of the tetramer in space filling representation. Part e is a representation of the streptavidin tetramer surface showing overall molecular shape. Weber et al. (1989) determined the X-ray structure of streptavidin and described the origins of its ability to bind the vitamin biotin. Although the biotin:streptavidin interaction is non-covalent, the biotin dissociation constant is about $10^{-14}$ M, so that the biotin:streptavidin bond is essentially irreversible. The strength of the biotin:streptavidin bond has led to the broad application of streptavidin in research and diagnostics applications where interaction specificity is required in a complex biological milieu.

In streptavidin, the biotin-binding sites are arranged as two pairs in an "H" orientation that facilitates specific pairwise binding. The biotin binding sites are arranged with D2 symmetry. When bound to the streptavidin biotin-binding sites, the biotin molecules have their terminal valeric acid chains (which are the usual chemical modification sites for generating biotin conjugated reagents) in extended conformation and oriented approximately parallel to one of the diad axes of the streptavidin tetramer. The distance between the two closest and roughly parallel pair of bound biotin chain termini is about 20.5 Angstroms. Thus, when serving as a strut, a streptavidin tetramer can be linked to two other biomolecular components, such as nodes, through biotin molecules. The streptavidin tetramer is approximately 60 Angstroms (6 nanometers) wide by 45 Angstroms (4.5 nanometers) deep by 50 Angstroms (5.0 nanometers) long in the direction that facilitates pairwise biotin interactions.

Although the present descriptions refer specifically to streptavidin, several related proteins are known (e.g., egg white avidin) that have similar amino acid sequence, structure, and biotin binding properties as streptavidin. For example, such a protein may have greater than about 80%, 90%, 95%, 98%, or 99% protein sequence similarity (homology) with streptavidin. For example, protein sequence similarity can refer to an amino acid composition similarity by relative proportion of amino acid composition. For the purposes of this work, the applications pertaining to "streptavidin" shall generally be construed to apply to all homologues or recombinantly produced variants of the naturally occurring streptavidin protein, or its homolog avidin, that incorporate 4 biotin binding sites arranged with same geometry as the native streptavidin or avidin tetramer. Variants include shortened or modified versions of the protein (Kopetzki, 1987, Cantor 1989, Goshorn et al. 2006, Sano et. al. 2000), versions where the binding affinity of the biotin binding sites have been modified through site-specific modification (Sano et. al. 2000, Staton 2000, 2005), or the chains corresponding too independent subunits in the native tetrameric protein have been interconnected or permuted using recombinant DNA technology (Nordland et. al. 2004, Stayton 2002). These proteins could be substituted for streptavidin in the applications described here. The invention encompasses such streptavidin analogs, both natural and synthetic homologs. For convenience, the term "streptavidin" as used herein, may include such variants.

Nodes

A node can connect three or more struts with predefined orientation of each strut with respect to the other connected struts.

For example, a node can be a symmetric protein multimer. For example, a node can be an enzyme that has catalytic binding sites with high binding specificity for certain substrates and cofactors. A naturally occurring protein can be used in its native state, or can be engineered, for example, using site-specific modification techniques, to render it suitable or optimal for an intended function as a node. Selection of a naturally occurring protein for use as a node can be made from the large number of X-ray crystal structures of stable protein multimers having different symmetries available. Alternatively, selection can be made from protein sequences that have over 70% sequence homology with sequences with known X-ray structures, since it is known that homologous protein sequences also have similar three-dimensional structures, and the multimeric state of a protein can be determined by physical methods like light scattering, electrophoresis, ultracentrifugation, gel exclusion chromatography, or other methods. For example, suitable natural symmetric protein multimers are available having 2-, 3-, 4-, 5-, 6-, 7-, and higher-fold symmetry useful for forming finite or extended planar nanoassemblies organized in two dimensions, as well as multimers having tetrahedral, octahedral, and other symmetries useful for forming three-dimensional nanoassemblies. Such multimers serving as nodes can be interconnected by biomolecular components serving as struts (such as streptavidin) to create nano-scale structures with defined two- and three-dimensional geometry, such as lattices.

For example, site-specific modification techniques can be used to introduce surface cysteine residues at pairs of points on the surface of a multimer to function as a node. Biotinylating reagents, for example, a thiol-reactive biotinylating reagent, can be covalently bonded to such surface cysteine residues to introduce biotin groups at defined, for example, at symmetric points. Thus, a node of defined geometry can be formed. The pairs of biotin groups on the multimer functioning as a node can then be bound to the binding sites on streptavidin tetramers, which can act as struts, to form a two- or three-dimensional nanostructure.

Figure 2:
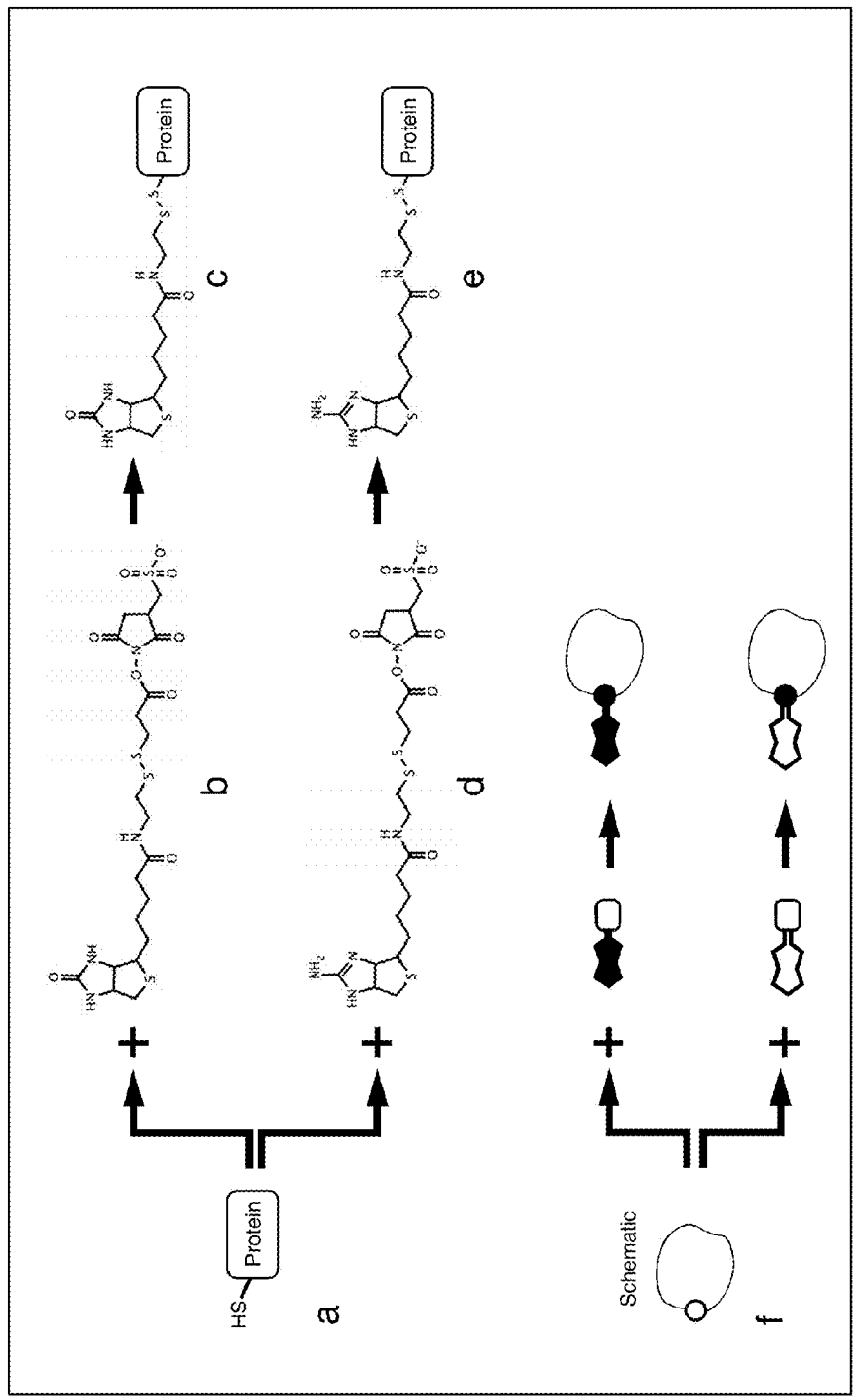
FIG. 2 shows the reaction of protein cysteine sulfhydryl groups with biotinylation reagents.

Reactions of biotinylating reagents that can modify protein cysteine sulfhydryl groups are presented in FIG. 2. Part a shows a free sulfhydryl group on a protein. Part b shows the biotinylation reagent Sulfosuccinimidyl 2-(biotinamido)-ethyl-1,3-dithiopropionate (EZ-Link Sulfo-NHS-SS-Biotin: Pierce). Part c shows the reaction product after biotinylation. Part d shows an analogous reagent for the introduction of 2-imino biotin groups. The binding of imino-biotin to streptavidin is pH dependent. At low pH (~pH4) the imino group becomes charged, causing imino-biotin displacement from the streptavidin biotin binding site. Part e shows the imino-biotin reaction product. Part f shows the reaction schemes schematically using the schema of FIG. 23. Additional chemical reagents useful in nanostructure assembly are presented in FIG. 23.

For example, FIG. 3 shows two-dimensional lattices formed using nodes with three-fold (C3) and four-fold (C4) rotational symmetry. Two types of symmetric 2D lattice structures that can be assembled through the association of biotin-modified symmetric node structures and streptavidin are illustrated. Part a shows part of a square 2D lattice incorporating tetrameric nodes b and connected through streptavidin tetramers c. Part d shows part of an hexagonal 2D lattice incorporating trimeric nodes e. Part f shows the hexagonal lattice of Part d that has been functionalized through specific attachment of an additional protein g such as an immunoglobulin. Biotin linking reagents can be covalently bound to engineered sites on the node proteins, so that they make rigid pairwise interactions with tetrameric streptavidin struts.

Node proteins can be based on template proteins derived from thermophiles, so that assembled nanodevices can be stable under a variety of manufacturing and storage conditions.

Single chain constructs of a node protein can be formed. For example, these fused protein multimers can be constructed by incorporating a DNA sequence coding for a polypeptide linker connecting the C-terminus of a first multimer gene to the N-terminus of a second multimer, and so on, to create a single contiguous gene coding for the complete multimer. This approach can allow for the subunits of a multimeric protein to be non-identical. For example, surface cysteine residues for biotinylation can be included in some subunits, but not in other subunits, so that struts can be attached at certain faces of the multimeric protein, but not at others. Herein, a protein having multiple subunits that are formed from a single polypeptide chain is termed a multimer, as is a protein having multiple subunits with each subunit formed from a separate polypeptide chain.

Figure 4:
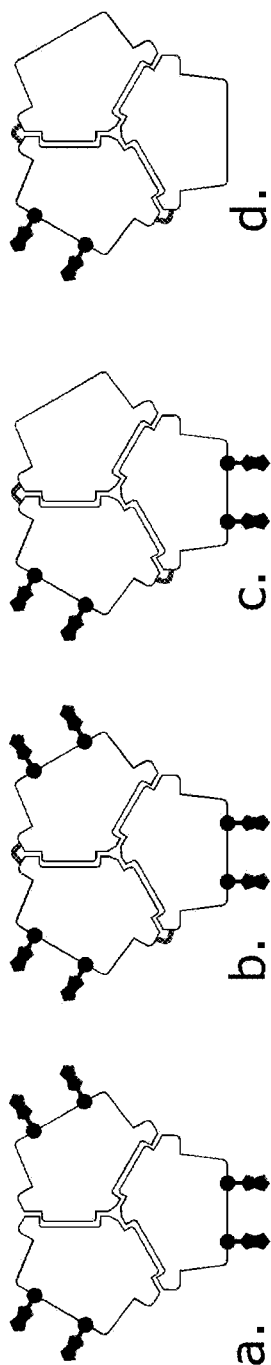
FIG. 4 presents cartoons of various three-fold symmetric nodes.
Figure 5:
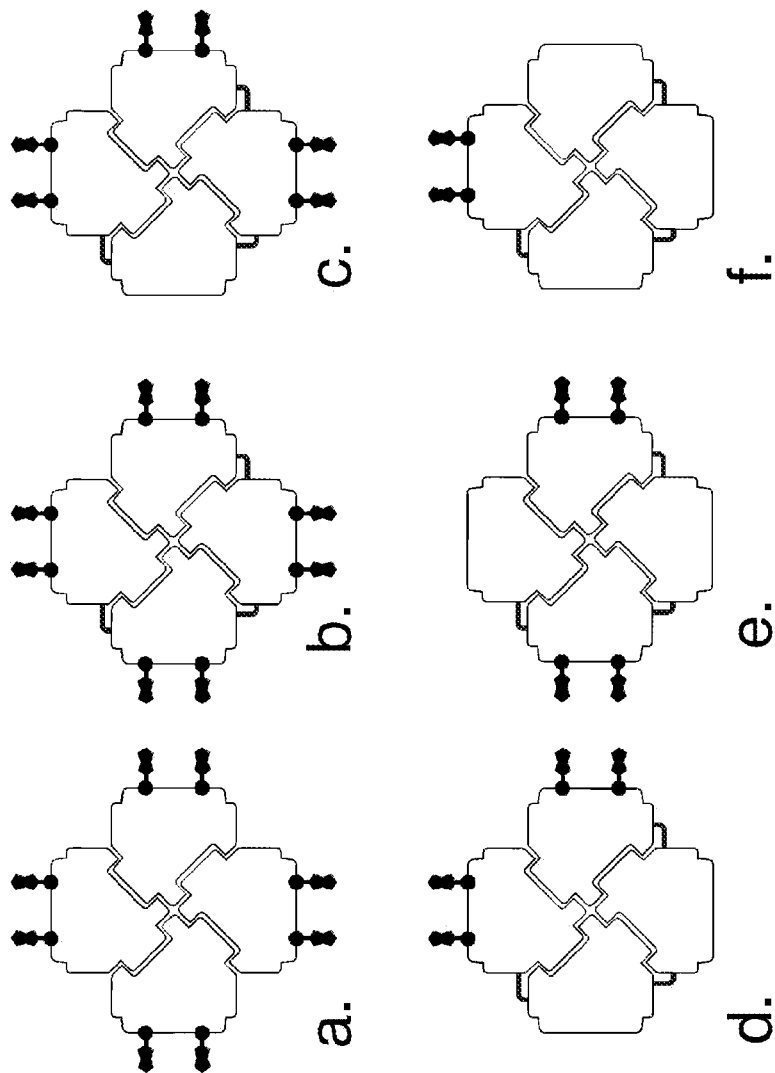
FIG. 5 presents cartoons of various four-fold symmetric nodes.

Some variations of the structure of multimeric nodes are illustrated in FIGS. 4 and 5. FIGS. 4a-4d show nodes based on a protein trimer having three-fold (C3) rotational symmetry. Each node is composed of a trimeric protein where the subunits have been modified through site-specific mutagenesis to introduce surface amino acid residues that can be chemically modified to introduce pairs of biotin groups with geometry that is complementary to two of the binding sites on the streptavidin tetramer. FIG. 4a shows a node that is a trimer as formed from three independent, identical chains that are not covalently associated. Two biotins are bound to each chain, so that a streptavidin strut can bind to each subunit. FIG. 4b shows a node based on a protein trimer formed from a single chain construct, that is, with each subunit linked to another by a polypeptide linker. That is, the individual chains of the non-covalently associated trimer have been covalently connected together in a single polypeptide chain. Two biotins are bound to each chain, so that a streptavidin strut can bind to each subunit. The structure shown in FIG. 4b is termed a protein trimer herein. FIG. 4c shows a node based on a protein trimer formed from a single chain construct. Two of the subunits of the trimer have bound biotin pairs, but the third does not. Thus, only two streptavidin struts can be linked to the trimer. As such, the trimer can serve as a connector between struts, but does not allow branching from one strut to two other struts. FIG. 4d shows a node based on a protein trimer formed from a single chain construct. Only one of the subunits of the trimer has a bound biotin pair; the other two do not. Thus, only one streptavidin strut can be linked to the trimer. As such, the trimer can serve as a terminator of a strut, and cannot serve as a connector or branch point between struts. Thus, FIGS. 4b through 4d illustrate nodes with various streptavidin binding geometry and valency.

FIGS. 5a through 5f show nodes based on a protein tetramer having four-fold (C4) rotational symmetry. Each node is composed of a tetrameric protein where the subunits have been modified through site-specific mutagenesis to introduce surface amino acid residues that can be chemically modified to introduce pairs of biotin groups with geometry that is complementary to two of the binding sites on the streptavidin tetramer. FIG. 5a shows a node that is a tetramer as formed from four independent, identical chains that are not covalently associated. All of the subunits of the tetramer are symmetrically equivalent. Two biotins are bound to each chain, so that a streptavidin strut can bind to each subunit. FIG. 5b shows a node based on a protein tetramer formed from a single chain construct, that is, with each subunit linked to another by a polypeptide linker. That is, in the structure shown in FIG. 5b the individual chains of the non-covalently associated tetramer are covalently connected together in a single polypeptide chain, i.e., a linear amino acid sequence. Two biotins are bound to each chain, so that a streptavidin strut can bind to each subunit. The structure shown in FIG. 5b is termed a protein tetramer herein. FIG. 5c shows a node based on a protein tetramer formed from a single chain construct. Three of the subunits of the tetramer have bound biotin pairs, but the fourth does not. Thus, only three streptavidin struts can be linked to the tetramer. As such, the tetramer can serve as a branch point for three struts. FIG. 5d shows a node based on a protein tetramer formed from a single chain construct. Two adjacent subunits of the trimer have bound biotin pairs, but the third and fourth subunits do not. Thus, only two streptavidin struts can be linked to the tetramer. As such, the tetramer can serve as a connector between struts, but does not allow branching from one strut to two or more other struts. The tetramer can serve, for example, to form a corner of a rectangular assembly. FIG. 5e shows a node based on a protein tetramer formed from a single chain construct. Two opposed subunits of the tetramer have bound biotin pairs; the first and third subunits do not. Because only two streptavidin struts can be linked to the tetramer, the tetramer can serve as a connector between struts, but does not allow branching from one strut to two or more other struts. The tetramer can serve, for example, to form a connector between two struts oriented along the same axis. FIG. 5f shows a node based on a protein tetramer formed from a single chain construct. Only one of the subunits of the tetramer has a bound biotin pair; the other three do not. Thus, only one streptavidin strut can be linked to the tetramer. As such, the tetramer can serve as a terminator of a strut, and cannot serve as a connector or branch point between struts. Thus, FIGS. 5c through 5f show covalently connected tetramers of which the surface binding sites on some subunits have been deleted, creating nodes with various streptavidin binding geometry and valency.

Nodes can also be functionalized by making a gene fusion between a node protein and a specific protein binding domain. For example, a gene fusion can be made between a node protein and a Protein A or Protein G domain that binds with high affinity to Immunoglobin Fc (fragment crystallizable) regions.

Additional information on proteins as nodes is presented in U.S. Provisional Application No. 61/136,097, filed Aug. 12, 2008, the specification of which is hereby incorporated by reference. For example, a method of using a template multimeric protein as a nanostructure node can include the following. A template multimeric protein can be connected with a nanostructure strut. The template multimeric protein can have a known 3-dimensional structure. The template multimeric protein can be derived from a thermostable microorganism. The template multimeric protein can have Cn, Dn, or higher symmetry. The template multimeric protein can incorporate a specific binding site for the attachment of at least one nanostructure strut with predefined stoichiometry and orientation. For example, methods of producing nanostructure nodes and nanostructure assemblies can include the following. A mathematical and/or computer graphic representation of the 3-dimensional molecular structure of a template multimeric protein and a streptavidin tetramer can be generated. Each surface cysteine residue of the template multimeric protein can be replaced with an alternative amino acid in the representation. Several spatial configurations of the streptavidin tetramer relative to the template multimeric protein can be iterated through in the representation, with the streptavidin tetramer in approximate Van der Waals contact with the template multimeric protein. For each spatial configuration, cysteine can be assigned to replace two amino acid side chains on the surface of the template multimeric protein that are geometrically complementary to positions in the streptavidin tetramer that correspond to the terminal chemical groups on biotin (e.g., the biotin valeric acid carbon atom) when bound to the streptavidin tetramer to generate a nanostructure node multimeric protein representation. A measure of quality can be assigned to each spatial configuration (e.g., root-mean-square (rms) error between the coordinates of the projected positions of valeric acid carbon atoms of a biotin group bound to the streptavidin tetramer and of the sulfur atoms of the nearest cysteine on the surface of the nanostructure node multimeric protein and/or the potential energy of electrostatic interaction between the nanostructure node multimeric protein and the streptavidin tetramer). Each spatial configuration and associated nanostructure node multimeric protein can be stored. An optimal nanostructure node multimeric protein can be selected for production (for example, based on the measure of quality associated with a spatial configuration of the optimal nanostructure node multimeric protein).

For example, a template multimeric protein with Cn subunit symmetry can be used to define the amino acid sequence of a nanostructure node multimeric protein that can form planar nanoassemblies incorporating Cn planar nodes and streptavidin or streptavidin-incorporating struts attached with predefined stoichiometry and orientation. A mathematical and/or computer graphic representation of the 3-dimensional molecular structure of the Cn symmetric template multimeric protein and a streptavidin tetramer can be generated. A computer graphics and/or mathematical method can be used to identify surface cysteine residues on the surface of the template multimeric protein. An alternative amino acid(s) (e.g., Ala, Serine, Asp, etc.) can be assigned to replace the identified surface cysteine residues in the template sequence. The mathematical and/or computer graphic representation can be used to initially position the 3-dimensional coordinates of the template multimeric protein and streptavidin tetramer, so that the Cn symmetry (or z) axis of the template multimeric protein is parallel to the streptavidin tetramer z-dyad axis or y-dyad axis, the centers of mass of the template multimeric protein and streptavidin coordinates have the same or nearly the same z coordinate, and the molecules do not physically intersect. The mathematical and/or computer graphic representation can be used to incrementally translate the 3-dimensional coordinates of the streptavidin tetramer along one of its dyad axes that is normal to and intersects the Cn axis of the template multimeric protein, until the template multimeric protein and streptavidin tetramer approximately reach Van der Waals contact. The computational and/or computer graphics method can be used to identify as specific amino acid reactive sites two amino acid residues on the surface of the template multimeric protein that are geometrically complementary to positions in the streptavidin tetramer that correspond to the terminal chemical groups on biotin (e.g., the biotin valeric acid carbon atom) when bound to the streptavidin tetramer. A cysteine can be assigned to replace each of two amino acid residues identified as specific amino acid reactive sites, wherein the assigned cysteine has an associated biotin group, to generate a nanostructure node multimeric protein. A computational and/or computer graphics method can be used to create a model of the complex formed between the nanostructure node multimeric protein, having the biotin groups associated with the assigned cysteines bound to the streptavidin tetramer, evaluating the overall quality of a potential linkage between the nanostructure node multimeric protein and the streptavidin tetramer, and assigning a measure of binding quality (e.g., root-mean-square (rms) error between the coordinates of the projected positions of valeric acid carbon atoms of the biotin group as bound to the streptavidin tetramer and of the sulfur atoms of the assigned cysteine with which the biotin group is associated). A computational and/or computer graphics method can be used to evaluate the overall quality of the complementarity of fit between the surface of the nanostructure node multimeric protein and the surface of the streptavidin tetramer. A measure of complementarity of fit and/or energetic stability can be assigned based on, e.g., steric and electrostatic complementarity of amino acid residues at the interface, maintenance of preferred amino acid side chain rotomer conformations, low potential energy as estimated using a computational method such as molecular mechanics, quantum mechanics, or potential energy calculations, or through experimental methods of measuring complex stability, including affinity measurements, calorimetry, or other experimental methods. The 3-dimensional coordinates of the nanostructure node multimeric protein:streptavidin complex can be stored along with quality measures in a database. Beginning with the initial orientation, a rotation of the template multimeric protein about the Cn axis can be incremented. The steps of positioning the 3-dimensional coordinates of the template multimeric protein and streptavidin tetramer through incrementing the rotation of the template multimeric protein can be repeated over an angular increment of at least 360/n degrees, where n defines the foldedness of the multimeric protein symmetry axis. Quality measures of stored nanostructure node multimeric protein:streptavidin complexes can be ranked and/or coordinates of stored nanostructure node multimeric protein: streptavidin complexes can be examined in selecting an optimal nanostructure node multimeric protein for production. Modifications of this approach can be used, for example, to design and produce nodes for use as an apex in a polyhedron or other geometrical structure; the nodes, for example, attached to each other by nanostructure struts. For example, in initially positioning the 3-dimensional coordinates of the template multimeric protein and streptavidin tetramer, the Cn symmetry (or z) axis of the template multimeric protein and streptavidin tetramer z-dyad axis or y-dyad axis can be oriented at an angle corresponding to a polyhedral node apex angle. The centers of mass of the template multimeric protein and streptavidin coordinates can be variably displaced along their z coordinates to facilitate the generation of polyhedron apex node geometry.

For example, a nanostructure node can include a nanostructure node multimeric protein comprising at least one polypeptide chain. The nanostructure node multimeric protein can have one or more of the following: a known 3-dimensional structure; essentially a Cn, Dn, or higher symmetry with a number of subunits; stability at a temperature of 70° C. or greater; an amino acid sequence not found in nature; and/or a specific binding site for the attachment of a nanostructure strut with predefined stoichiometry and orientation. The specific binding site can include at least two specific amino acid reactive residues. Each specific amino acid reactive residue can have a covalently attached biotin group. For example, two or more subunits can be covalently interconnected with a polypeptide linker. For example, the nanostructure node can be a planar node, and/or the nanostructure strut can be a streptavidin strut. The nanostructure node multimeric protein can include one polypeptide chain. For example, the nanostructure node multimeric protein can have an amino acid sequence with greater than 80 percent sequence identity with the amino acid sequence of a pdb code:1thj protein trimer.

Biomolecular Component Adaptors

SAMA, Biotinylation Reagent, and Biotin-Residue Linked Streptavidin:SAMA Complex Precision nanostructure assembly requires a much higher level of specific control over successive steps in the assembly process than can be achieved by a simple strategy of forming streptavidin-biotin-protein multimer links.

For a reliable process that can produce diverse, complex structures with high reliability and fidelity, ways of controlling assembly reactivity and diversifying the geometry of the biomolecular components are required. A controllable component adaptor can act as a protecting group for the end of a strut, to either allow or prevent the strut from linking to a node or another strut.

In developing a controllable component adaptor, natural proteins, which can be further tailored, can be considered. A computational approach, e.g., an algorithm, manual inspection, or a combination of automated and manual techniques can be used to analyze protein coordinate sets downloaded from the Protein Data Bank (see, www.rcsb.org) or another publicly available database to identify a suitable protein for use as a controllable component adaptor. For example, a suitable protein can have surface amino acids to which a linking molecule that can link to a strut can be bound. Alternatively, a protein can be tailored, for example, through genetic engineering techniques, to have surface amino acids to which a linking molecule that can link to a strut can be bound. If a strut has two or more sites to which a linking molecule can be bound, a suitable protein can have the surface amino acids located such that each bound linking molecule will bond to a site on the strut.

In an embodiment, a streptavidin macromolecular adaptor (SAMA) protein serves as a controllable component adaptor for a streptavidin strut. The SAMA can act as a reversible protecting group for pairs of streptavidin binding sites, and provide the required precise control over nanostructure assembly. The SAMA can provide key advantages known from solid-phase chemical synthesis (Merrifield & Stewart 1965; Merrifield et al. 1966) such as 1) geometrical control of reactivity, 2) a mechanism for specific immobilization of a growing molecular assembly, 3) the ability to drive reaction equilibria to completion using mass action, and 4) greatly facilitated ability to purify reaction products from reagents.

Figure 6:
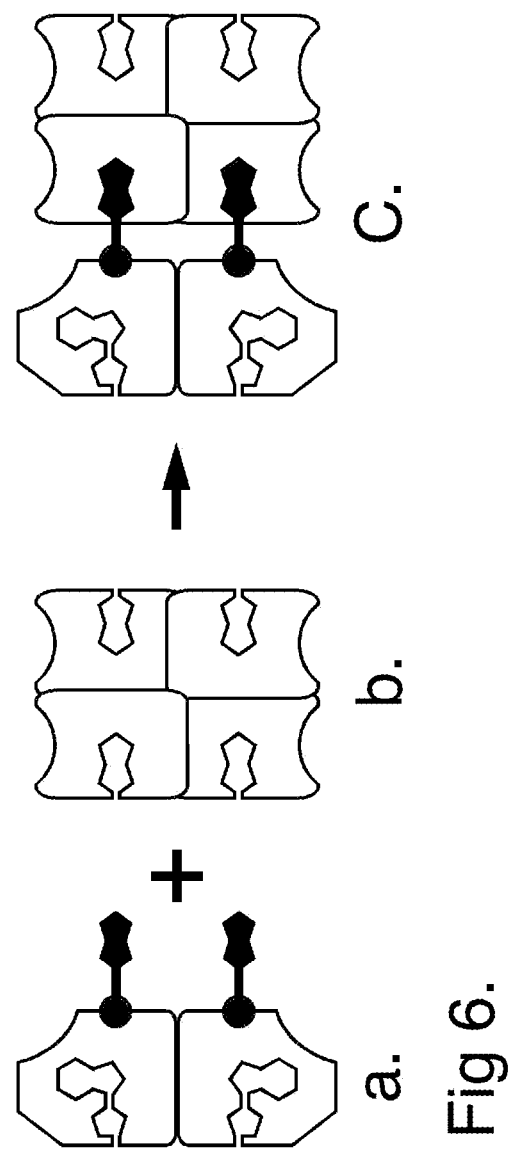
FIG. 6 presents steps in the assembly of a biotin-residue linked 1:1 streptavidin:SAMA complex.

FIG. 6c presents a cartoon of a 1:1 di-biotin linked streptavidin:SAMA complex. This complex can serve as a basic building block enabling the controlled assembly of nanostructures based on strut-node architecture. Furthermore, this complex can serve in streptavidin-based immobilization applications where improved control over immobilization chemistry is desired. Thus, a SAMA can function both as a protecting group and as an immobilization agent. FIG. 6a through 6c present steps in the assembly of the biotin-residue linked 1:1 streptavidin:SAMA complex shown in FIG. 6c. The molecules are in the complex linked through biotins occupying two of the four streptavidin biotin binding sites. Part a shows a schematic of the SAMA, part b shows the tetrameric protein streptavidin, and part c shows the 1:1 biotin-linked streptavidin:SAMA complex. This is an example of a basic nanostructure building block. Other examples of nanostructure building blocks, such as struts, are presented herein. Chemical structures for schematic representations of cross-link chemistry are given in FIG. 23.

Figure 7:
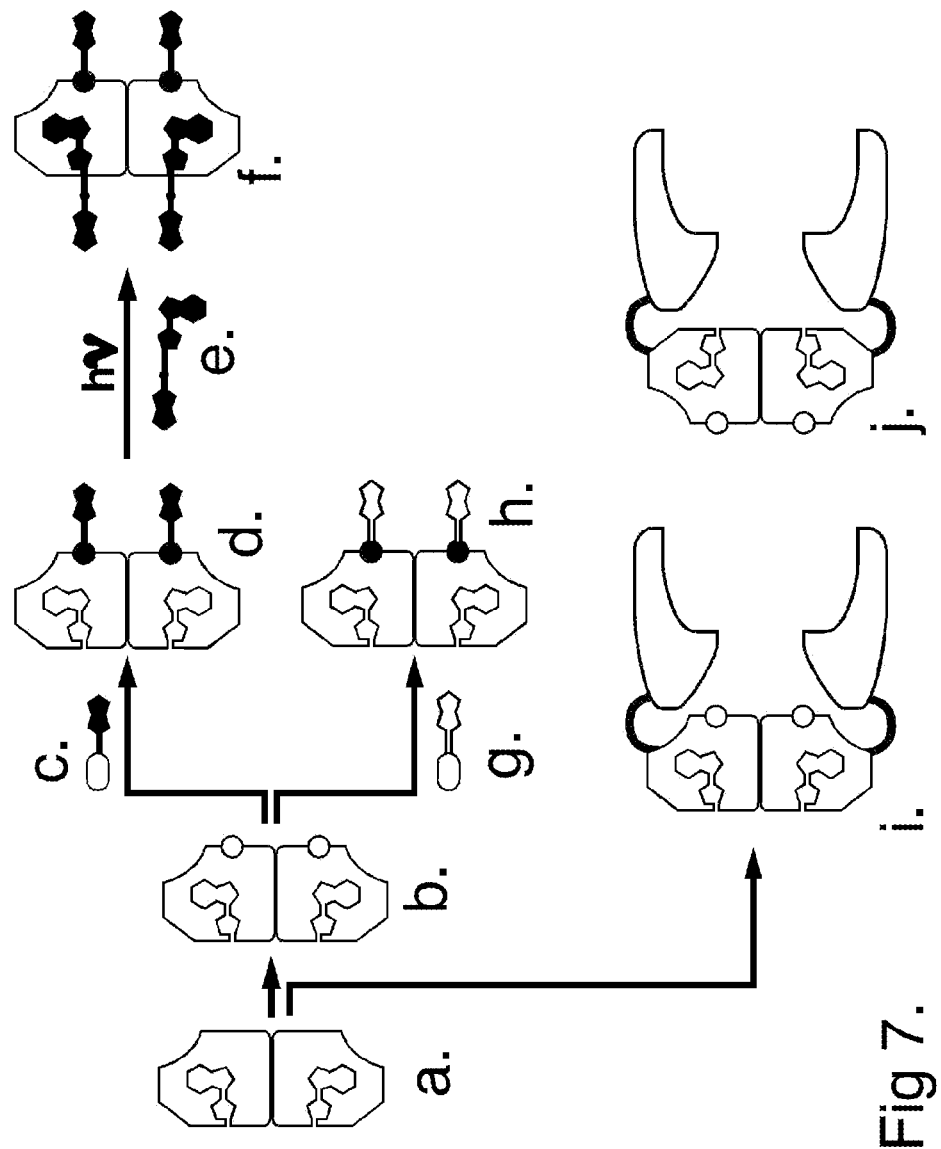
FIG. 7 presents steps in the formation and assembly of functionalized SAMA proteins.

FIG. 7 presents steps in the formation and assembly of several functionalized SAMA proteins. Chemical structures for schematic representations of cross-link chemistry are given in FIG. 23. FIG. 7, part a shows a schematic of a representative SAMA template protein, in this case a symmetric dimer with two ligand binding sites. Part b shows the introduction of a reactive surface amino acid residue into each monomer of the dimer so that the sites are separated by approximately 10.0 to 35.0 Angstroms and lie approximately in the same plane as two ligand binding sites on the dimer. The modified SAMA can be reacted with a biotinylating reagent c (e.g. FIG. 23a1 through 23a4) capable of reacting with the surface reactive amino acids introduced through site-specific modification of the native protein, producing the di-biotin-substituted SAMA d. The SAMA of part d may be further reacted with a bifunctional crosslinking reagent. In the example shown, a bifunctional crosslinker e incorporating biotin on one end and a photo-reactive analog of the SAMA ligand on the other binds to the protein and then becomes covalently attached through photo-crosslinking (e.g. FIGS. 23c1 and c2). This produces the modified SAMA f with four covalently bound biotin groups. The SAMA of part b may also be reacted with other reagents such as a reagent g (FIG. 23b1 through 23b4) that modifies the protein with 2-iminobiotin groups, allowing reversible, pH-dependent binding, e.g., between the MJ0577 SAMA embodiment and streptavidin.

A ligand interaction can be one in which a ligand moiety on the crosslinking reagent binds to a site on the SAMA, for example, wherein a nucleotide binds to a nucleotide binding site, or an enzyme inhibitor, substrate, or cofactor binds to an enzyme active site, or an antigen binds to an antibody domain. In such cases, the crosslinking reagent includes a moiety that is a nucleotide, an enzyme inhibitor, a substrate, a cofactor, or an antigen, respectively, or chemical analogs or derivatives of these. The SAMA protein binding site comprises a nucleotide binding site, an enzyme active site, or an antibody domain, respectively. The crosslinking reagent may comprise a derivative or chemical analog of the ligand moiety.

In developing a SAMA, thermostable proteins, which can be further tailored, for example, through genetic engineering techniques, can be considered. Thermostable proteins, derived from thermophilic organisms, offer many benefits. These include a high level of intrinsic stability that contributes to general experimental ease of handling, resistance to chemical degradation, stability at elevated temperature, and ease of purification when expressed in bacterial or other protein production systems. For example, a thermostable protein may be selected as a SAMA, so that the SAMA has a denaturation temperature in aqueous solution of at least about 60° C. and/or maintains secondary, tertiary, and quaternary structure in a solvent having a dielectric constant of at least about 15. A SAMA used as a biomolecular component can have a protein sequence homology (similarity) of at least about 50%, at least about 60%, at least about 70%, at least about 80%, at least about 90%, at least about 95%, at least about 98%, or at least about 99% with a sequence derived from a thermophilic organism, or can have complete sequence homology (similarity) with a sequence derived from a thermophilic organism except for one, two, or four amino acid residues at suitable positions on the surface of the SAMA to serve as designated amino acid residues for biotin binding sites.

Figure 27:
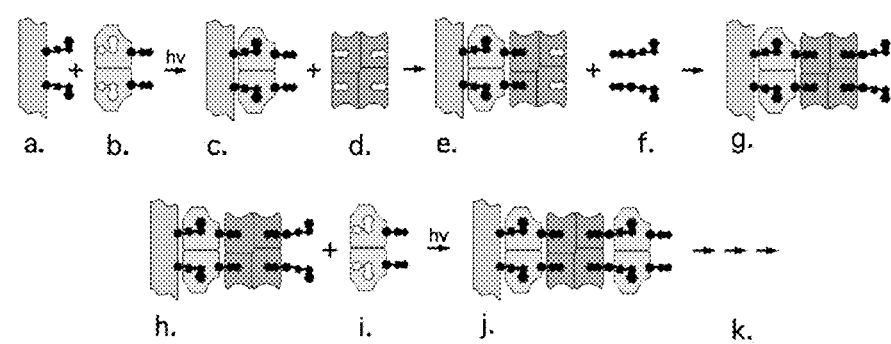
FIG. 27 shows the formation of a linear strut using a SAMA.

Thus, a SAMA can be easily produced in large quantities (e.g., isolation of the thermophile-derived SAMA protein from E. coli is significantly aided by heat denaturation of the E. coli native proteins) and can effectively function both as an immobilizing agent and as a reversible protecting group for two binding sites on streptavidin. FIG. 27 shows an example involving the formation of a linear strut. Part (a) shows a surface that has been functionalized with an azido-ATP reagent. Part (b) shows a dimeric SAMA molecule that has 2 ATP binding sites and has also been functionalized with biotin groups that are complementary to biotin binding sites on streptavidin. Part (c) shows the SAMA immobilized on the surface so that it can bind to 2 sites of a streptavidin tetramer (d). The immobilized complex (e) can then bind a biotin-azido-ATP crosslinking reagent (f) to form the modified complex (g). The resulting complex (h) can react with additional SAMAs (i) to form extended structures (j,k). The linear structure can be terminated with a wide variety of commercially available biotinylated proteins (e.g. Biotinylated Protein A that binds immunoglobulin Fc domains) to create functionalized assemblies on solid surfaces for devices such as biosensors.

For example, a suitable protein for a SAMA can have a longest dimension greater than about 20.5 Angstroms. A suitable protein for a SAMA can have at least two designated surface amino acid residues located 10 and 40 Angstroms apart, so that biotin linking molecules bound to these have a spacing sufficiently similar to that of biotin binding sites on streptavidin.

A designated surface amino acid is an amino acid on the exterior of a protein, such that the amino acid contacts the environment surrounding the protein, and that is intended to be reacted with a chemical group to impart a chemical functionality to the protein. For example, a cysteine on the exterior of a protein may serve as a designated surface amino acid, with which a thiol-reactive biotinylating reagent may react, so that biotin functionality is imparted to the protein. For example, a cysteine on the exterior of a protein may serve as a designated surface amino acid, with which a thiol-reactive ATP photo label, such as a 2-azido or 8-azido adenosine photo-crosslinking reagent functionalized to form S—S bonds with free sulfhydryl groups (FIG. 23d1 or 23d2) may react, so that ATP photo label functionality is imparted to the protein. Examples of such designated surface amino acid residues include cysteine, lysine, histidine, arginine, methionine, and tyrosine. For example, a designated surface amino acid residue can be the only amino acid of its type, for example, a cysteine, in a polypeptide chain or in a polypeptide chain that is on the surface of the protein. The two designated surface amino acid surface residues can be the same residue or different residues. A designated surface amino acid surface residue can include side chain atoms. The location of these designated surface amino acid surface residues can be termed a surface reactive region. For example, a sulfur-sulfur bond can be formed between the biotin-containing moiety of a biotinylation reagent and a surface cysteine on a SAMA protein, concurrent with the release of a chromogenic leaving group from the biotinylation reagent. A water-soluble biotin-derivative can be mixed with the SAMA protein solution and the time course of reaction followed colorimetrically by monitoring the release of the chromogenic group attached to the derivatized biotin (Green, 1975). Excess biotinylation reagent and/or multiple reaction cycles can be used to drive complete derivatization of the SAMA. A schematic diagram outlining the steps of site specific modification and biotinylation at the modified sites are illustrated in FIGS. 7a through 7d.

After biotinylation of a SAMA, a size exclusion chromatography (SEC) column can be used to completely remove any unreacted biotin reagent, and the extent of SAMA biotinylation can be measured by titration of any remaining free SAMA sulfhydryl groups with Ellman's Reagent (5,5'-dithiobis-(2-nitrobenzoic acid) or DTNB). DTNB readily forms a mixed disulfide with thiols to liberate 5-mercapto-2-nitrobenzoic acid, a chromophore with absorption maximum at 410 nm and extinction coefficient ~13,600 $cm^{-1}M^{-1}$. If analysis with DTNB indicates presence of any underivatized SAMA, an additional purification step involving passage of the biotinylated SAMA over a free thiol affinity column to remove any unreacted or mono-biotinylated SAMA can be performed for further purification to obtain di-biotinylated SAMA.

For example, a suitable protein for a SAMA can be a dimer of two subunits. The dimer can be formed of one or more polypeptide chains, for example, one or two polypeptide chains. Each subunit can be formed of a separate polypeptide chain, or the subunits can be formed of a single polypeptide chain. The dimer can be symmetric and the polypeptide chains can have the same amino acid sequence. The two subunits forming the dimer can be substantially structurally identical and/or substantially sequentially identical. For example, substantially structurally identical can mean that the secondary and tertiary structure of one subunit is similar to that of the other subunit, although there may be small differences, for example, in the position of secondary structures such as alpha helices and beta sheets. For example, substantially sequentially identical can mean that the amino acid sequence of the polypeptide forming one subunit is similar to that of the polypeptide forming the other subunit, although there may be small differences, for example, the addition (insertion) of one or a few amino acids, the deletion of one or a few amino acids, and/or the substitution of one or a few amino acids in a polypeptide. The polypeptide chains can be covalently linked. For example, a polypeptide chain forming a first subunit can be covalently linked to a polypeptide chain forming a second subunit. The surface reactive amino acid residues to which biotin can be bound, for example, each member of a pair of designated surface amino acid residues can be related by, e.g., be symmetric about, a dyad symmetry axis. The surface reactive amino acids can be introduced into the polypeptide chain at suitable positions determined through molecular modeling using methods of site-specific mutagenesis. Surface reactive amino acids can vary according to the chemistry used to introduce covalently bound biotin groups. In addition to cysteine, useful reactive amino acids include lysine, arginine, tyrosine, histidine, serine, and threonine, as well as the free amino terminus of the polypeptide chain. There can be a unique pairwise interaction between the biotins presented on the functionalized SAMA surface and two of the most closely spaced biotin binding sites on streptavidin, specifying an overall interaction with defined geometry. Each member of a pair of binding sites on the SAMA can be symmetric about a dyad symmetry axis, for example, about the same dyad symmetry axis about which each member of a pair of designated surface amino acid residues is symmetric. For example, such a dyad axis can span from a first end of the SAMA protein to a second end of the SAMA protein, with the second end being opposed to the first end, that is, with the first end on one side of the SAMA protein and the second end on the opposite side of the SAMA protein. For example, each member of a pair of binding sites can be symmetric about the dyad axis at the first end of the SAMA protein, and each member of a pair of designated surface amino acid residues can be symmetric about the dyad axis at the second end of the SAMA protein.

Thus, when the biotin groups on a SAMA bind to two biotin binding sites on streptavidin, the two binding sites are effectively "capped", in that they cannot react with any other available biotin molecules. That is, the SAMA serves as a protecting group, and can prevent the uncontrolled polymerization between streptavidin and biotin functionalized proteins observed by Ringler & Schulz (2003).

For example, biotin-type groups can be covalently bonded to each of a pair of designated surface amino acid residues on a SAMA protein. For example, a biotin-type group can include a biotin, an iminobiotin, a portion of a biotin or an iminobiotin, or a derivative or chemical analog of biotin or iminobiotin. A biotin-type group is capable of bonding with a biotin binding site on a streptavidin tetramer. A biotin-type group can also include a group capable of binding with another molecule, for example, a thiol group capable of covalently binding with a cysteine used as a designated surface amino acid on a protein, such as a SAMA protein. Each biotin-type group can be bound to a biotin binding site of a pair of biotin binding sites of a streptavidin tetramer. Alternatively, two bifunctional crosslinking reagents, each comprising a biotin-type moiety and a second moiety can be used to link a SAMA protein to a streptavidin tetramer. The biotin-type moiety can be bound to a biotin binding site of the pair of biotin binding sites of a streptavidin tetramer, and the second moiety can be bound to a binding site of the pair of binding sites of a SAMA protein. For example, the second moiety can include a nucleotide, an enzyme inhibitor, an enzyme substrate, an enzyme cofactor, derivatives of these, and/or chemical analogs of these. Each member of a pair of biotin binding sites can be symmetric about a dyad axis of a streptavidin tetramer. A dyad axis of the SAMA protein about which each member of a pair of designated surface amino acid residues and/or a pair of binding sites are symmetric can be colinear with a dyad axis of the streptavidin tetramer.

However, to allow for the construction of complex, predetermined structures of many biomolecular components, the biotin binding capability of the streptavidin should be able to be regenerated. Regeneration means that the capped binding sites can be linked through another protein to empty, available biotin binding sites. For example, in addition to a pair of designated surface amino acid residues to which biotin groups can be linked, the SAMA can include two or more binding sites. These binding sites can be, for example, separated from each other by from about 10 Angstroms to about 30 Angstroms. Each binding site can lie within about 8 Angstroms of a plane in which a side chain atom of each designated surface amino acid residue and the other binding site lie. The binding sites and the bifunctional crosslinking reagents which can bind to them are further discussed below.

Figure 8:
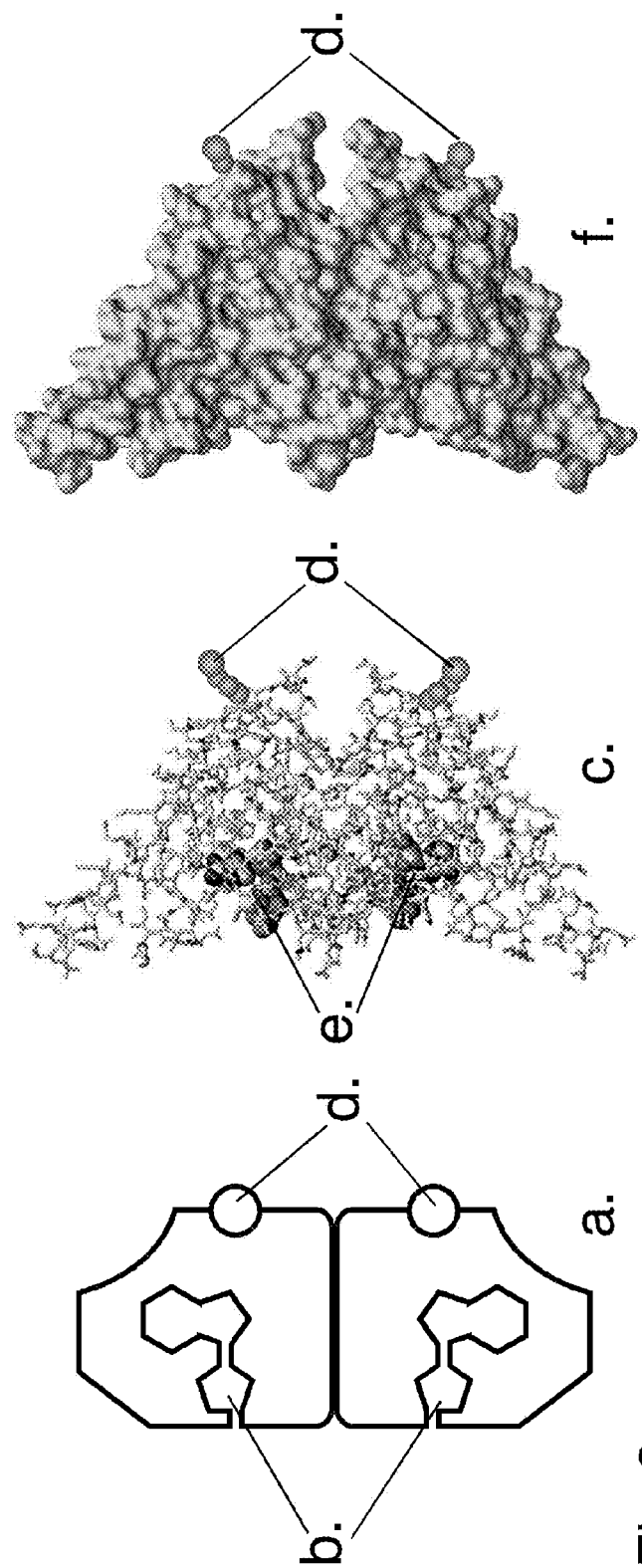
FIG. 8 presents a SAMA cartoon and computer representation of the MJ0577 protein dimer structure.

For example, the MJ0577 protein dimer isolated from the thermostable bacterium *Methanococcus jannaschii* can serve as a SAMA (see FIG. 8). MJ0577 belongs to a large family of proteins involved in stress responses, termed universal stress response proteins (Usp) (Sousa & McKay (2001); Saveanu et al. (2002)). The widespread occurrence of Usp domains either isolated or as parts of larger proteins suggests additional ligand-activated roles (Siegele 2005). Thus, other universal stress response proteins or universal stress response domains in large proteins may be used as SAMAs. For example, a SAMA can have an amino acid composition homology (similarity) by relative proportion of amino acid composition of at least about 50%, at least about 60%, at least about 70%, at least about 80%, at least about 90%, at least about 95%, at least about 98%, or at least about 99% to MJ0577 or to another naturally occurring protein, or can have complete sequence homology (similarity) with MJ0577 or another naturally occurring protein except for one, two, or four amino acid residues at suitable positions on the surface of the SAMA to serve as designated amino acid residues for biotin binding sites.

FIG. 8 presents a cartoon representation of a SAMA and a computer representation of the MJ0577 protein dimer structure. The streptavidin macromolecular adaptor (SAMA) embodiment, MJ0577, is a dimeric protein with C2 symmetry. Part a shows a cartoon of a SAMA. Part b designates binding sites for two specific binding ligands, such as nucleotides or nucleotide derivatives, related by a dyad axis of symmetry and spaced approximately 24.5 Angstroms apart. Part c shows an all atom (excluding hydrogen atoms) stick bond representation of an embodiment of a SAMA based on a modified form of the MJ0577 protein. Part d shows the positions of two surface reactive groups on the SAMA dimer allowing the covalent attachment of biotin groups through reaction with an appropriate chemical reagent. Part e shows two adenosine triphosphate (ATP) molecules, shown in space filling representation, bound to the MJ0577 protein and spaced approximately 24.5 Angstroms apart. Part f shows a surface representation of the MJ0577 SAMA embodiment showing overall shape. Chemical structures for schematic representations of cross-link chemistry are given in FIG. 23.

Several favorable characteristics of MJ0577 that make it suitable for use as a SAMA are as follows. MJ0577 has 162 residues with no cysteines, so that minimal tailoring or engineering is required and no stabilizing disulfides need to be removed. MJ0577 is thermostable to at least 80° C. (Zarembinski et al. 1998), and this thermostability implies the chemical stability required for chemical derivatization. The structure of MJ0577 has been determined to 1.7 Angstrom resolution (Zarembinski et al. 1998), and exhibits two-fold symmetry, and appropriate overall molecular dimensions and shape for a bidentate interaction with streptavidin. MJ0577 has been expressed in *E. coli*. Capitalizing on the protein's thermostability, the protein was purified by incubating the soluble protein extract at 80° C., and then removing denatured proteins by centrifugation. Subsequent anion exchange chromatography over DEAE Sepharose produced protein that readily crystallized. The protocol yielded about 2.5 mg of purified protein per liter of cell culture (Zarembinski et al. 1998). The expression and purification protocol used standard methods, so that MJ0577 can be routinely produced.

The structure of MJ0577 is such that an ATP (adenosine triphosphate) molecule can be fit to electron density at each ligand-binding pocket of the dimer (Zarembinski et al. 1998). Such binding to ATP can make MJ0577 suitable as an ATP-dependent molecular switch or ATPase. These ligand-binding pockets of MJ0577 can serve as binding sites so that the biotin binding capability of a streptavidin "capped" by MJ0577 can be regenerated. Thus, the high intrinsic stability, ease of production and purification, and ligand-binding capabilities of MJ0577 suggest its use as an integral biomolecular component of nanostructures and suggest its use in the solid-state synthesis of nanostructures. The SAMA based on MJ0577 is approximately 80 Angstroms (8 nanometers) wide by 50 Angstroms deep (5 nanometers) by 45 Angstroms (4.5 nanometers) long in the direction through which it is connected to streptavidin.

Figure 9:
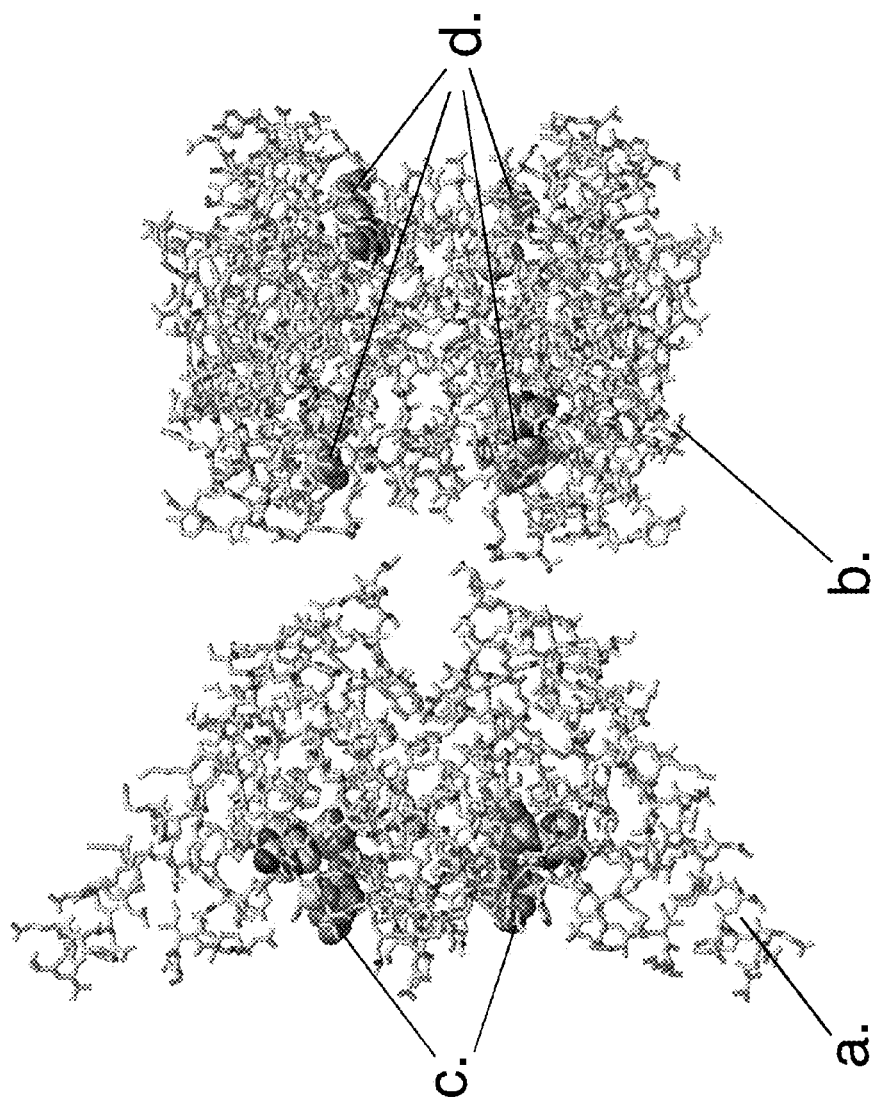
FIG. 9 presents a computer model showing the MJ0577 protein dimer and the streptavidin tetramer in apposition.

FIG. 9 presents a computer model showing apposition of the MJ0577 dimer (at left) and the streptavidin tetramer (at right). Biotins bound to streptavidin and ATPs bound to MJ0577 are shown as CPK-rendered groups (atoms are shown as spheres). FIG. 9a shows the MJ0577 SAMA embodiment in stick bond representation, and part b shows streptavidin in stick bond representation. The molecules are "docked" along a common two-fold symmetry axis. Parts c designates the ATP molecules bound to MJ0577 and part d designates biotin molecules bound to streptavidin. A detailed energetic analysis of the streptavidin-MJ0577 interaction can be performed. If necessary, unfavorable intermolecular electrostatic interactions can be minimized or eliminated through site specific modification of MJ0577, streptavidin, or both, so that a tight interface between streptavidin and MJ0577 is obtained. Computer modeling can be generally applied in the tailoring of natural proteins for their use as biomolecular components.

Figure 28:
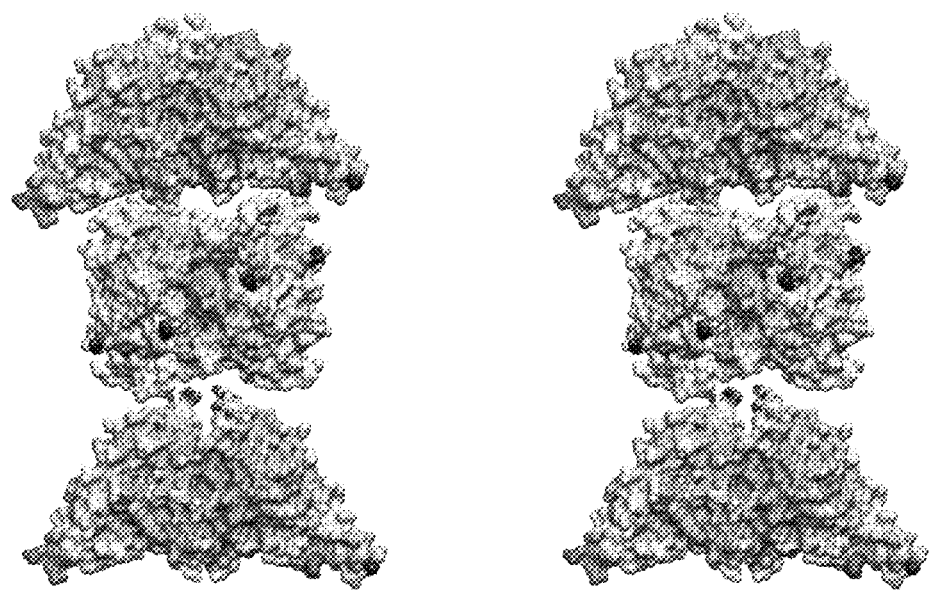
FIG. 28 is a stereoview that shows the excellent surface complementarity of both sides of the MJ0577 SAMA for streptavidin.

While MJ0577 is overall a neutral molecule, the charge distribution is somewhat asymmetric, and inspection of the modeled complex revealed that an electrostatically positive portion of MJ0577 is oriented toward electrostatically negative regions of streptavidin. As shown in FIG. 28, there is excellent surface complementarity between both sides of MJ0577 and streptavidin. The surface of streptavidin is shown in the middle. At the bottom, the SAMA is oriented as in complexes linked by biotin attached to surface cysteine side chains. The top molecule shows SAMA oriented toward SAV in an orientation to facilitate complexation via bifunctional ATP-biotin linkers. For clarity, molecules are translated apart along the interaction axis.

Figure 29:
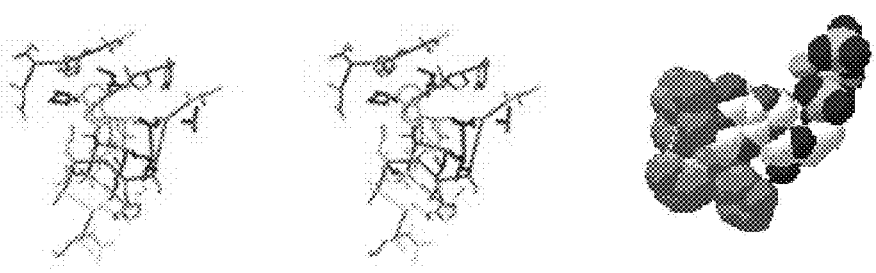
FIG. 29 shows the bound conformation of ATP in MJ0577.

There is a 16 Å distance between the MJ0577 ATP g-phosphate and streptavidin biotin carboxylate. This distance corresponds well to commercially available Biotin-(polyethylene oxide)-Azido-ATP cross linking reagents (see, FIG. 29). The left panel of FIG. 29 shows a stereoview of ATP (in the center of the image) bound to MJ0577. The right panel shows the van der Waals surfaces of the bound ATP and residues near the C2 of the adenine ring. ATP adopts a curved conformation in the bound state with the N6 and N7 atoms of the adenine ring, the g-phosphate, and associated Mn ion (green) exposed to solvent. As shown in the right, the environments of the adenine C2 and C8 atoms that are the usual sites for addition of the azido ($N_3$) photoreactive reagent differ. The C8 is tightly packed against the phosphate backbone, while a small pocket in the protein exists near C2. Although ATP immobilized though the g-phosphate appears suitable for capture of SAMA, resins with ATP immobilized through the N6 atom are also possible (Jena Bioscience).

Figure 30:
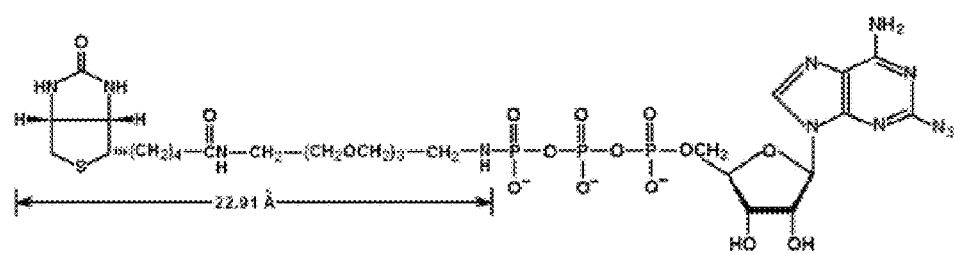
FIG. 30 shows a bifunctional linking reagent with biotin and photoreactive ATP.

In the MJ0577 X-ray structure (FIG. 29) ATP binds in a curved conformation with the N6 and N7 atoms of the adenine ring and the g-phosphate exposed to solvent. Available Azido-ATP compounds incorporate reactive azido groups on the C2 and C8 atoms of the adenine ring (FIG. 30). The reagent 2-Azidoadenosine 5'-triphosphate[g]-biotinyl-3, 6,9-trioxaundecanediamine ($2N_3$ATP[g]Biotin-LC-PEO-Amine) (ALT BioScience) shown in FIG. 30 has enough atoms linking the biotin and 2-azido ATP to span the distance (~16 Å) between molecules at the SAMA:streptavidin interface, as modeled. As shown in FIG. 29, the X-ray structure suggests that 2-azido derivatives have a less sterically hindered binding environment. We found that isolated, pre-reacted SAMA constructs have Tm >75° C. The thermal stability of constructs and complexes can be quantitatively measured throughout processing using a relatively efficient method for protein thermal stability characterization (Pantoliano et al. 2001). The method depends upon the fact that native folded proteins are highly organized structures that melt cooperatively at a specific melting temperature that is characteristic for each protein and representative of the free energy of stabilization of the protein's folded state. This melting effect can be efficiently measured in a microplate format by performing a thermal scan in a qPCR machine that measures the fluorescence of a dye (typically ANS) that only fluoresces when binding to the melted or "molten globule" state of the protein. In addition, the method can be used to determine effects of chemical modification or ligand binding on protein thermal stability. In addition to performing direct measurements of thermal stability, structural integrity and uniformity can be monitored using dynamic light scattering, alone and in combination with static light scattering. These methods from polymer physics provide measures of both particle size and anisotropy, and particle molecular weight that can be implemented in microliter formats making them practical as laboratory methods.

MJ0577 can be engineered using site-specific modification of the native MJ0577 gene to add surface cysteine residues. There are no cysteine residues present in the native MJ0577 structure, so there is no necessity to replace any cysteine residues in the native protein sequence. One surface cysteine residue can be placed in each monomer of the dimer. The cysteine residues can be placed to allow covalent attachment of biotin groups such that they uniquely can occupy only the closest pair of the streptavidin biotin binding sites, separated by about 20.5 Angstroms (the second possible pair of streptavidin biotin binding sites are separated by about 33.5 Angstroms). The thiol group of each surface cysteine residue can react with a thiol-reactive biotinylating reagent and thus serve as a covalent attachment site for a biotin alkylating reagent (FIG. 2).

The use of computer modeling methods suggests several alternative positions in the native MJ0577 protein sequence where an existing surface amino acid residue can be replaced by an amino acid with a reactive side chain allowing the chemical attachment of biotin. Examples of specific embodiments that are capable of biotinylation with the sulfhydryl reactive reagents shown in FIG. 2b include the following substitutions: K29 to C29, L31 to C31, K32 to C32, A33 to C33, E93 to C93, D94 to C94, V95 to C95, or G96 to C96, where a single residue in the native chain may be substituted by cysteine to provide for covalent attachment of one biotin group per SAMA subunit (FIG. 10). In the previous sentence, the letter is the standard abbreviation for an amino acid, and the number is the location of the amino acid in the protein sequence. For example, "L31" indicates the leucine at the 31 position. "L31 to C31" (L31=>C31) indicates a substitution of the leucine by a cysteine at the 31 position. FIG. 10 presents SAMA amino acid sequences based on the MJ0577 protein. Sequence A is the native sequence of the MJ0577 protein, a polypeptide containing 162 amino acid residues. Sequences B show alternative positions of 8 individual cysteine modifications (K29=>C29, L31=>C31, K32=>C32, A33=>C33, E93=>C93, D94=>C94, V95=>C94, G96=>C96), where a single residue in the native chain may be substituted by cysteine to provide for covalent attachment of one biotin group per SAMA subunit. Sequence(s) in C are variants of sequences B where either or both the amino and carboxy terminus of the polypeptide chains have been extended by the incorporation of functional polypeptide sequences (Sequences D and E) to aid in isolation, immobilization, or additional chemical functionalization of the SAMA. Preferably, the functional polypeptide sequences are connected to the SAMA or to each other by short linking sequences that may for example incorporate serine (S) and glycine (G) amino acid residues. For example, functional amino terminus extension Sequence D1 is a poly-histidine tag that binds to metals for immobilization or isolation, D2 is a polypeptide tag that binds to streptavidin, and sequences D3, D4, and D5 are streptococcal protein A or G sequences that bind to immunoglobulins. The sequence D0 is a specific protease cleavage site for the endoprotease Factor Xa. Inclusion of a protease site in the sequence allows controlled release or removal through proteolysis of one or more of the functional domains bound to SAMA. E Sequences are the same as D sequences, but are attached via linkers to the carboxy terminus of the SAMA polypeptide chain. Although the attached functional sequences shown in FIG. 10 C1, C2, etc. are shown with a particular order (e.g. D1D2 D3 etc., E1 E2 E3 etc.), arrangements with an alternative order of attached functional sequences (e.g. D1D3 D2 etc., E3 E1 E2 etc.) can also be constructed as required for specific applications, as can sequences with particular functional or linking sequences duplicated or deleted.

To select attachment sites, residues within 20 Å of the biotin carboxylate were identified. Two structural segments of MJ0577, a loop between two b-strands and a loop between a strand and helix, fell within this cutoff distance. Residues L31 and K32 of the b-loop and V95 (not G96) appeared as substitution candidates because they are solvent exposed to aid covalent attachment of linked biotin, and are situated in the same plane as the ATP binding sites in SAMA, so that twist is not be introduced into streptavidin-ligated structures as a result of the introduction of the SAMA protecting group. These sites can accommodate cysteine sidechains in several energetically favorable conformations. One allowed rotamer was selected in each case to model the covalent attachment of a linked biotin. First, MJ0577 and streptavidin were translated to nearly van der Waals contact. The biotin valeric acid side chain of streptavidin was next replaced with an extended hydrocarbon chain whose bonds could be rotated to find the most direct connection between the biotinylated SAMA and SAV. Using this procedure the minimum number of atoms between the SAMA cysteine SG and the biotin carboxylate could be estimated. The shortest linker was about 11 or 12 atoms for L31C and K32C and at least 19 atoms were needed between SAMA V95C and streptavidin. Molecular modeling was carried out with Deep View (Guex 1996; Guex et al. 1999) and VMD (Humphrey et al. 1996).

FIG. 11 shows a cartoon representation of a biotinylated SAMA and a molecular representation of the MJ0577 SAMA embodiment (L31=>C31) that has been modified by reaction with the biotinylation reagent of FIG. 2b and FIG. 23a1. Parts a and b show the MJ0577 SAMA embodiment (L31=>C31) that has been modified by reaction with a biotinylation reagent to covalently introduce two biotin groups. Part a shows a cartoon or schematic (used in other diagrams), part b shows an all atom representation of the SAMA embodiment MJ0577 in stick bond representation. Part c shows the covalently attached biotin moieties in schematic and in space filling representation, and part d shows the SAMA ATP binding sites in schematic and in space filling representation. Chemical structures for schematic representations of cross-link chemistry are given in FIG. 23.

Although the site-specific modification of individual residues is not expected to alter global properties of the native MJ0577 dimer, any such alterations can be monitored. Molecular properties of the engineered MJ0577 SAMA and the native MJ0577 from which it was derived can be monitored by SDS PAGE during the purification and verified by electrospray ionization mass spectroscopy (ESI MS) of the purified proteins. Comparison of the protein ionization patterns of the engineered MJ0577 SAMA with those of the native MJ0577 protein by ESI MS can provide a sensitive analytical tool for the identification of conformational changes in the global protein structure induced by site-specific modification. This can provide a general monitor of the conservation of protein tertiary structural integrity (Loo et al. 1990; Loo & Kilby 2002).

In addition to the symmetric dimer MJ0577 from *Methanococcus jannaschii*, other proteins that have appropriate geometrical and ligand binding properties can be used as frameworks for engineered streptavidin macromolecular adaptors (SAMAs). The various SAMAs made from these proteins can have a range of different types of ligand binding sites, so that the structures can be linked together with protein nodes or streptavidin using different types of bi-functional cross-linking chemistry. Each of these various SAMAs with different linking chemistry can be used independently of other types of SAMAs or in combination with other types of SAMA to expand the diversity and complexity of structures that can be assembled from protein building blocks. Some proteins in addition to MJ0577 that can be used as SAMA frameworks are now described.

The Universal Stress Protein from *Aquifex aeolicus* (Protein Data Bank (PDB) code 1q77) is an example of another dimeric protein besides MJ0577 that binds ATP ligands and can be engineered to produce a SAMA. The amino acid sequence is as follows:

(SEQ. ID NO. 1)
SNAMKVLLVLTDAYSDCEKAITYAVNFSEKLGAELDILAVLEDVYNLERA

NVTFGLPFPPEIKEESKKRIERRLREVWEKLTGSTEIPGVEYRIGPLSEE

VKKFVEGKGYELVVWACYPSAYLCKVIDGLNLASLIVK.

The Tryptophanyl-tRNA synthetase (EC 6.1.1.2) (tm0492) from *Thermotoga maritima* (PDB code 2g36) is an example of a dimeric protein that can be engineered to produce a SAMA. This protein has specific binding sites for the amino acid tryptophan, chemical derivatives of which can, for example, form one end of a SAMA bifunctional linking reagent. The amino acid sequence (including an N-terminal His tag incorporated for ease of isolation) is as follows:

(SEQ. ID NO. 2)
MGSDKIHHHHHHMRILSGMRPTGKLHIGHLVGALENWVKLQEEGNECFYV

ADWHALTTHYDDVSKLKEYTRDLVRGFLACGIDPEKSVIFVQSGVKEHAE

LALLFSMIVSVSRLERVPTYKEIKSELNYKDLSTAGFLIYPVLQAADILI

YKAEGVPVGEDQVYHIELTREIARRFNYLYDEVFPEPEAILSRVPKLPGT

DGRKMSKSYGNIINLEISEKELEQTILRMMTDPARVRRSDPGNPENCPVW

KYHQAFDISEEESKWVWEGCTTASIGCVDCKKLLLKNMKRKLAPIWENFR

KIDEDPYVDDVIMEGTKKAREVAAKTMEEVRRAMNLMF.

The Geranyltranstransferase enzyme (EC 2.5.1.10) (tm0161) from *Thermotoga maritima* (PDB code 2ftz) is an example of a dimeric protein that can be engineered to produce a SAMA. This protein has specific binding sites for various hydrocarbon chains, chemical derivatives of which can, for example, form one end of a SAMA bifunctional linking reagent. The amino acid sequence (including an N-terminal His tag incorporated for ease of isolation) is as follows:

(SEQ. ID NO. 3)
MGSDKIHHHHHHMKKEKVEERIREILRPGWDLLTEEAMLYSATVGGKRIR

PLLVLTLGEDLGVEEEKLLDVAVAVELFHTASLIHDDLPPIDNADFRRGK

PSCHRTYGEDIALLAGDGLFFLAFSQISKIGNSKIFEEFSETAYKLLLGE

AMDVEFERRKMEVSQEMVERMYAFKTGALFAFCFSAPFILKGKDHTKMKL

LGEKFGVAFQIYDDLKDILGSFEKVGKDLGKDTEKVTLVKKVGIQKAREM

ADKYYEEVLKGIESEGLFRTLFLLKELKQMVEER.

The 5-Methyltetrahydrofolate-Homocysteine S-Methyltransferase enzyme from *Thermotoga maritima* (PDB code 1Q8A) is an example of a dimeric protein that can be engineered to produce a SAMA. This protein has specific binding sites for various folate and folate analogs, chemical derivatives of which can, for example, form one end of a SAMA bifunctional linking reagent. The sequence of the first 566 residues of the chain that form an intact structural domain suitable for a SAMA is as follows:

(SEQ. ID NO. 4)
MRNRREVSKLLSERVLLLDGAYGTEFMKYGYDDLPEELNIKAPDVVLKVH

RSYIESGSDVILTNTFGATRMKLRKHGLEDKLDPIVRNAVRIARRAAGEK

LVFGDIGPTGELPYPLGSTLFEEFYENFRETVEIMVEEGVDGIIFETFSD

ILELKAAVLAAREVSRDVFLIAHMTFDEKGRSLTGTDPANFAITFDELDI

DALGINCSLGPEEILPIFQELSQYTDKFLVVEPNAGKPIVENGKTVYPLK

PHDFAVHIDSYYELGVNIFGGCCGTTPEHVKLFRKVLGNRKPLQRKKKRI

FAVSSPSKLVTFDHFVVIGERINPAGRKKLWAEMQKGNEEIVIKEAKTQV

EKGAEVLDVNFGIESQIDVRYVEKIVQTLPYVSNVPLSLDIQNVDLTERA

LRAYPGRSLFNSAKVDEEELEMKINLLKKYGGTLIVLLMGKDVPKSFEER

KEYFEKALKILERHDFSDRVIFDPGVLPLGAEGKPVEVLKTIEFISSKGF

NTTVGLSNLSFGLPDRSYYNTAFLVLGISKGLSSAIMNPLDETLMKTLNA

TLVILEKKELPRAEVK.

The dimeric Adenosine Monophosphate Binding Protein (tm1088a) from *Thermotoga maritima* (PDB code 2g1u) is an example of a dimeric protein that can be engineered to produce a SAMA. This protein has specific binding sites for adenosine monophosphate, chemical derivatives of which can, for example, form one end of a SAMA bifunctional linking reagent. The amino acid sequence (including an N-terminal His tag incorporated for ease of isolation) is as follows:

(SEQ. ID NO. 5)
MGSDKIHHHHHHMSKKQKSKYIVIFGCGRLGSLIANLASSSGHSVVVVDK

NEYAFHRLNSEFSGFTVVGDAAEFETLKECGMEKADMVFAFTNDDSTNFF

ISMNARYMFNVENVIARVYDPEKIKIFEENGIKTICPAVLMIEKVKEFII

GSEED.

The structures of these proteins that can serve as frameworks for SAMAs can be viewed at the Protein Data Bank (PDB) website (see, www.rcsb.org/pdb/home/home.do) by entering the appropriate PDB Code. The structures in the Protein Data Bank are hereby incorporated by reference.

A biotinylation reagent can be reacted with a designated surface amino acid residue on a SAMA to bond, for example, to covalently bond, a biotin group or biotin derivative group to the surface residue. A "biotin-type group" refers to a biotin group or a biotin derivative group that can include biotin, iminobiotin, derivatives of biotin and/or iminobiotin, and/or chemical analogs of biotin and/or iminobiotin. Biotinylation reagents can vary, for example, in the length of the chemical linker and chemical structure of the chromophore (FIG. 23). For example, a thiol-reactive biotinylation reagent can consist of biotin or a biotin derivative group, such as iminobiotin (FIG. 23b1), attached via an amide linkage to an aliphatic hydrocarbon chain linked to a chromophore by a sulfur-sulfur bond. A range of thiol-reactive biotinylating reagents is commercially available. Additional variations are known or can be readily synthesized (e.g., FIGS. 23b2 through b4). Such reagents can vary, for example, in the chemical structure of the leaving group, nature of the chemical groups forming the linker, number of methylene carbons between amide and S—S bond, and chemical structure of the biotin derivative. For example, sulfosuccinimidyl 2-biotinamido-ethyl-1,3-dithiopropionate (EZ-Link sulfo-NHS-SS-biotin, Pierce, Rockford Ill.) of which the structure is shown in FIG. 23a1, can be used.

FIG. 2c schematically depicts the S—S linkage formed between biotin and a SAMA protein. A biotinylation reagent with a chemical linker sufficiently long enough to bridge between a SAMA, such as MJ0577, and streptavidin should be selected. If the chemical linker is too short, then the SAMA and streptavidin cannot make a binary attachment. On the other hand, if the chemical linker is too long, only monovalent attachment of the SAMA to the streptavidin may occur and/or unintended high order aggregates may be formed.

Figure 12:
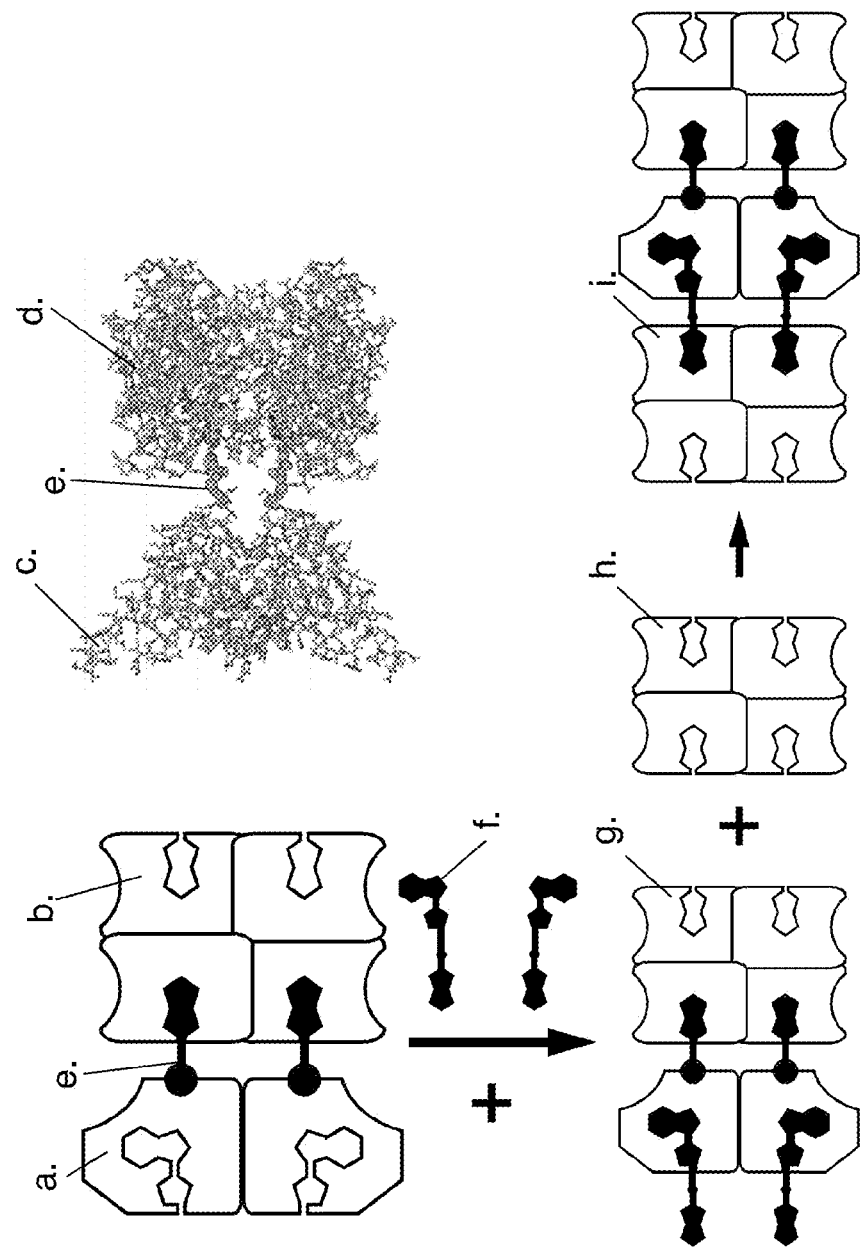
FIG. 12 presents a cartoon and a molecular model of a biotin-linked 1:1 SAMA:streptavidin complex based on the MJ0577 protein, and illustrates regeneration of binding capability to the complex.

A SAMA, such as MJ0577, biotinylated with a thiol-reactive biotinylating reagent at two selected surface residues, such as cysteine residues, can be linked to a streptavidin, in that each biotin group on the SAMA is bonded with a biotin binding site on streptavidin. Such a complex can be termed a biotin-residue linked 1:1 streptavidin complex. This complex is shown schematically and as a molecular model in FIG. 12. In the 1:1 streptavidin:SAMA complex, the streptavidin spans a distance of about 60 Angstroms along the common molecular two-fold axis and the SAMA spans a distance of about 50 Angstroms along the axis, so that the complex as a whole spans a distance of about 110 Angstroms along the axis. FIG. 12 presents a cartoon and a molecular model of a biotin-linked 1:1 SAMA:streptavidin complex based on the MJ0577 protein, and illustrates regeneration of binding capability of the complex. Part a shows a schematic view of the SAMA. Part b shows a schematic view of streptavidin. Part c shows a stick bond representation of the SAMA. Part d shows a stick bond representation of the streptavidin. Part e designates the covalently linked biotins linking the SAMA dimer and streptavidin tetramer in schematic and space filling representation. Part f shows the reaction of the 1:1 SAMA:streptavidin complex with a bifunctional linking reagent, producing the SAMA product g with regenerated ability to bind additional streptavidin tetramers h. Association of the streptavidin with the 1:1 SAMA:streptavidin produces a 1:2 SAMA:streptavidin complex i, that regenerates the biotin binding functionality lost on formation of the initial streptavidin:SAMA complex. Chemical structures for schematic representations of cross-link chemistry are given in FIG. 23.

In addition to the SAMA engineered protein, specialized surrogate ligands for biotin can be developed to act as temporary linking ligands for the biotin binding sites on streptavidin.

Controllable Bifunctional Crosslinking Agents

A thiol-reactive biotinylating reagent, such as the sulfosuccinimidyl 2-biotinamido-ethyl-1,3-dithiopropionate mentioned above, is a bifunctional crosslinking agent. The thiol-reactive group can covalently bond with the thiol group of a surface cysteine residue, such as on an engineered SAMA, and the biotin group can react with a biotin binding site, such as on streptavidin. However, once the covalent bond with the surface cysteine and the bond with the biotin binding site are formed, these are essentially irreversible. The biotin group of the bifunctional crosslinking agent will react with the complementary biotin binding site, and the thiol-reactive biotinylating reagent will react with the complementary cysteine residue whenever the complementary groups are present.

Controllable bifunctional crosslinking agents can facilitate the isolation and assembly of biomolecular components and building blocks of several biomolecular components into complex nanostructures. For example, controllable bifunctional crosslinking agents can be designed to fit into binding sites in order to provide biotin functionality or regenerate the biotin binding capacity of a SAMA-capped streptavidin. The controllable bifunctional crosslinking agent can be selected to undergo a chemical change when subjected to an external stimulus applied by a user. For example, the controllable bifunctional crosslinking agent can be selected to covalently bond to the ligand binding site of a SAMA when irradiated with light. As another example, the controllable bifunctional crosslinking agent can be selected to release from a streptavidin binding site when the pH drops below a predetermined value. The ability to use an external stimulus to trigger the formation or breaking of links between biomolecular components provides a way to control the assembly of complex nanostructures in defined stages.

A controllable bifunctional crosslinking reagent can include a first moiety and a second moiety. The first and/or the second moiety can be selected to bind only upon the application of an external stimulus or change in an environmental condition, such as irradiation with light, or to release binding upon the application of an external stimulus or change in an environmental condition, such as a decrease in ambient pH. Several examples are presented in FIG. 23.

FIG. 23 shows chemical structures and schematic illustrations of reagents (as used in other illustrations) used in streptavidin:SAMA nanostructure assembly. Parts a1 through a4 of FIG. 23 show a variety of biotinylation reagents that reacts with free sulfhydryl groups. Part a5 shows a biotin derivative functionalized by incorporation of the linker $H_2N((CH_2)_2)SH$ to provide a free SH group for subsequent reaction. Linker length can be varied by extension of the thiol alkyl amine moiety (e.g. $H_2N((CH_2)_2)SH$ moiety can be lengthened to $H_2N((CH_2)_n)SH$ as required). Parts b1 through b4 of FIG. 23 show a variety of biotinylation reagents that reacts with free sulfhydryl groups. Part b5 shows an iminobiotin derivative functionalized by incorporation of the linker $H_2N((CH_2)_2)SH$ to provide a free SH group for subsequent reaction. Linker length can be varied by extension of the thiol alkyl amine moiety (e.g. $H_2N((CH_2)_2)SH$ moiety can be lengthened to $H_2N((CH_2)_n)SH$ as required). Part c1 shows a bifunctional biotin-ATP photo crosslinking reagent incorporating the photo-crosslinking group 2-azido adenosine. Part c2 shows an alternate bifunctional biotin-ATP photo crosslinking reagent incorporating the photo-crosslinking group 8-azido adenosine. Part d1 shows a 2-azido adenosine photo-crosslinking reagent functionalized to form S—S bonds with free sulfhydryl groups. Part d2 shows an 8-azido adenosine photo-crosslinking reagent functionalized to form S—S bonds with free sulfhydryl groups. Part e1 shows a 2-azido adenosine photo-crosslinking reagent functionalized by incorporation of the linker $H_2N((CH_2)_2)SH$ to provide a free SH group for subsequent reaction. Linker length can be varied by extension of the thiol alkyl amine moiety (e.g. $H_2N((CH_2)_2)SH$ moiety can be lengthened to $H_2N((CH_2)_2)SH$ as required). Part e2 shows an 8-azido adenosine photo-crosslinking reagent functionalized by incorporation of the linker $H_2N((CH_2)_2)SH$ to provide a free SH group for subsequent reaction. Linker length can be varied by extension of the thiol alkyl amine moiety (e.g. $H_2N((CH_2)_2)SH$ moiety can be lengthened to $H_2N((CH_2)_n)SH$ as required). Part f1 shows a bifunctional di-biotin crosslinker formed by reaction of reagents a1 and a5. Part f2 shows a bifunctional di-biotin crosslinker with terminal groups interconnected by a polyethylene oxide linker. Part g shows a bifunctional biotin-photo-ATP crosslinker formed through reaction of reagents a5 and d1. An alternative structure can be formed by reaction of reagents a5 and d2. Part h shows a bifunctional photo-ATP crosslinker, formed by reaction of reagents d1 and e1, d1 and e2, or d2 and e2. Part i shows HABA, a dye that absorbs light when bound to streptavidin and which is useful in spectrophotometric monitoring of the assembly of biotin-linked streptavidin:SAMA complexes. Several HABA derivatives are also useful in this application. Part j shows an ATP derivative labeled with a fluorescent dye, which is useful in spectrophotometric monitoring of the assembly of ATP-linked streptavidin:SAMA complexes.

Iminobiotin Crosslinking Agent

For example, the first and/or the second moiety can be an iminobiotin group. At neutral pH values, iminobiotin strongly binds to a streptavidin binding site, with an iminobiotin dissociation constant of about $10^{-11}$ M (Hoffmann et al. 1980). Although this value is 3 orders of magnitude greater than the biotin-streptavidin dissociation constant, the binding of iminobiotin to streptavidin is nearly irreversible in the usual context of biochemical interactions. However, at pH values of less than or equal to about 4, the imino group on iminobiotin becomes charged, so that it is displaced from the streptavidin binding site. Thus, a structure can be temporarily formed using an iminobiotin-functionalized crosslinking reagent. Such a temporary structure can, for example, guide the formation of a permanent structure using a biotin-functionalized crosslinking reagent. Then, by lowering the pH below 4, the iminobiotin bonds can release, and components of the temporary structure can be washed away. Thus, a bifunctional crosslinking reagent with an iminobiotin group as the first and/or second moiety can be used to form a temporary scaffold, which assists in the construction of a permanent nanostructure.

The controllable and reversible nature of a link formed with an iminobiotin-functionalized crosslinking reagent can also be useful in allowing rearrangement of biomolecular components after initial binding in an "annealing" process. By analogy, annealing is known to be an important step in forming high quality crystals with a low density of defects. In the context of complex and extensive nanoassemblies, such "annealing" can be useful in "healing" defects arising during construction of the nanoassembly.

An example of a controllable bifunctional crosslinking reagent that can provide such reversible binding functionality is sulfosuccinimidyl 2-iminobiotinamido-ethyl-1,3-dithiopropionate, a reagent where the usual biotin group (FIG. 23*a*1 through *a*4 and FIG. 2*b*) is replaced by a 2-iminobiotin group (FIG. 23*b*1 through *b*4 and FIG. 2*d*). This chemical structure and others shown in FIG. 23 are either commercially available (Pierce, Rockford Ill.) or are readily synthesized using conventional organic chemistry methods by one skilled in the art. Thus, by analogy to the biotinylated SAMA described above, an iminobiotinylated SAMA can be formed by reacting the sulfosuccinimidyl leaving group to bind the iminobiotinylation agent with, for example, the thiol group of a surface cysteine residue, such as on an engineered SAMA. The iminobiotin group, now covalently attached to the SAMA, can then bind with the binding site on streptavidin. The result is an iminobiotin-residue linked streptavidin: SAMA complex. FIG. 7*h* shows a schematic of an iminobiotinylated SAMA.

Photoactivated Crosslinking Agents

Alternatively, the first and/or the second moiety of a controllable bifunctional crosslinking reagent can be selected to have binding with an intended site that is activated by an external stimulus or change in an environmental condition. For example, the first and/or the second moiety can be a photoactivated group, such as an azidoadenosine triphosphate group. When irradiated with light, the photoactivated group can form a covalent bond with a corresponding binding site. For example, when irradiated with light, an azidoadenosine triphosphate group can react to form a covalent bond with an ATP binding site, such as found on MJ0577.

Such binding that is activated by an external stimulus or environmental condition can be exploited, for example, as follows. In a first stage, a set of reactions can be carried out in darkness. The photoactive groups of controllable bifunctional crosslinking agents do not form bonds in the dark. After a sufficient time has passed for a first structure to form, reagents present may or may not be washed away, and additional reagents may or may not be introduced. Then, the reaction system can be irradiated with light. With the first structure in place, the photoactive groups can react with binding sites to form bonds and form a predetermined second structure. In this way, construction of a nanostructure can be carried out in defined, discrete stages controlled by exposure to light.

For example, adenosine triphosphate (ATP) crosslinking reagents can be used as controllable bifunctional crosslinking agents (FIGS. 23*c*1 and *c*2). ATP crosslinking reagents can use an alkyl diamine to couple the biotin valerate (forming an amide bond) and the gamma ATP phosphate group (forming an N-linked phosphamide). An example of a controllable bifunctional crosslinking agent whose binding is activated by exposure to light is 2-azidoadenosine 5'-triphosphate[g]-5 (biotinamido)pentylamine (FIG. 23*c*1) (Affinity Labeling Technologies, Lexington Ky.). The biotin group of this agent can bind with the streptavidin biotin binding site, and the 2-azidoadenosine 5'-triphosphate group can bind with the MJ0577 binding site when activated by light. Another example (FIG. 23*c*2) is 8-azidoadenosine 5'-triphosphate[g]- 5(biotinamido)pentylamine (Affinity Labeling Technologies, Lexington Ky.). These two controllable bifunctional crosslinking agents differ with respect to the position of the photo-active azido group on the adenine ring. One or the other of these reagents may be more suitable, for example, depending on the steric and electrostatic interactions with the selected binding site. For example, one of these reagents may form a bond more readily with the ATP binding site of MJ0577 when irradiated with light than the other reagent. To select an appropriate reagent, an energetic analysis of the binding can be performed or experiments can be conducted.

The biotin group of the bifunctional crosslinking agent can bind with the streptavidin biotin binding site, and the azidoadenosine triphosphate group can bind with the MJ0577 binding site when activated by light. Thus, a complex can be formed in which streptavidin is linked to a SAMA through a bifunctional crosslinking agent of which one end is a biotin bound to a binding site on streptavidin, and of which another end is a ligand bound to a binding site on the SAMA, for example, an adenosine triphosphate group bound to the ATP binding site on MJ0577.

S—S Linked Crosslinking Reagents

In addition to the crosslinking reagents outlined above, FIG. 23 illustrates several reagents that can be reacted to form bifunctional linkers that are linked through S—S bonds. Generally, the S—S linked bifunctional reagents are assembled through reaction of a reagent with a functional group bearing a free sulfhydryl group (e.g. FIG. 23 *a*5,*e*1,*e*2) and second reagent bearing a functional group and a thiol reactive leaving group (FIG. 23 *a*1 through *a*4, *b*1 through *b*4, *d*1 and *d*2). These linkers can be generated using commercially available reagents (Affinity Labeling Technologies, Lexington Ky.; Pierce, Rockford Ill.) or compounds readily synthesized by one with skill in the art. Bifunctional crosslinking agents linked through S—S bonds provide additional flexibility in the assembly of nanostructures, both by providing a greater variety of crosslinking functionality, such as FIGS. 23 *f*1,*f*2*g*, and *h*, and also as a means of changing the direction of assembly or polarity of a long assembly of SAMA:streptavidin complexes during the assembly process.

Numerous products can be made from reaction of reagents FIG. 23*a*1 through *a*4, *b*1 through 4, *d*1 and *d*2 with the reactants of FIG. 23*a*5,*e*1, and *e*2. These include, for example, the product of the reaction of reagents of FIG. 23*b*1 and *e*1, that can be used to assemble a controllable, S—S linked, bifunctional crosslinking agent having an iminobiotin group on one end and an azidoadenosine 5'-triphosphate group on the other. Each subunit of the MJ0577 SAMA embodiment has a binding site that precisely fits the adenine ring of ATP and ATP analogs and binds them with high specificity and reasonable (dissociation coefficient estimated to be approximately $10^{-5}$ M) affinity. The relatively weak binding of the ATP group and its azido-analogs are useful as this allows some degree of binding reversibility and "annealing" when assembling complex structures. However, irradiation of the azido-ATP reagent produces a covalent bond between the reagent and the protein, rendering the binding irreversible. Consequently, such a controllable bifunctional crosslinking agent can link two biomolecular components together upon exposure to light, and then release the two biomolecular components from each other when the pH is decreased below 4. Such an agent can be used, for example, to construct a complex, but still temporary scaffold that guides the construction of a permanent nanostructure.

Additional bifunctional crosslinking agents can be developed that enable functionalization of assemblies built using strut-node architecture. These agents incorporate a specific protein-reacting group (for example, a group able to react with cysteine side chain thiol group or a polypeptide chain terminal amine group) on one end of the linker and a protein-specific reactive agent on the other end. The aforementioned azido-ATP analogs represent one example, but many additional examples can be envisioned where other biochemical cofactors such as flavins, vitamins, and other biochemical cofactors that bind specifically to proteins can be chemically modified so that they can be photo-crosslinked to protein molecules functioning as either struts or nodes in assembled nanostructures. Since di- or multimeric strut or node proteins can be modified forms of enzymes that carry out specific catalytic processes on biochemical substrates, these enzymes will have generally active sites that bind substrates and catalyze reactions with great specificity. For many classes of enzymes, covalent inhibitors or suicide substrates are known that irreversibly inhibit the enzyme activity by forming a highly specific covalent bond with the catalytic amino acid side chain groups in the enzyme's active site. These agents are generally termed suicide substrates or covalent inhibitors of enzyme activity. These agents, when connected to one end of a bifunctional crosslinking reagent as described above, can provide a means of specific immobilization of a protein to an underlying strut-node architecture. For example, immunoglobulins, lectins, or other specific binding molecules could be linked to nanostructures constructed of struts and nodes using this means, as outlined in FIG. 3f. Such functionalization can be used in nanostructures intended to serve in, for example, filters, diagnostics, or biological sensing applications.

Other controllable bifunctional crosslinking reagents that can be activated to bind and/or be induced to release from binding can be used. The binding and/or release from binding can be triggered by one or more external stimuli or changes in environmental conditions, including, for example, temperature, visible light, ultraviolet light, change in pH, change in concentration of ionic species other than $H^+$ or $OH^-$, temperature, binding of specific molecules, and other conditions. In addition to serving in the construction of complex nanostructure by allowing for controlled staging or the use of temporary scaffolds, the changes, for example, binding or release from binding, exhibited by controllable bifunctional crosslinking reagents can be themselves used for sensing or transduction applications.

SAMAs Engineered for Additional Binding Properties

In addition to the use of chemical crosslinking agents as a way to couple proteins to an underlying strut-node structure, it is possible to engineer either nodes or SAMAs where the nucleotide sequence coding for the SAMA domain is modified by a sequence insertion or extended at either the amino or carboxy with nucleotide sequences coding for additional binding function. When these fused genes are expressed, the result will be a single continuous polypeptide chain incorporating the encoded polypeptide chains. The attached sequences can have utility in both protein isolation and in creating protein assemblies. Examples of such binding sequences include immunoglobulin domains, polyhistidine sequences, polypeptide sequences that bind to streptavidin, for example, Streptag™ (Skerra & Schmidt, 2000), for example, the polypeptide sequences WSHPQFEK (SEQ ID NO: 6) or AWRHPQFGG (SEQ ID NO: 7), *Staphylococcus* Protein-A, *Staphylococcus* Protein-G, and others together with sequences designed to be linkers with greater or lesser conformational flexibility (FIG. 10). FIGS. 7i and 7j show a cartoon of SAMAs where each chain of the SAMA dimer has been extended at its amino terminus through a polypeptide linker with a specific binding sequence.

FIG. 7 presents steps in the formation and assembly of several functionalized SAMA proteins. Part a shows a schematic of a representative SAMA template protein, in this case a symmetric dimer with two ligand binding sites. Part b shows the introduction of a reactive surface amino acid residue into each monomer of the dimer so that the sites are separated by approximately 10.0 to 35.0 Angstroms and lie approximately in the same plane as two ligand binding sites on the dimer. The modified SAMA can be reacted with a biotinylating reagent c (e.g., FIG. 23a1 through a4) capable of reacting with the surface reactive amino acids introduced through site-specific modification of the native protein, producing the di-biotin-substituted SAMA d. The SAMA of part d may be further reacted with a bifunctional crosslinking reagent. In the example shown, a bifunctional crosslinker e incorporating biotin on one end and a photo-reactive analog of the SAMA ligand on the other binds to the protein and then becomes covalently attached through photo-crosslinking (e.g., FIG. 23c1,c2). This produces the modified SAMA f with 4 covalently bound biotin groups. The SAMA of part b may also be reacted with other reagents such as a reagent g (FIG. 23b through b4) that modifies the protein with 2-iminobiotin groups, allowing reversible, pH-dependent binding, e.g., between the MJ0577 SAMA embodiment and streptavidin. Parts i and j schematically show engineered forms of SAMA where the SAMA gene has been extended at either end with a gene coding for a linker sequence and a polypeptide sequence corresponding to a binding domain. Examples of such binding sequences include immunoglobulin domains, polyhistidine sequences, polypeptide sequences that bind to streptavidin (Streptag™), *Staphylococcus* Protein A, and *Staphylococcus* Protein G. Depending on the length of the linkers either or both of the binding functions shown in part f can be preserved. Chemical structures for schematic representations of cross-link chemistry are given in FIG. 23.

Agents may serve to provide information to the user on the state of a nanoassembly. Such agents could, for example, serve to indicate the arrangement of a nanoassembly under construction and thus guide the subsequent steps a user takes during construction. As another example, such agents could serve to indicate the arrangement of a nanoassembly whose structure is sensitive to an environmental condition and thus provide a readout for a nanoassembly intended as a sensor. For example, 4'-hydroxyazobenzene-2-carboxylic acid (HABA) and derivatives thereof can serve as biotin displacement detection dyes. These dyes absorb light and/or fluoresce when bound to the biotin binding site in streptavidin. Absorption and/or fluorescence is diminished or abolished when HABA is displaced by biotin.

Biotin-Nucleotide Linked Streptavidin:SAMA Complex

A biotin-nucleotide bifunctional crosslinking reagent of which a first moiety is a biotin-type group, such as a biotin or a biotin derivative, and a second moiety is a nucleotide, nucleotide derivative, ligand, enzyme inhibitor, enzyme substrate, enzyme cofactor, derivatives of these, and/or chemical analogs of these that binds to, for example, that binds specifically to, a SAMA protein can be used to link a SAMA to streptavidin. The biotin or biotin derivative of the bifunctional crosslinking agent can bind with streptavidin and the nucleotide or nucleotide derivative can bind with a binding site on the SAMA. The resulting complex can be termed a biotin-nucleotide linked 1:1 streptavidin:SAMA complex. The SAMA can be selected or engineered, so that it is sterically complementary to streptavidin at the streptavidin:SAMA interface. Furthermore, the SAMA can be so selected or engineered, so that ligand binding pockets for a nucleotide or a nucleotide derivative on the SAMA have a favorable position and orientation with respect to the biotin binding sites on streptavidin. A bifunctional crosslinking agent can be selected, for example, to have the appropriate length, so that its biotin group binds with the binding site on streptavidin and its nucleotide or nucleotide derivative group binds with the binding site on the SAMA. For example, the bifunctional crosslinking agent can include a photo-crosslinkable adenosine triphosphate derivative. For example, 2-azidoadenosine 5'-triphosphate[g]-5(biotinamido)pentylamine or 8-azidoadenosine 5'-triphosphate[g]-5(biotinamido)pentylamine can be used. In an embodiment, the bifunctional crosslinking agent can include a moiety having a binding property that varies with pH, such as iminobiotin.

For example, MJ0577 has two adenosine triphosphate (ATP) binding sites. When ATP molecules are bound to these sites, the ATP terminal phosphate groups are spaced approximately 24.5 Angstroms apart. This is similar to the spacing between the termini of two biotin molecules bound to the closest sites on streptavidin, about 20.5 Angstroms. Furthermore, as shown in FIG. 9, the biotin "tails" are oriented in an approximately horizontal direction in the reference frame of the picture as are the phosphate terminal chains of the ATPs. These similarities can be exploited to link MJ0577 and streptavidin together by a bifunctional crosslinking agent bound at one end to the ATP binding site on MJ0577 and bound at the other end to the biotin-binding site on streptavidin. As discussed above, when linking two biomolecular components with a bifunctional crosslinking agent, the bifunctional crosslinking agent can be selected to have a length sufficiently long to bridge the space between the areas of attachment on each biomolecular component, but not so long that aggregation results or, if a link through multiple bifunctional crosslinking agents is intended, only a link through a single bifunctional crosslinking agent results.

Figure 13:
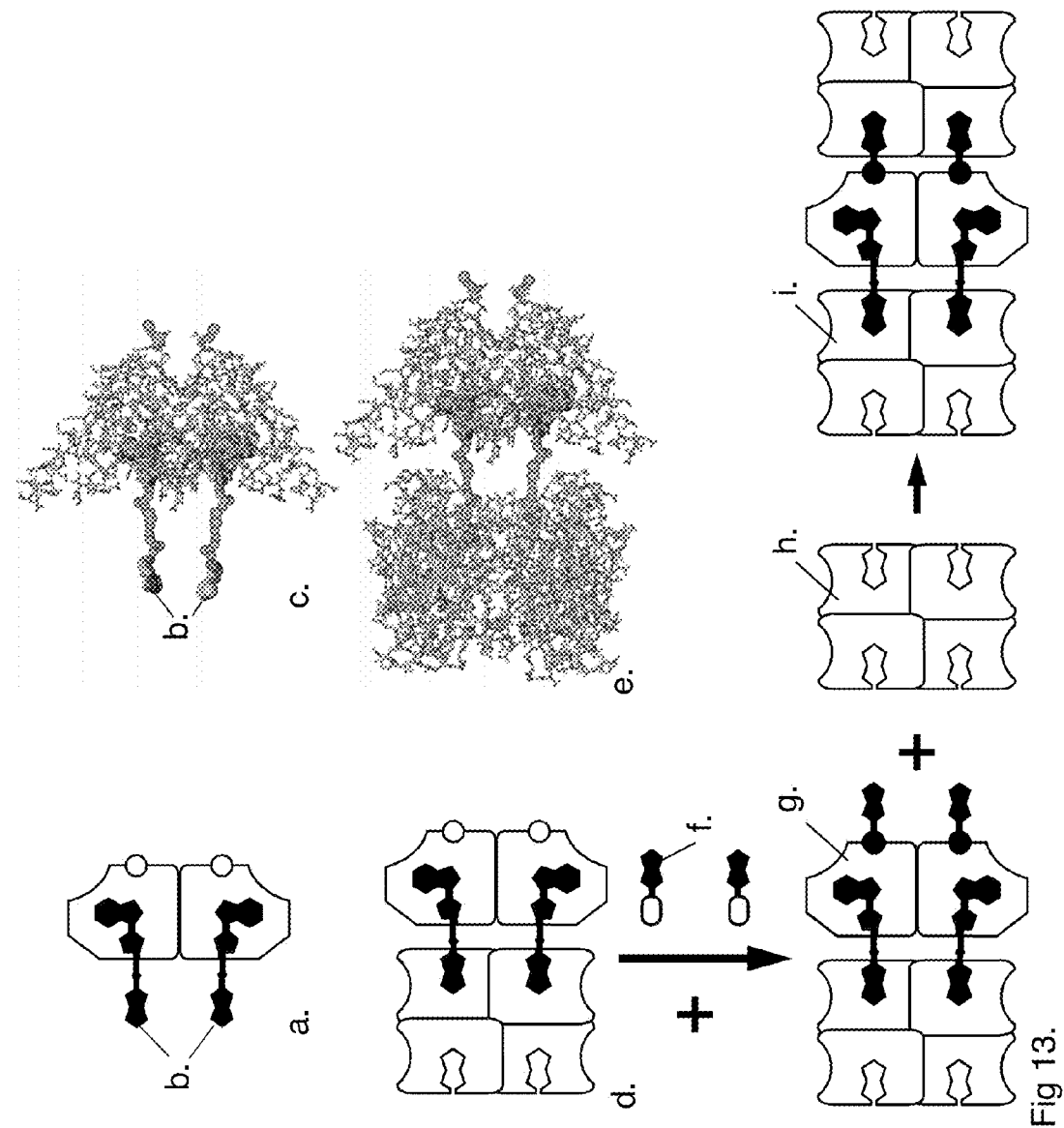
FIG. 13 presents a cartoon and a molecular model of a biotin-photo-ATP crosslinked 1:1 SAMA:streptavidin complex based on the MJ0577 protein, and illustrates regeneration of binding capability to the complex.

Thus, in the case of linking MJ0577 at the ATP binding site with streptavidin at the biotin binding site, the bifunctional crosslinking agent can be selected to accommodate SAMA:streptavidin steric interactions and the approximately 4 Angstroms spacing difference between biotin binding sites on streptavidin and ATP binding sites on an MJ0577 SAMA. Both 2-azidoadenosine 5'-triphosphate[g]-5(biotinamido) pentylamine or 8-azidoadenosine 5'-triphosphate[g]-5(biotinamido)pentylamine have an appropriate length to link MJ0577 at the ATP binding site with streptavidin at the biotin binding site and form a tight connection between MJ0577 and streptavidin to obtain a rigid complex after the photo ATP reagent is irradiated and forms a covalent bond with MJ0577. The two crosslinking agents differ with respect to the position of the photo-active azido group on the adenine ring. One or the other of these agents may be more suitable, for example, may form a more favorable bonding arrangement with residues in the ATP binding site of MJ0577 when irradiated with light than the other agent. To select an appropriate agent, an energetic analysis of the binding can be performed or experiments can be conducted. Purification steps can be used to obtain functionalized, ATP-free SAMA. FIG. 13 illustrates the biotin-photo-ATP crosslinker bound to the MJ0577 SAMA embodiment together with the 1:1 complex formed with streptavidin with a cartoon and a molecular model and illustrates regeneration of binding capability to the complex. Part a shows a schematic of the SAMA with two bound biotin-photo-ATP crosslinks b. Part c shows a stick bond representation of the SAMA structure with the crosslink shown in space-filling representation. Part d shows a schematic of the 1:1 streptavidin:SAMA biotin-photo-ATP-linked complex. Part e shows a stick bond representation of the complex with the crosslink shown in space-filling representation. Part f shows the reaction of the 1:1 SAMA:streptavidin complex with a biotin linking reagent, producing the SAMA product g with regenerated ability to bind additional streptavidin tetramers h. Association of the streptavidin with the 1:1 SAMA:streptavidin produces a 1:2 SAMA:streptavidin complex i, that regenerates the biotin binding functionality lost on formation of the initial streptavidin:SAMA complex. Chemical structures for schematic representations of cross-link chemistry are given in FIG. 23.

Regenerating Biotin Binding Capability of SAMA Capped Streptavidin

A SAMA can prevent the uncontrolled polymerization between streptavidin and biotin functionalized proteins by "capping" the biotin-binding sites on streptavidin. However, to serve usefully as a protecting group, a SAMA should allow for regeneration of the biotin-binding capability of a capped SAMA.

A SAMA can be functionalized both by reaction of surface reactive amino acid residues with a biotinylating reagent, providing two biotin binding groups at one side of the SAMA, and by reaction with a bifunctional crosslinker that binds to specific binding sites on the SAMA, providing two additional biotin groups at the opposite side of the SAMA. For example, a thiol-reactive biotinylation reagent, having a biotin group at one end and a thiol-reactive group at the other end, can be covalently bonded by the thiol-reactive group to a designated surface amino acid residue on the SAMA. A bifunctional crosslinking reagent having a biotin group at one end and a nucleotide, nucleotide derivative, or ligand at the other end can be bound by the nucleotide, nucleotide derivative, or ligand binding site on the SAMA. All four of the biotin groups of the fully biotinylated SAMA can be coplanar. This can be useful in creating extended structures of defined geometry.

For example, a thiol-reactive biotinylation reagent can be covalently bonded to a surface cysteine residue on an engineered MJ0577 protein that serves as a SAMA, and a controllable bifunctional crosslinking reagent having a biotin group on one end and a photoactivated group, such as an azidoadenosine triphosphate group, on the other end can be bound by the photoactivated group to the binding site on MJ0577. Steps that can be used to form such a SAMA bearing two pairs of biotin groups are illustrated in FIGS. 7a through 7f.

Such a fully biotinylated SAMA is illustrated in FIG. 14, both in cartoon form in part a and as a molecular model of the SAMA embodiment MJ0577 in part b. The fully biotinylated SAMA shown in FIG. 14 incorporates four biotin groups introduced through reaction with crosslinking reagents. The SAMA is reacted with a biotin-photo-ATP crosslinking agent c at two ligand binding sites and biotinylated on two specific surface sites d. Because the chemistry involved in the introduction of the two pairs of biotins on the SAMA are different, the scheme can be used for the controlled sequential assembly of biotin-streptavidin linked structures. Chemical structures for schematic representations of cross-link chemistry are given in FIG. 23.

A streptavidin can be "capped" by a SAMA, where two biotin binding sites on a side of the streptavidin tetramer are occupied by biotin groups of a biotinylation reagent covalently bonded to a surface residue on the SAMA. The biotinylation reagent can be covalently bonded to suitable surface amino acids on the SAMA. For example, cysteine surface residues on an engineered SAMA can be reacted to covalently bind with a thiol-reactive biotinylating reagent. For example, sulfosuccinimidyl 2-biotinamido-ethyl-1,3-dithiopropionate can be the thiol-reactive biotinylation reagent. Such a configuration is illustrated in FIG. 12. The streptavidin and the SAMA can have steric complementarity at the interface where they meet. The surface residues to which the biotinylation reagent is bound and the biotin binding sites on streptavidin can be located such that there is a unique pairwise interaction between the biotins presented on the functionalized SAMA surface and two of the most closely spaced biotin binding sites on streptavidin.

The ability of the "capped" streptavidin to form additional biotin-linked interactions on the same side of the complex occupied by the SAMA can be regenerated as follows (FIG. 12 *f,g,h,i*). Exposed binding sites on the face of the SAMA opposite the SAMA-streptavidin interface can be reacted with a bifunctional crosslinking agent of which one end is a ligand (such as an ATP group) that binds to the exposed binding site on the SAMA and the other end is a biotin or biotin derivative group. The exposed biotin groups of the bifunctional crosslinking agent bound to the SAMA can then react with two biotin-binding sites on one side of an additional streptavidin tetramer. The two biotin-binding sites on the other side of the additional streptavidin tetramer are then available for receiving biotin groups, so that the biotin-streptavidin binding capability of the streptavidin has been regenerated.

A streptavidin can also be "capped" by a SAMA, through an interaction where two biotin binding sites on a side of the streptavidin are occupied by biotin groups of a bifunctional crosslinking reagent, the other end of which is a nucleotide (such as ATP), nucleotide derivative, or ligand bound to a binding site on the SAMA. For example, 2-azidoadenosine 5'-triphosphate[g]-5(biotinamido)pentylamine or 8-azidoadenosine 5'-triphosphate[g]-5(biotinamido)pentylamine can be the bifunctional crosslinking reagent. Such a configuration is illustrated in FIGS. 13*d* and 13*e*. The streptavidin and the SAMA can have steric complementarity at the interface where they meet. The SAMA ligand binding site (shown as an ATP binding site) and the biotin binding sites on streptavidin can be located such that there is a unique pairwise interaction between the biotins presented on the functionalized SAMA surface and two of the most closely spaced biotin binding sites on streptavidin.

The ability of the "capped" streptavidin to form additional biotin-linked interactions on the same side of the complex occupied by the SAMA can be regenerated as follows (FIG. 13 *f,g,h,i*). A biotinylation reagent can be covalently bonded to suitable surface amino acids on the face of the SAMA opposite the SAMA-streptavidin interface. The exposed biotin groups linked through the biotinylation reagent to the SAMA can then react with two biotin-binding sites on one side of an additional streptavidin tetramer. The two biotin-binding sites on the other side of the additional streptavidin tetramer are then available for receiving biotin groups, so that the biotin-binding capability of the streptavidin has been regenerated.

The molecular model of FIG. 9, in which MJ0577 and streptavidin are shown placed along a common diad axis, shows that an orientation provides good complementarity of the facing MJ0577 and streptavidin surfaces, the ATP groups bound to MJ0577 lie in the same plane as the biotin valerate groups bound to streptavidin, and the phosphate terminal chains of the ATP groups are approximately parallel to the biotin tails of the groups bound to streptavidin. This demonstrates, for example, that a complex formed of a streptavidin tetramer and an MJ0577 SAMA linked by biotin-nucleotide bifunctional crosslinking agents can be a tight structure, useful for assembling larger structures.

A SAMA can have an asymmetrical structure or a symmetrical structure. For example, the MJ0577 protein dimer can be viewed as a template for an asymmetrical SAMA. An asymmetric non-biotinylated SAMA is shown in FIG. 8, and an asymmetric biotinylated SAMA is shown in FIG. 11. Such an asymmetrical SAMA can have chemical groups with different binding properties at opposite ends. For example, the asymmetric SAMA of FIG. 8 has ligand binding sites, e.g., nucleotide binding sites (such as adenosine triphosphate (ATP) binding sites), on its left side (FIG. 8*b*) and has surface reactive groups, e.g., cysteine residues, on its right side (FIG. 8*d*). For example, the asymmetric SAMA of FIG. 11 has ligand binding sites, e.g., nucleotide binding sites (such as adenosine triphosphate (ATP) binding sites), on its left side (FIG. 11*d*) and has biotin or biotin-type groups, on its right side (FIG. 11*c*). An asymmetrical SAMA can be viewed as having a chemical functional "polarity".

Alternatively, a SAMA can have a symmetrical structure. A SAMA with a symmetrical structure can be formed of a single protein subunit or of a single protein multimer. Alternatively, a SAMA with a symmetrical structure can be formed of subcomponents; such subcomponents can include symmetric or asymmetric SAMAs. For example, two asymmetric SAMAs, such as shown in FIG. 11, can be linked to each other at ends having the same type of chemical functionality, e.g., the same type of ligand binding sites (FIG. 11*d*) can be linked to each other by a bifunctional crosslinking reagent, such as the di-photo ATP bifunctional reagent of FIG. 23*h*. The resultant symmetric SAMA can have two biotin or biotin-type groups on each of two opposite ends. As another example, the two asymmetric SAMAs shown in FIG. 8 can be linked to each other by a bifunctional reagent of which either end can bind with, e.g., covalently bind to, the designated surface amino acid residues (FIG. 8*d*). The resultant symmetric SAMA can have two ligand binding sites, e.g., nucleotide binding sites (such as ATP binding sites) on each of two opposite ends.

Nanostructure Building Blocks

Two or more biomolecular components can be linked together to form a nanostructure building block. For example, a biotin-residue linked 1:1 streptavidin:SAMA complex in which two biotins are covalently bonded to surface residues of the SAMA and are bound to binding sites on the streptavidin, such as illustrated by the cartoon of FIG. 6*c*, can serve as a nanostructure building block.

Figure 15:
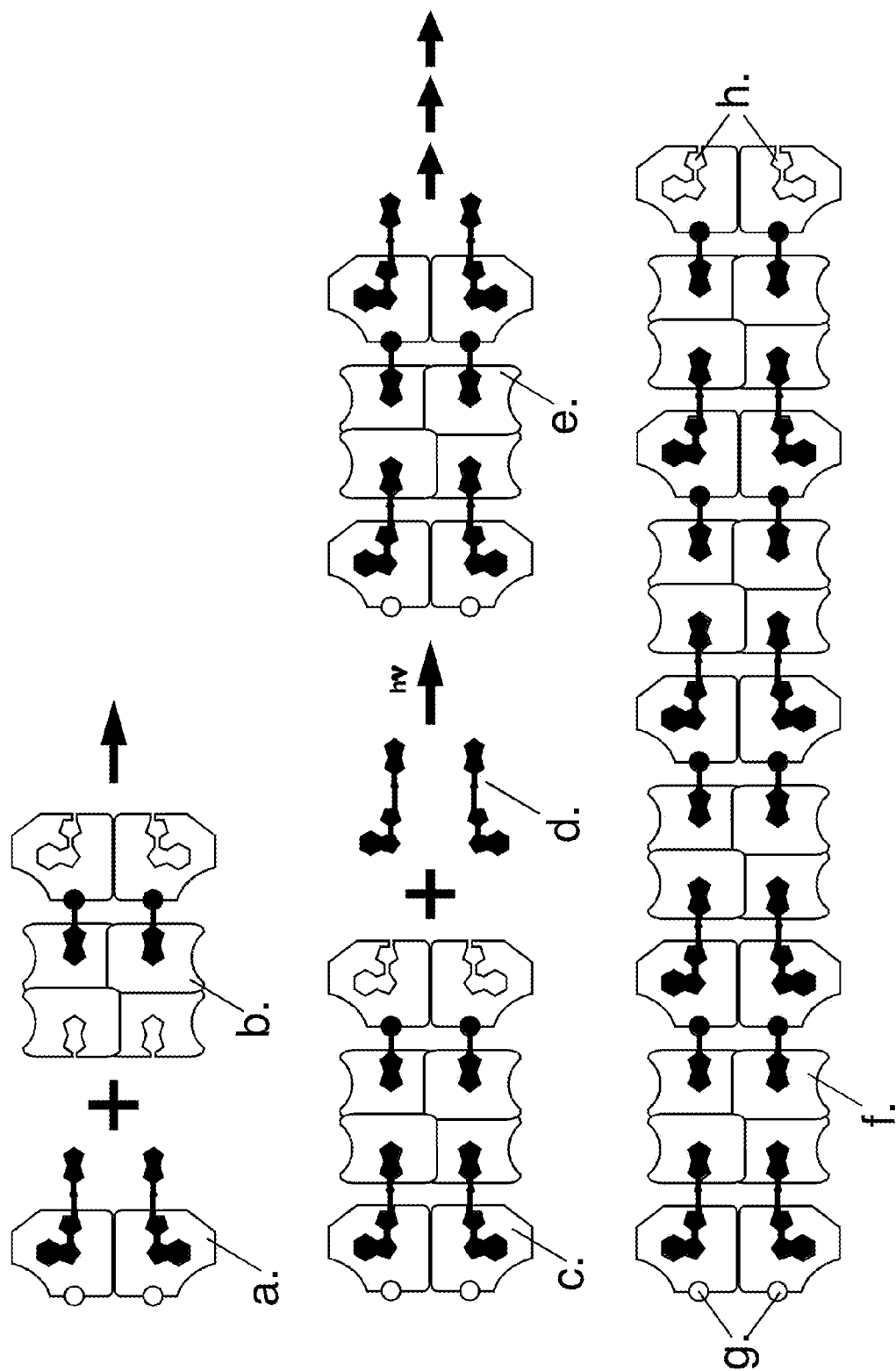
FIG. 15 presents a cartoon outlining steps in assembling a 3:4 streptavidin:SAMA strut in solution.

Such a biotin-residue linked 1:1 streptavidin:SAMA building block can be used to form, for example, longer struts of predetermined length having alternating streptavidin and SAMA biomolecular components, as discussed below. For example, a 4:5 streptavidin:SAMA strut, as illustrated in FIG. 15, can be formed.

Such a streptavidin:SAMA strut can have a defined "polarity". That is, one end of the strut can include a streptavidin with a biotin binding site. The other end of the strut can include a SAMA, either not biotinylated (and thus not "primed" to bind to another streptavidin) or biotinylated (and thus "primed" to bind to another streptavidin). For example, a system can be developed in which the SAMA, after biotinylation, can only bind to another streptavidin, and a streptavidin can only bind to a biotinylated SAMA.

In addition to the biotin-residue linked 1:1 streptavidin:SAMA shown in the cartoon FIG. 6*c*, the biotin-nucleotide linked 1:1 streptavidin:SAMA illustrated in the cartoon FIG. 13*d* can also be considered as a nanostructure building block.

Figure 16:
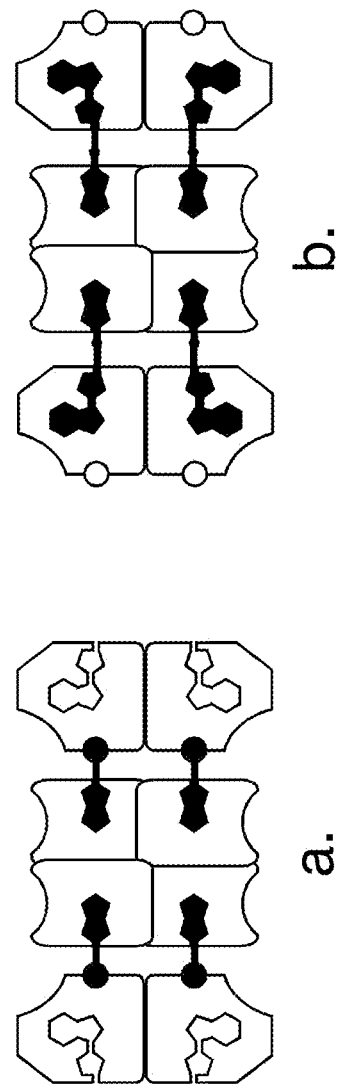
FIG. 16 presents cartoons of various streptavidin:SAMA complexes.

In the biotin-nucleotide linked 1:1 streptavidin:SAMA of FIG. 13d, a streptavidin is capped at one end by a SAMA in which the biotins are part of a bifunctional crosslinking reagent bound through an ATP group to the binding site on the SAMA. FIG. 16 presents cartoons of some 1:2 streptavidin: SAMA building blocks. FIG. 16a illustrates a streptavidin capped at both ends by biotin-residue linked SAMAs in which the biotins are covalently bound to the SAMA designated surface amino acid residues, for example, cysteine groups. This symmetric complex can be termed a biotin-residue-linked 1:2 streptavidin:SAMA complex. The biotin-residue-linked 1:2 streptavidin:SAMA complex FIG. 16a can be formed from reaction of a biotinylated SAMA FIG. 6a with a 1:1 di-biotin linked streptavidin: SAMA complex FIG. 6c. FIG. 16b illustrates a streptavidin capped at both ends by SAMAs in which the biotins are part of a bifunctional crosslinking reagent bound through a group, for example, a nucleotide or nucleotide derivative, such as an ATP group, to the binding site on a SAMA. This symmetric complex can be termed a biotin-nucleotide-linked 1:2 streptavidin:SAMA complex, and can be, for example, a streptavidin:SAMA 1:2 biotin-photo-ATP linked complex. The biotin-nucleotide-linked 1:2 streptavidin:SAMA complex FIG. 16b can be formed from reaction of a SAMA biotinylated through interactions at nucleotide binding sites FIG. 13a with a biotin-nucleotide linked 1:1 streptavidin:SAMA FIG. 13d. Chemical structures for schematic representations of cross-link chemistry are given in FIG. 23. Longer struts can themselves serve as building blocks.

EXAMPLE

Antibody Biosensor

Figure 17:
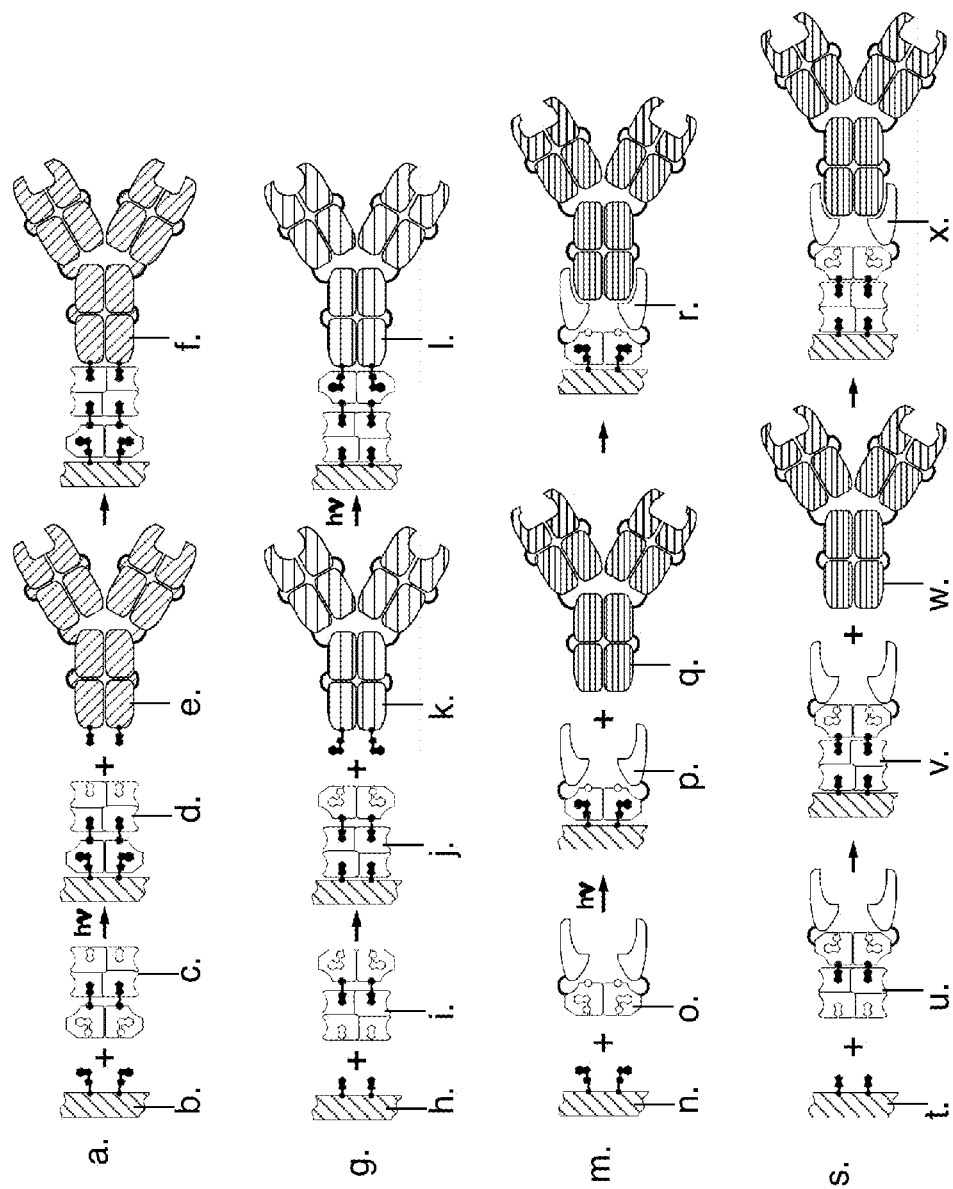
FIG. 17 presents methods of assembly of various biosensors incorporating antibodies.

The biomolecular components, such as the SAMA, and building blocks, such as the biotin-residue linked 1:1 streptavidin:SAMA complex can be used to construct engineered protein assemblies. For example, FIG. 17 presents synthetic steps for generating an antibody-based biosensor. FIG. 17a shows the irradiation induced reaction of a biotin-residue linked 1:1 streptavidin:SAMA complex FIG. 17c with a substrate FIG. 17b that has been functionalized by reaction with a reagent that can bind to a binding site on a SAMA and form a photo-crosslink on irradiation (for example, an ATP photo label, such as the azo-ATP derivatives of FIGS. 23e1 and e2). The resultant streptavidin:SAMA complex is bound to the substrate as an immobilized streptavidin:SAMA complex FIG. 17d. An immunoglobulin or antibody FIG. 17e, labeled, for example, covalently functionalized, on its Fc region, e.g., the Fc chain termini, with biotin groups, can then be bound to the immobilized streptavidin, to form the biosensor construct FIG. 17f, an immobilized and oriented immunoglobulin complex.

An alternative approach to construction of a biosensor is shown in FIG. 17g through 17l. FIG. 17g shows the reaction of a biotin-residue linked 1:1 streptavidin:SAMA complex FIG. 17i with a substrate FIG. 17h that has been functionalized by reaction with a biotinylation reagent (for example, FIG. 23a5). The complex binds with the functionalized substrate to form the substrate-immobilized streptavidin:SAMA complex FIG. 17j. An immunoglobulin or antibody FIG. 17k, labeled, for example, covalently functionalized, on its Fc region, e.g., the Fc chain termini, with a nucleotide or nucleotide derivative, such as a photo-ATP reagent, can then be bound to the SAMA to form the biosensor construct FIG. 17l, an immobilized and oriented immunoglobulin complex. In an embodiment, a substrate can be patterned to be functionalized with biotin in certain areas and functionalized with a ligand for a SAMA (for example, ATP or an ATP derivative) in other areas. The antibody shown in FIG. 17e can be a first antibody type different from a second antibody type shown in FIG. 17k, so that when the antibodies are reacted with the patterned, functionalized substrate, the first and second types of antibodies are bound to different areas on the substrate.

An alternative approach to construction of a biosensor is shown in FIG. 17m through 17r. FIG. 17m shows the reaction of a SAMA protein FIG. 17o that has been modified through incorporation of an antibody binding sequence, for example, a Staphylococcus Protein-A or Protein-G domain FIG. 10, with a substrate FIG. 17n that has been functionalized by reaction with a reagent (for example, the azo-ATP derivatives of FIGS. 23e1 and e2) that can bind to a binding site on a SAMA and form a photo-crosslink on irradiation. A Protein-A or Protein-G domain can be, for example, covalently incorporated into a SAMA through fusion of the SAMA gene and genes coding for the Protein-A or Protein-G domains. Protein-A and Protein-G domains can fold spontaneously into compact domains that bind strongly to the Fc regions of immunoglobulins. Thus, after irradiation, the modified SAMA is bound to the substrate to form the immobilized complex FIG. 17p. An immunoglobulin or antibody FIG. 17q can then be bound to the immobilized SAMA via the specific interactions made between the antibody Fc region and the SAMA bound protein-A or Protein-G domains to form the biosensor construct FIG. 17r, an immobilized and oriented immunoglobulin complex.

An alternative approach to construction of a biosensor is shown in FIG. 17s through 17x. In FIG. 17s is shown a substrate FIG. 17t that has been functionalized by reaction with a biotinylation reagent. FIG. 17u shows a biotin-linked streptavidin:SAMA complex formed between the biotinylated SAMA of FIG. 7j and streptavidin. The complex binds with the functionalized substrate to form a substrate-immobilized streptavidin:SAMA complex FIG. 17v. An immunoglobulin or antibody FIG. 17w, can then be bound to the immobilized SAMA via interactions between the antibody Fc region and the SAMA bound protein-A or Protein-G domains to form the biosensor construct FIG. 17x, an immobilized and oriented immunoglobulin complex. Chemical structures for schematic representations of cross-link chemistry are given in FIG. 23.

An advantage of the approaches shown in FIG. 17m and in FIG. 17s, in which an antibody or immunoglobulin is bound by an antibody binding sequence, such as a Staphylococcus Protein-A or Protein-G domain, is that there is no need to chemically modify the antibody itself. By contrast, in the approaches shown in FIG. 17a and in FIG. 17g, the antibody or immunoglobulin must be modified by first binding to it a biotin or biotin derivative or a nucleotide or nucleotide derivative.

A wide range of materials can be used as a substrate, for example, for the methods illustrated in FIG. 17. For example, the substrate can be a metal. For example, the substrate can be a noble metal, such as gold, silver, platinum, palladium, or rhodium. For example, the substrate can be a base metal, such as iron, copper, nickel, zinc, or lead. For example, the substrate can be a metal alloy. For example, the substrate can be a non-metal, such as carbon, e.g., graphite or diamond. For example, the substrate can be a metalloid, such as boron, silicon, or germanium. For example, the substrate can be a metal oxide, such as copper oxide, or a metalloid oxide, such as silicon oxide. For example, the substrate can be a ceramic. For example, the substrate can be a compound of nonmetallic elements or a compound of nonmetallic and metallic elements. For example, the substrate can be a liquid crystal.

In an embodiment, a substrate can be patterned to be functionalized with biotin in certain areas and functionalized with a ligand for a SAMA (for example, ATP or an ATP derivative) in other areas. The antibodies shown in FIGS. 17e, 17k, 17q, and 17w can be antibody types with different recognition specificities, so that when the antibodies are reacted with the patterned, functionalized substrate, the different types of antibodies are bound to different areas on the substrate.

Figure 18:
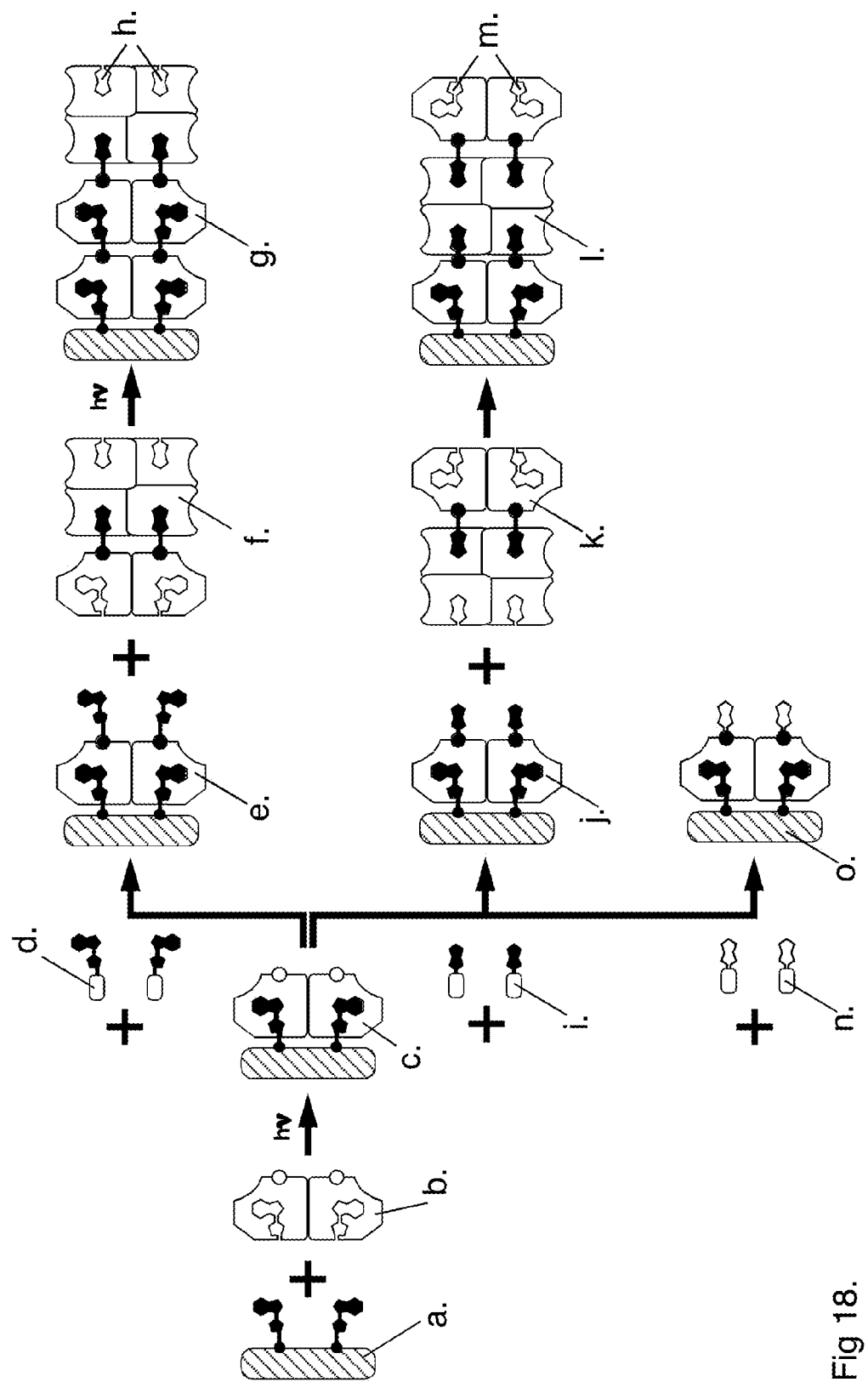
FIG. 18 presents methods for altering the assembly polarity of structures assembled from SAMA and streptavidin.

Orthogonal immobilization allowing the independent attachment of biomolecules to assemblies or substrates is useful in many contexts. FIG. 18 schematically illustrates a method of altering the polarity of a streptavidin:SAMA nanostructure during its assembly that depends upon modification of an immobilized SAMA that is subsequently modified using the S—S linked crosslink chemistry described in FIG. 23. FIG. 18a shows a substrate functionalized by reaction with a nucleotide, such as an ATP photo label. Combination with the SAMA of FIG. 18b (FIG. 7b) produces the immobilized SAMA complex FIG. 18c having designated surface amino acid residues, such as free cysteine sulfhydryl groups. Chemical modification of the immobilized SAMA FIG. 18c with different reagents can produce streptavidin:SAMA complexes with different exposed binding functionality.

For example, reaction of the immobilized SAMA FIG. 18c with a photo-ATP reagent FIG. 18d produces the immobilized complex FIG. 18e. When the immobilized complex FIG. 18e is combined with a 1:1 biotin-linked streptavidin:SAMA complex (FIG. 18f) and irradiated, a structure is produced (FIG. 18g) where the biotin binding sites (FIG. 18f) on the immobilized streptavidin:SAMA complex are exposed for further reaction.

Reaction of the immobilized SAMA (FIG. 18c) with a biotinylation reagent FIG. 18i produces the immobilized complex FIG. 18j. When FIG. 18j is combined with a 1:1 biotin-linked streptavidin:SAMA complex FIG. 18k, an immobilized structure FIG. 18l is produced where the photo-ATP binding sites FIG. 18m on the immobilized streptavidin:SAMA complex are exposed for further reaction.

The structure, or strut, formed from SAMA and streptavidin shown in FIG. 18l can be further extended. For example, a bifunctional crosslinking reagent having a nucleotide on each end, such as the S—S linked di-photo ATP (2-azido ATP) shown in FIG. 23h, can be bound at the ATP binding sites FIG. 18m of the SAMA farthest from the substrate FIG. 18a. A SAMA:streptavidin:SAMA structure, with the binding sites of the SAMAs facing away from the streptavidin in the center of the structure, can then be bound to the exposed nucleotide of the bifunctional crosslinking reagent linked to the ATP binding site FIG. 18m. The resultant structure, or strut, will then have the form SAMA(d):streptavidin:SAMA(n):SAMA(d):streptavidin:SAMA(n). SAMA(d) indicates a SAMA with the designated surface amino acid residues, to which biotins or iminobiotins are bound in FIG. 18, facing away from the substrate FIG. 18a. SAMA(n) indicates a SAMA with the ATP binding sites facing away from the substrate FIG. 18a. Thus, a SAMA in the SAMA(d) orientation can be viewed as having a polarity opposite to that of a SAMA in the SAMA(n) orientation. Such a SAMA(d):streptavidin:SAMA(n):SAMA(d):streptavidin:SAMA(n) structure may be advantageous in certain situations. For example, the location of the designated surface amino acid residues on the SAMA can be selected so that their separation is close to 20.5 Å, which is the separation between biotin binding sites on streptavidin. Therefore, the distance between, for example, a thiol group and a biotin group on a reagent that links the SAMA to the streptavidin, for example, the thiol-functionalized biotin linking reagent shown in FIG. 23a5, can be minimized. Alternatively, if a reagent is selected for linking the SAMA to the streptavidin for a certain application, and the reagent selected has a certain predetermined distance between, say, a thiol group and a biotin group, the location of the designated surface amino acid residues on the SAMA can be selected so that the spacing between the designated surface amino acid residues is optimal. For example, the location may be selected so that the spacing is such that the distance between the thiol group and the biotin group of the selected reagent is long enough to span between the designated surface amino acid residue on the SAMA and the biotin binding site on the streptavidin, but short enough so that there is not excessive "play" in the selected reagent and the SAMA and streptavidin are locked rigidly together. Furthermore, an adjacent SAMA(n) and SAMA(d) on consecutive SAMA(d):streptavidin:SAMA(n) blocks will have their ends with the ATP binding sites facing each other. The separation between the ATP binding site on one subunit and the ATP binding site of the other subunit on a given SAMA (SAMA(d) or SAMA(n)) can necessarily be the same as the separation between ATP binding sites on the opposing SAMA (SAMA(n) or SAMA(d)). Therefore, the distance between nucleotide ends on a bifunctional crosslinking, such as shown in FIG. 23h can be minimized.

Reaction of FIG. 18c with a 2-imino-biotinylation reagent FIG. 18n produces the immobilized complex FIG. 18o. This substrate provides a pH-dependent binding function for the assembly of streptavidin:SAMA nanoassemblies.

Figure 19:
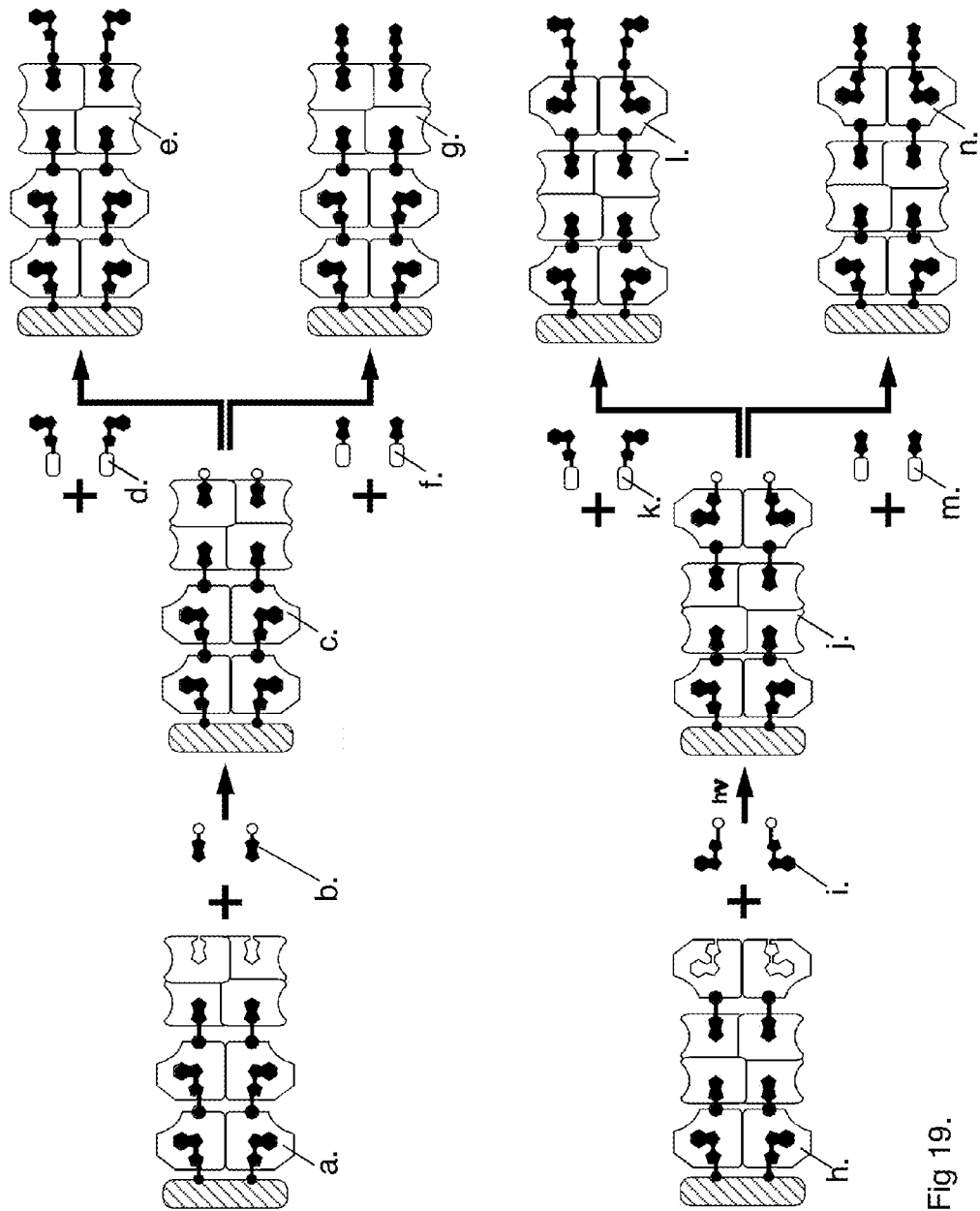
FIG. 19 presents methods for altering the assembly polarity of structures assembled from SAMA and streptavidin using SS-linked crosslinking reagents.

FIG. 19 presents methods for altering the assembly polarity of structures assembled from SAMA and streptavidin using sulfur-sulfur-linked crosslinking reagents (SS-linked crosslinking reagents). FIG. 19a shows the immobilized complex of FIG. 18g. When reacted with a biotin derivative functionalized with a reactive linking group FIG. 19b (such as the thiol substituted biotin reagent of FIG. 23a5), an immobilized complex FIG. 19c is produced with two reactive linking groups. Reaction of the product FIG. 19c with the reagent of FIG. 19d (such as the thiol-reactive photo-ATP reagents of FIG. 23d1,d2) produces the immobilized complex FIG. 19e, with, e.g., photo-ATP groups exposed to allow additional specific structure assembly or immobilization. Reaction of the complex FIG. 19c with the reagent of FIG. 19f (such as the thiol-reactive biotinylation reagent of FIG. 23a1 through a4) produces the immobilized complex FIG. 19g, with, e.g., free biotin groups exposed to allow additional specific structure assembly or immobilization.

FIG. 19h shows the immobilized complex of FIG. 18l. When reacted with a nucleotide or nucleotide derivative (e.g., a photo-ATP derivative) functionalized with a reactive linking group (such as the thiol substituted photo-ATP reagent of FIG. 23e1,e2), an immobilized complex FIG. 19j is produced with two reactive linking groups. Reaction of the product FIG. 19j with the reagent FIG. 19k (such as the thiol-reactive photo-ATP reagents of FIG. 23d1,d2) produces the immobilized complex FIG. 19l, with, e.g., photo-ATP groups exposed to allow additional specific structure assembly or immobilization. Reaction of the immobilized complex FIG. 19j with the reagent of FIG. 19m (such as the thiol-reactive biotinylation reagent of FIG. 23a1 through a4) produces the immobilized complex FIG. 19n, with, e.g., free biotin groups exposed to allow additional specific structure assembly or immobilization. Chemical structures for schematic representation of cross-link chemistry are given in FIG. 23.

Thus, the polar nature of the streptavidin:SAMA complex allows for orthogonal immobilization reactions to be carried out using a number of different approaches.

Methods of Making

Biotinylation of SAMA Surface Residues

Generation of a SAMA biotinylated at surface residues (FIG. 11) can be carried out as follows (FIG. 7b,c,d). A SAMA protein having two designated reactive surface amino acid residues separated by from about 10 Angstroms to about 35 Angstroms can be formed by site specific modification techniques. In the present 162 amino acid residue MJ0577 embodiment (FIG. 10) the reactive amino acids are cysteine residues that have been introduced alternatively at sequence positions 29, 31, 32, 33, 93, 94, 95, or 96, preferably at positions 31 or 33.

The SAMA protein can be mixed with at least 2 molar equivalents of a thiol-reactive biotinylation reagent, such as sulfosuccinimidyl-2-biotinamido-ethyl-1,3-dithiopropionate (FIG. 23a1) to form a reaction solution. The SAMA protein and the thiol-reactive biotinylation reagent can be allowed to react to form a biotinylated SAMA protein. Following the biotinylation reaction, size exclusion chromatography can be used to completely remove any unreacted biotin reagent, and the extent of SAMA biotinylation measured by removal of an aliquot of the reaction product solution and titration of any remaining free SAMA sulfhydryl groups with Ellman's Reagent (5,5'-dithiobis-(2-nitrobenzoic acid) or DTNB). DTNB readily forms a mixed disulfide with thiols to liberate 5-mercapto-2-nitrobenzoic acid, a chromophore with absorption maximum at 410 nm and extinction coefficient ~13,600 cm$^{-1}$M$^{-1}$. If analysis with DTNB indicates presence of any underivatized SAMA, an additional reaction step and/ or purification step involving passage of the biotinylated SAMA over a free thiol affinity column to remove any unreacted or mono-biotinylated SAMA will be performed to obtain purified, di-biotinylated SAMA.

Biotinylation of SAMA at Nucleotide Binding Sites:

Generation of a SAMA biotinylated through interactions at nucleotide binding sites (FIG. 13a) can be carried out as follows. A SAMA protein having two nucleotide binding sites, such as binding sites for ATP, can be selected or engineered. The SAMA protein can be mixed with at least about 2 molar equivalents of the bifunctional crosslinking reagent to form a reaction solution. The bifunctional crosslinking reagent can include a biotin moiety and a photo-reactive nucleotide moiety, for example the reagents of FIGS. 23c1 and c2. The SAMA protein and the bifunctional crosslinking reagent can be allowed to associate and are irradiated to induce the formation of photo cross-links between the azido-ATP moiety of the cross-linking reagent and the SAMA protein to form a biotin-nucleotide functionalized SAMA protein. Conditions for the reaction can be optimized by performing test reactions in the presence of an ATP analog that binds to the crosslinking ATP binding site and is displaced during the cross-linking reaction. An example of such a reagent (FIG. 23j) is the fluorescently tagged ATP reagent Adenosine 5'-triphosphate[7]-1-Naphthalenesulfonic acid-5 (2-Aminoethylamide) (ATP[γ]-1,5-EDANS). The reaction solution can be purified to obtain a substantially pure biotin-nucleotide functionalized SAMA protein. Purification can include, for example, subjecting the reaction solution to one or more of the techniques of size exclusion chromatography, ion exchange chromatography, electrophoresis, or free thiol affinity column chromatography.

Solution Synthesis of Biotin-Linked 1:1 Streptavidin:SAMA Complex

A biotin-residue linked 1:1 streptavidin:SAMA complex (FIG. 12a,b) can be formed in solution as follows. A SAMA protein in which biotin or biotin derivative groups are covalently bonded to designated surface amino acid residues can be provided in solution. This biotinylated SAMA protein can be mixed with about a molar equivalent of streptavidin tetramer in solution to form a reaction solution. The biotinylated SAMA protein and the streptavidin tetramer can be allowed to react to form a biotin-residue linked 1:1 streptavidin:SAMA complex. The procedure may result in the formation of the biotin-residue linked 1:2 streptavidin:SAMA complex (FIG. 16a) as well. The reaction solution can be purified to obtain a substantially pure biotin-residue linked 1:1 streptavidin:SAMA complex. Purifying can include, for example, subjecting the reaction solution to one or more of the techniques of electrophoresis, size exclusion chromatography, ion exchange chromatography, and high performance liquid chromatography.

In forming the biotin-residue linked 1:1 streptavidin:SAMA complex in solution, the extent of reaction between streptavidin and SAMA can be monitored through dye displacement from streptavidin biotin binding sites. A series of diazo dyes binding to the streptavidin biotin binding site with dissociation affinities ranging from $K_d=1\times10^{-5}$ M to $K_d=1\times10^{-8}$ M have been synthesized and characterized (e.g., FIG. 23i) (Weber et al. 1994). These diazo dyes are intensely absorbent or fluorescent when bound to streptavidin, but cease or lessen to absorb or fluoresce when displaced by the higher-affinity biotin ligand. Therefore, the dyes can be used as spectroscopic probes to directly and quantitatively measure biotin binding to streptavidin (Green 1965). More generally, the dyes can be used to monitor the assembly of streptavidin-linked nanostructures. Several derivatives of the prototype diazo reporter dye, 2-(4'-hydroxyazobenzene)benzoic acid (HABA), are available commercially. To monitor the progress of reaction, the biotinylated SAMA can be added to a streptavidin solution that has been saturated with HABA. Formation of the streptavidin:SAMA complex can then be monitored spectrophotometrically by measuring the release of HABA.

Before or after purification, reaction products can be analyzed by SDS PAGE (sodium dodecyl sulfate polyacrylamide gel electrophoresis). The high affinity for biotin and the thermostability of the streptavidin:biotin complex allows analysis of tetrameric streptavidin by SDS PAGE under conditions that denature most proteins (e.g. Gonzalez et al. 1997). SDS PAGE determination of a molecular weight of about 90 kiloDalton can indicate formation of the 1:1 streptavidin:SAMA complex, and determination of a molecular weight of about 120 kiloDalton can indicate formation of the 1:2 streptavidin:SAMA complex. Products isolated by size exclusion chromatography or high performance liquid chromatography can be analyzed using DLS (dynamic light scattering), ESI MS (electrospray ionization mass spectroscopy), ultraviolet (UV) light detection, refractive index, and/or viscosity measurements to verify molecular weights and characterize the structural integrity and molecular weight dispersity of products.

Solid Matrix Synthesis of Biotin-Linked 1:1 Streptavidin:SAMA Complex

Figure 20:
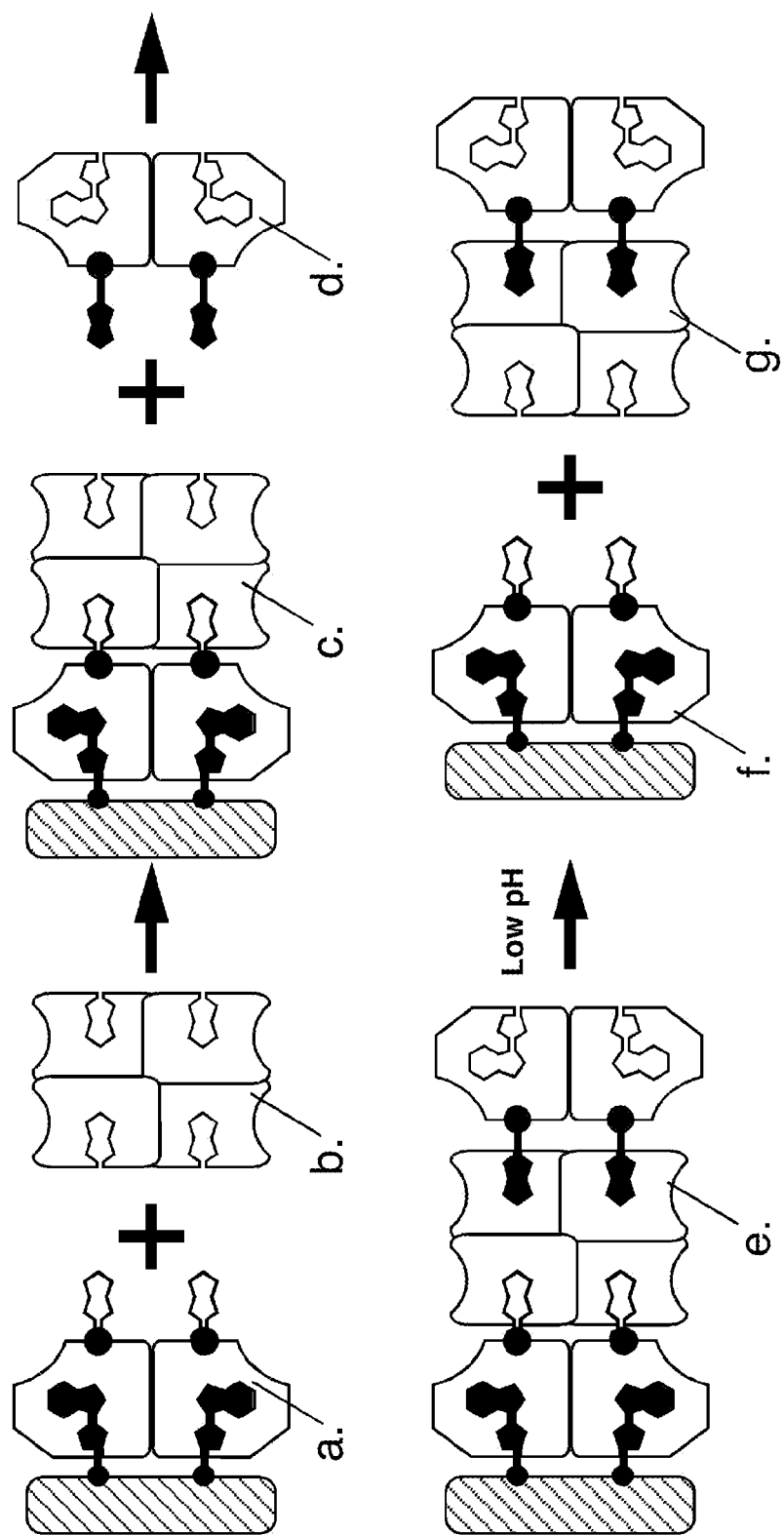
FIG. 20 presents steps in assembling a biotin-residue linked 1:1 streptavidin:SAMA complex using a support matrix.

A biotin-residue linked 1:1 streptavidin:SAMA complex can be formed on an immobilized resin serving as a support matrix as follows. This procedure may produce a higher fraction of 1:1 streptavidin:SAMA complex than the solution procedure. In this resin-based scheme the complex is immobilized on particles of a support resin that can be present, for example, as a slurry or as a bed in a flow-through reaction column. In either case, the support matrix resin is easily washed, so that any unreacted or excess reagents can be removed, and additional increments of reagents may be added or reaction steps repeated to obtain high product yields. The procedure is illustrated in FIG. 20. FIG. 20a shows a schematic of a solid matrix (such as a surface or resin) that has been derivatized with a SAMA (FIG. 18o) that has been functionalized with, for example, 2-iminobiotin. Reaction of about 1 molar equivalent of streptavidin tetramer FIG. 20b with the solid matrix at a pH greater than about 6.5 produces the immobilized streptavidin complex FIG. 20c. Because of the "opposite facing" orientation of the pairs of biotin binding sites on the streptavidin tetramer, and the geometrical alignment of the biotin binding sites with the matrix-bound SAMA, the streptavidin is expected to bind to the column resin predominantly through a single pair of the biotin binding sites. In order to allow monitoring of progress of subsequent reaction of the streptavidin with SAMA, the solution of streptavidin can be saturated with HABA (FIG. 23i). HABA binds 5 orders of magnitude more weakly to streptavidin than does iminobiotin and binds 8 orders of magnitude more weakly to streptavidin than does biotin. Addition of at least one molar equivalent of a SAMA protein FIG. 20d in which biotin or biotin derivative groups are covalently bonded to designated surface amino acid residues results in formation of the immobilized complex FIG. 20e. For example, the biotinylated SAMA protein solution can be flowed over the column to form an immobilized complex, the resin bound biotin-residue linked 1:1 streptavidin:SAMA complex FIG. 20e. It is understood that even though biotin binds more strongly to streptavidin than does iminobiotin, the biotinylated SAMA protein FIG. 20d will essentially not displace the substrate bound SAMA functionalized with iminobiotin FIG. 20a from the streptavidin FIG. 20b. This is because for such a displacement to occur, both iminobiotins would have to dissociate from the biotin binding sites on the streptavidin. The probability of both iminobiotins dissociating from the streptavidin during the time the biotinylated SAMA protein solution is flowed over the column is very small. This indicates an advantage of the pairwise binding approach to making a 1:1 streptavidin:SAMA complex and larger struts.

Following formation of the resin bound biotin-residue linked 1:1 streptavidin:SAMA complex FIG. 20e, a solution having pH of less than about 4 can then be flowed over the column to release the biotin-residue linked 1:1 streptavidin:SAMA complex into an eluted solution (see, FIGS. 20f and 20g). On reduction of pH in the solution around the support matrix or resin, iminobiotin becomes charged, releasing the 1:1 streptavidin:SAMA complex. The eluted solution can be purified to obtain a substantially pure biotin-residue linked 1:1 streptavidin:SAMA complex. Purifying can include, for example, subjecting the reaction solution to one or more of the techniques of electrophoresis, size exclusion chromatography, ion exchange chromatography and high performance liquid chromatography. The analytical techniques used with the solution reaction can also be used with this immobilized resin reaction. Steps can be carried out in a different order than presented above. Chemical structures for schematic representations of cross-link chemistry are given in FIG. 23.

Solution Synthesis of Biotin-Nucleotide Linked 1:1 Streptavidin:SAMA Complex

A biotin-nucleotide linked 1:1 streptavidin:SAMA complex (FIG. 13d) can be formed in solution as follows. A SAMA protein that has been functionalized through reaction with a biotin-nucleotide photo-crosslink (FIG. 13a and synthesis described above), and having 2 attached biotin groups geometrically situated to react with one pair of binding sites on streptavidin, can be mixed with a solution containing about a molar equivalent of streptavidin tetramer to form a reaction solution. The progress of the association reaction can be monitored by displacement of the dye HABA (FIG. 23i) from the streptavidin binding biotin sites when the SAMA biotin groups bind. In addition to the 1:1 complex, 1:2 streptavidin:SAMA biotin-nucleotide linked complexes may be formed. The reaction solution can be purified to obtain a substantially pure biotin-nucleotide linked 1:1 streptavidin:SAMA complex. Purifying can include, for example, subjecting the reaction solution to one or more of the techniques of electrophoresis, size exclusion chromatography, ion exchange chromatography, and high performance liquid chromatography.

Figure 21:
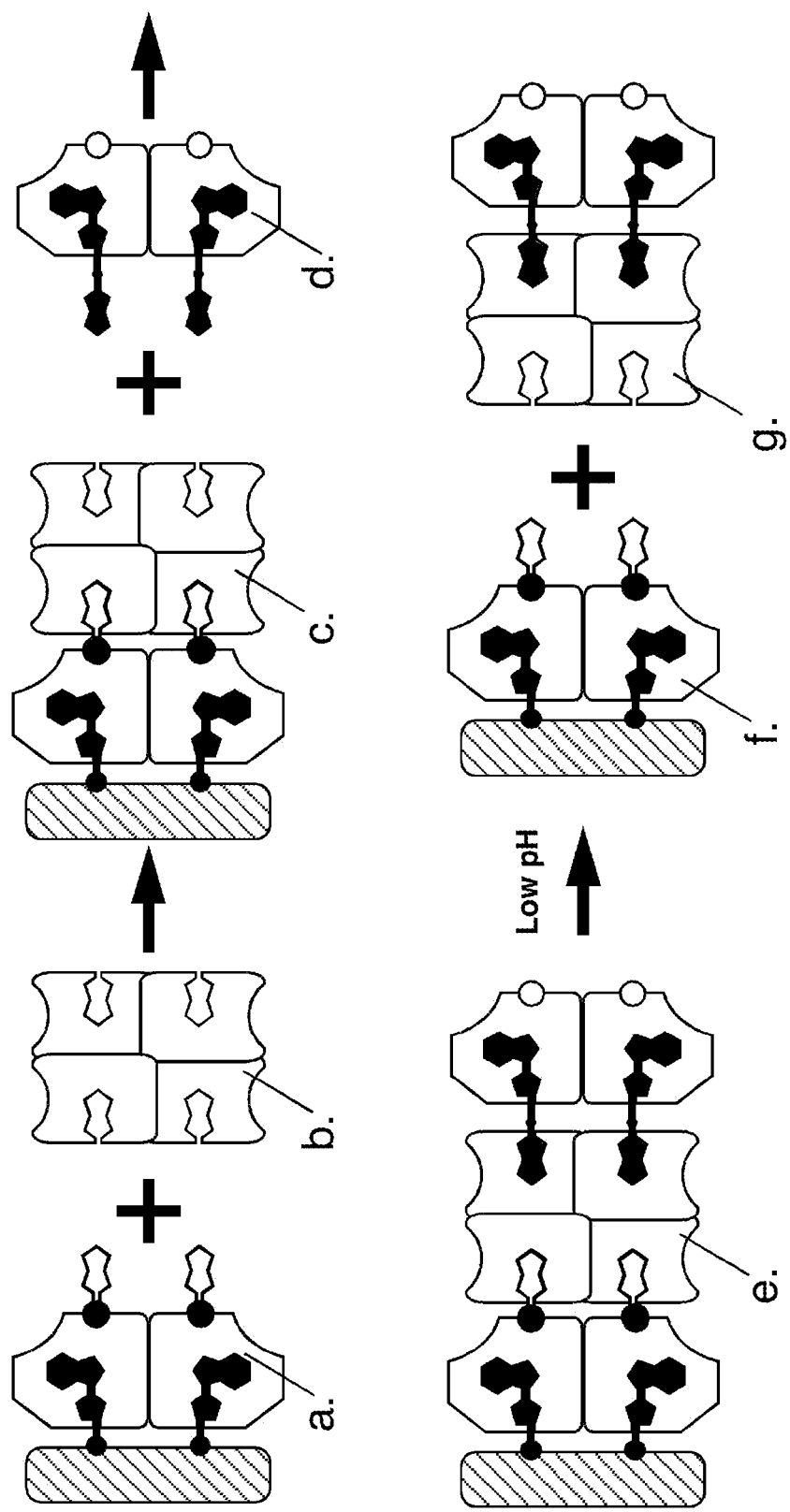
FIG. 21 presents steps in assembling a biotin-photo-ATP linked 1:1 streptavidin:SAMA complex using a support matrix.

Solid Matrix Synthesis of Biotin-Nucleotide Linked 1:1 Streptavidin:SAMA Complex A biotin-nucleotide linked 1:1 streptavidin:SAMA complex can be formed on a support matrix or immobilized resin as follows. This procedure may produce a higher fraction of 1:1 streptavidin:SAMA complex than the solution procedure. In this resin-based scheme the complex is immobilized on particles of a support resin that can be present as a slurry or as a bed in a flow-through reaction column. In either case, the support matrix resin is easily washed, so that any unreacted or excess reagents can be removed, and additional increments of reagents may be added or reaction steps repeated to obtain high product yields. The procedure is illustrated in FIG. 21. FIG. 21a shows a schematic of a solid matrix, such as a surface or resin, that has been derivatized with a SAMA (FIG. 18o) that has been functionalized with 2-iminobiotin. Reaction of about 1 molar equivalent of streptavidin tetramer FIG. 21b with the solid matrix at a pH greater than about 6.5 produces the immobilized streptavidin complex FIG. 21c. Because of the "opposite facing" orientation of the pairs of biotin binding sites on the streptavidin tetramer, and the geometrical alignment of the biotin binding sites with the matrix-bound SAMA, the streptavidin is expected to bind to the column resin predominantly through a single pair of the biotin binding sites. In order to allow monitoring of progress of subsequent reaction of the streptavidin with SAMA, the solution of streptavidin can be saturated with HABA (FIG. 23i). HABA binds 5 orders of magnitude more weakly to streptavidin than does iminobiotin and 8 orders of magnitude more weakly to streptavidin than does biotin. Addition of at least one molar equivalent of a SAMA protein FIG. 21d (also shown in FIG. 13a) in which biotin or biotin derivative groups are covalently bonded to a nucleotide, for example, a photo crosslinking reagent, such as a photo-ATP functionalized SAMA, results in the formation of an immobilized complex FIG. 21e. For example, the solution of SAMA protein functionalized with the covalently bound nucleotide crosslink can be flowed over the column to form the resin bound 1:1 streptavidin:SAMA complex FIG. 21e. A solution having pH of less than about 4 can be flowed over the column to release the biotin-nucleotide linked 1:1 streptavidin:SAMA complex into an eluted solution (FIGS. 21f and 21g). On reduction of pH in the solution around the support matrix or resin, iminobiotin becomes charged, releasing the biotin-nucleotide linked 1:1 streptavidin:SAMA complex FIG. 21g. The eluted solution can be purified to obtain a substantially pure biotin-residue linked 1:1 streptavidin:SAMA complex. Purifying can include, for example, subjecting the reaction solution to one or more of the techniques of electrophoresis, size exclusion chromatography, ion exchange chromatography and high performance liquid chromatography. The analytical techniques used with the solution reaction can also be used with this immobilized resin reaction. This process can also be performed with some steps carried out in a different order. Chemical structures for schematic representations of cross-link chemistry are given in FIG. 23.

Solution Synthesis of 4:5 Streptavidin:SAMA Strut

Long, directional strut structures can be formed by solution techniques or immobilized resin techniques. For example, FIG. 15 illustrates the formation of a 4:5 streptavidin:SAMA strut formed in solution. This structural assembly uses the biotin-residue linked 1:1 streptavidin:SAMA complex as a basic building block. FIG. 15a shows a cartoon of a SAMA whose binding sites have been modified by reaction with a bifunctional crosslinking agent having a biotin moiety and a ligand (for example, a nucleotide moiety) attached. For example, FIG. 15a can be the biotin-ATP SAMA construct of FIG. 13a. Mixing this SAMA in solution with a solution containing an approximate molar equivalent of a biotin-residue 1:1 streptavidin:SAMA complex (FIG. 15b) can produce a 1:2 streptavidin:SAMA complex FIG. 15c. The formation of the 1:2 streptavidin:SAMA complex FIG. 15c may be monitored using HABA displacement as described above and the resulting solution may be subjected to purification to separate the pure 1:2 complex from any unreacted materials. The 1:2 complex of FIG. 15c can be reacted in solution with at least 2 molar equivalents of a bifunctional crosslinking agent having a biotin moiety and a ligand (for example, a photoactivated-nucleotide moiety, such as the biotin-ATP crosslinking agent shown in FIG. 23c1,c2) (FIG. 15d), and the solution irradiated with light to functionalize the available binding sites on a SAMA with biotins and form a reactivated complex, the biotin functionalized 1:2 streptavidin:SAMA complex shown in FIG. 15e. The formation of FIG. 15e may be monitored using ATP[γ]-1,5-EDANS (FIG. 23j) as described above, and the resulting solution may be subjected to purification to separate the pure complex FIG. 15e from any unreacted materials. The steps of reaction with a biotin-residue linked 1:1 streptavidin complex and functionalization of binding sites on the SAMA with the photo-activated bifunctional crosslinking reagent can be repeated as desired to form a polar strut of predetermined length. In FIG. 15f, a 4:5 streptavidin: SAMA strut is shown. Because of the separation of the step in which the biotin-residue linked 1:1 streptavidin complex is added from the step in which the bifunctional crosslinking agent is added and the solution is irradiated with light, the user has precise control over the length of the strut constructed. The strut has additional binding sites for functionalization at both ends enabling connection of the strut to nodes or other biomolecules in a directional and controlled manner. The polar strut FIG. 15f has different chemical binding reactivity sites 15g and 15h at each end of the strut. Chemical structures for schematic representations of cross-link chemistry are given in FIG. 23.

Solid Matrix Synthesis of 4:4 Streptavidin:SAMA Strut

Figure 22:
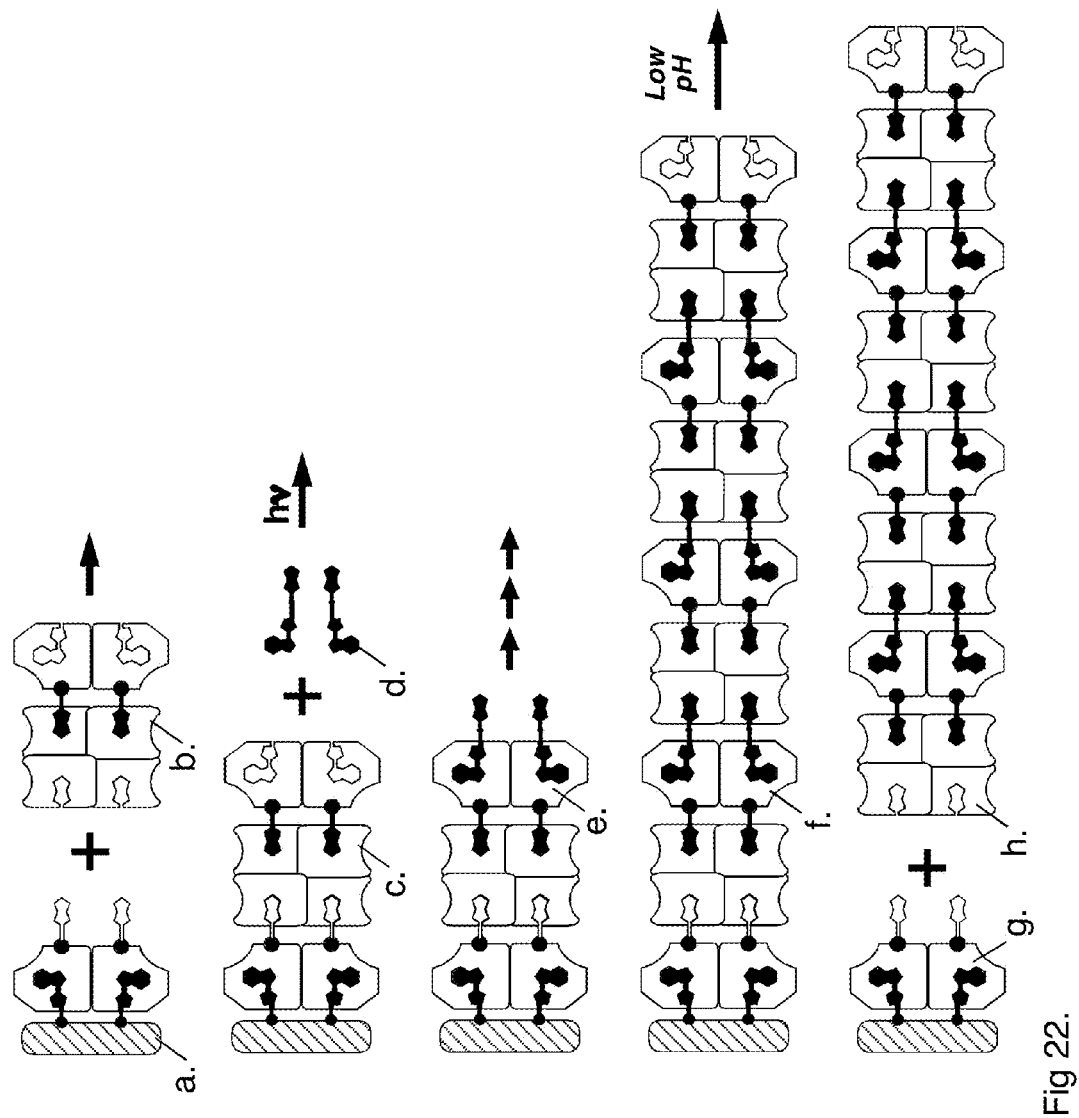
FIG. 22 presents steps in assembling a 4:4 streptavidin:SAMA strut using a support matrix.

FIG. 22 illustrates the formation of a 4:4 streptavidin: SAMA strut by a solid support matrix or an immobilized resin technique. In this resin-based scheme the growing strut is immobilized on particles of a support resin that can be present as a slurry or as a bed in a flow-through reaction column. In either case, the support matrix resin is easily washed, so that any unreacted or excess reagents can be removed, and additional increments of reagents may be added or reaction steps repeated to obtain high product yields. FIG. 22a shows a schematic of a solid matrix (such as a surface or resin) that has been derivatized with a SAMA (FIG. 18o) that has been functionalized with 2-iminobiotin. Reaction of about 1 molar equivalent of a biotin-residue linked 1:1 streptavidin:SAMA complex FIG. 22b with the SAMA-derivatized solid matrix at a pH greater than about 6.5 produces the immobilized 1:2 streptavidin:SAMA complex FIG. 22c. The formation of the 1:2 streptavidin:SAMA complex FIG. 22c may be monitored using HABA displacement as described above and the immobilized complex washed to separate the pure 1:2 streptavidin: SAMA complex FIG. 22c from any unreacted materials. The 1:2 streptavidin:SAMA complex FIG. 22c is reacted with at least 2 molar equivalents of a bifunctional crosslinking agent having a biotin moiety and a ligand FIG. 22d (for example, a photoactivated-nucleotide moiety FIG. 23c1,c2), such as a biotin-photo-ATP crosslinking reagent, and the reaction mixture is irradiated with light to functionalize the available binding sites on a SAMA with biotins and form the immobilized biotin-nucleotide functionalized 1:2 streptavidin: SAMA complex FIG. 22e. The newly incorporated biotin binding sites allow for the addition of another 1:1 biotin-linked streptavidin:SAMA complex. The formation of FIG. 22e may be monitored using ATP[γ]-1,5-EDANS (FIG. 23j) as described above, and the solid matrix washed and reacted additional times as necessary to insure most complete product formation. The steps of reaction with a biotin-residue linked 1:1 streptavidin complex and functionalization of binding sites on the SAMA with a photo-activated bifunctional crosslinking reagent can be repeated as desired to form a strut of predetermined length FIG. 22f. After the desired number of steps, a solution having pH of less than about 4 can then be flowed over the column or slurry to release the strut complex from the support matrix into an eluted solution (FIGS. 22g and 22h). On reduction of pH in the solution around the support matrix or resin, the iminobiotin becomes charged, releasing the streptavidin: SAMA complex. The eluted solution can be purified to obtain a substantially pure 4:4 streptavidin:SAMA complex. Purifying can include, for example, subjecting the eluted solution to one or more of the techniques of electrophoresis, size exclusion chromatography, ion exchange chromatography and high performance liquid chromatography. This process can also be performed if some steps are carried out in different order. The analytical techniques used with the solution reaction can also be used with this immobilized resin reaction. Chemical structures for schematic representations of cross-link chemistry are given in FIG. 23.

The location of designated surface amino acid residues on a SAMA can be selected so as to preserve or induce a change in orientation of the SAMA and streptavidin components as a strut is traversed along its length. For example, in the case of the D2 symmetric tetramer streptavidin, a line joining the two biotin binding sites on one end of the streptavidin is at a relative angle of about 36 degrees with respect to a line joining the biotin binding sites on the opposite end of the streptavidin. That is, in considering FIG. 1a, an observer looking in a direction extending from left to right through the streptavidin would see that the relative orientation of the two biotin binding sites on the left side of the streptavidin differed by 36 degrees from the relative orientation of the two biotin binding sites on the right side of the streptavidin. In considering FIG. 8a, an observer looking in a direction extending from left to right through the SAMA would see the binding sites FIG. 8b (e.g., a nucleotide binding site, such as an ATP binding site) on the left side of the SAMA in a relative orientation to each other and would see the designated surface amino acid residues FIG. 8d on the right side of the SAMA in a relative orientation to each other. The location of the designated surface amino acid residues FIG. 8d can be selected, so that the relative orientation of the binding sites on the left side is the same as or similar to the relative orientation of the designated surface amino acid residues on the right side. That is, the location of the designated surface amino acid residues on the right side can be selected so that a line connecting them would be parallel or nearly parallel to a line connecting the binding sites on the left side. Alternatively, the location of the designated surface amino acid residues FIG. 8*d* can be selected, so that the relative orientation of the binding sites on the left side is different from the relative orientation of the designated surface amino acid residues on the right side. That is, an observer looking left to right through the SAMA of FIG. 8*a* would see a line connecting the biotin binding sites at an angle with respect to a line connecting the designated surface amino acid residues. The location of the biotin binding sites can be selected, so that this angle is or approximates a predetermined, desired value.

For example, an observer looking left to right through the strut of FIG. 22*h* will see that the relative orientation of the biotin binding sites on the right side (for the observer, the far side) of the first streptavidin is about 36 degrees clockwise with respect to the relative orientation of the biotin binding sites on the left side (for the observer, the near side) of the streptavidin. With the observer continuing to look left to right through the strut, the location of the designated surface amino acid residues on the left side (for the observer, the near side) of the first SAMA can be selected so that the relative orientation of the binding sites (e.g., nucleotide binding site, such as an ATP binding site) on the right side (for the observer, the far side) of the SAMA is about 36 degrees counterclockwise with respect to the designated surface amino acid residues on the left side (for the observer, the near side) of the SAMA. That is, the location of the designated surface amino acid residues on the SAMA can be selected so that, from the perspective of an observer traveling from left to right through the strut of FIG. 22*h*, the relative rotation of 36 degrees clockwise from the orientation of the near to the far biotin binding sites on the streptavidin is canceled by the relative rotation of 36 degrees counterclockwise from the orientation of the near designated surface amino acid residues to the far binding sites on the subsequent SAMA. With such a selection of designated surface amino acid residues on the SAMA, the net twist of the relative orientation of the left (for the observer, the near) biotin binding sites of the first streptavidin, through a single streptavidin:SAMA repeating unit, to the relative orientation of the left biotin binding sites of the second, subsequent streptavidin of the next repeating unit can be zero or approximately zero. That is, the relative orientation of streptavidin:SAMA repeating units along the strut can be the same.

As another example, with an observer looking left to right through the strut of FIG. 22*h*, the location of the designated surface amino acid residues on the left side (for the observer, the near side) of the SAMA can be selected so that the relative orientation of the binding sites (e.g., nucleotide binding site, such as an ATP binding site) on the right side (for the observer, the far side) of the SAMA is zero (or approximately zero) degrees with respect to the designated surface amino acid residues on the left side (for the observer, the near side) of the SAMA. That is, the location of the designated surface amino acid residues on the left side of the SAMA can be selected so that their relative orientation is parallel to the relative orientation of the binding sites on the right side of the SAMA. With such a selection of the location of the designated surface amino acid residues on the SAMA, the net twist of the relative orientation of the left (for the observer, the near) biotin binding sites of the first streptavidin, through a single streptavidin: SAMA repeating unit, to the relative orientation of the left biotin binding sites of the second, subsequent streptavidin of the next repeating unit of the FIG. 22*h* strut can be 36 degrees (or approximately 36 degrees) clockwise. With such a selection of the location of designated surface amino acid residues, after 5 streptavidin:SAMA repeating units, the net twist can be 180 degrees (or approximately 180 degrees) clockwise. Because the streptavidin tetramer is D2 symmetric, if the SAMA is, for example, C2 symmetric (such as MJ0577), the orientation of the sixth streptavidin repeating unit will be the same as the orientation of the first streptavidin repeating unit. In this case, subsequent orientation of the repeating units in the strut lends the strut the appearance of a right-handed helix.

Other selections of repeating units, for example SAMA(d): streptavidin:SAMA(n), SAMA(d):SAMA(d):streptavidin, or others, with appropriate reagents to link the SAMA and streptavidin components to each other and the repeating units to each other, along with appropriate selection of the locations of designated surface amino acid residues on the SAMAs, can be made to obtain a strut that preserves orientation among all repeating units (i.e., all repeating units have the same orientation) or can be made to obtain a strut that has essentially any desired rate of twist from one repeating unit to the next with the strut having the form of a right-handed or left-handed helix. The design and construction of a strut with repeating units having the same orientation or a twist in orientation so that the strut has the form of helix can be made based upon the intended application of the strut. In addition to struts composed of identical repeating units composed of streptavidin(s) and SAMA(s), struts can be formed from streptavidin(s) and SAMA(s) arranged in a quasiperiodic or an aperiodic order. Such struts formed from streptavidin(s) and SAMA(s) arranged in a quasiperiodic or an aperiodic order can be designed, so that streptavidins and/or SAMAs at selected portions of the chain have a predetermined orientation with respect to each other.

Because of the separation of the step in which the biotin-residue linked 1:1 streptavidin complex is added from the step in which the bifunctional crosslinking agent is added and the solution is irradiated with light, the user has precise control over the length of the strut constructed. The progress of the reaction can be monitored using the spectroscopic methods outlined above, for example, using HABA and/or ATP[γ]-1, 5-EDANS (FIG. 23*i,j*). SDS PAGE, high performance liquid chromatography, and DLS can be used to characterize and/or purify struts such as the 4:4 streptavidin:SAMA complex. Detection methods can include ultraviolet (UV), ultraviolet-visible (UV-Vis), refractive index (RI), and viscosity methods. The extent and uniformity of the structures produced may be determined through direct visualization, for example, with atomic force microscopy (AFM) and electron microscopy (EM). For example, a 4:4 streptavidin:SAMA strut has dimensions of about 400 Angstroms (40 nanometers) long by about 80 Angstroms (8 nanometers) in broadest cross section, so that it should be clearly visible with either atomic force microscopy or electron microscopy (see Cherny et al. 1998).

The biomolecular components and building blocks of several biomolecular components described herein can be functionalized with chemical and/or biochemical groups. For example, the SAMA and/or the streptavidin component of a 1:1 SAMA:streptavidin complex can be functionalized with biocompounds, inorganic compounds, organic compounds, and/or organometallic compounds. For example, a biomolecular component can be functionalized with one or more organometallic compounds, such as chelate complexes, porphyrins, hemes, chlorophylls, and ferrocene. A biomolecular component can be functionalized with one or more metalloproteins, such as metalloenzymes, iron-sulfur proteins, e.g., ferredoxin, hemoproteins, e.g., cytochrome and hemoglobin. A biomolecular component can be functionalized with inorganic compounds, such as metals, semiconductors, iron-sulfur compounds, and metal and semiconductor nanostructures, such as quantum dots. A biomolecular component can be functionalized with organic compounds. A biomolecular component can be functionalized with organic nanostructures, such as fullerenes and carbon nanotubes and with organometallic nanostructures. A biomolecular component can be functionalized with organic biocompounds, such as proteins, carbohydrates, and glycoproteins. A biomolecular component can be functionalized with a compound, group, or structure that exhibits useful electrical, optical, chemoelectrical, or chemooptical properties. A biomolecular component can be functionalized with a compound, group, or structure to make the biomolecular component useful as a sensor. A biomolecular component can be functionalized, so that its electrical and/or optical properties change in the presence or absence of particular chemical species.

The control that can be exerted by the methods described above over the form of a structure, such as a SAMA:streptavidin strut, can be used in conjunction with functionalization of the biomolecular components. For example, the spacing between functional groups can be controlled. For example, a functional group may be placed on each SAMA and each streptavidin of a SAMA:streptavidin strut, only on the SAMAs, or only on the streptavidins. A functional group may be placed only on every other 1:1 SAMA:streptavidin building block. Two different functional groups may alternate on consecutive 1:1 SAMA:streptavidin building blocks. More complex periodic or aperiodic patterns of one or multiple types of functional groups along a structure, such as a SAMA:streptavidin strut, can be made. The control over the spacing between one or multiple types of functional groups on a structure, such as a SAMA:streptavidin strut, can be used to control emergent properties arising from interactions among individual functional groups, such as quantum tunneling effects.

EXPERIMENTAL EXAMPLES

1) Construction of SAMA Genes for Heterologous Expression

Genes encoding MJ0577 wt and three variants L31C, K32C and V95C were synthesized by Blue Heron Bio (www.blueheronbio.com) using the Blue Heron GeneMaker, an automated, high throughput gene synthesis platform. Gene sequences differ from those found in nature because codon usage was chosen to optimize expression in the bacterial host strain, *Escherichia coli*. The MJ0577 wt gene sequence (with the open reading frame in upper case, the ribosome binding site (RBS) in lower case and italics, initiating methionine codon in bold and stop codon in bold) follows:

(SEQ ID NO: 8)
gaaggagatatacatATGAGCGTCATGTATAAAAAAATCCTGTATCCGAC

CGACTTTAGCGAAACCGCCGAAATTGCACTGAAACATGTTAAAGCATTTA

AAACCCTGAAAGCCGAAGAAGTGATCCTGCTGCATGTCATCGACGAACGC

GAAATTAAAAAACGTGATATTTTTAGCCTGCTGCTGGGTGTTGCCGGTCT

GAACAAAAGCGTGGAAGAATTCGAAAATGAACTGAAAAATAAACTGACCG

AAGAAGCGAAAAATAAATGGAAAATATTAAAAAAGAACTGGAAGACGTG

GGCTTTAAAGTCAAGGATATTATTGTTGTGGGCATTCCGCATGAAGAAAT

TGTTAAAATTGCAGAAGATGAAGGCGTGGATATTATCATTATGGGCAGCC

ATGGCAAAACCAATCTGAAAGAAATTCTGCTGGGCAGCGTGACCGAAAAT

GTGATTAAAAAAAGCAATAAACCGGTTCTGGTCGTCAAACGTAAAAATAG

CTAA

The L31C gene sequence (with the open reading frame in upper case, the ribosome binding site (RBS) in lower case and italics, initiating methionine codon in bold and stop codon in bold) follows:

(SEQ ID NO: 9)
gaaggagatatacatATGAGCGTCATGTATAAAAAAATCCTGTATCCGAC

CGACTTTAGCGAAACCGCCGAAATTGCACTGAAACATGTTAAAGCATTTA

AAACCTGTAAAGCCGAAGAAGTGATCCTGCTGCATGTCATCGACGAACGC

GAAATTAAAAAACGTGATATTTTTAGCCTGCTGCTGGGTGTTGCCGGTCT

GAACAAAAGCGTGGAAGAATTCGAAAATGAACTGAAAAATAAACTGACCG

AAGAAGCGAAAAATAAATGGAAAATATTAAAAAAGAACTGGAAGACGTG

GGCTTTAAAGTCAAGGATATTATTGTTGTGGGCATTCCGCATGAAGAAAT

TGTTAAAATTGCAGAAGATGAAGGCGTGGATATTATCATTATGGGCAGCC

ATGGCAAAACCAATCTGAAAGAAATTCTGCTGGGCAGCGTGACCGAAAAT

GTGATTAAAAAAAGCAATAAACCGGTTCTGGTCGTCAAACGTAAAAATAG

CTAA

The V95C gene sequence (with the open reading frame in upper case, the ribosome binding site (RBS) in lower case and italics, initiating methionine codon in bold and stop codon in bold) follows:

(SEQ ID NO: 10)
gaaggagatatacatATGAGCGTCATGTATAAAAAAATCCTGTATCCGAC

CGACTTTAGCGAAACCGCCGAAATTGCACTGAAACATGTTAAAGCATTTA

AAACCCTGAAAGCCGAAGAAGTGATCCTGCTGCATGTCATCGACGAACGC

GAAATTAAAAAACGTGATATTTTTAGCCTGCTGCTGGGTGTTGCCGGTCT

GAACAAAAGCGTGGAAGAATTCGAAAATGAACTGAAAAATAAACTGACCG

AAGAAGCGAAAAATAAATGGAAAATATTAAAAAAGAACTGGAAGACTGT

GGCTTTAAAGTCAAGGATATTATTGTTGTGGGCATTCCGCATGAAGAAAT

TGTTAAAATTGCAGAAGATGAAGGCGTGGATATTATCATTATGGGCAGCC

ATGGCAAAACCAATCTGAAAGAAATTCTGCTGGGCAGCGTGACCGAAAAT

GTGATTAAAAAAAGCAATAAACCGGTTCTGGTCGTCAAACGTAAAAATAG

CTAA.

The MJ0577 wt amino acid sequence, in standard 1-letter code and also shown in FIG. 10, is:

(SEQ ID NO: 11)
MSVMYKKILYPTDFSETAEIALKHVKAFKTLKAEEVILLHVIDEREIKKR

DIFSLLLGVAGLNKSVEEFENELKNKLTEEAKNKMENIKKELEDVGFKVK

DIIVVGIPHEEIVKIAEDEGVDIIIMGSHGKTNLKEILLGSVTENVIKKS

NKPVLVVKRKNS..

The L31C amino acid sequence, in standard 1-letter code and also shown in FIG. 10, is (SEQ ID NO: 12)
MSVMYKKILYPTDFSETAEIALKHVKAFKTCKAEEVILLHVIDEREIKKR

DIFSLLLGVAGLNKSVEEFENELKNKLTEEAKNKMENIKKELEDVGFKVK

DIIVVGIPHEEIVKIAEDEGVDIIIMGSHGKTNLKEILLGSVTENVIKKS

NKPVLVVKRKNS.

The V95C amino acid sequence, in standard 1-letter code and also shown in FIG. 10, is (SEQ ID NO: 13)
MSVMYKKILYPTDFSETAEIALKHVKAFKTLKAEEVILLHVIDEREIKKR

DIFSLLLGVAGLNKSVEEFENELKNKLTEEAKNKMENIKKELEDCGFKVK

DIIVVGIPHEEIVKIAEDEGVDIIIMGSHGKTNLKEILLGSVTENVIKKS

NKPVLVVKRKNS.

Figure 24:
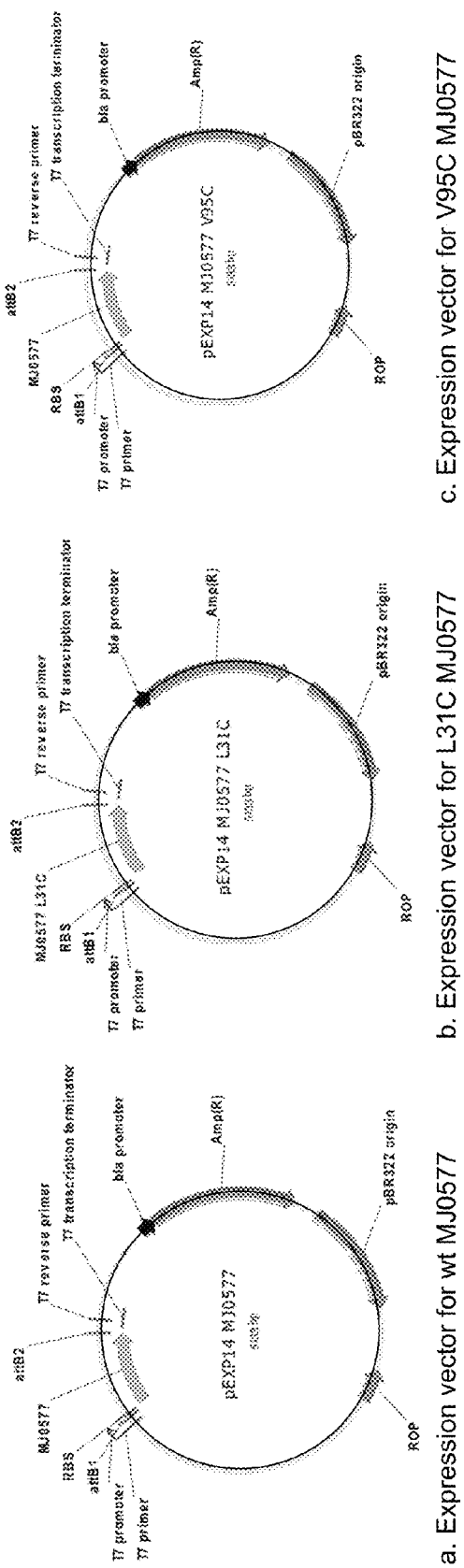
FIG. 24 illustrates the structures of the expression vectors for expression of MJ0577 protein and L31C and V95C SAMA variants.

Expression vectors for MJ0577 wt, L31C and V95C are diagrammed in FIG. 24.

2) Heterologous Expression of SAMA Genes in *E. coli*.

Expression of Wild Type MJ0577

MJ0577 wt was expressed in bacterial cells. *Escherichia coli* strain BL21 Star™ (DE3), a bacterial expression strain of Invitrogen Corp, harboring expression vector pEXP14 MJ0577 wt (FIG. 24a) was grown in Terrific Broth (Invitrogen) culture media supplemented with 100 μg/mL of the antibiotic ampicillin. An initial culture of cells was grown overnight to an optical density at 600 nm ($OD_{600}$) of 6.03. 265 mL of this culture were used to inoculate a 16 L flask maintained at 37° C. with the growth chamber flask temperature shifted to 25° C. when the cell culture density reached an optical density at 600 nm ($OD_{600}$) of 0.915. Expression of MJ0577 wt was induced by addition of 1 mM isopropyl β-D-1-thiogalactopyranoside (IPTG) when the culture temperature was 27.7° C. and cell culture optical density $OD_{600}$ was 1.239. Cells were harvested by centrifugation after 20 hours of growth, and at that time the cell density $OD_{600}$ was 1.36. The yield of cells as a wet paste was 48.6 g. The wet paste was frozen and stored at −80° C.

Expression of L31C SAMA Variant Based on MJ0577

L31C was expressed in bacterial cells. *Escherichia coli* strain BL21 Star™ (DE3), a bacterial expression strain of Invitrogen Corp, harboring expression vector pEXP14 MJ0577 L31C (FIG. 24b) was grown in Terrific Broth (Invitrogen) culture media supplemented with 100 μg/mL of the antibiotic ampicillin. An initial culture of cells was grown overnight to an optical density at 600 nm ($OD_{600}$) of 6.17. 260 mL of this culture were used to inoculate a 16 L flask maintained at 37° C. with the growth chamber flask temperature shifted to 25° C. when the culture density reached an optical density at 600 nm ($OD_{600}$) of 0.815. Expression of MJ0577 L31C was induced by addition of 1 mM isopropyl β-D-1-thiogalactopyranoside (IPTG) when the culture temperature was 27.9° C. and cell culture optical density $OD_{600}$ was 1.113. Cells were harvested by centrifugation after 20 hours of growth and at that time the cell density $OD_{600}$ was 1.11. The yield of cells as a wet paste was 35.7 g. The wet paste was frozen and stored at −80° C.

Expression of V95C SAMA Variant Based on MJ0577

V95C was expressed in bacterial cells. *Escherichia coli* strain BL21 Star™ (DE3) pLysS, a bacterial expression strain of Invitrogen Corp, harboring expression vector pEXP14 MJ0577 V95C (FIG. 24c) was grown in Luria Bertani Broth (Invitrogen) culture media supplemented with 100 μg/mL of the antibiotic ampicillin and with 34 μg/mL of the antimicrobial agent chloramphenicol. An initial culture of cells was grown overnight to an optical density at 600 nm ($OD_{600}$) of 3.58. 450 mL of this culture were used to inoculate a 16 L flask maintained at 37° C. with the growth chamber flask temperature shifted to 25° C. when the culture density reached an optical density at 600 nm ($OD_{600}$) of 0.934. Expression of MJ0577 V95C was induced by addition of 1 mM isopropyl β-D-1-thiogalactopyranoside (IPTG) when the culture temperature was 29.9° C. and cell culture optical density $OD_{600}$ was 1.313. Cells were harvested by centrifugation after 19 hours of growth and at that time the cell density $OD_{600}$ was 2.137. The yield of cells as a wet paste was 47.4 g. The wet paste was frozen and stored at −80° C.

3) Purification Methods for MJ0577 wt and SAMA Variant Proteins

MJ0577 wt and SAMA variants, L31C and V95C, were purified to at least 80% homogeneity by the following procedure. 17g of frozen cells were suspended in 150 mL of phosphate buffered saline (PBS) pH 7.4 supplemented with 5 mM dithiothreitol (DTT) and stirred for 30 minutes in the cold (4° C.). Cells were disrupted by sonication in 4 30-second sequences of pulsed sonication using a microtip sonicator operating at 20% power. Following sonication, 1 pellet Roche protease inhibitor cocktail (Roche), 1.5 mg DNAse 1 and 150 mg hen egg white lysozyme were added and the solution stirred in the cold (4° C.) for 30 min. The whole cell lysate was stirred and heated to a temperature between 50 and 70° C. for 30 min. The lysate was clarified by centrifugation at 12 000×g for 15 minutes. The supernatant was made 0.7M in ammonium sulfate by addition of solid salt and applied to a 10 mL Butyl Sepharose Fast Flow column (Pharmacia) previously equilibrated with 25 mM sodium phosphate buffer pH 7.0, 5 mM DTT, 0.5M $(NH_4)_2SO_4$. The column was washed with 3 column volumes of the equilibrating buffer, then washed with 3 column volumes of 10 mM sodium phosphate buffer pH 7.0, 0.2M $(NH_4)_2SO_4$. MJ0577 wt, L31C or V95C were eluted from the column with a 4-column volume linear gradient starting with 10 mM sodium phosphate buffer pH 7.0, 5 mM DTT, 0.2M $(NH_4)_2SO_4$ and ending with 5 mM DTT. MJ0577 wt-, L31C- or V95C-containing fractions, as determined by uv absorbance at 280 nm and polyacrylamide gel electrophoresis (PAGE), eluted near the end of the gradient. These fractions were loaded into dialysis tubing (Spectra/Por, 5 000 mW cutoff dialysis tubing, Cole-Palmer), then dialyzed against at least two changes of 25 mM sodium acetate buffer pH 5.2, 2 mM DTT, each at least 10 times the dialysate volume. The dialysate was loaded onto a 10 mL CM Sepharose Fast Flow (Pharmacia) column equilibrated with 25 mM sodium acetate pH 5.2, 2 mM DTT. After washing the column with 3 column volumes of 25 mM sodium acetate pH 5.2, 2 mM DTT, MJ0577 wt, L31C or V95C was eluted using a 5-column volume linear gradient starting with 25 mM sodium acetate pH 5.2, 2 mM DTT and ending with 25 mM sodium acetate pH 5.2, 2 mM DTT, 1M NaCl. MJ0577 wt-, L31C- or V95C-containing fractions, as determined by uv absorbance at 280 nm and polyacrylamide gel electrophoresis (PAGE), eluted near the end of the gradient. The Butyl Sepharose Fast Flow chromatography could be repeated to improve protein purity. MJ0577 wt, L31C or V95C near 85% purity as determined by PAGE (FIG. 25, lane 1) could be obtained. Protein concentration was estimated using an extinction coefficient of 2980 $M^{-1}$ $cm^{-1}$ calculated from the amino acid composition (www.ca.expasy.org/tools/protparam.html).

Because MJ0577 contains no tryptophan residues, the calculated extinction coefficient, as stated on the website, could be in error. Determination of the number of free cysteines using Ellman's reagent and estimation of the protein concentration by a Bradford assay (Pierce) both indicated that the calculated extinction coefficient overestimates the protein concentration by about 50%. We envision determining the extinction coefficient analytically.

The protein identity was confirmed by 8 cycles of N-terminal sequencing (M-Scan, Inc, West Chester Pa.). MJ0577 and the L31C and V95C variants were essentially indistinguishable during the purification procedures, indicating that incorporation of cysteines does not significantly alter the protein's structure.

In development of the purification protocol, it was found that MJ0577 has low affinity for HIC resins, low substitution phenyl superose and alkyl superose. In addition to the high binding affinity for butyl Sepharose FF, MJ0577 also binds high substitution phenyl sepharose and octyl sepharose. Butyl sepharose FF was selected because fewer other proteins eluted with MJ0577. HIC interactions on the high substitution phenyl Sepharose resin were independent of pH for experiments at pH 5.5 mL-histidine buffer, pH 8.3 in TRIS buffer and pH 8.9 in CHES buffer.

ATP-free MJ0577 SAMA can be prepared, ATP and Biotin-ATP linker binding constants can be determined, and the binding constants of ATP and the photo-ATP crosslinking reagent can be determined. The structure of MJ0577 was determined in the context of a structural genomics project aimed at elucidating protein function through 3D structural studies. When the X-ray structure of MJ0577 was initially solved, an ATP molecule could be fit to electron density at each ligand-binding pocket of the dimer (Zarembinski et al. 1998). Because the nucleotide was not added to buffers used during purification and crystallization, the authors concluded that ATP was scavenged from the growth media. Our initial approach for isolation of the ATP-free MJ0577 was to prepare the protein in the absence of added ATP. Because the purification protocol developed here includes heating and dialysis at pH 5.2 steps, we believed that it was possible that the protein would be isolated as the ATP-free form. To test this hypothesis, the affinity of purified MJ0577 for the nucleotide mimicking resin, Cibacron Blue, was tested following the procedure successfully applied in the purification of an MJ0577 structural relative, *E. coli* YnaF (Saveanu et al. 2002). No binding was observed for MJ0577 in 25 mM sodium phosphate buffer pH 7.6. Next a procedure developed for removal of ATP from the protease resistant core of actin (Jacobson & Rosenbusch 1976) was tested. MJ0577 was dialyzed overnight against 8 M guanidinium HCl (GuHCl) 0.2 M TRIS pH 8.2, 5 mM DTT, then dialyzed overnight against 8 M urea, and finally equilibrated to non-denaturing conditions by dialysis against 25 mM sodium phosphate buffer pH 7.6. In a separate experiment, MJ0577 was dialyzed overnight against 2 M GuHCl in 25 mM L-histidine pH 5.6, 2 M GuHCl in 25 mM CHES pH 9.8, and 2 M GuHCl in 25 mM sodium phosphate buffer pH 7.8, 20% DMSO. Half of each sample was then heated at 40° C. for one hour. Removal of ATP was tested by binding the protein to ATP immobilized on a resin by attachment via the g-phosphate (ProteoEnrich ATP-binders Kit, Novagen). This resin is a good candidate to capture MJ0577 because the ATP in the MJ0577 crystal structure is observed with the g-phosphate exposed to solvent. Portions of the adenine ring are also exposed to solvent, a structural feature that could potentially allow binding to a Cibacron Blue resin. Analysis by PAGE showed essentially no interaction between MJ0577 and the ATP resin. ESI and/or MALDI-TOF MS can be used to analyze the isolated MJ0577 samples to determine the extent of complex formation with ATP. Procedures designed to assay noncovalent complexes can be employed (e.g., Hernandez & Robinson 2001; Potier et al. 2003; Krishnaswamy et al. 2006). The resulting data can guide subsequent experiments. It is possible that either the protein as isolated or following the dialysis procedures was free of ATP, but did not bind ATP in the configurations immobilized on the resins. Such results can enable the ready establishment of proper conditions for a biotin-ATP substituted SAMA.

Thus, ATP- or Cibacron-resin binding affinity can be used to measure the binding of ATP. Approaches to removal of ATP can involve experimentation with conditions or the use of denaturing agents such as hexafluoroisopropanol (HFIP), a solvent widely used in polyamide polymer synthesis.

4) Biotin Functionalization of L31C and V95C SAMA Variants

Figure 25:
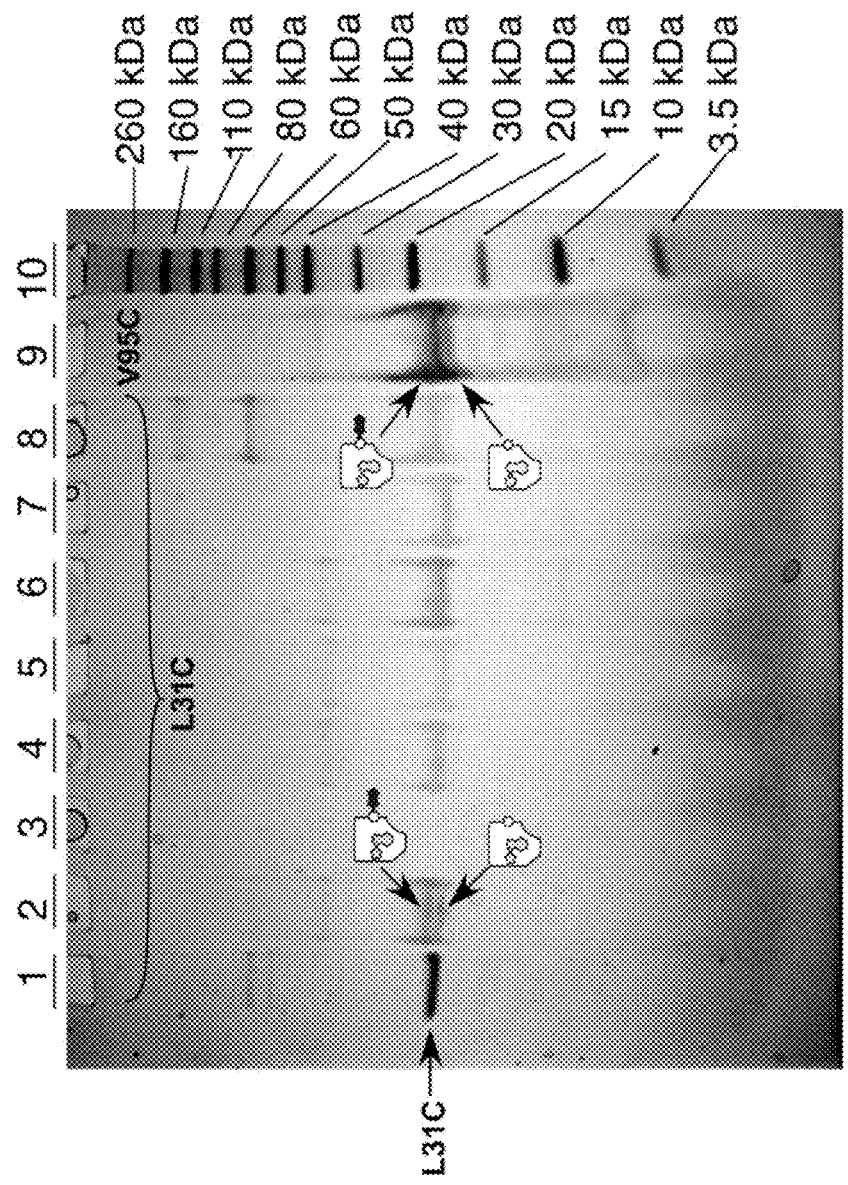
FIG. 25 shows Polyacrylamide Gel Electrophoresis (PAGE) separations of SAMA and chemically modified forms of SAMA.

Biotin- and iminobiotin-containing reagents were covalently linked to free cysteine residues on L31C or V95C using the following procedure. The protein was equilibrated in 20 mM sodium phosphate buffer pH 6.8 for reaction with biotin-linking reagents MAL PEO3 (FIG. 23 *a*3) and MAL PEO11 (FIG. 23 *a*4) or iminobiotin-linking reagent MAL PEO3 (FIG. 23 *b*3) or equilibrated in 20 mM sodium phosphate buffer pH 7.6 for reaction with biotin-linking reagent EZ-Link HPDP (FIG. 23 *a*2) by either dialysis (Spectra/Por, 5 000 mW cutoff dialysis tubing, Cole-Palmer) or by using centrifugal protein concentrators (PierceNet) to concentrate the protein to about 10 µL followed by adding 2 mL of the appropriate buffer. Protein was then concentrated to a volume of about 0.5 mL and a concentration of least 1 mg/mL using centrifugal protein concentrator (PierceNet) and protein concentration determined by using an extinction coefficient of 2980 $M^{-1}$ $cm^{-1}$. Solutions of biotin- and iminobiotin-containing reagents were prepared by adding solid reagent to an appropriate buffer. For maleimide-reactive reagents (such as MAL PEO3 (FIG. 23 *a*3 and FIG. 23 *b*3) and MAL PEO11 (FIG. 23 *a*4)), the buffer was 20 mM sodium phosphate buffer pH 6.8 and for the sulfur-reactive biotin-linking reagent EZ-Link HPDP (FIG. 23 *a*2), the dissolving solution was dimethyl sulfoxide (DMSO). Maleimide-reactive reagents were added to the L31C or V95C solutions immediately after dissolution of the solid reagent. The molar concentrations of reagent solutions were at least 20 times that of L31C or V95C. At least a 10-fold molar excess of reagent was added to L31C or V95C, and the reaction allowed to progress for at least 2 hours. FIG. 23 shows the chemical structures of the maleimide-reactive biotin-linking reagents MAL PEO3 (FIG. 23 *a*3) and MAL PEO11 (FIG. 23 *a*4), the maleimide-reactive iminobiotin-linking reagent MAL PEO3 (FIG. 23 *b*3), and the sulfur-reactive biotin-linking reagent (EZ-Link HPDP (FIG. 23 *a*2)). The extent of derivatization was estimated by PAGE (FIG. 25). In FIG. 25, a PAGE analysis using 12% Bis(2-hydroxyethyl)iminotris(hydroxymethyl)methane (Bis-Tris) polyacrylamide gel with 2-(N-Morpholino)ethanesulfonic acid (MES), sodium dodecyl sulfate (SDS) running buffer is shown. Lanes are numbered from left to right. Lane 1 shows purified and unreacted L31C. Lanes 2&8 show L31C reacted with biotin-linking reagent MAL PEO11 (FIG. 23 *a*4). Lane 3 is blank. Lanes 4&6 show L31C reacted with biotin-linking reagent MAL PEO3 (FIG. 23 *a*3). Lanes 5&7 show L31C reacted with biotin-linking reagent EZ-Link HPDP (FIG. 23 *a*2). Lane 9 shows V95C reacted with biotin-linking reagent MAL PEO11 (FIG. 23 *a*4). Samples of L31C used in reactions 2, 4, and 5 were purified independently of those used to prepare samples shown in lanes 8, 6 and 7. An upward shift in protein band relative to the purified and unreacted L31C indicates derivatization. Larger upward shifts are expected for L31C and V95C reacted with biotin-linking reagent MAL PEO11 (FIG. 23 a4) than with either biotin-linking reagent MAL PEO3 (FIG. 23 a3) or biotin-linking reagent (EZ-Link HPDP (FIG. 23 a2) because the biotin-linking reagent MAL PEO11 (FIG. 23 a4) molecular weight of 922.09 Da is larger than the molecular weights of biotin-linking reagent MAL PEO3 (FIG. 23 a3, MW 597.73 Da) and biotin-linking reagent EZ-Link HPDP (FIG. 23 a2, MW 539.78 Da). A doublet of bands as seen in Lanes 2 and 9 indicates incomplete derivatization. Lane 10 shows molecular weight standards (NovexSharp Standards, Invitrogen) with MWs from top to bottom of 260 kDa, 160 kDa, 110 kDa, 80 kDa, 60 kDa, 50 kDa, 40 kDa, 30 kDa, 20 kDa, 15 kDa, 10 kDa and 3.5 kDa. Underivatized L31C migrates between the 20 kDa and 15 kDa standards, as expected for a monomer MW of ~18 330 kDa.

Figure 32:
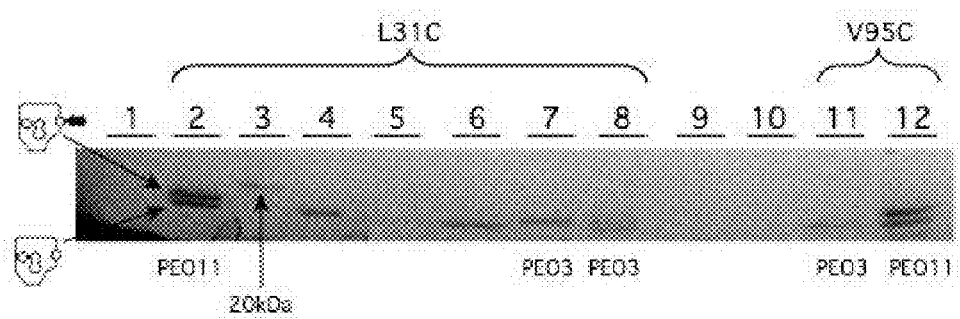
FIG. 32 shows Polyacrylamide Gel Electrophoresis (PAGE) separations of SAMA and chemically modified forms of SAMA.

In FIG. 32, a similar analysis of derivatized SAMAs is shown as in FIG. 25, except that the SAMAs were separated by electrophoresis on 4-12% Bis-TRIS gels with 3-(N-Morpholino)propanesulfonic acid (MOPS) SDS running buffer to provide greater separation between derivatized and unreacted SAMAs.

In general, higher concentrations of both reagent and SAMA, and higher molar ratios of reagent to SAMA favored derivatization.

Reagents used in preparation and assembly of SAMA and SAMA-based nanoassemblies are shown in FIG. 23. Chemical structures of the maleimide-reactive biotin- linking reagents MAL PEO3 (FIG. 23 a3) and MAL PEO11 (FIG. 23 a4), the maleimide-reactive iminobiotin-linking reagent MAL PEO3 (FIG. 23 b3), and the sulfur-reactive biotin-linking reagent, EZ-Link HPDP (FIG. 23 a2), are shown along with a schematic representation used elsewhere. The PEO-containing reagents with ethylene glycol-based chains were selected because they are more water-soluble than their aliphatic counterparts. The MAL-containing reagents contain a terminal maleimide that forms a covalent S—C bond on reaction with the cysteine sulfhydryl, while a reversible S—S bond is formed by reaction with EZ-Link HPDP. Three of the reagents, MAL PEO3 biotin and imino biotin, and EZ-Link HPDP, have ~20 atoms to span between the biotin carboxylate and the SAMA cysteine sulfur, while the MAL PEO11 reagent has ~42 intervening atoms. According to the model, the shorter reagents are suitable for linking L31C SAMA to streptavidin. The longer reagent, PEO11, was included to determine if complexation could occur.

An imino-biotin thiol-reactive biotinylation reagent (FIG. 23 b3) was developed and synthesized. Unlike biotin, the streptavidin:imino-biotin interaction is pH-dependent and offers useful options for assembly of SAMA:SAV complexes. PEO linkers provide both excellent reagent water solubility and flexibility in controlling cross linker length. The iminobiotin reagent was difficult to purify, and the initial sample was ~75% pure. Gel analysis showed that the reagent complexed with free cysteines on SAMA. This material can be purified further using supercritical chromatography.

5) Solution Assembly of SAV:SAMA Complexes

Following derivatization of L31C or V95C by covalent addition of biotin via a linker where the linker is bonded to a cysteine sulfur on a SAMA, excess and unreacted linking reagent was removed by centrifugation through a desalting column (Zeba Desalting Column, PierceNet). SAMA concentrations near 0.2 mM were achieved by dilution of a more concentrated solution with 50 mM sodium phosphate buffer pH 6.8 or by concentrating via centrifugal protein concentrators (PierceNet). The concentration of SAMA was estimated using an $A_{280}$ extinction coefficient of 2980 $M^{-1}$ $cm^{-1}$. Solutions of L31C and V95C previously derivatized by using biotin-linking reagent MAL PEO3 (FIG. 23 a3), biotin-linking reagent MAL PEO11 (FIG. 23 a4), iminobiotin-linking reagent MAL PEO3 (FIG. 23 b3), and biotin-linking reagent EZ-Link HPDP (FIG. 23 a2) were prepared in this manner.

A solution of *Streptomyces avidinii* streptavidin was prepared by dissolving lyophilized streptavidin (ProZyme) in 50 mM sodium phosphate buffer pH 6.8. Excess NaCl present in the lyophilized SAV was removed by dialysis against 50 mM sodium phosphate buffer pH 6.8. SAV concentrations of at least twice the SAMA concentration were achieved by dilution of a more concentrated solution with 50 mM sodium phosphate buffer pH 6.8 or by concentrating via centrifugal protein concentrators (PierceNet). The concentration of SAV was estimated using an $A_{280}$ extinction coefficient of 41326 $M^{-1}$ $cm^{-1}$.

Figure 26:
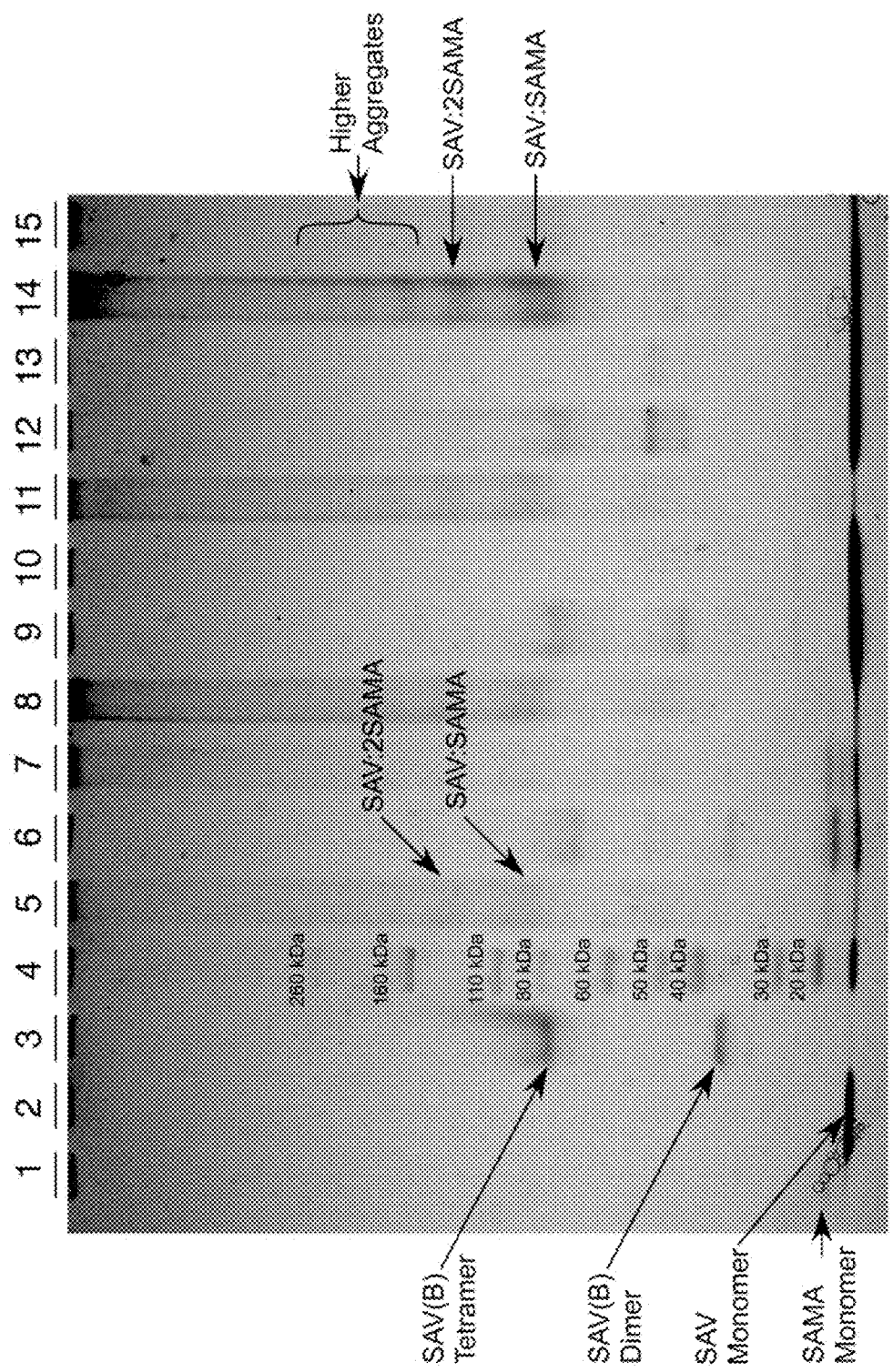
FIG. 26 shows Polyacrylamide Gel Electrophoresis (PAGE) separations of SAMA: streptavidin complexes.

Streptavidin (herein, SAV) and SAMA solutions were mixed to allow formation of SAV:SAMA and SAV:2SAMA complexes. Streptavidin was added to the individual solutions of derivatized V95C and L31C in 2 to 4 aliquots until 2- to 3-fold molar excesses were achieved. Total reaction volumes ranged from 75 to 800 μL. Each mixture was allowed to react for at least 2 hours. Analyses by PAGE show formation of the SAV:SAMA and SAV:2SAMA complexes (FIG. 26). FIG. 26 shows a 4-12% Tris-glycine PAGE analysis of several mixtures where solutions of derivatized L31C and derivatized V95C were combined with solutions of SAV. Samples were heated at 70° C. for 10 min prior to loading on the gel. The Tris-glycine gel running buffer (Invitrogen) contained 0.1% sodium dodecyl sulfate (SDS). No reducing agents were included in the running buffer. Under these conditions, the streptavidin biotin tetramer (SAV(B)) is stable, as shown in FIG. 26 lane 3, but unliganded streptavidin is not, as evidenced by a single band of about 14 kDa in FIG. 26 lane 2. Uncomplexed SAMA is also dissociated under these conditions, as evidenced by a single band near 18 kDa in FIG. 26 lane 1. SAV:SAMA complexes migrate as diffuse bands of molecular weights higher than that of the SAV(B) tetramer. As indicated in FIG. 26 lane 14 SAV:SAMA (SAV:L31C derivatized with biotin-linking reagent MAL PEO11 (FIG. 23 a4)) and SAV:2SAMA (SAV:2L31C biotin-linking reagent MAL PEO11 (FIG. 23 a4)) complexes are observed, for example, SAV:SAMA and SAMA:SAV:SAMA complexes, along with higher molecular weight aggregates. Similarly, FIG. 26 lane 5 shows SAV in complex with V95C derivatized with biotin-linking reagent MAL PEO11 (FIG. 23 a4).

Figure 33:
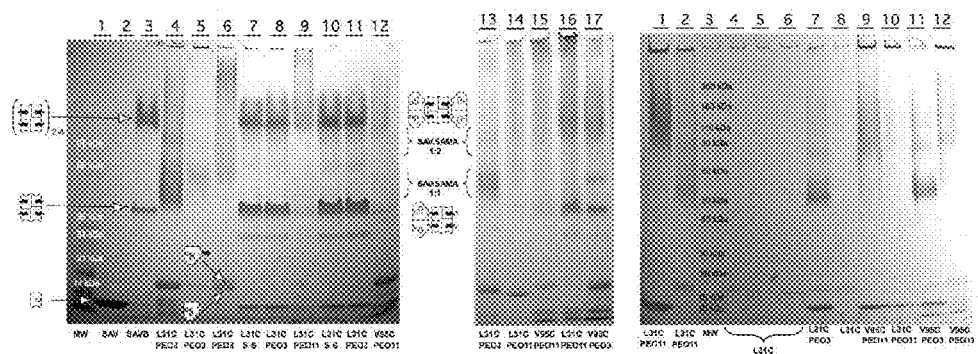
FIG. 33 shows results from SDS PAGE analysis of SAMA: SAV complexes.

We established optimal conditions for complex formation. One issue involved the existence of stable dimeric, trimeric and higher aggregates of streptavidin in most preparations (Sano & Cantor 1990b; Kurzban et al. 1991; Waner et al. 2004). We found the aggregates of liganded and unliganded streptavidin stable to heating at 70° C. and the liganded streptavidin aggregates also stable in SDS PAGE running buffers (FIG. 33). We exploited these features in a gel assay to help assess complexation in both denaturing and native gels (see FIG. 33). The left and middle panels of FIG. 33 show complexes of SAMA and streptavidin analyzed on 4-12% Bis-TRIS gels with 3-(N-Morpholino)propanesulfonic acid (MOPS) SDS running buffer. Before analysis, samples were prepared as described above then treated with excess biotin to stabilize any unliganded SAV. Prior to loading, samples were heated at 70° C. for 10 minutes together with reducing agent and SDS. Lanes are numbered on the top and the sample identity (SAMA and linking reagent) given below. Mark12 MW standards (Invitrogen) are in Lane 1. Under these conditions streptavidin is denatured (Lane 2) but the streptavidin: biotin tetramer remains folded and the higher order aggregates remain associated (Lane 3). Schematics on the left indicate the electrophoretic mobilities of control molecules including the streptavidin monomer, derivatized and underivatized SAMA monomers, the streptavidin:biotin tetramer and higher order aggregates of the streptavidin:biotin tetramer. Brackets and schematics on the right indicate probable electrophoretic mobilities of SAMA:SAV complexes. Definition of the complexes by MALDI MS is envisioned, so that gels can be used as a laboratory screen of complex formation. Bands for complexes are broadened, because while the streptavidin:biotin is not denatured under these conditions, SAMA, initially bound as a dimer, may be denatured into monomers during sample preparation and electrophoresis. Higher molecular weight SAV:SAMA complexes, presumably formed by SAMA bridging streptavidin tetramers are evident at the tops of Lanes 6 & 9. Changes in gel patterns for the lanes with the same SAMA and linker labels reflect differences in sample preparation conditions. The right panel shows analysis of similar samples on the same gel system except that excess biotin was not added prior to electrophoresis. Lanes are numbered on the top, and SAMA and linkers labeled at the bottom. Molecular weight standards (Novex Sharp, Invitrogen) are in Lane 3. Comparison of Lanes 12 and 10 on the right with lanes 12 and 9, respectively, on the left demonstrates how complete formation of the streptavidin: biotin complex changes and clarifies the gel pattern. In the left gel, the SAV:SAMA complex is better defined for V95C with the PEO11 linked biotin. In the left gel, Lane 9 shows a distinct band for high MW aggregates that appear along with the streptavidin:biotin tetramer while the same sample appears only as a very broad band in Lane 10 on the right. It is also informative to compare Lane 7 on the right with Lane 5 on the left to illustrate how the mixture of the streptavidin: SAMA complexes having open biotin binding sites such as the 1:1 complex and the 1:2 SAV:SAMA complexes gives rise to more bands than samples with excess biotin. The excess bands presumably arise because of the overwhelming tendency for fully liganded streptavidin:biotin tetramers to form in the presence of mixed ligation species as also observed by Sano & Cantor 1990, Gonzalez et al. 1997, and others.

We created about ~100 mg of purified L31C SAMA and cell paste for V95C SAMA. We generated MJ0577 SAMA dimers with no bound ATP and with free sulfhydryls on the cysteines, with sulfhydryl groups linked to biotin, and with sulfhydryl groups linked to imino-biotin.

Complexes using both the MAL PEO3 and MAL PEO11 reagents were assembled using two SAMAs, L31C and V95C. In general and in agreement with the molecular model, the shorter PEO3 linkers produced clearer patterns corresponding to 1:1 and 2:1 SAMA:SAV complexes, while as anticipated from the modeling some higher molecular weight species formed with the PEO11 reagent.

The Biotin-Azido-ATP can be reacted to generate an Azido-ATP linked SAMA and the modified SAMA product can be characterized. The ATP binding sites on SAMA allow for versatility in nanostructure assembly. Range-finding experiments with 2-Azido ATP reagents coupled to fluorescent reporting groups can be performed to establish optimal reaction conditions prior to using the more expensive photo-ATP biotin linked reagents (FIG. 29). Conditions for reaction with the Azido-ATP biotin reagent can be monitored by MS analyses to determine extent of reaction. Unreacted SAMAs can be separated by affinity chromatography or by differential heating, because ligation may induce changes in thermal stability between reacted and unreacted SAMAs. For example, this approach can be tested with both SAMA L31C and SAMA V95C. Iminobiotin reagents can be purified, for example, by supercritical chromatography.

Figure 31:
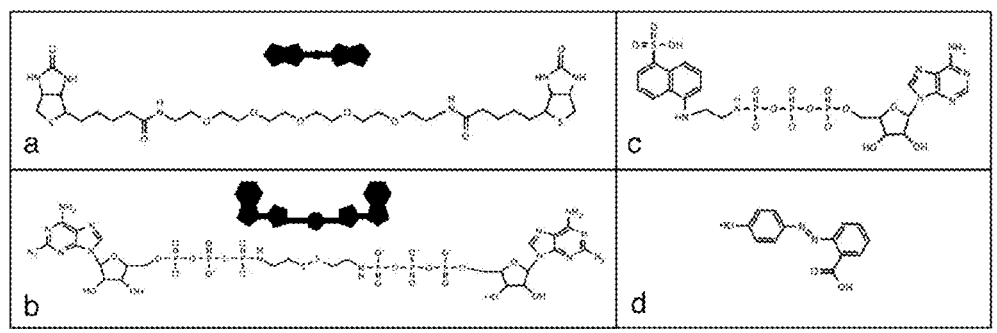
FIG. 31 shows several designed reagents for SAV:SAMA based nanofabrication.

FIG. 31 shows several designed reagents for SAV:SAMA based nanofabrication. Part a shows a PEO-based di-biotin crosslinker and Part b shows a linked di-Azido-ATP crosslinker. Part d shows a biotin displacement detection dye (2-(4-Hydroxyphenylazo)benzoic acid, HABA, Pierce). Part c shows a fluorescently-labeled ATP for monitoring ATP binding (ATP[g]-1,5-EDANS, ALT BioScience).

6) Assembly of a SAV:SAMA Complex on a Solid Support

Following derivatization of SAMA by covalent addition of biotin via a linker where the linker is bonded to a cysteine sulfur on SAMA so that the biotin heterocycle is solvent exposed and available for interaction with SAV, excess and unreacted linking reagent is removed by centrifugation through a desalting column (Zeba Desalting columns, PierceNet). A solution of *Streptomyces avidinii* streptavidin is prepared by dissolving lyophilized streptavidin (ProZyme) in 50 mM sodium phosphate buffer pH 6.8. Excess NaCl in the SAV solution is removed by dialysis against 50 mM sodium phosphate buffer pH 6.8. SAMA is bound to a solid matrix known to mimic nucleotides or a resin of immobilized ATP. Resins such as Cibacron Blue (GE Life Sciences) and ProteoEnrich ATP-Binders (EMD Biochemicals) bind SAMA via the SAMA ATP binding sites. The SAMA in complex with the solid matrix is separated from unbound SAMA by centrifugation. The SAMA in complex with the solid matrix is resuspended in a solution of 50 mM sodium phosphate buffer pH 6.8. Streptavidin is then aliquoted into the suspension of SAMA in complex with the solid matrix and the reaction allowed to proceed for at least 2 hours. Any excess SAV solution is separated from the SAV:SAMA complex bound to the solid matrix via the SAMA ATP binding sites by centrifugation. The SAV:SAMA complex bound to the solid matrix via the SAMA ATP binding sites is resuspended in a solution of 50 mM sodium phosphate buffer pH 6.8. Addition of ATP (or nucleotide analog) to the suspension releases the SAV:SAMA complex from the solid matrix.

SAMA yields during development of purification protocols were approximately 2-4 mgs per gm of wet cell paste obtained from 16 liter fermentations.

Expression vectors and systems were developed for 2 SAMA variants using heterologous expression in *E. coli* from 16 liter fermentations that gave expression levels of about 2-4 mgs SAMA per gm of wet cell paste after purification. This was an efficient approach for performing gene design, sequence verification, vector production and protein expression.

The ability to achieve a substantial purification of the thermally stable SAMAs from the proteins in the background expression organism is advantageous. Recovery after the heating step can be optimized by determining the melting temperature of each SAMA protein as described above, then experimenting with heating protocols of the cell lysate within a few degrees of the SAMA Tm to determine conditions of optimum recovery. Structurally intact SAMA may be entrained in thermally denatured *E. coli* proteins during the heating step. For example, an ATP-fluorescent dye conjugate can be used to detect SAMA bound to the *E. coli* protein precipitate obtained after the heating step. The Butyl Sepharose FF and CM Sepharose chromatography steps performed after the initial heat fractionation are optimized. The SAMAs bind with high affinity and elute near the ends of the applied elution gradients. The extinction coefficient at A280 (or the maximum absorbance wavelength in that region) for each SAMA can be determined, so that in subsequent reactions reaction stoichiometry can be accurately controlled. An ESI-MS QC procedure for release of protein batches can be developed to ensure protein amino acid identity and existence of completely reduced cysteine sulfhydryls.

EDTA can be used to prevent metal-promoted oxidation of free cysteine during SAMA isolation should ESI MS studies show that cysteine oxidation occurs. Several reagents have only limited solubility in aqueous solution. Ratios of SAMA and linking reagents in reaction mixtures and acceptable solvent conditions can be evaluated. SAMA is fully stable in 20% DMSO solutions. Other organic solvents (e.g. DMF) can also be evaluated.

The fidelity of nanostructure assembly can be dependent on the purity and homogeneity of the molecular components. Consequently, it can be important to achieve good separation of unreacted and derivatized SAMAs. If experiments in PAGE gels run at different pHs show differences in the mobility of fully reacted SAMAs and partially reacted products, this may be the basis for an empirical ion-exchange chromatographic separation approach using the appropriate resin and buffer conditions. Alternatively, analyses of reaction products using ESI MS can be used to show more or less exactly which impurities are present and a more focused approach applied. For example, unreacted cysteine residues can be removed through chromatography using thiol-affinity resins. Alternatively, cysteine residues can be rendered unreactive through oxidation or unanticipated side reactions. Using ESI MS data as a guide, adducts can be eliminated by removal of a reactant (e.g. removal of b-mercaptoethanol (BME) would prevent formation of BME adducts). The formation of unreacted sulfinic acids can be avoided by careful elimination of oxygen from reaction mixtures or they can be enzymatically reduced to thiols (Biteau et al. 2003; Woo et al. 2003).

The SAMAs incorporating biotin and Azido-ATP linkers are completely novel constructs providing unique capabilities for controlled nanostructure assembly.

Figure 34:
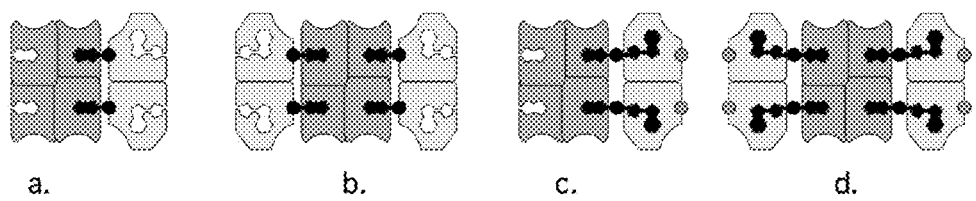
FIG. 34 shows several SAMA:SAV complexes.

We envision preparing SAMA:SAV complexes for commercialization. Several SAV:SAMA complexes are presented in FIG. 34. These include a 1:1 sulfhydryl-biotin-linked SAV: SAMA complex (FIG. 34a), a 1:2 sulfhydryl-biotin-linked SAV:SAMA complex (FIG. 34b), a 1:1 Azido-ATP-linked SAV:SAMA complex (FIG. 34c), and a 1:2 Azido-ATP-linked SAV:SAMA complex (FIG. 34d).

FIGS. 34a and 34b show the structures of the 1:1 and 1:2 biotin-linked SAV:SAMA complexes. We have demonstrated the formation of these complexes together with appearance of some higher MW aggregates (fewer high-order aggregates formed when short PEO3 linkers were used). MALDI or ESI MS can be used to characterize the species. For example, an iminobiotin column can reversibly capture the 1:1, but not the 1:2 biotin-linked SAV:SAMA complex. FIGS. 34c and 34d show the structures of the 1:1 and 1:2 Azido-ATP-linked SAV:SAMA complexes. Spectroscopic methods can be used to monitor SAV:SAMA complex formation using a dye displacement approach and using DLS alone or combined with static light scattering. Formation of the biotin linked complex can be followed spectroscopically (Green 1965) by measuring the displacement of the dye (2-(4-Hydroxyphenylazo) benzoic acid) (HABA, Table 31d (Pierce)). The HABA dye binds to streptavidin to produce a yellow-orange colored complex which absorbs at 500 nm. Free biotin displaces the HABA dye and causes the absorbance to decrease. A standard curve can be established using the free biotin to estimate the number of moles of biotin incorporated complex formation. The availability of a number of easily synthesized HABA analogs with a graded range of streptavidin binding constants ranging from HABA Kd~$10^{-6}$ to Kd~$10^{-9}$ M can extend the flexibility of this approach (Weber et al. 1994).

Figure 35:
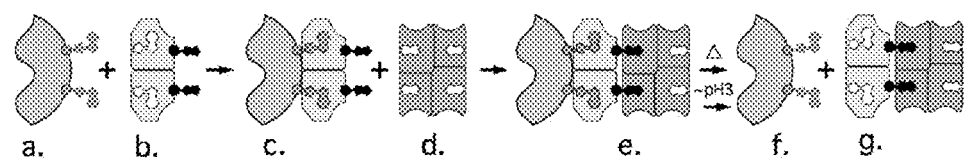
FIG. 35 shows a resin-based synthesis scheme for a biotin-linked 1:1 SAV:SAMA complex.
Figure 36:
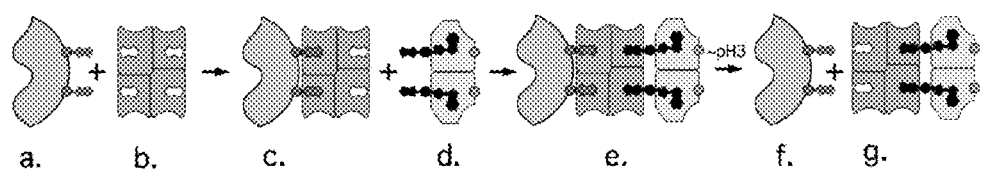
FIG. 36 shows a resin-based synthesis scheme for an ATP-linked 1:1 SAV:SAMA complex.

The minimum number of components offering the maximum flexibility can be used for nanostructure assembly and efficiency of synthesis. Some flexible components are the 1:1 SAV:SAMA complexes (FIGS. 34a and 34c). 1:1 SAV: SAMA complexes can be synthesized in high yield on resin-bound templates. FIGS. 35 and 36 illustrate processes for improving the yield and homogeneity of SAV:SAMA complexes. Both schemes involve the initial immobilization of either ATP (FIG. 35) or imino-biotin (FIG. 36) to allow the sequential assembly of SAV and SAMA components to the immobilized resin, followed by a step to release the SAV: SAMA complex from the resin. In the case of the iminobiotin-linked 1:1 SAV:SAMA complex combinations of organic solvents, heat treatment, and acid conditions can be used to release the complex (FIG. 35g). In the case of the Azido-ATP linked 1:1 SAV:SAMA complex we can exploit the pH-dependent binding of iminobiotin as a method to release the complex from the support resin. Resin immobilization brings several advantages to synthesis including ability to drive reaction equilibria to completion using mass action, and a facilitated ability to purify reaction products from reagents. Availability of a number of HABA analogs with a range of streptavidin binding constants can extend the flexibility of this approach (Weber et al. 1994).

A resin with ATP immobilized though the g-phosphate is suitable for capture of SAMA, and experiments can guide selection of the best resin for immobilization of SAMA through the ATP sites. In addition to the g-phosphate, the N6 position of the adenine ring can be exposed in the ATP-ligated MJ0577 structure, suggesting that resins with ATP immobilized through the N6 atom (Jena Bioscience) can be useful immobilization agents. Additional versions of a reagent such as the MAL PEO3 iminobiotin linking reagent with different PEO linker lengths or linkers with constrained geometries, can be made to meet geometric or steric requirements.

The SAV:SAMAs complexes are completely novel constructs providing unique capabilities for controlled nanostructure assembly.

The SAMA ATP binding site can be modified to enhance or alter its binding properties, surface features can be engineered for an improved complimentary fit with streptavidin, and fusion proteins with "reporter domains" or other functionalities can be developed.

Crystals can be prepared and structures of purified SAMA and SAV:SAMA complexes can be determined. Although molecular modeling approaches together with available crystal structures can be used to initially develop models of second-generation SAMAs, we envision carrying out crystal structure determinations in parallel. Target structures include SAMA structures with ATP analogs, post reaction with Azido-ATP, and various SAMA:SAV complexes. Owing to the overall stability of the SAMA proteins (Tm >75° C.), crystals of well-purified materials should be formed. SAMA variants can be purified and screened for crystallization conditions, X-ray data collection, and structure determination, for example, using an X-ray suite including crystallization robotics and a rotating anode X-ray generator. Structure solution can proceed rapidly using molecular replacement methods.

SAMAs with modified ATP binding sites can be engineered. As illustrated in FIG. 29, ATP forms a number of close interactions in the native MJ0557 structure. Harsh conditions were tested to insure the complete removal of any bound ATP to SAMAs as isolated. If ATP is extremely tightly bound to SAMA and removal through alteration of solvent conditions causes protein denaturation, a SAMA with reduced ATP binding affinity can be engineered. A binding site that better accommodates the Azido-ATP SAMA photo products can be engineered, although, as shown in FIG. 29, it appears as if the reaction product of the 2-Azido ATP might be accommodated in the ATP binding site of MJ0557. If biophysical results suggest that modifications of the ATP site are required, modeling shows that the 2-azidoadenosine analog can be more readily accommodated in the ATP-binding pocket if Pro11 is changed to Gly, and Ile112 is changed to Ala or Val. The SAMA nucleotide binding affinity can be altered from ATP to another other nucleotide. Molecular modeling tools used to build X-ray crystal structure models (A. Jones xray.bmc.u-u.se; www.ccp14.ac.uk/solution/macromolecular_software) can be used and complemented by energy minimization methods (Cornell et al. 1995). There have been significant advances in protein modeling with the advent of methods that employ various types of heuristic potentials and large-scale statistical sampling methods. Examples range from modeling novel ligand binding sites (e.g. Allert et al. 2004) to predictions of protein folding (e.g., Das & Baker 2008). Heuristic approaches for a number of different protein modeling tasks including definition of b-sheet geometry have been developed (Salemme 1982), using substructure libraries to fit protein electron density maps (Finzel et al. 1990), and repacking protein interiors using side chain rotamer libraries incorporating sequence and secondary structure-dependant amino acid side-chain rotamer probability distributions (Wendoloski & Salemme 1992). These approaches can also be used in a modeling context, particularly if combined with an efficient sampling algorithm, and have been implemented in various forms in crystallographic modeling software packages.

The natural steric and electrostatic complementarity between streptavidin and MJ0557 is good. However, for at least some advanced 2D and 3D nonstructural applications the complementarity of these surfaces can be improved to insure the preservation of geometrical accuracy over long distances. A surface side chain backbone loop/rotamer search with a highly constrained relative orientation between SAMA and streptavidin can be done. Conventional modeling approaches can be complemented by applying large-scale statistical sampling methods.

Figure 37:
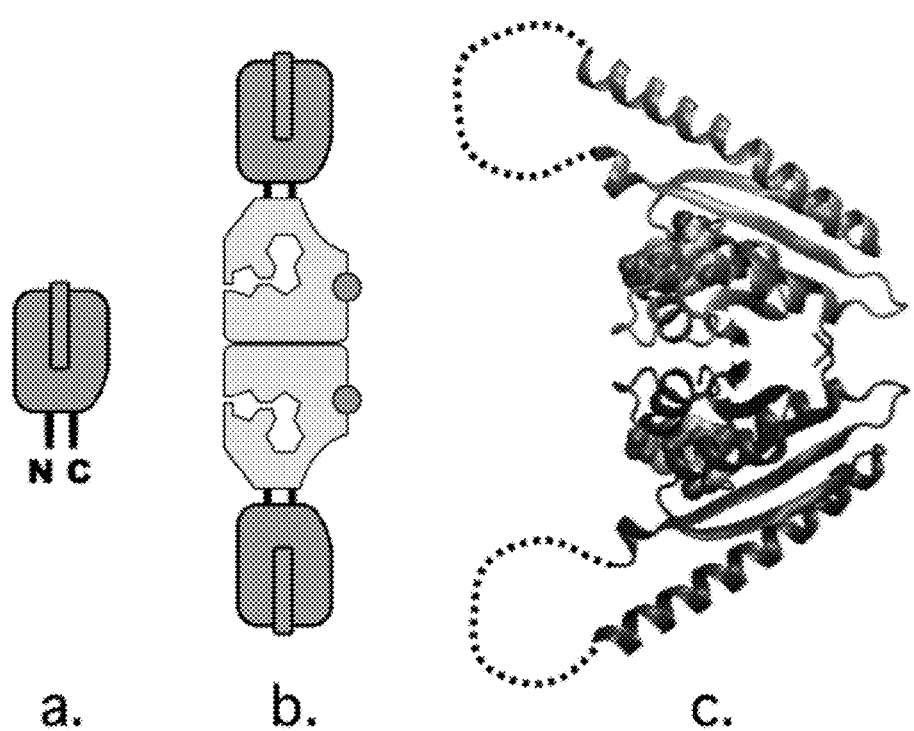
FIG. 37 shows a SAMA with functionalized loops.

SAMAs with functionalized loops, as shown in FIG. 37, can be engineered. Part a shows a ligand binding or other functional domain where the N and C polypeptide termini are situated proximally in the native structure. Part b shows a SAMA based on the MJ0577 protein where ligand binding domains have been fused to the SAMA subunits, essentially as inserted loops. Part c shows a ribbon diagram of the MJ0577 crystal structure, where the loop connecting Residues 48 to 65 (here shown by a dotted line) is disordered in both subunits. As illustrated in FIG. 37, each monomer of the MJ0557 structure has 2 a-helices connected by a loop that forms "wings" on the dimeric structure. The interconnecting loop is disordered in the MJ0557 crystal structure and in those of some orthologs, thus this could be a position for insertion of a functional protein domain. Some proteins whose amino and carboxy polypeptide chain termini are relatively closely situated in their native structures (thus lending them to insertion into the SAMA sequence as an extended loop) include green fluorescent protein (pdb code 1kyr) and relative, aequorin (pdb code: 1uhh), and cytochrome b562 (pdb code: 256b), a heme containing protein.

Destabilizing effects on the structure from the introduction of point mutations or loops associated with functional modifications can be minimized High-throughput and efficient biophysical measurements, including temperature-dependent fluorescence and dynamic light scattering, can be used to monitor protein stability and conformation and focus necessary alternative sequence or process changes.

7) "Streptavipol" for Branched Nanoassembly Construction

Figure 38:
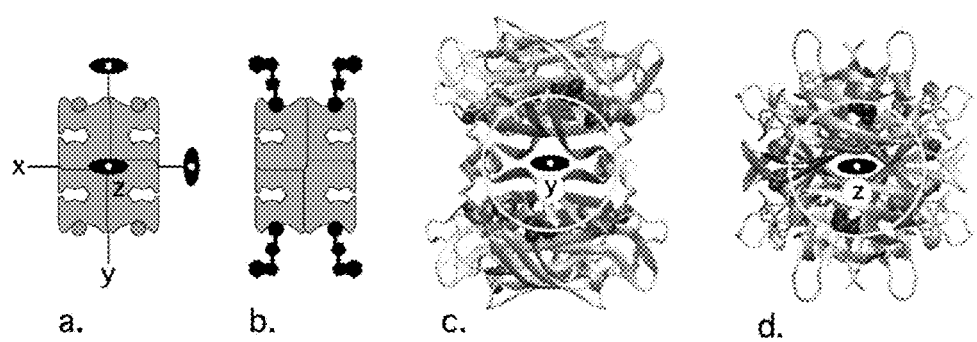
FIG. 38 shows a modified streptavidin (Streptavipol) allowing branched nanostructure formation.

A modified streptavidin "Streptavipol" can be engineered for branched nanoassembly construction. Streptavidin is a tetramer with D2 symmetry with 4 biotin-binding sites that basically align the bound biotin groups parallel to one of the molecular dyad symmetry axes. Part a of FIG. 38 shows a schematic of the D2-symmetric streptavidin tetramer. Part b shows modified versions substituted with Azido-ATP groups, providing orthogonal SAMA binding capability. Part c shows a projection down the streptavidin "y" dyad axis. The circle in parts c and d shows loci of symmetrically situated amino acids that are separated by 20.5 Å and is complementary to the ATP-binding sites on SAMA (or equivalently, the biotin binding sites on streptavidin). Part d shows representative alternatives for connection sites along the streptavidin "z" dyad axis. Certain residue positions (shown in space-filling representation at the front of the molecules at the top and bottom of the circle in parts c and d) are compatible with the formation of planar 2D and regular 3D lattices interconnected with streptavidin struts. Formation of the "Streptavipol" structure includes introducing one or two cysteine residues into each amino acid chain of each subunit or monomer (streptavidin has no naturally occurring cysteine residues), so that the modified Streptavpol can bind SAMAs along dyad axes not "occupied" by the preexisting biotin groups. FIG. 38b shows that most assembly flexibility is gained when the newly introduced cysteine groups are derivatized with Azido-ATP groups, as this allows "orthogonal" attachment of biotin-linked and Azido-ATP-linked SAV:SAMA complexes to the Streptavipol. That, is the Azido-ATP groups can be linked, for example, covalently bonded, to the cysteine groups. We have developed a simple geometrical approach to identify residues on nodes that can be sites of site-specific modification to introduce biotin functionalization sites (e.g., cysteine residues) on proteins that are geometrically complementary to the biotin binding sites on streptavidin. As shown in FIGS. 38c and 38d, there are several solutions for streptavidin. Substitution can be at groups that are sterically masked from direct interaction in solution, so as to avoid uncontrolled Streptavipol tetramer polymerization through S—S bond formation.

Streptavipol can be expressed, purified, and characterized. Streptavidin and many variant forms have been expressed in E. coli at high levels (Thompson & Weber 1993; Sano et al. 1995; Wu & Wong 2005). Gene synthesis and construction of expression vectors can be conducted. Purification protocols that rely on the pH-dependence of imino-biotin affinity (Suter et al. 1988; Sano & Cantor 1990a; Sano et al. 1995) can be used. Following an initial scaleup at the 15-20 liter level, we can employ protocols that rely on the intrinsic thermal stability of unliganded streptavidin (Tm ~75° C., Weber et al. 1992) and/or the pH-dependence of imino-biotin binding affinity (Green 1975) to purify the protein. For example, a procedure can involve a heating step followed by binding to an imino-biotin affinity column, followed by a low pH wash to elute the purified Streptavipol.

Figure 39:
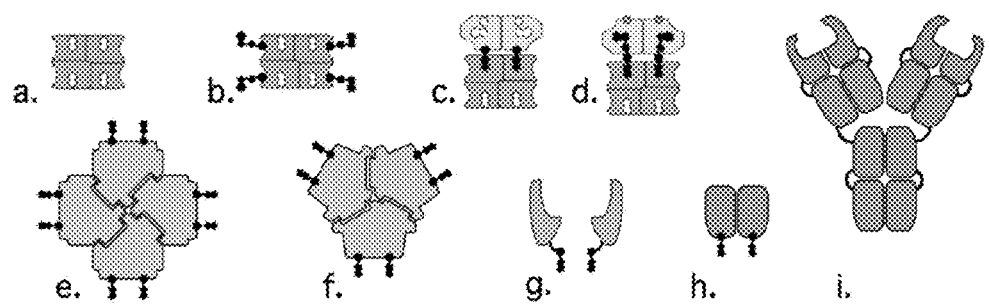
FIG. 39 shows several protein components for nanoassembly fabrication.

We term several basic architectural building blocks for nanoassembly "struts" and "nodes". Struts are basically linear structural elements, while nodes are generally polymeric protein structures with Cn rotational or 3-dimensional point group symmetry. Struts can incorporate streptavidin, a tetramer with D2 symmetry that incorporates 4 high-affinity ($K_d$~$10^{-14}$) biotin binding sites oriented approximately as the legs of an "H". Nodes can be site-modified proteins with plane or point group symmetry (typically protein multimers) that incorporate covalently bound biotin groups that are pair-wise-complementary to the biotin binding sites on streptavidin, and allow the assembly of 1D, 2D, or 3D structures with defined geometrical organization. Examples of components are shown in FIG. 39. Part a shows streptavidin (SAV), part b shows a modified streptavidin, Streptavipol, functionalized with azido-ATP groups, part c shows a biotin-linked 1:1 SAV:SAMA complex, part d shows an azido-ATP-linked 1:1 SAV:SAMA complex, part e shows a C4 symmetric node functionalized with biotin groups, part f shows a C3 symmetric node functionalized with biotin groups, part g shows biotinylated Protein A or Protein G (these protein bind specifically to the Fc regions of immunoglobulins), part h shows an dimeric protein of arbitrary function functionalized with biotin, and part i schematically shows an immunoglobulin molecule. Complexes c and d were developed.

Figure 40:
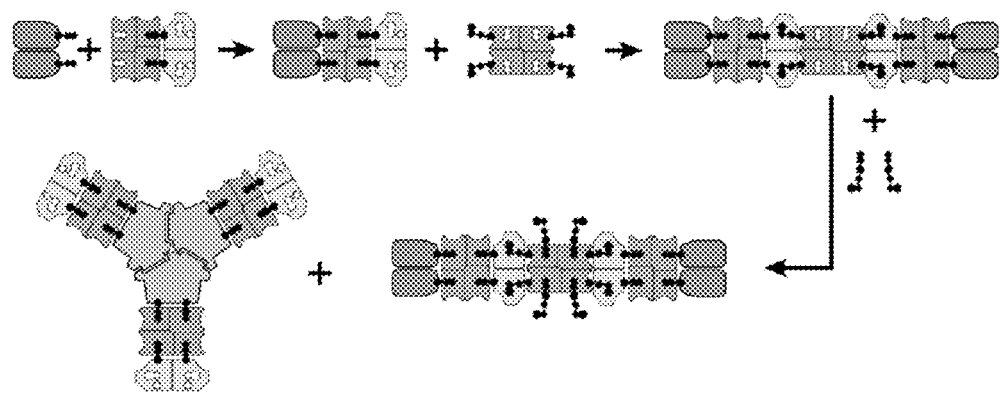
FIG. 40 shows assembly of a functionalized strut component.
Figure 41:
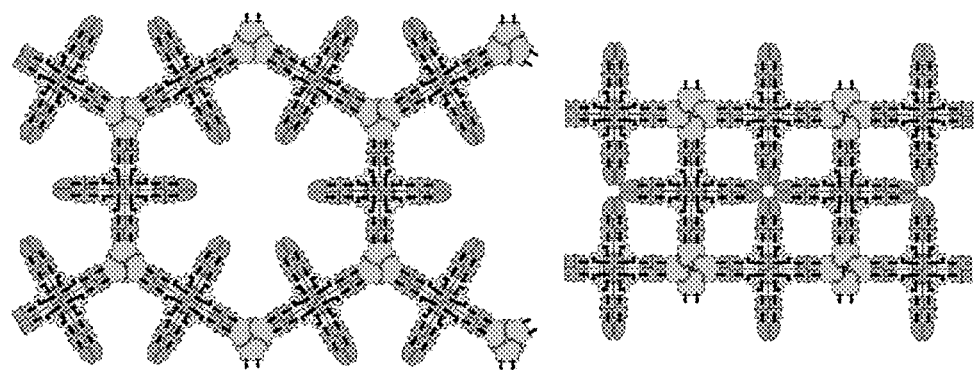
FIG. 41 shows 2D hexagonal and square nanolattices.

Examples of 2D structures incorporating streptavidin containing struts and Cn symmetric nodes are shown in FIG. 40. Such structures can be functionalized by providing various means of attachment for additional biomolecules (e.g. antibodies, as described below) to struts and nodes. In other cases, "function" can be an intrinsic property of node proteins that, e.g., incorporate prosthetic groups or are themselves enzymes. The Streptavidin Macromolecular Adapter (SAMA) can effectively function as a chemical protecting group for 2 of the biotin binding groups on streptavidin. Functionalized SAMAs, SAV:SAMA complexes, and a modified streptavidin "Streptavipol" can allow the assembly of struts that are functionalized through the incorporation of additional proteins. The step-wise assembly of a functionalized strut incorporating Streptavipol is shown in FIG. 40. The strut component incorporates a central streptavipol component functionalized with azido-ATP groups that can bind to ATP binding sites on Cn nodes incorporating 1:1 SAV:SAMA complexes, to form 2D lattices (FIG. 41). FIG. 41 shows 2D hexagonal and square nanolattices composed of biotinylated Cn-symmetric nodes and streptavidin struts incorporating components shown in FIG. 39. The lattices are "functionalized" through attachment of dimeric proteins (FIG. 39h) to the streptavipol struts interconnecting the nodes. Such structures can be constructed on self assembling monolayers where node proteins are anchored through their polypeptide chain termini to a lipid soluble component, allowing 2-dimensional diffusion of node proteins during the assembly process.

Figure 42:
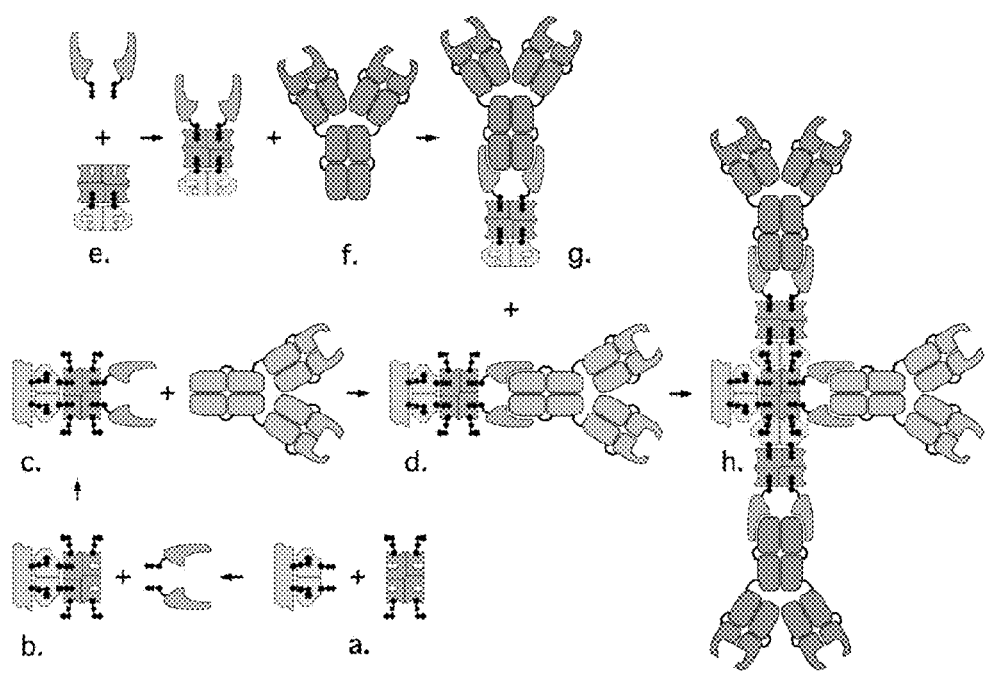
FIG. 42 shows assembly of an immobilized arrangement of antibodies.
Figure 43:
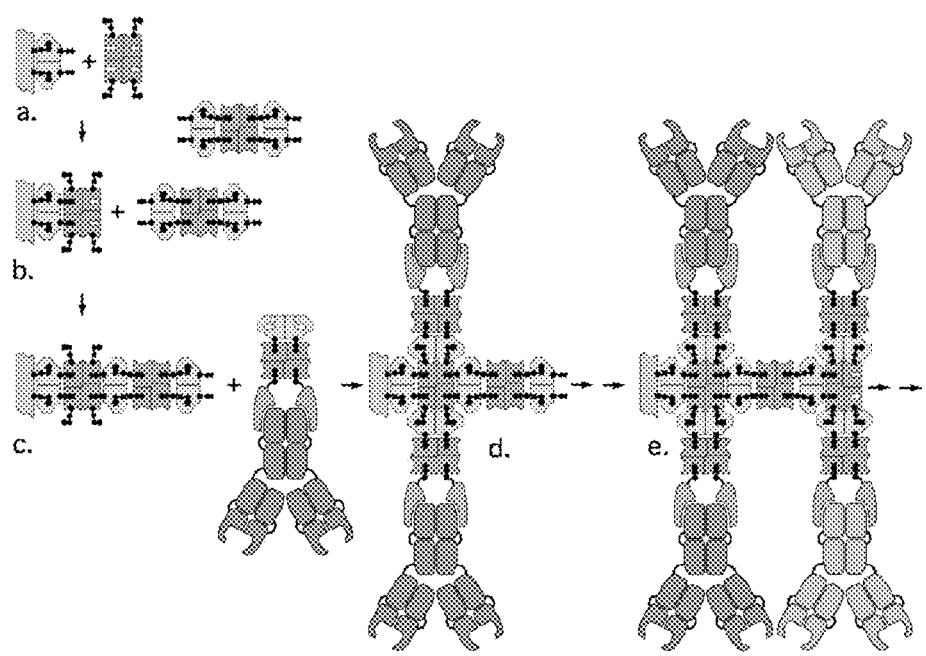
FIG. 43 shows assembly of an immobilized linear arrangement of antibodies.

Functionalized lattice structures such as those illustrated in FIG. 41 can allow investigation of a host of new biomimetic materials and functional applications. Examples of applications of our technology include facilitation of the assembly of diagnostic devices and sensors incorporating multiple molecular detectors whose relative geometry and stoichiometry are precisely controlled. An advantage of such structures is that they potentially offer much greater detection sensitivity and specificity than a detection system incorporating a single antibody (or single-chain Fv, etc.), since two different antibodies can be geometrically constrained, so that they potentially interact with the same antigen simultaneously. For example, FIGS. 42 and 43 illustrate antibody-based biosensor structures assembled of surfaces (e.g., through thiol-reactive azido-ATP reagents reacting with a thiol-functionalized metal surface) incorporating two different monoclonal antibodies recognizing different epitopes of the same antigen. That is, FIG. 42 shows the assembly of an immobilized arrangement of two different (monoclonal) antibodies. The precise geometry and stoichiometry of such arrays is expected to result in enhanced antigen detection affinity and specificity. FIG. 43 shows the assembly of an immobilized linear arrangement of two different antibodies. Thus, use of the nanoscale components described herein can enable improvements in detection sensitivity and specificity.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

References

Blum A S, Soto C M, Wilson C D, Cole J D, Kim M, Gnade B, Chatterji A, Ochoa W F, Lin T, Johnson J, Ratna B R "Cowpea mosaic virus as a scaffold for 3-D patterning of gold nanoparticles" *Nano Lett* (2004) 4:867.

Blum A S, Soto C M, Wilson C D, Brower T L, Pollack S K, Schull T L, Chatterji A, Lin T, Johnson J E, Amsinck C, Franzon P, Shashidhar R, Ratna B R "An engineered virus as a scaffold for three-dimensional self-assembly on the nanoscale" *Small* (2005) 1:702.

Cantor, C R, et. al., U.S. Pat. No. 4,839,293—DNA encoding streptavidin, streptavidin produced therefrom, fused polypeptides which include amino acid sequences present in streptavidin and uses thereof (1989)

Castro G R, Knubovets T "Homogeneous biocatalysis in organic solvents and water-organic mixtures" *Crit Rev Biotechnol* (2003) 23:195-231.

Chatterji A, Ochoa W F, Paine M, Ratna B R, Johnson J E, Lin T "New addresses on an addressable virus nanoblock; uniquely reactive Lys residues on cowpea mosaic virus" *Chem Biol* (2004) 11:855.

Chatterji A, Ochoa W F, Ueno T, Lin T, Johnson J E "A virus-based nanoblock with tunable electrostatic properties" *Nano Lett* (2005) 5:597.

Cherny D I, Fourcase A, Svinarchuk F, Nielson P E, Malvy C, Delain E "Analysis of Various Sequence-Specific Triplexes by Electron and Atomic Force Microscopies" *Biophysical J* (1998) 74:1015-1023.

Eigler D M, Schweizer E K "Positioning single atoms with a scanning tunnelling microscope" *Nature* (1990) 344:524-526.

Falkner J C, Turner M E, Bosworth J K, Trentler T J, Johnson J E, Lin T, Colvin V L "Virus crystals as nanocomposite scaffolds" *J Am Chem Soc* (2005) 127:5274.

Fitzpatrick P A, Steinmetz A C U, Ringe D, Klibanov A M "Enzyme Crystal Structure in a Neat Organic Solvent" *Proc Nat Acad Sci USA* (1993) 90:8653.

Gonzalez M, Bagatolli L A, Echabe I, Arrondo J L R, Argarana C E, Cantor C R, Fidelio G D "Interaction of Biotin with Streptavidin" *J Biol Chem* (1997) 272:112288-11294.

Goshorn, S G et al., U.S. Pat. No. 7,144,991—Streptavidin expressed gene fusions and methods of use thereof (2006)

Green N M "A Spectrophotometric Assay for Avidin and Biotin Based on Binding of Dyes by Avidin" *Biophys J* (1965) 294:23c-24c.

Green N M "Avidin" *Adv Prot Chem* (1975) 29:85-133.

Green N M "Avidin and Streptavidin" *Meth Enzymol* (1990) 243:51-67.

Gupta M N, Roy I "Enzymes in organic media: Forms, functions and applications" *Eur J Biochem* (2004) 271:2575-2583.

Hartmann E, Enachescu M, Radojkovic P, Schwartzkopff M, Koch F "Imaging and manipulation properties of nanoparticles in scanning tunneling microscopy" *Nanotechnology* (1996) 7:376-380.

Hla S W, Rieder K H "STM Control Of Chemical Reactions: Single-Molecule Synthesis" *Annu Rev Phys Chem* (2003) 54:307-309.

Hofmann K, Wood S W, Brinton C C, Montibeller J A, Finn F M "Iminobiotin affinity columns and their application to retrieval of streptavidin" *Proc Natl Acad Sci USA* (1980) 77:4666-4668.

Jones A "O" www.bioxray.dk/~mok/o-files.html.

Kopetzki E, et. al. U.S. Pat. No. 5,672,691—Recombinant core streptavidin (1997)

Lawrence M C, Colman P M "Shape complementarity at protein/protein interfaces" *J Mol Biol* (1993) 234:946-950.

Lee K B, Park S, Mirkin C A, Smith J C, Mrksich M "Protein Nanoarrays Generated By Dip-Pen Nanolithography" *Science* (2002) 295:1702-1705.

Liu G Y, Xu S, Qian Y "Nanofabrication of Self-Assembled Monolayers Using Scanning Probe Lithography" *Nanotechnology* (1996) 7:376-380.

Liu G Y, Amro N A "Positioning protein molecules on surfaces: A nanoengineering approach to supramolecular chemistry" *Proc Nat Acad Sci* (2002) 99:5165-5170.

Loo J A, Edmonds C G, Udseth H R, Smith R D "Effect of reducing disulfide-containing proteins on electrospray ionization spectra" *Anal Chem* (1990) 62:693-698.

Loo J A, Kilby G W "Electrospray Ionization Mass Spectrometry of Peptides and Proteins" in Applied Electrospray Mass Spectrometry (B N Pramanik, A K Ganguly & M L Gross, eds.) Marcel Dekker, NY.

Merrifield R B, Stewart J M "Automated Peptide Synthesis" *Nature* (1965) 207:522-523.

Merrifield R B, Stewart J M, Jernberg N "An instrument for automated synthesis of peptides" *Anal Chem* (1966) 38:1905-1914.

Nordlund, H R, et. al. Construction of a Dual Chain Pseudotetrameric Chicken Avidin by Combining Two Circularly Permuted Avidins J. Biol. Chem. 279:36715-36719 (2004)

Padilla J E, Colovos C, Yeates T O "Nanohedra: Using symmetry to design self-assembling protein cages, layers, crystals, and filaments" *Proc Nat Acad Sci USA* (2001) 98:2217-2221.

Pantoliano M P, Petrella E, Kwasnoski J, Lobannov V, Myslik J, Graf E, Carver T, Asel E, Springer B, Salemme F R "High Density Miniaturized Thermal Shift Assay as a General Strategy for Drug Discovery" *J Biomol Screening* (2001) 6:429-440.

Protein Data Bank www.rcsb.org/pdb/.

Ringler P, Schulz G "Self-Assembly of Proteins into Designed Networks" *Science* (2003) 302:106-109.

Rothemund P W K "Folding DNA to create nanoscale shapes and patterns" *Nature* (2006) 440:297-302.

Rupley J A, Careri G "Protein hydration and function" *Adv Protein Chem* (1991) 41:37-172.

Sano, T et. al., U.S. Pat. No. 6,022,951—Streptavidin mutants (2000)

Saveanu C, Miron S, Borza T, Craescu C T, Labesse G, Gagyi C, Popescu A, Schaeffer F, Namane A, Laurent-Winter C, Barzu O, Gilles A-M "Structural and nucleotide-binding properties of YajQ and YnaF, two *Escherichia coli* proteins of unknown function" *Prot Sci* (2002) 11:2551-2560.

Schulten K "VMD" www.ks.uiuc.edu/Research/vmd.

Schwarzenbacher R, Canaves J M, Brinen L S, Dai X, Deacon A M, Elsliger M A, Eshaghi S, Floyd R, Godzik A, Grittini C, Grzechnik S K, Guda C, Jaroszewski L, Karlak C, Klock H E, Koesema E, Kovarik J S, Kreusch A, Kuhn P, Lesley S A, McMullan D, McPhillips T M, Miller M A, Miller M D, Morse A, Moy K, Ouyang J, Robb A, Rodrigues K, Selby T L, Spraggon G, Stevens R C, van den Bedem H, Valasquez J, Vincent J, Wang X, West B, Wolf G, Hodgson K O, Wooley J, Wilson I A, "Crystals Structure of Uronate Isomerase (TM0064) From *Thermotoga maritima* at 2.85 A Resolution" *Proteins: Struct, Funct & Bioinform* (2003) 53:142-145.

Seeman N C "From Genes to Machines: DNA Nanomechanical Devices" *Trends in Biochemical Sciences* (2005a) 30:119-235.

Seeman N C "Structural DNA Nanotechnology: An Overview" Methods in Molecular Biology 303: Bionanotechnology Protocols, Editors, Sandra J. Rosenthal and David W. Wright, Humana Press, Totowa, N.J. (2005b) pp. 143-166.

Shih W M, Quispe J D, Joyce G F A "1.7-kilobase single-stranded DNA that folds into a nanoscale octahedron" *Nature* (2004) 427:618-621.

Siegele D A "Universal Stress Proteins in *Escherichia coli*" *J Bacteriol* (2005) 187:6253-6254.

Skerra A, Schmidt, T G M "Use of the Strep-tag and Streptavidin for Detection and Purification of Recombinant Proteins" *Meth. Enzymology* (2000) 326:271-204

Sligar S G, Salemme F R "Protein engineering for molecular electronics" *Curr Opin Biotechnol* (1992) 3:388-393.

Sousa M C, McKay D B "Structure of the universal stress protein of *Haemophilus influenzae*" *Structure* (2001) 9:1135-1141.

Stayton. P S, U.S. Pat. No. 6,156,493—Modified-affinity streptavidin (2005)

Stayton, P S, U.S. Pat. No. 6,165,750—Modified-affinity streptavidin (2000)

Stayton, P S, U.S. Pat. No. 6,492,492—Circularly permuted biotin binding proteins (2002)

Wada T, Park S.-Y, Tame R H, Kuramitsu S, Yokoyama S "Crystal Structure of IPP isomerase at P43212" To be Published as reported in the PDB, 2006

Weber P C, Ohlendorf D H, Wendoloski J J, Salemme F R "Structural Origins of High Affinity Biotin Binding to Streptavidin" *Science* (1989) 243:85-88.

Weber P C, Wendoloski J J, Pantoliano M W, Salemme F R "Crystallographic and Thermodynamic Comparison of Natural and Synthetic Ligands Bound to Streptavidin" *J Amer Chem Soc* (1992) 114:3197-3200.

Weber P C, Wendoloski J J, Pantoliano M W, Salemme F R "Structure-Based Design of Synthetic Azobenzene Ligands for Streptavidin" *J Amer Chem Soc* (1994)116: 2717-2724.

Whitesides G M, Boncheva M "Beyond molecules: Self-assembly of mesoscopic and macroscopic components" *Proc Nat Acad Sci USA* (2002) 99:4769-4774.

Zaks A, Klibanov A M "Enzymatic catalysis in nonaqueous solvents" *J Biol Chem* (1988) 263:3194-3201.

Zarembinski T I, Hung L-W, Mueller-Dieckmann H-J, Kim, K-K, Yokota H, Kim R, Kim S-H "Structure-based assignment of the biochemical function of a hypothetical protein: A test case of structural genomics" *Proc Natl Acad Sci USA* (1998) 95:15189-15193.

Allert M, Rizk S, Looger L L, Hellinga H W "Computational design of receptors for an organophosphate surrogate of the nerve agent soman" Proc Natl Acad Sci (2004) 101:7907-7912.

Ashwell G, Wahba A J, Hickman J "Uronic Acid Metabolism in Bacteria I. Purification and Properties of Uronic Acid Isomerase in *Escherichia coli*" *J Biol Chem* (1960) 235: 1559-1565.

Biteau B, Labarre J, Toledano M B "ATP-dependent reduction of cysteine-sulfinic acid by *S. cerevisiae* sulphredoxin" *Nature* (2003) 425:980-984.

Carvalho-Alves P C, Oliveira C R G, Verjovski-Almeida S "Stoichiometric Photolabeling of Two Distinct Low and High Affinity nucleotide Sites in Sarcoplasmic Reticulum ATPase" *J Biol Chem* (1985) 260:4282-4287.

Cornell W D, Cieplak P, Bayly C I, Gold I R, Merz K M, Ferguson D M, Spellmeyer D C, Fox F, Caldwell J W, Kollman P A "A Second Generation Force Field for the Simulation of Proteins, Nucleic Acids, and Organic Molecules" *J Amer Chem Soc* (1995) 117:5179-5197.

Das R, Baker D "Macromolecular Modeling with Rosetta" *Annu Rev Biochem* (2008) 77:363-82.

Finzel B C, Kimatian S, Ohlendorf D H, Wendoloski J J, Levitt M, Salemme F R "Molecular Modeling with Substructure Libraries Derived from Known Protein Structures" In Crystallographic and Modeling Methods in Molecular Design (S Ealick & C Bugg eds.) Springer Verlag, New York (1990) 175-189.

Guex N "Swiss-PdbViewer: A new fast and easy to use PDB viewer for the Macintosh" *Experientia* (1996) 52:A26.

Guex N, Diemand A, and M. C. Peitsch M C "Protein Modelling for All" *Trends Biochem Sci* (1999) 24:364-367.

Hernandez H, Robinson CV "Dynamic Protein Complexes: Insights from Mass Spectrometry" *J Biol Chem* (2001) 276:46685-46688.

Horovitz A, Levitzki A "An accurate method for determination of receptor-ligand and enzyme-inhibitor dissociation constants from displacement curves" *Proc Natl Acad Sci USA* (1987) 84:6654-6658.

Humphrey W, Dalke A, Schulten K "VMD: visual molecular dynamics" *J Mol Graph* (1996) 14:33-8 & 27-8.

Jacobson G R, Rosenbusch J P "ATP binding to a protease-resistant core of actin" *Proc Nat Acad Sci* (1976) 73:2742-2746.

Krishnaswamy S R, Williams E R, Kirsch J F "Free energies of protein-protein association determined by electrospray ionization mass spectrometry correlate accurately with values obtained by solution methods" *Protein Sci* (2006) 15:1465-1475.

Kurzban G P, Bayer E A, Wilchek M, Horowitz P M "The Quaternary Structure of Streptavidin in Urea" *J Biol Chem* (1991) 266:14470-14477.

Matulis D, Kranz J K, Salemme F R, Todd M J "Thermodynamic Stability of Carbonic Anhydrase: Measurements of Binding Affinity and Stoichiometry Using ThermoFluor" *Biochemistry* (2005) 44:5258-66.

Potier N, Billas I M L, Steinmetz A, Schaeffer C, van Dorsselaer A, Moras D, Renaud J-P "Using nondenaturing mass spectrometry to detect fortuitous ligands in orphan nuclear receptors" *Protein Sci* (2003) 12:725.

Salemme F R "Conformational Flexibility and Amide Exchange Stability in Protein β-Sheets" *Nature* (1982) 299:754-756.

Sano T, Cantor C R "Expression of a cloned streptavidin gene in *Escherichia coli*" *Proc Natl Acad Sci USA* (1990a) 87:142-146.

Sano T, Cantor C R "Cooperative Biotin Binding by Streptavidin Electrophoretic Behavior and Subunit Association of Streptavidin in the Presence of 6M Urea" *J Biol Chem* (1990b) 265:3369-3373.

Sano T, Pandori M W, Chen X, Smith C L, Cantor C R "Recombinant Core Streptavidins A Minimum-sized Core Streptavidin has Enhanced Structural Stability and Higher Accessibility to Biotinylated Macromolecules" *J Biol Chem* (1995) 270:28204-28209.

Shimkus M, Levy J, Herman T "A chemically cleavable biotinylated nucleotide: Usefulness in the recovery of protein-DNA complexes from avidin affinity columns" *Proc Natl Acad Sci USA* (1985) 82:2593-2597.

Suter M, Cazin J Jr, Butler J E, Mock D M "Isolation and Characterization of Highly Purified Streptavidin Obtained in a Two-Step Purification Procedure from *Streptomyces avidinii* Grown in a Synthetic Medium" *J Immunol Meth* (1988) 113:83-91.

Thompson L D, Weber P C "Expression of Streptavidin from a Synthetic Gene" *Gene* (1993) 136:243-6

Waner M J, Navrotskaya I, Bain A, Oldham E D, Mascotti D P "Thermal and Sodium Dodecylsulfate Induced Transitions of Streptavidin" *Biophys J* (2004) 87:2701-2713.

Wang H, Boisvert D, Kim K K, Kim R, Kim S H "Crystal structure of a fibrillarin homologue from *Methanococcus jannaschii*, a hyperthermophile, at 1.6 A resolution" *EMBO J* (2000) 19:317-23.

Weber P C, Ganguly A K, Kaler E W U.S. Pat. No. 5,948,688 Method of Determining Monomeric Drug Content Weber P C, Pantoliano M W, Simons D M, Salemme F R "Structure-Based Design of Synthetic Azobenzene Ligands for Streptavidin" *J Amer Chem Soc* (1994) 116: 2717-2724.

Wendoloski J J, Salemme F R "PROBIT: A Statistical Approach to Modeling Proteins from Partial Coordinate Data Using Substructure Libraries" *J Molecular Graphics* (1992) 10:124-126.

Woo H A, Chae H Z, Hwang S C, Yang K S, Kang S W, Kim K, Rhee S G "Reversing the inactivation of peroxlredoxins caused by cysteine sulfinic acid formation Science (2003) 300:653-658.

Wu S S J, Martin D L "Binding of ATP to brain glutamate decarboxylase as studied by affinity chromatography" *J Neurochem* (1984) 42:1607-1612.

Wu S-C, Wong S-L "Engineering Soluble Monomeric Streptavidin with Reversible Biotin Binding Capability" *J Biol Chem* (2005) 280:23225-23231.

We claim:

1. A biotinylated streptavidin macromolecular adaptor (SAMA) protein, comprising:
   a SAMA protein having a first end and a second end opposite of the first end, a dyad axis spanning from the first end to the second end, a pair of designated surface amino acid residues at the first end, and a pair of ligand binding sites at the second end; and
   a biotin-type group covalently bonded to each designated surface amino acid residue and positioned to bind to a biotin binding site of a streptavidin tetramer, and/or
   a biotin-ligand crosslinking reagent having a ligand moiety bound to each ligand binding site and having a biotin-type moiety positioned to bind to a biotin binding site of a streptavidin tetramer,
   wherein the pair of designated surface amino acid residues is symmetric about the dyad axis at the first end, and the pair of ligand binding sites is symmetric about the dyad axis at the second end.

2. The biotinylated SAMA protein of claim 1, wherein the biotin-type moiety is iminobiotin, and wherein the ligand moiety is selected from the group consisting of a nucleotide, nucleotide derivative, chemical analog of a nucleotide, a photo-activated nucleotide crosslinking group that binds specifically to the ligand binding site of the SAMA protein, and a photo-activated adenosine triphosphate (ATP) crosslinking group that binds specifically to the ligand binding site of the SAMA protein.

3. The biotinylated SAMA protein of claim 1, wherein the biotin-type group is a biotin or an iminobiotin group, and wherein the SAMA protein is a dimer or a symmetric dimer.

4. The biotinylated SAMA protein of claim 1, wherein the SAMA protein comprises a dimer having two subunits, and wherein a first subunit of the dimer is covalently connected to a second subunit of the dimer, so that the two subunits consist of one polypeptide chain.

5. The biotinylated SAMA protein of claim 1, further comprising
   a binding domain having a binding polypeptide chain; and
   a linker peptide,
   wherein the binding polypeptide chain is covalently bonded to the linker peptide,
   wherein the linker peptide is covalently bonded to a polypeptide chain of the SAMA protein, and
   wherein the binding polypeptide chain is selected from the group consisting of an immunoglobulin polypeptide, a polyhistidine polypeptide, a streptavidin binding polypeptide, Streptag, an antibody binding sequence, staphylococcus Protein A, and staphylococcus Protein G.

6. A binding sequence linked antibody sensor, comprising:
   the biotinylated SAMA protein of claim 5;
   a substrate functionalized with nucleotides or nucleotide derivatives; and
   an antibody,
   wherein the binding polypeptide chain of the functionalized SAMA protein has an antibody binding polypeptide,
   wherein the antibody is bound to the antibody binding polypeptide, and
   wherein the ligand binding sites of the biotinylated SAMA protein are bound with the nucleotide or nucleotide derivatives with which the substrate is functionalized.

7. A binding sequence linked antibody sensor, comprising:
   the biotinylated SAMA protein of claim 5;
   a substrate functionalized with biotin-type groups;
   a streptavidin tetramer having biotin binding sites; and
   an antibody,
   wherein the binding polypeptide chain of the biotinylated SAMA protein has an antibody binding polypeptide,
   wherein the antibody is bound to the antibody binding polypeptide,
   wherein each biotin-type group of the biotinylated SAMA protein is bound to a separate biotin binding site on the streptavidin tetramer,
   wherein a pair of biotin binding sites on the streptavidin tetramer are bound to the biotin-type groups with which the substrate is functionalized.

8. The biotinylated SAMA protein of claim 1, further comprising a functional polypeptide sequence bound to a polypeptide chain of the SAMA protein, wherein the functional polypeptide sequence is covalently bound to an amino or carboxy terminus of a polypeptide chain of the SAMA protein, the functional polypeptide sequence is within a surface loop of the polypeptide chain of the SAMA protein, and/or the functional polypeptide sequence is an Fab (fragment, antigen binding) sequence.

9. The biotinylated SAMA protein of claim 1, wherein a polypeptide chain of the SAMA protein has a protein sequence similarity of at least about 70% with a protein derived from a thermophilic organism and wherein the protein derived from a thermophilic organism is selected from the group consisting of MJ0577, the universal stress response protein from *Aquifex aeolicus* (Protein Data Bank (PDB) code 1q77), the Tryptophanyl-tRNA synthetase (EC 6.1.1.2) (tm0492) from *Thermotoga maritima* (PDB code 2g36), the Geranyltranstransferase enzyme (EC 2.5.1.10) (tm0161) from *Thermotoga maritime* (PDB code 2ftz), the 5-Methyltetrahydrofolate-Homocysteine S-Methyltransferase enzyme from *Thermotoga maritima* (PDB code 1Q8A), and the dimeric Adenosine Monophosphate Binding Protein (tm1088a) from *Thermotoga maritima* (PDB code 2g1u).

10. The biotinylated SAMA protein of claim 1, comprising the amino acid sequence of MJ0577, except at least one amino acid residue at positions 29, 31, 32, 33, 93, 94, 95, and/or 96 on each polypeptide chain is substituted by cysteine.

11. The biotinylated SAMA protein of claim 1, having a denaturation temperature in aqueous solution of at least about 60° C. and maintaining secondary, tertiary, and quaternary structure in a solvent having a dielectric constant of at least about 15.

12. The biotinylated SAMA protein of claim 1, comprising a universal stress response protein or a universal stress response protein domain.

13. The biotinylated SAMA protein of claim 1, comprising two polypeptide sequences independently selected from the group consisting of Sequence A (SEQ ID NO: 11), Sequence B1 (SEQ ID NO: 14), Sequence B2 (SEQ ID NO: 15), Sequence B3 (SEQ ID NO: 16), Sequence B4 (SEQ ID NO: 17), Sequence B5 (SEQ ID NO: 18), Sequence B6 (SEQ ID NO: 19), Sequence B7 (SEQ ID NO: 20), and Sequence B8 (SEQ ID NO: 21) of FIG. 10.

14. The biotinylated SAMA protein of claim 1, comprising a polypeptide sequence having an amino acid composition similarity by relative proportion of amino acid composition of greater than 90% to Sequence A (SEQ ID NO: 11) of FIG. 10.

15. The biotinylated SAMA protein of claim 1, wherein the designated surface amino acid residue is selected from the group consisting of cysteine, lysine, histidine, arginine, methionine, and tyrosine.

16. The biotinylated SAMA protein of claim 1,
wherein the pair of ligand binding sites are separated by from about 10 Angstroms to about 30 Angstroms,
wherein each designated surface amino acid residue comprises side chain atoms, and
wherein a first ligand binding site is less than 5 Angstroms from a plane in which a side chain atom of each designated surface amino acid residue and a second ligand binding site lie.

17. The biotinylated SAMA protein of claim 16, wherein each ligand binding site is an adenosine triphosphate (ATP) binding site.

18. A streptavidin:SAMA complex, comprising:
the biotinylated streptavidin macromolecular adaptor (SAMA) protein of claim 1; and
a streptavidin tetramer having biotin binding sites;
wherein the SAMA protein has the biotin-type group covalently bonded to each of the designated surface amino acid residues bound to the biotin binding site of the streptavidin tetramer.

19. The streptavidin:SAMA complex of claim 18, wherein a dyad axis of the streptavidin tetramer is colinear with the dyad axis of the SAMA protein.

20. A strut, comprising:
at least two streptavidin:SAMA complexes of claim 18,
two biotin-ligand crosslinking reagents having a biotin-type moiety and a ligand moiety,
wherein each biotin-type moiety is bound to a biotin binding site of the streptavidin tetramer of a first streptavidin:SAMA complex,
wherein each ligand moiety is bound to a ligand binding site of the SAMA protein of a second streptavidin:SAMA complex, and
wherein each streptavidin:SAMA complex is attached to at least one and at most two streptavidin:SAMA complexes.

21. A nucleotide-linked antibody biosensor, comprising:
the streptavidin:SAMA complex of claim 18; and
a substrate functionalized with biotin-type groups;
an antibody having two Fc chain termini,
wherein two biotin binding sites of the streptavidin of the streptavidin:SAMA complex are bound with the biotin-type groups with which the substrate is functionalized,
wherein each Fc chain terminus is functionalized with a nucleotide or nucleotide derivative, and
wherein each nucleotide or nucleotide derivative with which an Fc chain terminus is functionalized is bound to a ligand binding site of the SAMA of the streptavidin:SAMA complex.

22. A biotin-linked antibody biosensor, comprising:
the streptavidin:SAMA complex of claim 18;
a substrate functionalized with nucleotides or nucleotide derivatives; and
an antibody having two Fc chain termini,
wherein two ligand binding sites of a SAMA of the streptavidin:SAMA complex are bound with the nucleotide or nucleotide derivative groups with which the substrate is functionalized,
wherein each Fc chain terminus is functionalized with a biotin-type group, and
wherein each biotin-type group with which an Fc chain terminus is functionalized is bound to a biotin binding site of the streptavidin of the streptavidin:SAMA complex.

23. A biotin binding site exposed assembly, comprising:
the streptavidin:SAMA complex of claim 18,
a substrate functionalized with nucleotides or nucleotide derivatives; and
a first SAMA protein having a pair of ligand binding sites and a pair of designated surface amino acid residues with a nucleotide or nucleotide derivative covalently bound to each designated surface amino acid residue,
wherein the nucleotides or nucleotide derivatives of the substrate are bound to each ligand binding site of the first SAMA protein and
wherein each nucleotide or nucleotide derivative covalently bound to the first SAMA protein is bound to a ligand binding site of the SAMA protein of the biotin-residue linked 1:1 streptavidin: SAMA complex.

24. An assembly, comprising:
the biotin binding site exposed assembly of claim 23; and
a crosslinking reagent, comprising a biotin-type moiety bonded to a ligand moiety or to a biotin-type moiety,
wherein the ligand moiety is selected from the group consisting of a nucleotide or a nucleotide derivative,
wherein the biotin-type moiety of each biotin-ligand crosslinking reagent is bound to a biotin binding site of the streptavidin tetramer.

25. A binding site exposed assembly, comprising:
the biotin-residue linked 1:1 streptavidin:SAMA complex of claim 18,
a substrate functionalized with nucleotides or nucleotide derivatives; and a first SAMA protein having a pair of binding sites and a pair of designated surface amino acid residues with a biotin-type group covalently bound to each designated surface amino acid residue;
wherein the nucleotides or nucleotide derivatives of the substrate are bound to each binding site of the first SAMA protein and
wherein each biotin-type group covalently bound to the first SAMA protein is bound to a biotin binding site of the streptavidin tetramer of the streptavidin:SAMA complex.

26. A nucleotide exposed assembly, comprising:
the binding site exposed assembly of claim 25; and
a crosslinking reagent, comprising a nucleotide or nucleotide derivative moiety bonded to a nucleotide or nucleotide-derivative moiety or comprising a nucleotide or nucleotide derivative moiety bonded to a biotin-type moiety,
wherein a nucleotide or nucleotide derivative moiety of the crosslinking reagent is bound to a ligand binding site of the SAMA protein of the streptavidin:SAMA complex.

27. A method, comprising:
providing a SAMA protein;
mixing the SAMA protein with a thiol-reactive biotinylation reagent that has a biotin-type group and a thiol-group to form a reaction solution; and
allowing the SAMA protein and the thiol-reactive biotinylation reagent to react to form a biotin-residue functionalized SAMA protein,
wherein the SAMA protein has a first end and an opposite second end, a dyad axis spanning from the first end to the second end, a pair of designated surface amino acid residues at the first end, and a pair of ligand binding sites at the second end,
wherein the pair of designated surface amino acid residues is symmetric about the dyad axis at the first end, and the pair of ligand binding sites is symmetric about the dyad axis at the second end,
wherein the thiol group of the thiol-reactive biotinylation reagent is capable of bonding with a designated surface amino acid residue, and wherein each biotin of the biotin-residue functionalized SAMA protein is positioned to bind with a separate biotin binding site of a streptavidin tetramer.

28. A method, comprising:
making a biotin-residue functionalized SAMA protein according to the method of claim 27;
mixing the biotin-residue functionalized SAMA protein with a streptavidin tetramer to form a reaction solution; and
allowing the biotin-residue functionalized SAMA protein and the streptavidin tetramer to react to form a biotin-residue linked 1:1 streptavidin:SAMA complex.

29. A method, comprising:
making a biotin-residue functionalized SAMA protein according to the method of claim 27,
putting the biotin-residue functionalized SAMA protein into solution,
immobilizing streptavidin tetramer on a column comprising a resin derivatized with iminobiotin at a pH greater than about 6.5,
flowing the biotin-residue functionalized SAMA protein solution over the column to form a resin bound biotin-residue linked 1:1 streptavidin:SAMA complex, and
flowing a solution having pH of less than about 4 over the column to release a biotin-residue linked 1:1 streptavidin:SAMA complex into an eluted solution.

30. A method, comprising:
providing a SAMA protein;
mixing the SAMA protein with a biotin-ligand crosslinking reagent having a biotin-type moiety and a ligand moiety to form a reaction solution; and
allowing the SAMA protein and the biotin-ligand crosslinking reagent to react to form a biotin-ligand functionalized SAMA protein;
wherein the SAMA protein has a first end and an opposite second end, a dyad axis spanning from the first end to the second end, a pair of designated surface amino acid residues at the first end, and a pair of ligand binding sites at the second end,
wherein the pair of designated surface amino acid residues is symmetric about the dyad axis at the first end, and the pair of ligand binding sites is symmetric about the dyad axis at the second end,
wherein the ligand moiety of the biotin-ligand crosslinking reagent is capable of bonding with the ligand binding site, and
wherein each biotin-type moiety of the biotin-ligand functionalized SAMA protein moiety is positioned to bind with a separate biotin binding site of a streptavidin tetramer.

31. The method of claim 30, further comprising subjecting the reaction solution to light irradiation, wherein the ligand moiety of the biotin-ligand crosslinking reagent is a photo-activated nucleotide crosslinking group that binds specifically to the ligand binding site.

32. A method, comprising:
making a biotin-ligand functionalized SAMA protein according to the method of claim 30;
mixing the biotin-ligand functionalized SAMA protein with a streptavidin tetramer to form a reaction solution; and
allowing the biotin-ligand functionalized SAMA protein and the streptavidin tetramer to react to form a biotin-ligand linked 1:1 streptavidin:SAMA complex.

33. A method, comprising:
immobilizing streptavidin tetramer on a column comprising a resin derivatized with iminobiotin at a pH greater than about 6.5;
flowing a solution comprising the biotin-ligand crosslinking reagent over the column to form a resin bound biotin-ligand functionalized streptavidin tetramer;
mixing the SAMA protein with the resin bound biotin-ligand functionalized streptavidin tetramer according to claim 30 to form a resin bound biotin-ligand linked 1:1 streptavidin:SAMA complex; and
flowing a solution having pH of less than about 4 over the column to release a biotin-ligand linked 1:1 streptavidin:SAMA complex into an eluted solution.

34. A streptavidin:SAMA complex, comprising:
the biotinylated streptavidin macromolecular adaptor (SAMA) protein of claim 1; and
a streptavidin tetramer having biotin binding sites,
wherein the biotin-type moiety of the biotin-ligand crosslinking reagent is bound to the biotin binding site of the streptavidin tetramer.

35. A biotinylated streptavidin, comprising:
a streptavidin tetramer having 4 subunits;
each subunit having a biotin binding site;
each subunit having an introduced cysteine residue; and
an azido-ATP group linked to each introduced cysteine residue.

36. A functionalized strut, comprising:
a biotinylated streptavidin according to claim 35;
a streptavidin macromolecular adapter (SAMA) bound to an ATP group of the biotinylated streptavidin;
a functional protein, such as Protein A or Protein G, functionalized with a biotin group;
the biotin group of the functional protein bound to a biotin binding site of the biotinylated streptavidin or bound to a biotin binding site of a streptavidin tetramer of which a second biotin binding site is bound to a biotin with which the SAMA is functionalized.

37. An antibody structure, comprising:
a biotinylated streptavidin according to claim 35;
a functional protein, such as Protein A or Protein G, functionalized with a biotin group;
the biotin group of the functional protein bound to a biotin binding site of the biotinylated streptavidin;
an antibody bound to the functional protein.

38. An antibody structure, comprising:
a biotinylated streptavidin according to claim 35;
a streptavidin macromolecular adapter (SAMA) bound to an ATP group of the biotinylated streptavidin;
the SAMA being functionalized with a biotin group;
the biotin group of the SAMA bound to a biotin binding site of a streptavidin tetramer;
a functional protein, such as Protein A or Protein G, functionalized with a biotin group;
the biotin group of the functional protein bound to a biotin binding site of the streptavidin tetramer;
an antibody bound to the functional protein.

39. The biotinylated SAMA protein of claim 1, wherein a polypeptide chain of the SAMA protein has a protein sequence similarity of at least about 70% with MJ0577.

40. The biotinylated SAMA protein of claim 1, wherein a polypeptide chain of the SAMA protein has a protein sequence similarity of at least about 70% with the universal stress response protein from *Aquifex aeolicus* (Protein Data Bank (PDB) code 1q77).

41. The biotinylated SAMA protein of claim 1, wherein a polypeptide chain of the SAMA protein has a protein sequence similarity of at least about 70% with the Tryptophanyl-tRNA synthetase (EC 6.1.1.2) (tm0492) from *Thermotoga maritime* (PDB code 2g36).

42. The biotinylated SAMA protein of claim 1, wherein a polypeptide chain of the SAMA protein has a protein sequence similarity of at least about 70% with the Geranyltranstransferase enzyme (EC 2.5.1.10) (tm0161) from *Thermotoga maritime* (PDB code 2ftz).

43. The biotinylated SAMA protein of claim 1, wherein a polypeptide chain of the SAMA protein has a protein sequence similarity of at least about 70% with the 5-Methyltetrahydrofolate-Homocysteine S-Methyltransferase enzyme from *Thermotoga maritima* (PDB code 1Q8A).

44. The biotinylated SAMA protein of claim 1, wherein a polypeptide chain of the SAMA protein has a protein sequence similarity of at least about 70% with the dimeric Adenosine Monophosphate Binding Protein (tm1088a) from *Thermotoga maritima* (PDB code 2g1u).

45. The biotinylated SAMA protein of claim 1, comprising a biotin-type group covalently bonded to each designated surface amino acid residue and positioned to bind to a biotin binding site of a streptavidin tetramer.

46. The biotinylated SAMA protein of claim 1, comprising a biotin-ligand crosslinking reagent having a ligand moiety bound to each ligand binding site and having a biotin-type moiety positioned to bind to a biotin binding site of a streptavidin tetramer.

47. The biotinylated SAMA protein of claim 1, wherein the designated surface amino acid residue is cysteine.

48. The biotinylated SAMA protein of claim 1, wherein the biotin-type group is biotin-linking reagent (MAL PEO3)

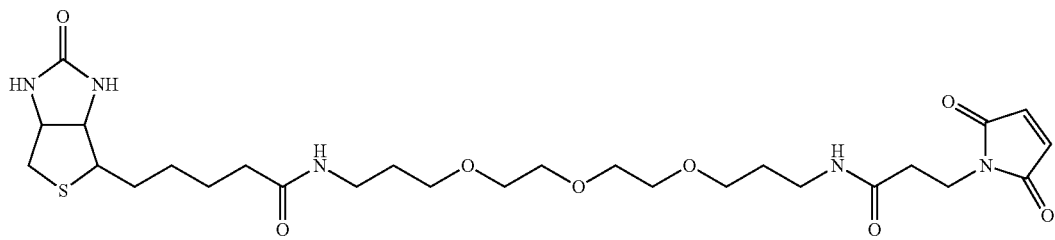

or biotin-linking reagent (MAL PEO11)

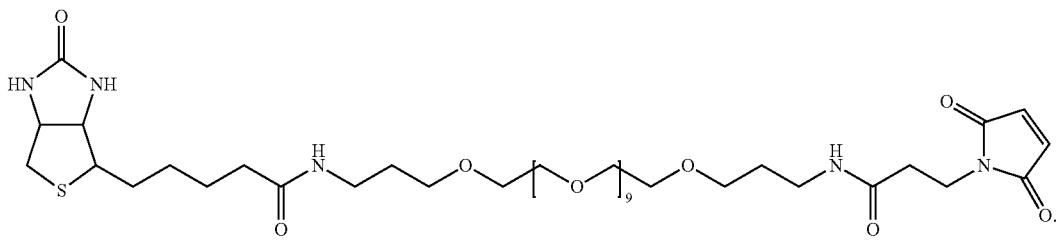

49. The biotinylated SAMA protein of claim 1, wherein the biotin-type group is biotin-linking reagent
(EZ Link HPDP)
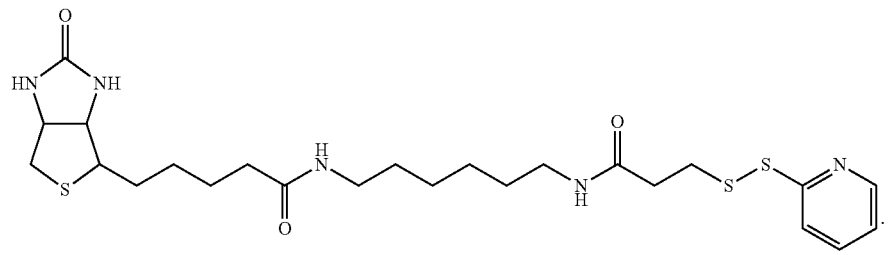
50. The biotinylated SAMA protein of claim 1, wherein the biotin-type group is iminobiotin-linking reagent
(MAL PEO3)
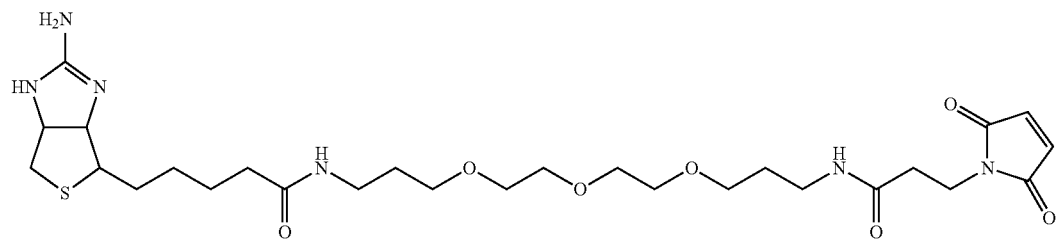
or iminobiotin-linking reagent
(MAL PEO11)
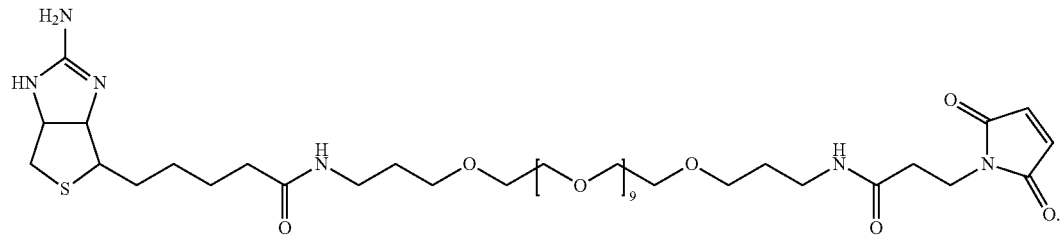
\* \* \* \* \*

SEQUENCE LISTING

<160> NUMBER OF SEQ ID NOS: 28

<210> SEQ ID NO 1
<211> LENGTH: 138
<212> TYPE: PRT
<213> ORGANISM: Aquifex aeolicus

<400> SEQUENCE: 1

Ser Asn Ala Met Lys Val Leu Leu Val Leu Thr Asp Ala Tyr Ser Asp
1               5                   10                  15

Cys Glu Lys Ala Ile Thr Tyr Ala Val Asn Phe Ser Glu Lys Leu Gly
            20                  25                  30

Ala Glu Leu Asp Ile Leu Ala Val Leu Glu Asp Val Tyr Asn Leu Glu
        35                  40                  45

Arg Ala Asn Val Thr Phe Gly Leu Pro Phe Pro Glu Ile Lys Glu
    50                  55                  60

Glu Ser Lys Lys Arg Ile Glu Arg Arg Leu Arg Glu Val Trp Glu Lys
65                  70                  75                  80

Leu Thr Gly Ser Thr Glu Ile Pro Gly Val Glu Tyr Arg Ile Gly Pro
                85                  90                  95

Leu Ser Glu Glu Val Lys Lys Phe Val Glu Gly Lys Gly Tyr Glu Leu
            100                 105                 110

Val Val Trp Ala Cys Tyr Pro Ser Ala Tyr Leu Cys Lys Val Ile Asp
            115                 120                 125

Gly Leu Asn Leu Ala Ser Leu Ile Val Lys
        130                 135

<210> SEQ ID NO 2
<211> LENGTH: 338
<212> TYPE: PRT
<213> ORGANISM: Thermotoga maritima

<400> SEQUENCE: 2

Met Gly Ser Asp Lys Ile His His His His His Met Arg Ile Leu
1               5                   10                  15

Ser Gly Met Arg Pro Thr Gly Lys Leu His Ile Gly His Leu Val Gly
            20                  25                  30

Ala Leu Glu Asn Trp Val Lys Leu Gln Glu Gly Asn Glu Cys Phe
        35                  40                  45

Tyr Val Ala Asp Trp His Ala Leu Thr Thr His Tyr Asp Asp Val Ser
    50                  55                  60

Lys Leu Lys Glu Tyr Thr Arg Asp Leu Val Arg Gly Phe Leu Ala Cys
65                  70                  75                  80

Gly Ile Asp Pro Glu Lys Ser Val Ile Phe Val Gln Ser Gly Val Lys
                85                  90                  95

Glu His Ala Glu Leu Ala Leu Leu Phe Ser Met Ile Val Ser Val Ser
            100                 105                 110

Arg Leu Glu Arg Val Pro Thr Tyr Lys Glu Ile Lys Ser Glu Leu Asn
        115                 120                 125

Tyr Lys Asp Leu Ser Thr Ala Gly Phe Leu Ile Tyr Pro Val Leu Gln
    130                 135                 140

Ala Ala Asp Ile Leu Ile Tyr Lys Ala Glu Gly Val Pro Val Gly Glu
145                 150                 155                 160

Asp Gln Val Tyr His Ile Glu Leu Thr Arg Glu Ile Ala Arg Arg Phe
                165                 170                 175

Asn Tyr Leu Tyr Asp Glu Val Phe Pro Glu Pro Glu Ala Ile Leu Ser
            180                 185                 190

Arg Val Pro Lys Leu Pro Gly Thr Asp Gly Arg Lys Met Ser Lys Ser
        195                 200                 205

Tyr Gly Asn Ile Ile Asn Leu Glu Ile Ser Glu Lys Glu Leu Glu Gln
    210                 215                 220

Thr Ile Leu Arg Met Met Thr Asp Pro Ala Arg Val Arg Arg Ser Asp
225                 230                 235                 240

```
Pro Gly Asn Pro Glu Asn Cys Pro Val Trp Lys Tyr His Gln Ala Phe
                245                 250                 255

Asp Ile Ser Glu Glu Ser Lys Trp Val Trp Glu Gly Cys Thr Thr
            260                 265                 270

Ala Ser Ile Gly Cys Val Asp Cys Lys Lys Leu Leu Leu Lys Asn Met
            275                 280                 285

Lys Arg Lys Leu Ala Pro Ile Trp Glu Asn Phe Arg Lys Ile Asp Glu
290                 295                 300

Asp Pro Tyr Val Asp Asp Val Ile Met Glu Gly Thr Lys Lys Ala Arg
305                 310                 315                 320

Glu Val Ala Ala Lys Thr Met Glu Glu Val Arg Arg Ala Met Asn Leu
                325                 330                 335

Met Phe

<210> SEQ ID NO 3
<211> LENGTH: 284
<212> TYPE: PRT
<213> ORGANISM: Thermotoga maritima

<400> SEQUENCE: 3

Met Gly Ser Asp Lys Ile His His His His His Met Lys Lys Glu
1               5                   10                  15

Lys Val Glu Glu Arg Ile Arg Glu Ile Leu Arg Pro Gly Trp Asp Leu
                20                  25                  30

Leu Thr Glu Glu Ala Met Leu Tyr Ser Ala Thr Val Gly Gly Lys Arg
            35                  40                  45

Ile Arg Pro Leu Leu Val Leu Thr Leu Gly Glu Asp Leu Gly Val Glu
50                  55                  60

Glu Glu Lys Leu Leu Asp Val Ala Val Ala Val Glu Leu Phe His Thr
65                  70                  75                  80

Ala Ser Leu Ile His Asp Asp Leu Pro Pro Ile Asp Asn Ala Asp Phe
                85                  90                  95

Arg Arg Gly Lys Pro Ser Cys His Arg Thr Tyr Gly Glu Asp Ile Ala
            100                 105                 110

Leu Leu Ala Gly Asp Gly Leu Phe Phe Leu Ala Phe Ser Gln Ile Ser
            115                 120                 125

Lys Ile Gly Asn Ser Lys Ile Phe Glu Glu Phe Ser Glu Thr Ala Tyr
130                 135                 140

Lys Leu Leu Leu Gly Glu Ala Met Asp Val Glu Phe Glu Arg Arg Lys
145                 150                 155                 160

Met Glu Val Ser Gln Glu Met Val Glu Arg Met Tyr Ala Phe Lys Thr
                165                 170                 175

Gly Ala Leu Phe Ala Phe Cys Phe Ser Ala Pro Phe Ile Leu Lys Gly
            180                 185                 190

Lys Asp His Thr Lys Met Lys Leu Leu Gly Glu Lys Phe Gly Val Ala
            195                 200                 205

Phe Gln Ile Tyr Asp Asp Leu Lys Asp Ile Leu Gly Ser Phe Glu Lys
        210                 215                 220

Val Gly Lys Asp Leu Gly Lys Asp Thr Glu Lys Val Thr Leu Val Lys
225                 230                 235                 240

Lys Val Gly Ile Gln Lys Ala Arg Glu Met Ala Asp Lys Tyr Tyr Glu
                245                 250                 255

Glu Val Leu Lys Gly Ile Glu Ser Glu Gly Leu Phe Arg Thr Leu Phe
            260                 265                 270
```

```
Leu Leu Lys Glu Leu Lys Gln Met Val Glu Glu Arg
        275                 280
```

<210> SEQ ID NO 4
<211> LENGTH: 566
<212> TYPE: PRT
<213> ORGANISM: Thermotoga maritima

<400> SEQUENCE: 4

```
Met Arg Asn Arg Arg Glu Val Ser Lys Leu Leu Ser Glu Arg Val Leu
1               5                   10                  15

Leu Leu Asp Gly Ala Tyr Gly Thr Glu Phe Met Lys Tyr Gly Tyr Asp
            20                  25                  30

Asp Leu Pro Glu Glu Leu Asn Ile Lys Ala Pro Asp Val Val Leu Lys
        35                  40                  45

Val His Arg Ser Tyr Ile Glu Ser Gly Ser Asp Val Ile Leu Thr Asn
    50                  55                  60

Thr Phe Gly Ala Thr Arg Met Lys Leu Arg Lys His Gly Leu Glu Asp
65                  70                  75                  80

Lys Leu Asp Pro Ile Val Arg Asn Ala Val Arg Ile Ala Arg Arg Ala
                85                  90                  95

Ala Gly Glu Lys Leu Val Phe Gly Asp Ile Gly Pro Thr Gly Glu Leu
            100                 105                 110

Pro Tyr Pro Leu Gly Ser Thr Leu Phe Glu Glu Phe Tyr Glu Asn Phe
        115                 120                 125

Arg Glu Thr Val Glu Ile Met Val Glu Gly Val Asp Gly Ile Ile
    130                 135                 140

Phe Glu Thr Phe Ser Asp Ile Leu Glu Leu Lys Ala Ala Val Leu Ala
145                 150                 155                 160

Ala Arg Glu Val Ser Arg Asp Val Phe Leu Ile Ala His Met Thr Phe
                165                 170                 175

Asp Glu Lys Gly Arg Ser Leu Thr Gly Thr Asp Pro Ala Asn Phe Ala
            180                 185                 190

Ile Thr Phe Asp Glu Leu Asp Ile Asp Ala Leu Gly Ile Asn Cys Ser
        195                 200                 205

Leu Gly Pro Glu Glu Ile Leu Pro Ile Phe Gln Glu Leu Ser Gln Tyr
    210                 215                 220

Thr Asp Lys Phe Leu Val Val Glu Pro Asn Ala Gly Lys Pro Ile Val
225                 230                 235                 240

Glu Asn Gly Lys Thr Val Tyr Pro Leu Lys Pro His Asp Phe Ala Val
                245                 250                 255

His Ile Asp Ser Tyr Tyr Glu Leu Gly Val Asn Ile Phe Gly Gly Cys
            260                 265                 270

Cys Gly Thr Thr Pro Glu His Val Lys Leu Phe Arg Lys Val Leu Gly
        275                 280                 285

Asn Arg Lys Pro Leu Gln Arg Lys Lys Arg Ile Phe Ala Val Ser
    290                 295                 300

Ser Pro Ser Lys Leu Val Thr Phe Asp His Phe Val Val Ile Gly Glu
305                 310                 315                 320

Arg Ile Asn Pro Ala Gly Arg Lys Lys Leu Trp Ala Glu Met Gln Lys
                325                 330                 335

Gly Asn Glu Glu Ile Val Ile Lys Glu Ala Lys Thr Gln Val Glu Lys
            340                 345                 350

Gly Ala Glu Val Leu Asp Val Asn Phe Gly Ile Glu Ser Gln Ile Asp
```

```
                355                 360                 365
Val Arg Tyr Val Glu Lys Ile Val Gln Thr Leu Pro Tyr Val Ser Asn
            370                 375                 380

Val Pro Leu Ser Leu Asp Ile Gln Asn Val Asp Leu Thr Glu Arg Ala
385                 390                 395                 400

Leu Arg Ala Tyr Pro Gly Arg Ser Leu Phe Asn Ser Ala Lys Val Asp
                405                 410                 415

Glu Glu Glu Leu Glu Met Lys Ile Asn Leu Leu Lys Lys Tyr Gly Gly
            420                 425                 430

Thr Leu Ile Val Leu Leu Met Gly Lys Asp Val Pro Lys Ser Phe Glu
                435                 440                 445

Glu Arg Lys Glu Tyr Phe Glu Lys Ala Leu Lys Ile Leu Glu Arg His
            450                 455                 460

Asp Phe Ser Asp Arg Val Ile Phe Asp Pro Gly Val Leu Pro Leu Gly
465                 470                 475                 480

Ala Glu Gly Lys Pro Val Glu Val Leu Lys Thr Ile Glu Phe Ile Ser
                485                 490                 495

Ser Lys Gly Phe Asn Thr Thr Val Gly Leu Ser Asn Leu Ser Phe Gly
            500                 505                 510

Leu Pro Asp Arg Ser Tyr Tyr Asn Thr Ala Phe Leu Val Leu Gly Ile
                515                 520                 525

Ser Lys Gly Leu Ser Ser Ala Ile Met Asn Pro Leu Asp Glu Thr Leu
            530                 535                 540

Met Lys Thr Leu Asn Ala Thr Leu Val Ile Leu Glu Lys Lys Glu Leu
545                 550                 555                 560

Pro Arg Ala Glu Val Lys
                565

<210> SEQ ID NO 5
<211> LENGTH: 155
<212> TYPE: PRT
<213> ORGANISM: Thermotoga maritima

<400> SEQUENCE: 5

Met Gly Ser Asp Lys Ile His His His His His His Met Ser Lys Lys
1               5                   10                  15

Gln Lys Ser Lys Tyr Ile Val Ile Phe Gly Cys Gly Arg Leu Gly Ser
            20                  25                  30

Leu Ile Ala Asn Leu Ala Ser Ser Gly His Ser Val Val Val
            35                  40                  45

Asp Lys Asn Glu Tyr Ala Phe His Arg Leu Asn Ser Glu Phe Ser Gly
        50                  55                  60

Phe Thr Val Val Gly Asp Ala Ala Glu Phe Glu Thr Leu Lys Glu Cys
65                  70                  75                  80

Gly Met Glu Lys Ala Asp Met Val Phe Ala Phe Thr Asn Asp Asp Ser
                85                  90                  95

Thr Asn Phe Phe Ile Ser Met Asn Ala Arg Tyr Met Phe Asn Val Glu
            100                 105                 110

Asn Val Ile Ala Arg Val Tyr Asp Pro Glu Lys Ile Lys Ile Phe Glu
        115                 120                 125

Glu Asn Gly Ile Lys Thr Ile Cys Pro Ala Val Leu Met Ile Glu Lys
    130                 135                 140

Val Lys Glu Phe Ile Ile Gly Ser Glu Glu Asp
145                 150                 155
```

<210> SEQ ID NO 6
<211> LENGTH: 8
<212> TYPE: PRT
<213> ORGANISM: Artificial Sequence
<220> FEATURE:
<223> OTHER INFORMATION: Description of artificial sequence: Synthetic construct

<400> SEQUENCE: 6

Trp Ser His Pro Gln Phe Glu Lys
1               5

<210> SEQ ID NO 7
<211> LENGTH: 9
<212> TYPE: PRT
<213> ORGANISM: Artificial Sequence
<220> FEATURE:
<223> OTHER INFORMATION: Description of artificial sequence: Synthetic construct

<400> SEQUENCE: 7

Ala Trp Arg His Pro Gln Phe Gly Gly
1               5

<210> SEQ ID NO 8
<211> LENGTH: 504
<212> TYPE: DNA
<213> ORGANISM: Artificial Sequence
<220> FEATURE:
<223> OTHER INFORMATION: Description of artificial sequence: Synthetic construct

<400> SEQUENCE: 8

```
gaaggagata tacatatgag cgtcatgtat aaaaaaatcc tgtatccgac cgactttagc      60
gaaaccgccg aaattgcact gaaacatgtt aaagcattta aaaccctgaa agccgaagaa     120
gtgatcctgc tgcatgtcat cgacgaacgc gaaattaaaa acgtgatat ttttagcctg      180
ctgctgggtg ttgccggtct gaacaaaagc gtggaagaat cgaaaatga actgaaaaat     240
aaactgaccg aagaagcgaa aaataaaatg gaaatatta aaaagaact ggaagacgtg      300
ggctttaaag tcaaggatat tattgttgtg ggcattccgc atgaagaaat tgttaaaatt    360
gcagaagatg aaggcgtgga tattatcatt atgggcagcc atggcaaaac caatctgaaa   420
gaaattctgc tgggcagcgt gaccgaaaat gtgattaaaa aagcaataa accggttctg    480
gtcgtcaaac gtaaaaatag ctaa                                          504
```

<210> SEQ ID NO 9
<211> LENGTH: 504
<212> TYPE: DNA
<213> ORGANISM: Artificial Sequence
<220> FEATURE:
<223> OTHER INFORMATION: Description of artificial sequence: Synthetic construct

<400> SEQUENCE: 9

```
gaaggagata tacatatgag cgtcatgtat aaaaaaatcc tgtatccgac cgactttagc      60
gaaaccgccg aaattgcact gaaacatgtt aaagcattta aaccctgtaa agccgaagaa    120
gtgatcctgc tgcatgtcat cgacgaacgc gaaattaaaa acgtgatat ttttagcctg      180
ctgctgggtg ttgccggtct gaacaaaagc gtggaagaat cgaaaatga actgaaaaat     240
aaactgaccg aagaagcgaa aaataaaatg gaaatatta aaaagaact ggaagacgtg      300
ggctttaaag tcaaggatat tattgttgtg ggcattccgc atgaagaaat tgttaaaatt    360
```

```
gcagaagatg aaggcgtgga tattatcatt atgggcagcc atggcaaaac caatctgaaa    420
gaaattctgc tgggcagcgt gaccgaaaat gtgattaaaa aaagcaataa accggttctg    480
gtcgtcaaac gtaaaaatag ctaa                                          504
```

```
<210> SEQ ID NO 10
<211> LENGTH: 504
<212> TYPE: DNA
<213> ORGANISM: Artificial Sequence
<220> FEATURE:
<223> OTHER INFORMATION: Description of artificial sequence: Synthetic
      construct

<400> SEQUENCE: 10
```

```
gaaggagata tacatatgag cgtcatgtat aaaaaaatcc tgtatccgac cgactttagc     60
gaaaccgccg aaattgcact gaaacatgtt aaagcattta aaaccctgaa agccgaagaa    120
gtgatcctgc tgcatgtcat cgacgaacgc gaaattaaaa aacgtgatat ttttagcctg    180
ctgctgggtg ttgccggtct gaacaaaagc gtggaagaat cgaaaatgaa actgaaaaat    240
aaactgaccg aagaagcgaa aataaaaatg gaaatatatt aaaaagaact ggaagactgt    300
ggctttaaag tcaaggatat tattgttgtg ggcattccgc atgaagaaat tgttaaaatt    360
gcagaagatg aaggcgtgga tattatcatt atgggcagcc atggcaaaac caatctgaaa    420
gaaattctgc tgggcagcgt gaccgaaaat gtgattaaaa aaagcaataa accggttctg    480
gtcgtcaaac gtaaaaatag ctaa                                          504
```

```
<210> SEQ ID NO 11
<211> LENGTH: 162
<212> TYPE: PRT
<213> ORGANISM: Methanococcus jannaschii

<400> SEQUENCE: 11
```

Met Ser Val Met Tyr Lys Lys Ile Leu Tyr Pro Thr Asp Phe Ser Glu
1               5                   10                  15

Thr Ala Glu Ile Ala Leu Lys His Val Lys Ala Phe Lys Thr Leu Lys
            20                  25                  30

Ala Glu Glu Val Ile Leu Leu His Val Ile Asp Glu Arg Glu Ile Lys
        35                  40                  45

Lys Arg Asp Ile Phe Ser Leu Leu Leu Gly Val Ala Gly Leu Asn Lys
    50                  55                  60

Ser Val Glu Glu Phe Glu Asn Glu Leu Lys Asn Lys Leu Thr Glu Glu
65                  70                  75                  80

Ala Lys Asn Lys Met Glu Asn Ile Lys Lys Glu Leu Glu Asp Val Gly
                85                  90                  95

Phe Lys Val Lys Asp Ile Ile Val Gly Ile Pro His Glu Glu Ile
            100                 105                 110

Val Lys Ile Ala Glu Asp Glu Gly Val Asp Ile Ile Met Gly Ser
        115                 120                 125

His Gly Lys Thr Asn Leu Lys Glu Ile Leu Leu Gly Ser Val Thr Glu
    130                 135                 140

Asn Val Ile Lys Lys Ser Asn Lys Pro Val Leu Val Val Lys Arg Lys
145                 150                 155                 160

Asn Ser

```
<210> SEQ ID NO 12
<211> LENGTH: 162
```

-continued

<212> TYPE: PRT
<213> ORGANISM: Artificial Sequence
<220> FEATURE:
<223> OTHER INFORMATION: Description of artificial sequence: Synthetic
      construct

<400> SEQUENCE: 12

Met Ser Val Met Tyr Lys Lys Ile Leu Tyr Pro Thr Asp Phe Ser Glu
1               5                   10                  15

Thr Ala Glu Ile Ala Leu Lys His Val Lys Ala Phe Lys Thr Cys Lys
            20                  25                  30

Ala Glu Glu Val Ile Leu Leu His Val Ile Asp Glu Arg Glu Ile Lys
        35                  40                  45

Lys Arg Asp Ile Phe Ser Leu Leu Leu Gly Val Ala Gly Leu Asn Lys
    50                  55                  60

Ser Val Glu Glu Phe Glu Asn Glu Leu Lys Asn Lys Leu Thr Glu Glu
65                  70                  75                  80

Ala Lys Asn Lys Met Glu Asn Ile Lys Lys Glu Leu Glu Asp Val Gly
                85                  90                  95

Phe Lys Val Lys Asp Ile Ile Val Val Gly Ile Pro His Glu Glu Ile
            100                 105                 110

Val Lys Ile Ala Glu Asp Glu Gly Val Asp Ile Ile Met Gly Ser
        115                 120                 125

His Gly Lys Thr Asn Leu Lys Glu Ile Leu Leu Gly Ser Val Thr Glu
    130                 135                 140

Asn Val Ile Lys Lys Ser Asn Lys Pro Val Leu Val Val Lys Arg Lys
145                 150                 155                 160

Asn Ser

<210> SEQ ID NO 13
<211> LENGTH: 162
<212> TYPE: PRT
<213> ORGANISM: Artificial Sequence
<220> FEATURE:
<223> OTHER INFORMATION: Description of artificial sequence: Synthetic
      construct

<400> SEQUENCE: 13

Met Ser Val Met Tyr Lys Lys Ile Leu Tyr Pro Thr Asp Phe Ser Glu
1               5                   10                  15

Thr Ala Glu Ile Ala Leu Lys His Val Lys Ala Phe Lys Thr Leu Lys
            20                  25                  30

Ala Glu Glu Val Ile Leu Leu His Val Ile Asp Glu Arg Glu Ile Lys
        35                  40                  45

Lys Arg Asp Ile Phe Ser Leu Leu Leu Gly Val Ala Gly Leu Asn Lys
    50                  55                  60

Ser Val Glu Glu Phe Glu Asn Glu Leu Lys Asn Lys Leu Thr Glu Glu
65                  70                  75                  80

Ala Lys Asn Lys Met Glu Asn Ile Lys Lys Glu Leu Glu Asp Cys Gly
                85                  90                  95

Phe Lys Val Lys Asp Ile Ile Val Val Gly Ile Pro His Glu Glu Ile
            100                 105                 110

Val Lys Ile Ala Glu Asp Glu Gly Val Asp Ile Ile Met Gly Ser
        115                 120                 125

His Gly Lys Thr Asn Leu Lys Glu Ile Leu Leu Gly Ser Val Thr Glu
    130                 135                 140

Asn Val Ile Lys Lys Ser Asn Lys Pro Val Leu Val Val Lys Arg Lys

```
145                 150                 155                 160

Asn Ser

<210> SEQ ID NO 14
<211> LENGTH: 162
<212> TYPE: PRT
<213> ORGANISM: Artificial Sequence
<220> FEATURE:
<223> OTHER INFORMATION: Description of artificial sequence: Synthetic
      construct

<400> SEQUENCE: 14

Met Ser Val Met Tyr Lys Lys Ile Leu Tyr Pro Thr Asp Phe Ser Glu
1               5                   10                  15

Thr Ala Glu Ile Ala Leu Lys His Val Lys Ala Phe Cys Thr Leu Lys
                20                  25                  30

Ala Glu Glu Val Ile Leu Leu His Val Ile Asp Glu Arg Glu Ile Lys
            35                  40                  45

Lys Arg Asp Ile Phe Ser Leu Leu Leu Gly Val Ala Gly Leu Asn Lys
        50                  55                  60

Ser Val Glu Glu Phe Glu Asn Glu Leu Lys Asn Lys Leu Thr Glu Glu
65                  70                  75                  80

Ala Lys Asn Lys Met Glu Asn Ile Lys Lys Glu Leu Glu Asp Val Gly
                85                  90                  95

Phe Lys Val Lys Asp Ile Ile Val Gly Ile Pro His Glu Glu Ile
            100                 105                 110

Val Lys Ile Ala Glu Asp Glu Gly Val Asp Ile Ile Met Gly Ser
        115                 120                 125

His Gly Lys Thr Asn Leu Lys Glu Ile Leu Leu Gly Ser Val Thr Glu
    130                 135                 140

Asn Val Ile Lys Lys Ser Asn Lys Pro Val Leu Val Val Lys Arg Lys
145                 150                 155                 160

Asn Ser

<210> SEQ ID NO 15
<211> LENGTH: 162
<212> TYPE: PRT
<213> ORGANISM: Artificial Sequence
<220> FEATURE:
<223> OTHER INFORMATION: Description of artificial sequence: Synthetic
      construct

<400> SEQUENCE: 15

Met Ser Val Met Tyr Lys Lys Ile Leu Tyr Pro Thr Asp Phe Ser Glu
1               5                   10                  15

Thr Ala Glu Ile Ala Leu Lys His Val Lys Ala Phe Lys Thr Cys Lys
                20                  25                  30

Ala Glu Glu Val Ile Leu Leu His Val Ile Asp Glu Arg Glu Ile Lys
            35                  40                  45

Lys Arg Asp Ile Phe Ser Leu Leu Leu Gly Val Ala Gly Leu Asn Lys
        50                  55                  60

Ser Val Glu Glu Phe Glu Asn Glu Leu Lys Asn Lys Leu Thr Glu Glu
65                  70                  75                  80

Ala Lys Asn Lys Met Glu Asn Ile Lys Lys Glu Leu Glu Asp Val Gly
                85                  90                  95

Phe Lys Val Lys Asp Ile Ile Val Gly Ile Pro His Glu Glu Ile
            100                 105                 110
```

Val Lys Ile Ala Glu Asp Glu Gly Val Asp Ile Ile Met Gly Ser
            115                 120                 125

His Gly Lys Thr Asn Leu Lys Glu Ile Leu Leu Gly Ser Val Thr Glu
    130                 135                 140

Asn Val Ile Lys Lys Ser Asn Lys Pro Val Leu Val Lys Arg Lys
145                 150                 155                 160

Asn Ser

<210> SEQ ID NO 16
<211> LENGTH: 162
<212> TYPE: PRT
<213> ORGANISM: Artificial Sequence
<220> FEATURE:
<223> OTHER INFORMATION: Description of artificial sequence: Synthetic
      construct

<400> SEQUENCE: 16

Met Ser Val Met Tyr Lys Lys Ile Leu Tyr Pro Thr Asp Phe Ser Glu
1               5                   10                  15

Thr Ala Glu Ile Ala Leu Lys His Val Lys Ala Phe Lys Thr Leu Cys
            20                  25                  30

Ala Glu Glu Val Ile Leu Leu His Val Ile Asp Glu Arg Glu Ile Lys
        35                  40                  45

Lys Arg Asp Ile Phe Ser Leu Leu Gly Val Ala Gly Leu Asn Lys
    50                  55                  60

Ser Val Glu Glu Phe Glu Asn Glu Leu Lys Asn Lys Leu Thr Glu Glu
65                  70                  75                  80

Ala Lys Asn Lys Met Glu Asn Ile Lys Lys Glu Leu Glu Asp Val Gly
                85                  90                  95

Phe Lys Val Lys Asp Ile Ile Val Val Gly Ile Pro His Glu Glu Ile
            100                 105                 110

Val Lys Ile Ala Glu Asp Glu Gly Val Asp Ile Ile Met Gly Ser
        115                 120                 125

His Gly Lys Thr Asn Leu Lys Glu Ile Leu Leu Gly Ser Val Thr Glu
    130                 135                 140

Asn Val Ile Lys Lys Ser Asn Lys Pro Val Leu Val Lys Arg Lys
145                 150                 155                 160

Asn Ser

<210> SEQ ID NO 17
<211> LENGTH: 162
<212> TYPE: PRT
<213> ORGANISM: Artificial Sequence
<220> FEATURE:
<223> OTHER INFORMATION: Description of artificial sequence: Synthetic
      construct

<400> SEQUENCE: 17

Met Ser Val Met Tyr Lys Lys Ile Leu Tyr Pro Thr Asp Phe Ser Glu
1               5                   10                  15

Thr Ala Glu Ile Ala Leu Lys His Val Lys Ala Phe Lys Thr Leu Lys
            20                  25                  30

Cys Glu Glu Val Ile Leu Leu His Val Ile Asp Glu Arg Glu Ile Lys
        35                  40                  45

Lys Arg Asp Ile Phe Ser Leu Leu Gly Val Ala Gly Leu Asn Lys
    50                  55                  60

Ser Val Glu Glu Phe Glu Asn Glu Leu Lys Asn Lys Leu Thr Glu Glu
65                  70                  75                  80

Ala Lys Asn Lys Met Glu Asn Ile Lys Lys Glu Leu Glu Asp Val Gly
            85                  90                  95

Phe Lys Val Lys Asp Ile Ile Val Val Gly Ile Pro His Glu Glu Ile
            100                 105                 110

Val Lys Ile Ala Glu Asp Glu Gly Val Asp Ile Ile Met Gly Ser
            115                 120                 125

His Gly Lys Thr Asn Leu Lys Glu Ile Leu Leu Gly Ser Val Thr Glu
        130                 135                 140

Asn Val Ile Lys Lys Ser Asn Lys Pro Val Leu Val Val Lys Arg Lys
145                 150                 155                 160

Asn Ser

<210> SEQ ID NO 18
<211> LENGTH: 162
<212> TYPE: PRT
<213> ORGANISM: Artificial Sequence
<220> FEATURE:
<223> OTHER INFORMATION: Description of artificial sequence: Synthetic
      construct

<400> SEQUENCE: 18

Met Ser Val Met Tyr Lys Lys Ile Leu Tyr Pro Thr Asp Phe Ser Glu
1               5                   10                  15

Thr Ala Glu Ile Ala Leu Lys His Val Lys Ala Phe Lys Thr Leu Lys
            20                  25                  30

Ala Glu Glu Val Ile Leu Leu His Val Ile Asp Glu Arg Glu Ile Lys
        35                  40                  45

Lys Arg Asp Ile Phe Ser Leu Leu Gly Val Ala Gly Leu Asn Lys
    50                  55                  60

Ser Val Glu Glu Phe Glu Asn Glu Leu Lys Asn Lys Leu Thr Glu Glu
65                  70                  75                  80

Ala Lys Asn Lys Met Glu Asn Ile Lys Lys Glu Leu Cys Asp Val Gly
            85                  90                  95

Phe Lys Val Lys Asp Ile Ile Val Val Gly Ile Pro His Glu Glu Ile
            100                 105                 110

Val Lys Ile Ala Glu Asp Glu Gly Val Asp Ile Ile Met Gly Ser
            115                 120                 125

His Gly Lys Thr Asn Leu Lys Glu Ile Leu Leu Gly Ser Val Thr Glu
        130                 135                 140

Asn Val Ile Lys Lys Ser Asn Lys Pro Val Leu Val Val Lys Arg Lys
145                 150                 155                 160

Asn Ser

<210> SEQ ID NO 19
<211> LENGTH: 162
<212> TYPE: PRT
<213> ORGANISM: Artificial Sequence
<220> FEATURE:
<223> OTHER INFORMATION: Description of artificial sequence: Synthetic
      construct

<400> SEQUENCE: 19

Met Ser Val Met Tyr Lys Lys Ile Leu Tyr Pro Thr Asp Phe Ser Glu
1               5                   10                  15

Thr Ala Glu Ile Ala Leu Lys His Val Lys Ala Phe Lys Thr Leu Lys
            20                  25                  30

Ala Glu Glu Val Ile Leu Leu His Val Ile Asp Glu Arg Glu Ile Lys

```
                35                  40                  45
Lys Arg Asp Ile Phe Ser Leu Leu Gly Val Ala Gly Leu Asn Lys
     50                  55                  60

Ser Val Glu Glu Phe Glu Asn Glu Leu Lys Asn Lys Leu Thr Glu Glu
 65                  70                  75                  80

Ala Lys Asn Lys Met Glu Asn Ile Lys Lys Glu Leu Glu Cys Val Gly
                 85                  90                  95

Phe Lys Val Lys Asp Ile Ile Val Val Gly Ile Pro His Glu Glu Ile
                100                 105                 110

Val Lys Ile Ala Glu Asp Glu Gly Val Asp Ile Ile Ile Met Gly Ser
                115                 120                 125

His Gly Lys Thr Asn Leu Lys Glu Ile Leu Leu Gly Ser Val Thr Glu
            130                 135                 140

Asn Val Ile Lys Lys Ser Asn Lys Pro Val Leu Val Val Lys Arg Lys
145                 150                 155                 160

Asn Ser

<210> SEQ ID NO 20
<211> LENGTH: 162
<212> TYPE: PRT
<213> ORGANISM: Artificial Sequence
<220> FEATURE:
<223> OTHER INFORMATION: Description of artificial sequence: Synthetic
      construct

<400> SEQUENCE: 20

Met Ser Val Met Tyr Lys Lys Ile Leu Tyr Pro Thr Asp Phe Ser Glu
 1               5                  10                  15

Thr Ala Glu Ile Ala Leu Lys His Val Lys Ala Phe Lys Thr Leu Lys
                 20                  25                  30

Ala Glu Glu Val Ile Leu Leu His Val Ile Asp Glu Arg Glu Ile Lys
             35                  40                  45

Lys Arg Asp Ile Phe Ser Leu Leu Gly Val Ala Gly Leu Asn Lys
     50                  55                  60

Ser Val Glu Glu Phe Glu Asn Glu Leu Lys Asn Lys Leu Thr Glu Glu
 65                  70                  75                  80

Ala Lys Asn Lys Met Glu Asn Ile Lys Lys Glu Leu Glu Asp Cys Gly
                 85                  90                  95

Phe Lys Val Lys Asp Ile Ile Val Val Gly Ile Pro His Glu Glu Ile
                100                 105                 110

Val Lys Ile Ala Glu Asp Glu Gly Val Asp Ile Ile Ile Met Gly Ser
                115                 120                 125

His Gly Lys Thr Asn Leu Lys Glu Ile Leu Leu Gly Ser Val Thr Glu
            130                 135                 140

Asn Val Ile Lys Lys Ser Asn Lys Pro Val Leu Val Val Lys Arg Lys
145                 150                 155                 160

Asn Ser

<210> SEQ ID NO 21
<211> LENGTH: 162
<212> TYPE: PRT
<213> ORGANISM: Artificial Sequence
<220> FEATURE:
<223> OTHER INFORMATION: Description of artificial sequence: Synthetic
      construct

<400> SEQUENCE: 21
```

```
Met Ser Val Met Tyr Lys Lys Ile Leu Tyr Pro Thr Asp Phe Ser Glu
1               5                   10                  15

Thr Ala Glu Ile Ala Leu Lys His Val Lys Ala Phe Lys Thr Leu Lys
            20                  25                  30

Ala Glu Glu Val Ile Leu Leu His Val Ile Asp Glu Arg Glu Ile Lys
        35                  40                  45

Lys Arg Asp Ile Phe Ser Leu Leu Leu Gly Val Ala Gly Leu Asn Lys
    50                  55                  60

Ser Val Glu Glu Phe Glu Asn Glu Leu Lys Asn Lys Leu Thr Glu Glu
65                  70                  75                  80

Ala Lys Asn Lys Met Glu Asn Ile Lys Lys Glu Leu Gly Asp Val Cys
            85                  90                  95

Phe Lys Val Lys Asp Ile Ile Val Val Gly Ile Pro His Glu Glu Ile
            100                 105                 110

Val Lys Ile Ala Glu Asp Gly Val Asp Ile Ile Met Gly Ser
        115                 120                 125

His Gly Lys Thr Asn Leu Lys Glu Ile Leu Leu Gly Ser Val Thr Glu
    130                 135                 140

Asn Val Ile Lys Lys Ser Asn Lys Pro Val Leu Val Lys Arg Lys
145                 150                 155                 160

Asn Ser

<210> SEQ ID NO 22
<211> LENGTH: 746
<212> TYPE: PRT
<213> ORGANISM: Artificial Sequence
<220> FEATURE:
<223> OTHER INFORMATION: Description of artificial sequence: Synthetic
      construct
<220> FEATURE:
<221> NAME/KEY: MOD_RES
<222> LOCATION: (1)..(4)
<223> OTHER INFORMATION: May or may not be present
<220> FEATURE:
<221> NAME/KEY: MOD_RES
<222> LOCATION: (5)..(5)
<223> OTHER INFORMATION: May or may not be present
<220> FEATURE:
<221> NAME/KEY: MOD_RES
<222> LOCATION: (6)..(6)
<223> OTHER INFORMATION: May or may not be present
<220> FEATURE:
<221> NAME/KEY: MOD_RES
<222> LOCATION: (7)..(7)
<223> OTHER INFORMATION: May or may not be present
<220> FEATURE:
<221> NAME/KEY: MOD_RES
<222> LOCATION: (8)..(8)
<223> OTHER INFORMATION: May or may not be present
<220> FEATURE:
<221> NAME/KEY: MOD_RES
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: May or may not be present
<220> FEATURE:
<221> NAME/KEY: MOD_RES
<222> LOCATION: (11)..(11)
<223> OTHER INFORMATION: May or may not be present
<220> FEATURE:
<221> NAME/KEY: MOD_RES
<222> LOCATION: (12)..(12)
<223> OTHER INFORMATION: May or may not be present
<220> FEATURE:
<221> NAME/KEY: MOD_RES
<222> LOCATION: (13)..(13)
```

```
<223> OTHER INFORMATION: May or may not be present
<220> FEATURE:
<221> NAME/KEY: MOD_RES
<222> LOCATION: (14)..(14)
<223> OTHER INFORMATION: May or may not be present
<220> FEATURE:
<221> NAME/KEY: MOD_RES
<222> LOCATION: (15)..(16)
<223> OTHER INFORMATION: May or may not be present
<220> FEATURE:
<221> NAME/KEY: MOD_RES
<222> LOCATION: (17)..(18)
<223> OTHER INFORMATION: May or may not be present
<220> FEATURE:
<221> NAME/KEY: MOD_RES
<222> LOCATION: (19)..(20)
<223> OTHER INFORMATION: May or may not be present
<220> FEATURE:
<221> NAME/KEY: MOD_RES
<222> LOCATION: (21)..(22)
<223> OTHER INFORMATION: May or may not be present
<220> FEATURE:
<221> NAME/KEY: MOD_RES
<222> LOCATION: (23)..(24)
<223> OTHER INFORMATION: May or may not be present
<220> FEATURE:
<221> NAME/KEY: MOD_RES
<222> LOCATION: (25)..(26)
<223> OTHER INFORMATION: May or may not be present
<220> FEATURE:
<221> NAME/KEY: MOD_RES
<222> LOCATION: (27)..(30)
<223> OTHER INFORMATION: May or may not be present
<220> FEATURE:
<221> NAME/KEY: MOD_RES
<222> LOCATION: (31)..(38)
<223> OTHER INFORMATION: May or may not be present
<220> FEATURE:
<221> NAME/KEY: MOD_RES
<222> LOCATION: (39)..(40)
<223> OTHER INFORMATION: May or may not be present
<220> FEATURE:
<221> NAME/KEY: MOD_RES
<222> LOCATION: (41)..(42)
<223> OTHER INFORMATION: May or may not be present
<220> FEATURE:
<221> NAME/KEY: MOD_RES
<222> LOCATION: (43)..(44)
<223> OTHER INFORMATION: May or may not be present
<220> FEATURE:
<221> NAME/KEY: MOD_RES
<222> LOCATION: (45)..(46)
<223> OTHER INFORMATION: May or may not be present
<220> FEATURE:
<221> NAME/KEY: MOD_RES
<222> LOCATION: (47)..(48)
<223> OTHER INFORMATION: May or may not be present
<220> FEATURE:
<221> NAME/KEY: MOD_RES
<222> LOCATION: (49)..(50)
<223> OTHER INFORMATION: May or may not be present
<220> FEATURE:
<221> NAME/KEY: MOD_RES
<222> LOCATION: (51)..(54)
<223> OTHER INFORMATION: May or may not be present
<220> FEATURE:
<221> NAME/KEY: MOD_RES
<222> LOCATION: (55)..(110)
<223> OTHER INFORMATION: May or may not be present
<220> FEATURE:
<221> NAME/KEY: MOD_RES
<222> LOCATION: (111)..(112)
<223> OTHER INFORMATION: May or may not be present
<220> FEATURE:
<221> NAME/KEY: MOD_RES
<222> LOCATION: (113)..(114)
<223> OTHER INFORMATION: May or may not be present
<220> FEATURE:
<221> NAME/KEY: MOD_RES
```

```
<222> LOCATION: (115)..(116)
<223> OTHER INFORMATION: May or may not be present
<220> FEATURE:
<221> NAME/KEY: MOD_RES
<222> LOCATION: (117)..(118)
<223> OTHER INFORMATION: May or may not be present
<220> FEATURE:
<221> NAME/KEY: MOD_RES
<222> LOCATION: (119)..(120)
<223> OTHER INFORMATION: May or may not be present
<220> FEATURE:
<221> NAME/KEY: MOD_RES
<222> LOCATION: (121)..(122)
<223> OTHER INFORMATION: May or may not be present
<220> FEATURE:
<221> NAME/KEY: MOD_RES
<222> LOCATION: (123)..(126)
<223> OTHER INFORMATION: May or may not be present
<220> FEATURE:
<221> NAME/KEY: MOD_RES
<222> LOCATION: (127)..(182)
<223> OTHER INFORMATION: May or may not be present
<220> FEATURE:
<221> NAME/KEY: MOD_RES
<222> LOCATION: (183)..(184)
<223> OTHER INFORMATION: May or may not be present
<220> FEATURE:
<221> NAME/KEY: MOD_RES
<222> LOCATION: (185)..(186)
<223> OTHER INFORMATION: May or may not be present
<220> FEATURE:
<221> NAME/KEY: MOD_RES
<222> LOCATION: (187)..(188)
<223> OTHER INFORMATION: May or may not be present
<220> FEATURE:
<221> NAME/KEY: MOD_RES
<222> LOCATION: (189)..(190)
<223> OTHER INFORMATION: May or may not be present
<220> FEATURE:
<221> NAME/KEY: MOD_RES
<222> LOCATION: (191)..(192)
<223> OTHER INFORMATION: May or may not be present
<220> FEATURE:
<221> NAME/KEY: MOD_RES
<222> LOCATION: (193)..(194)
<223> OTHER INFORMATION: May or may not be present
<220> FEATURE:
<221> NAME/KEY: MOD_RES
<222> LOCATION: (195)..(198)
<223> OTHER INFORMATION: May or may not be present
<220> FEATURE:
<221> NAME/KEY: MOD_RES
<222> LOCATION: (199)..(278)
<223> OTHER INFORMATION: May or may not be present
<220> FEATURE:
<221> NAME/KEY: MOD_RES
<222> LOCATION: (279)..(280)
<223> OTHER INFORMATION: May or may not be present
<220> FEATURE:
<221> NAME/KEY: MOD_RES
<222> LOCATION: (281)..(282)
<223> OTHER INFORMATION: May or may not be present
<220> FEATURE:
<221> NAME/KEY: MOD_RES
<222> LOCATION: (283)..(284)
<223> OTHER INFORMATION: May or may not be present
<220> FEATURE:
<221> NAME/KEY: MOD_RES
<222> LOCATION: (285)..(286)
<223> OTHER INFORMATION: May or may not be present
<220> FEATURE:
<221> NAME/KEY: MOD_RES
<222> LOCATION: (287)..(288)
<223> OTHER INFORMATION: May or may not be present
<220> FEATURE:
<221> NAME/KEY: MOD_RES
<222> LOCATION: (289)..(290)
<223> OTHER INFORMATION: May or may not be present
<220> FEATURE:
```

```
<221> NAME/KEY: MOD_RES
<222> LOCATION: (291)..(294)
<223> OTHER INFORMATION: May or may not be present
<220> FEATURE:
<221> NAME/KEY: MOD_RES
<222> LOCATION: (323)..(323)
<223> OTHER INFORMATION: Lys or Cys
<220> FEATURE:
<221> NAME/KEY: MOD_RES
<222> LOCATION: (325)..(325)
<223> OTHER INFORMATION: Leu or Cys
<220> FEATURE:
<221> NAME/KEY: MOD_RES
<222> LOCATION: (326)..(326)
<223> OTHER INFORMATION: Lys or Cys
<220> FEATURE:
<221> NAME/KEY: MOD_RES
<222> LOCATION: (327)..(327)
<223> OTHER INFORMATION: Ala or Cys
<220> FEATURE:
<221> NAME/KEY: MOD_RES
<222> LOCATION: (387)..(387)
<223> OTHER INFORMATION: Glu or Cys
<220> FEATURE:
<221> NAME/KEY: MOD_RES
<222> LOCATION: (388)..(388)
<223> OTHER INFORMATION: Asp or Cys
<220> FEATURE:
<221> NAME/KEY: MOD_RES
<222> LOCATION: (389)..(389)
<223> OTHER INFORMATION: Val or Cys
<220> FEATURE:
<221> NAME/KEY: MOD_RES
<222> LOCATION: (390)..(390)
<223> OTHER INFORMATION: Gly or Cys
<220> FEATURE:
<221> NAME/KEY: MOD_RES
<222> LOCATION: (457)..(460)
<223> OTHER INFORMATION: May or may not be present
<220> FEATURE:
<221> NAME/KEY: MOD_RES
<222> LOCATION: (461)..(462)
<223> OTHER INFORMATION: May or may not be present
<220> FEATURE:
<221> NAME/KEY: MOD_RES
<222> LOCATION: (463)..(464)
<223> OTHER INFORMATION: May or may not be present
<220> FEATURE:
<221> NAME/KEY: MOD_RES
<222> LOCATION: (465)..(466)
<223> OTHER INFORMATION: May or may not be present
<220> FEATURE:
<221> NAME/KEY: MOD_RES
<222> LOCATION: (467)..(468)
<223> OTHER INFORMATION: May or may not be present
<220> FEATURE:
<221> NAME/KEY: MOD_RES
<222> LOCATION: (469)..(470)
<223> OTHER INFORMATION: May or may not be present
<220> FEATURE:
<221> NAME/KEY: MOD_RES
<222> LOCATION: (471)..(472)
<223> OTHER INFORMATION: May or may not be present
<220> FEATURE:
<221> NAME/KEY: MOD_RES
<222> LOCATION: (473)..(552)
<223> OTHER INFORMATION: May or may not be present
<220> FEATURE:
<221> NAME/KEY: MOD_RES
<222> LOCATION: (553)..(556)
<223> OTHER INFORMATION: May or may not be present
<220> FEATURE:
<221> NAME/KEY: MOD_RES
<222> LOCATION: (557)..(558)
<223> OTHER INFORMATION: May or may not be present
<220> FEATURE:
<221> NAME/KEY: MOD_RES
<222> LOCATION: (559)..(560)
<223> OTHER INFORMATION: May or may not be present
```

```
<220> FEATURE:
<221> NAME/KEY: MOD_RES
<222> LOCATION: (561)..(562)
<223> OTHER INFORMATION: May or may not be present
<220> FEATURE:
<221> NAME/KEY: MOD_RES
<222> LOCATION: (563)..(564)
<223> OTHER INFORMATION: May or may not be present
<220> FEATURE:
<221> NAME/KEY: MOD_RES
<222> LOCATION: (565)..(566)
<223> OTHER INFORMATION: May or may not be present
<220> FEATURE:
<221> NAME/KEY: MOD_RES
<222> LOCATION: (567)..(568)
<223> OTHER INFORMATION: May or may not be present
<220> FEATURE:
<221> NAME/KEY: MOD_RES
<222> LOCATION: (569)..(624)
<223> OTHER INFORMATION: May or may not be present
<220> FEATURE:
<221> NAME/KEY: MOD_RES
<222> LOCATION: (625)..(628)
<223> OTHER INFORMATION: May or may not be present
<220> FEATURE:
<221> NAME/KEY: MOD_RES
<222> LOCATION: (629)..(630)
<223> OTHER INFORMATION: May or may not be present
<220> FEATURE:
<221> NAME/KEY: MOD_RES
<222> LOCATION: (631)..(632)
<223> OTHER INFORMATION: May or may not be present
<220> FEATURE:
<221> NAME/KEY: MOD_RES
<222> LOCATION: (633)..(634)
<223> OTHER INFORMATION: May or may not be present
<220> FEATURE:
<221> NAME/KEY: MOD_RES
<222> LOCATION: (635)..(636)
<223> OTHER INFORMATION: May or may not be present
<220> FEATURE:
<221> NAME/KEY: MOD_RES
<222> LOCATION: (637)..(638)
<223> OTHER INFORMATION: May or may not be present
<220> FEATURE:
<221> NAME/KEY: MOD_RES
<222> LOCATION: (639)..(640)
<223> OTHER INFORMATION: May or may not be present
<220> FEATURE:
<221> NAME/KEY: MOD_RES
<222> LOCATION: (641)..(696)
<223> OTHER INFORMATION: May or may not be present
<220> FEATURE:
<221> NAME/KEY: MOD_RES
<222> LOCATION: (697)..(700)
<223> OTHER INFORMATION: May or may not be present
<220> FEATURE:
<221> NAME/KEY: MOD_RES
<222> LOCATION: (701)..(702)
<223> OTHER INFORMATION: May or may not be present
<220> FEATURE:
<221> NAME/KEY: MOD_RES
<222> LOCATION: (703)..(704)
<223> OTHER INFORMATION: May or may not be present
<220> FEATURE:
<221> NAME/KEY: MOD_RES
<222> LOCATION: (705)..(706)
<223> OTHER INFORMATION: May or may not be present
<220> FEATURE:
<221> NAME/KEY: MOD_RES
<222> LOCATION: (707)..(708)
<223> OTHER INFORMATION: May or may not be present
<220> FEATURE:
<221> NAME/KEY: MOD_RES
<222> LOCATION: (709)..(710)
<223> OTHER INFORMATION: May or may not be present
<220> FEATURE:
<221> NAME/KEY: MOD_RES
<222> LOCATION: (711)..(712)
```

<223> OTHER INFORMATION: May or may not be present
<220> FEATURE:
<221> NAME/KEY: MOD_RES
<222> LOCATION: (713)..(720)
<223> OTHER INFORMATION: May or may not be present
<220> FEATURE:
<221> NAME/KEY: MOD_RES
<222> LOCATION: (721)..(724)
<223> OTHER INFORMATION: May or may not be present
<220> FEATURE:
<221> NAME/KEY: MOD_RES
<222> LOCATION: (725)..(726)
<223> OTHER INFORMATION: May or may not be present
<220> FEATURE:
<221> NAME/KEY: MOD_RES
<222> LOCATION: (727)..(728)
<223> OTHER INFORMATION: May or may not be present
<220> FEATURE:
<221> NAME/KEY: MOD_RES
<222> LOCATION: (729)..(730)
<223> OTHER INFORMATION: May or may not be present
<220> FEATURE:
<221> NAME/KEY: MOD_RES
<222> LOCATION: (731)..(732)
<223> OTHER INFORMATION: May or may not be present
<220> FEATURE:
<221> NAME/KEY: MOD_RES
<222> LOCATION: (733)..(734)
<223> OTHER INFORMATION: May or may not be present
<220> FEATURE:
<221> NAME/KEY: MOD_RES
<222> LOCATION: (735)..(736)
<223> OTHER INFORMATION: May or may not be present
<220> FEATURE:
<221> NAME/KEY: MOD_RES
<222> LOCATION: (737)..(737)
<223> OTHER INFORMATION: May or may not be present
<220> FEATURE:
<221> NAME/KEY: MOD_RES
<222> LOCATION: (738)..(738)
<223> OTHER INFORMATION: May or may not be present
<220> FEATURE:
<221> NAME/KEY: MOD_RES
<222> LOCATION: (739)..(739)
<223> OTHER INFORMATION: May or may not be present
<220> FEATURE:
<221> NAME/KEY: MOD_RES
<222> LOCATION: (740)..(740)
<223> OTHER INFORMATION: May or may not be present
<220> FEATURE:
<221> NAME/KEY: MOD_RES
<222> LOCATION: (741)..(741)
<223> OTHER INFORMATION: May or may not be present
<220> FEATURE:
<221> NAME/KEY: MOD_RES
<222> LOCATION: (742)..(742)
<223> OTHER INFORMATION: May or may not be present
<220> FEATURE:
<221> NAME/KEY: MOD_RES
<222> LOCATION: (743)..(743)
<223> OTHER INFORMATION: May or may not be present
<220> FEATURE:
<221> NAME/KEY: MOD_RES
<222> LOCATION: (744)..(744)
<223> OTHER INFORMATION: May or may not be present
<220> FEATURE:
<221> NAME/KEY: MOD_RES
<222> LOCATION: (745)..(745)
<223> OTHER INFORMATION: May or may not be present
<220> FEATURE:
<221> NAME/KEY: MOD_RES
<222> LOCATION: (746)..(746)
<223> OTHER INFORMATION: May or may not be present

<400> SEQUENCE: 22

Ile Glu Gly Arg His His His His His His His His His Ser Gly
1               5                   10                  15

```
Ser Gly Ser Gly Ser Gly Ser Gly Ser Gly Ile Glu Gly Arg Trp Ser
        20                  25                  30

His Pro Gln Phe Glu Lys Ser Gly Ser Gly Ser Gly Ser Gly
        35                  40                  45

Ser Gly Ile Glu Gly Arg Ala Gln His Asp Glu Ala Gln Gln Asn Ala
        50                  55                  60

Phe Tyr Gln Val Leu Asn Met Pro Asn Leu Asn Ala Asp Gln Arg Asn
 65                 70                  75                  80

Gly Phe Ile Gln Ser Leu Lys Asp Asp Pro Ser Gln Ser Ala Asn Val
                85                  90                  95

Leu Gly Glu Ala Gln Lys Leu Asn Asp Ser Gln Ala Pro Lys Ser Gly
            100                 105                 110

Ser Gly Ser Gly Ser Gly Ser Gly Ile Glu Gly Arg Met Thr
        115                 120                 125

Tyr Lys Leu Ile Leu Asn Gly Lys Thr Leu Lys Gly Glu Thr Thr Thr
        130                 135                 140

Glu Ala Val Asp Ala Ala Thr Ala Glu Lys Val Phe Lys Gln Tyr Ala
145                 150                 155                 160

Asn Asp Asn Gly Val Asp Gly Glu Trp Thr Tyr Asp Asp Ala Thr Lys
                165                 170                 175

Thr Phe Thr Val Thr Glu Ser Gly Ser Gly Ser Gly Ser Gly
            180                 185                 190

Ser Gly Ile Glu Gly Arg Met Asp Pro Gly Asp Ala Ser Glu Leu Thr
        195                 200                 205

Pro Ala Val Thr Thr Tyr Lys Leu Val Ile Asn Gly Lys Thr Leu Lys
210                 215                 220

Gly Glu Thr Thr Thr Lys Ala Val Asp Ala Glu Thr Ala Glu Lys Ala
225                 230                 235                 240

Phe Lys Gln Tyr Ala Asn Asp Asn Gly Val Asp Gly Val Trp Thr Tyr
                245                 250                 255

Asp Asp Ala Thr Lys Thr Phe Thr Val Thr Glu Met Val Thr Glu Val
            260                 265                 270

Pro Val Ala Ser Lys Arg Ser Gly Ser Gly Ser Gly Ser Gly
        275                 280                 285

Ser Gly Ile Glu Gly Arg Met Ser Val Met Tyr Lys Lys Ile Leu Tyr
        290                 295                 300

Pro Thr Asp Phe Ser Glu Thr Ala Glu Ile Ala Leu Lys His Val Lys
305                 310                 315                 320

Ala Phe Xaa Thr Xaa Xaa Xaa Glu Glu Val Ile Leu Leu His Val Ile
                325                 330                 335

Asp Glu Arg Glu Ile Lys Lys Arg Asp Ile Phe Ser Leu Leu Leu Gly
            340                 345                 350

Val Ala Gly Leu Asn Lys Ser Val Glu Glu Phe Glu Asn Glu Leu Lys
        355                 360                 365

Asn Lys Leu Thr Glu Glu Ala Lys Asn Lys Met Glu Asn Ile Lys Lys
        370                 375                 380

Glu Leu Xaa Xaa Xaa Xaa Phe Lys Val Lys Asp Ile Ile Val Val Gly
385                 390                 395                 400

Ile Pro His Glu Glu Ile Val Lys Ile Ala Glu Asp Glu Gly Val Asp
                405                 410                 415

Ile Ile Ile Met Gly Ser His Gly Lys Thr Asn Leu Lys Glu Ile Leu
            420                 425                 430

Leu Gly Ser Val Thr Glu Asn Val Ile Lys Lys Ser Asn Lys Pro Val
```

```
            435                 440                 445
Leu Val Val Lys Arg Lys Asn Ser Ile Glu Gly Arg Ser Gly Ser Gly
        450                 455                 460

Ser Gly Ser Gly Ser Gly Ser Gly Met Asp Pro Gly Asp Ala Ser Glu
465                 470                 475                 480

Leu Thr Pro Ala Val Thr Thr Tyr Lys Leu Val Ile Asn Gly Lys Thr
                485                 490                 495

Leu Lys Gly Glu Thr Thr Thr Lys Ala Val Asp Ala Glu Thr Ala Glu
            500                 505                 510

Lys Ala Phe Lys Gln Tyr Ala Asn Asp Asn Gly Val Asp Gly Val Trp
        515                 520                 525

Thr Tyr Asp Asp Ala Thr Lys Thr Phe Thr Val Thr Glu Met Val Thr
    530                 535                 540

Glu Val Pro Val Ala Ser Lys Arg Ile Glu Gly Arg Ser Gly Ser Gly
545                 550                 555                 560

Ser Gly Ser Gly Ser Gly Ser Gly Met Thr Tyr Lys Leu Ile Leu Asn
                565                 570                 575

Gly Lys Thr Leu Lys Gly Glu Thr Thr Thr Glu Ala Val Asp Ala Ala
            580                 585                 590

Thr Ala Glu Lys Val Phe Lys Gln Tyr Ala Asn Asp Asn Gly Val Asp
        595                 600                 605

Gly Glu Trp Thr Tyr Asp Asp Ala Thr Lys Thr Phe Thr Val Thr Glu
    610                 615                 620

Ile Glu Gly Arg Ser Gly Ser Gly Ser Gly Ser Gly Ser Gly Ser Gly
625                 630                 635                 640

Ala Gln His Asp Glu Ala Gln Gln Asn Ala Phe Tyr Gln Val Leu Asn
                645                 650                 655

Met Pro Asn Leu Asn Ala Asp Gln Arg Asn Gly Phe Ile Gln Ser Leu
            660                 665                 670

Lys Asp Asp Pro Ser Gln Ser Ala Asn Val Leu Gly Glu Ala Gln Lys
        675                 680                 685

Leu Asn Asp Ser Gln Ala Pro Lys Ile Glu Gly Arg Ser Gly Ser Gly
    690                 695                 700

Ser Gly Ser Gly Ser Gly Ser Gly Trp Ser His Pro Gln Phe Glu Lys
705                 710                 715                 720

Ile Glu Gly Arg Ser Gly Ser Gly Ser Gly Ser Gly Ser Gly Ser Gly
                725                 730                 735

His His His His His His His His His
            740                 745

<210> SEQ ID NO 23
<211> LENGTH: 4
<212> TYPE: PRT
<213> ORGANISM: Artificial Sequence
<220> FEATURE:
<223> OTHER INFORMATION: Description of artificial sequence: Synthetic
      construct

<400> SEQUENCE: 23

Ile Glu Gly Arg
1

<210> SEQ ID NO 24
<211> LENGTH: 10
<212> TYPE: PRT
<213> ORGANISM: Artificial Sequence
<220> FEATURE:
```

```
<223> OTHER INFORMATION: Description of artificial sequence: Synthetic
      construct
<220> FEATURE:
<221> NAME/KEY: misc_feature
<222> LOCATION: (1)..(10)
<223> OTHER INFORMATION: This sequence may encompass 0-10 "His" residues

<400> SEQUENCE: 24

His His His His His His His His His
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Description of artificial sequence: Synthetic
      construct

<400> SEQUENCE: 25

Trp Ser His Pro Gln Phe Glu Lys
1               5

<210> SEQ ID NO 26
<211> LENGTH: 56
<212> TYPE: PRT
<213> ORGANISM: Artificial Sequence
<220> FEATURE:
<223> OTHER INFORMATION: Description of artificial sequence: Synthetic
      construct

<400> SEQUENCE: 26

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 27
<211> LENGTH: 56
<212> TYPE: PRT
<213> ORGANISM: Artificial Sequence
<220> FEATURE:
<223> OTHER INFORMATION: Description of artificial sequence: Synthetic
      construct

<400> SEQUENCE: 27

Met Thr Tyr Lys Leu Ile Leu Asn Gly Lys Thr Leu Lys Gly Glu Thr
1               5                   10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 28
<211> LENGTH: 80
<212> TYPE: PRT
<213> ORGANISM: Artificial Sequence
```

```
<220> FEATURE:
<223> OTHER INFORMATION: Description of artificial sequence: Synthetic
      construct

<400> SEQUENCE: 28

Met Asp Pro Gly Asp Ala Ser Glu Leu Thr Pro Ala Val Thr Thr Tyr
1               5                   10                  15

Lys Leu Val Ile Asn Gly Lys Thr Leu Lys Gly Glu Thr Thr Thr Lys
            20                  25                  30

Ala Val Asp Ala Glu Thr Ala Glu Lys Ala Phe Lys Gln Tyr Ala Asn
        35                  40                  45

Asp Asn Gly Val Asp Gly Val Trp Thr Tyr Asp Asp Ala Thr Lys Thr
    50                  55                  60

Phe Thr Val Thr Glu Met Val Thr Glu Val Pro Val Ala Ser Lys Arg
65                  70                  75                  80
```